US012667546B2

(12) United States Patent
Tam et al.

(10) Patent No.: US 12,667,546 B2
(45) Date of Patent: Jun. 30, 2026

(54) METHODS FOR MANIPULATING CELL STATE TRANSITIONS IN CANCER

(71) Applicant: AGENCY FOR SCIENCE, TECHNOLOGY AND RESEARCH, Singapore (SG)

(72) Inventors: Wai Leong Tam, Singapore (SG); Ser Yue Loo, Singapore (SG); Li Ping Toh, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 719 days.

(21) Appl. No.: 17/293,362

(22) PCT Filed: Nov. 11, 2019

(86) PCT No.: PCT/SG2019/050549
§ 371 (c)(1),
(2) Date: May 12, 2021

(87) PCT Pub. No.: WO2020/101571
PCT Pub. Date: May 22, 2020

(65) Prior Publication Data
US 2022/0008358 A1 Jan. 13, 2022

(30) Foreign Application Priority Data
Nov. 12, 2018 (SG) ........................... 10201810070Y

(51) Int. Cl.
| | |
|---|---|
| *A61P 35/04* | (2006.01) |
| *A61K 31/07* | (2006.01) |
| *A61K 31/513* | (2006.01) |
| *A61K 45/06* | (2006.01) |
| *A61P 35/00* | (2006.01) |

(52) U.S. Cl.
CPC ............ *A61K 31/07* (2013.01); *A61K 31/513* (2013.01); *A61K 45/06* (2013.01); *A61P 35/00* (2018.01); *A61P 35/04* (2018.01)

(58) Field of Classification Search
CPC ...... A61K 45/06; A61K 31/07; A61K 31/192; A61K 31/337; A61K 31/513; A61P 35/00
See application file for complete search history.

(56) References Cited

U.S. PATENT DOCUMENTS

| | | | | |
|---|---|---|---|---|
| 9,953,129 B2 * | 4/2018 | Thiery | ................... | G16B 20/00 |
| 10,398,672 B2 * | 9/2019 | Pattabiraman | ....... | C12N 5/0093 |
| 2014/0357693 A1 | 12/2014 | Shaul et al. | | |
| 2017/0049745 A1 * | 2/2017 | Pattabiraman | ..... | G01N 33/5041 |

FOREIGN PATENT DOCUMENTS

| | | | | |
|---|---|---|---|---|
| WO | WO-2009017833 A2 * | 2/2009 | ......... | A61K 39/3955 |
| WO | WO-2010099138 A2 * | 9/2010 | ......... | G01N 33/5017 |

OTHER PUBLICATIONS

Meyskens et al., "Cancer Prevention: Obstacles, Challenges, and the Road Ahead", 2016, J Natl Cancer Inst, pp. 1-8 (Year: 2016).*
Chengye et al., "Metformin reverses bFGF-induced epithelial-mesenchymal transition in HCC cells", 2017, Oncology, 8, pp. 104247-104257 (Year: 2017).*
Gudas, "Retinoids induce stem cell differentiation via epigenetic changes", 2013, Semin. Cell Dev. Biol., 24, pp. 1-11 (Year: 2013).*
Ampuero et al., "Metformin inhibits glutaminase activity and protects against hepatic encephalopathy", 2012, PLOS One, 7, pp. 1-6 (Year: 2012).*
Montagner et al., "Beta-catenin oncogenic activation rewires fatty acid catabolismo fuel hepatocellular carcinoma", 2018, Gut, 0, pp. 1-2 (Year: 2018).*
Cao et al., "Chemical reprogramming of mouse embryonic and adult fibroblast into endoderm lineage", 2017, J. Biol. Chem., 292, pp. 19122-19132 (Year: 2017).*
Biddle et al., "Phenotypic Plasticity Determines Cancer Stem Cell Therapeutic Resistance in Oral Squamous Cell Carcinoma", 2016 , EBioMedicine, 4, pp. 138-145 (Year: 2016).*
Gonzalez-Baro et al., "Mitochondrial acyltransferases and glycerophospholipid metabolism", 2017, Biochimica et Biophysica Acta, 1862, pp. 49-55 (Year: 2017).*
Merino et al., "Combined Treatment with Epigenetic, Differentiating, and Chemotherapeutic Agents Cooperatively Targets Tumor-Initiating Cells in Triple-Negative Breast Cancer", 2016, Cancer Research, 76, pp. 2013-2024 (Year: 2016).*
Connolly et al., "Molecular Pathways: Current Role and Future Directions of the Retinoic Acid Pathway in Cancer Prevention and Treatment", 2013, Molecular Pathways, 19, pp. 1651-1659 (Year: 2013).*
Wright et al., "CDCP1 drives triple-negative breast cancer metastasis through reduction of lipid-droplet abundance and stimulation of fatty acid oxidation", 2017, PNAS, 114, E6556-E6565 (Year: 2017).*
Tsuchiya et al., "Characteristic interactivity of landiolol, an ultra-short-acting highly selective β1 blocker, with biomimetic membranes : comparisons with β1-selective esmolol and non-selective propranolol and alprenolol", 2013, Frontiers in Pharmacology; 4, pp. 1-8 (Year: 2013).*

(Continued)

*Primary Examiner* — Brenda L Coleman
*Assistant Examiner* — Madeline E Braun
(74) *Attorney, Agent, or Firm* — Sterne, Kessler, Goldstein & Fox P.L.L.C.

(57) ABSTRACT

The present invention relates to a method of inducing mesenchymal-epithelial transition (MET) in a basal-like (or mesenchymal-like) cancer cell by contacting the cancer cell with an inducer of mesenchymal-epithelial transition for a time and under conditions sufficient to induce MET in the cell. Additionally, there is also provided a method of inhibiting epithelial-mesenchymal transition (EMT) of a cancer in a subject, the method comprising administering an inhibitor or regulator of lipid metabolism for a sufficient time and under conditions to inhibit epithelial mesenchymal transition (EMT) of the cancer in the subject.

9 Claims, 68 Drawing Sheets
Specification includes a Sequence Listing.

(56) References Cited

OTHER PUBLICATIONS

Bushue et al., "Retinoid pathway and cancer therapeutics", 2010, Advanced Drug Delivery Reviews, 62, pp. 1285-1298 (Year: 2010).*

Saurat, "Retinoids and psoriasis: Novel issues in retinoid pharmacology and implications for psoriasis treatment", 1999, J Am Acad Dermatol, 41, S1-S6 (Year: 1999).*

McKeown et al., "Superenhancer Analysis Defines Novel Epigenomic Subtypes of Non-APL AML, Including an RARa Dependency Targetable by SY-1425, a Potent and Selective RARa agonist", 2017, Cancer Discovery, pp. 1137-1153 (Year: 2017).*

Green et al., "RARy is a negative regulator of osteoclastogenesis", 2015, Journal of Steroid Biochemistry & Molecular Biology, 150, pp. 46-53 (Year: 2015).*

Huang et al., "Characterization of the interactions of potent allosteric inhibitors with glutaminase C, a key enzyme in cancer cell glutamine metabolism", 2018, J Biol Chem, 293, pp. 3535-3545 (Year: 2018).*

Lee et al., "DIx-2 and glutaminase upregulate epithelial-mesenchymal transition and glycolytic switch", 2016, Oncotarget, 7, pp. 7925-7939 (Year: 2016).*

Feng et al., "M3 muscarinic acetylcholine receptors regulate epithelial-mesenchymal transition, perineural invasion, and migration/metastasis in cholangiocarcinoma through the AKT", 2018, Cancer Cell International, 18, pp. 1-12 (Year: 2018).*

Zanetti et al., "All-trans-retinoic Acid Modulates the Plasticity and Inhibits the Motility of Breast Cancer Cells", 2015, The Journal of Biological Chemistry, 290, pp. 17690-17709 (Year: 2015).*

Pubchem, "5-[3-bromo-4-(dimethylamino)phenyl]-2,2-dimethyl-2,3,5,6-tetrahydrobenzo[a]phenanthridin-4(1H)-one", first available 2005, National Library of Medicine, 18 pgs. (Year: 2005).*

Zhang et al., "Norepinephrine induced epithelial-mesenchymal transition in HT-29 and A549 cells in vitro", 2016, Journal of Cancer Research and Clinical Oncology, 142, pp. 423-435 (Year: 2016).*

Wagner et al., "Propranolol for the treatment of vascular sarcomas", 2018, Journal of Experimental Pharmacology, 10, pp. 51-58 (Year: 2018).*

Elks (ed.), "The Dictionary of Drugs: Chemical Data, Structures and Bibliographies", 2014, Springer, p. 1258 (Year: 2014).*

Ramírez-Merino et al., "Chemotherapy for cholangiocarcinoma: An update", 2013, World Journal of Gastrointestinal Oncology, 5, pp. 171-176 (Year: 2013).*

Chen et al., "Targeting Glutamine Induces Apoptosis: A Cancer Therapy Approach", 2015, International Journal of Molecular Sciences, 16, pp. 22830-22855 (Year: 2015).*

Lampa et al., "Glutaminase is essential for the growth of triple-negative breast cancer cells with a deregulated glutamine metabolism pathway and its suppression synergizes with mTOR", 2017, PLOS One, 12, pp. 1-24 (Year: 2017).*

Bevill, "Transcriptional Adaptation to Targeted Inhibitors via Bet Bromodomain Proteins in Triple-Negative Breast Cancer", 2019, University of North Carolina at Chapel Hill Graduate School, 205 pgs. (Year: 2019).*

Vijay et al., "GSK3β regulates epithelial-mesenchymal transition and cancer stem cell properties in triple-negative breast cancer", 2019, Breast Cancer Research, 21, 257 pgs. (Year: 2019).*

Biddle, A., "Phenotypic Plasticity Determines Cancer Stem Cell Therapeutic Resistance in Oral Squamous Cell Carcinoma," *EBioMedicine* 4:138-45, Elsevier, Netherlands (2016).

Biorad., "ChemiDoc™ and ChemiDoc MP Imaging Systems with Image Lab™ Touch Software," Catalog No. 17001401, 39 pages.

Buijs, J.T., et al., "BMP7, A Putative Regulator of Epithelial Homeostasis in the Human Prostate, Is a Potent Inhibitor of Prostate Cancer Bone Metastasis in Vivo," *The American Journal of Pathology* 171(3):1047-1057, American Association of Pathologists, United States (2007).

Doctoral Thesis-Epigenetic Mechanisms Regulating Epithelial-mesenchymal Plasticity in Breast Cancer, [Retrieved from https://edoc.unibas.ch/59030/ on Jan. 17, 2020] (Jun. 2017).

Hernandez, A., et al., "Role of Lipid Droplets in Metastasis and Drug Resistance," Abstract CHED-1169, 255th ACS National Meeting & Exposition (2018).

International Search Report and Written Opinion for Application No. PCT/SG2019/050549, mailed on Feb. 5, 2020, 18 pages.

Nath, A and Chan, C., "Genetic Alterations in Fatty Acid Transport and Metabolism Genes Are Associated With Metastatic Progression and Poor Prognosis of Human Cancers," *Scientific Reports* 6:18669, Nature Publishing Group, England (2016).

NCBI, "ChIP-Seq N8 S159," Accession No. GSE119824, available at https://www.ncbi.nlm.nih.gov/geo/query/acc.cgi?acc=GSE119824, 2 pages.

Origene., CPT1A (NM_001031847) Human Tagged ORF Clone—Cat No. RC200485L1, Product sheet, 5 pages.

Pattabiraman, D.R., et al., "Activation of PKA Leads to Mesenchymal-to-Epithelial Transition and Loss of Tumor-Initiating Ability," *Science* 351(6277):aad3680, American Association for the Advancement of Science, United States (2016).

SRA database, "Rewiring of Lipid Metabolism Is Essential for Cell State Transition in Breast Cancer," Accession No. SRP152713, available at https://trace.ncbi.nlm.nih.gov/Traces/sra/?study=SRP152713.

Thermofisher Scientific., "SuperSignal™ West Dura Extended Duration Substrate," Cat No. 34075, 5 pages.

Ulanet, D.B., et al., "Mesenchymal Phenotype Predisposes Lung Cancer Cells to Impaired Proliferation and Redox Stress in Response to Glutaminase Inhibition," *PLoS One* 9(12):e115144, Public Library of Science, United States (2014).

Viotti, M., et al., "SUV420H2 Is an Epigenetic Regulator of Epithelial/mesenchymal States in Pancreatic Cancer," *The Journal of Cell Biology* 217(2):763-777, Rockefeller University Press, United States (2018).

Wu, M.J., et al., "Retinoic Acid Directs Breast Cancer Cell State Changes Through Regulation of TET2-PKCζ Pathway," Oncogene 36(22):3193-3206, Nature Publishing Group, England (2017).

Zhou, P., et al., "The Epithelial to Mesenchymal Transition (EMT) and Cancer Stem Cells: Implication for Treatment Resistance in Pancreatic Cancer," *Molecular Cancer* 16(1):52: 1-11, BioMed Central, England (2017).

* cited by examiner

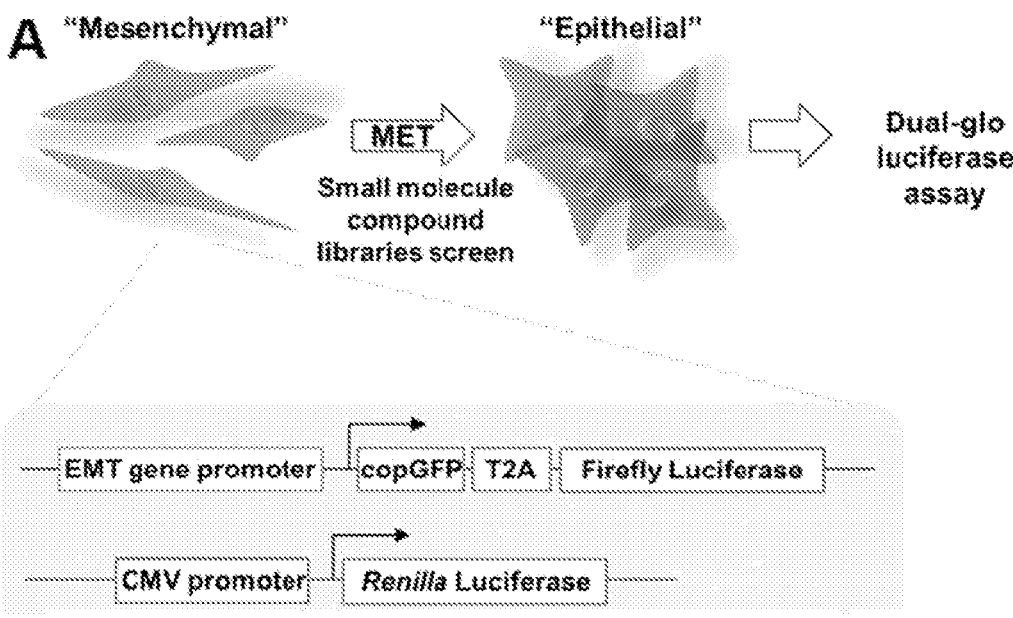
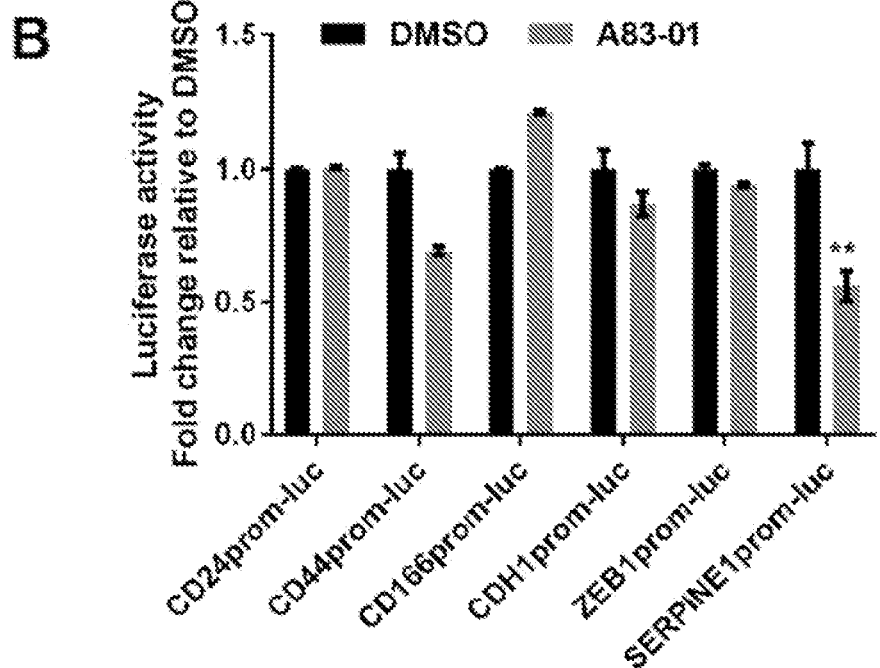
Figure 1 (A)-(B) (continued)

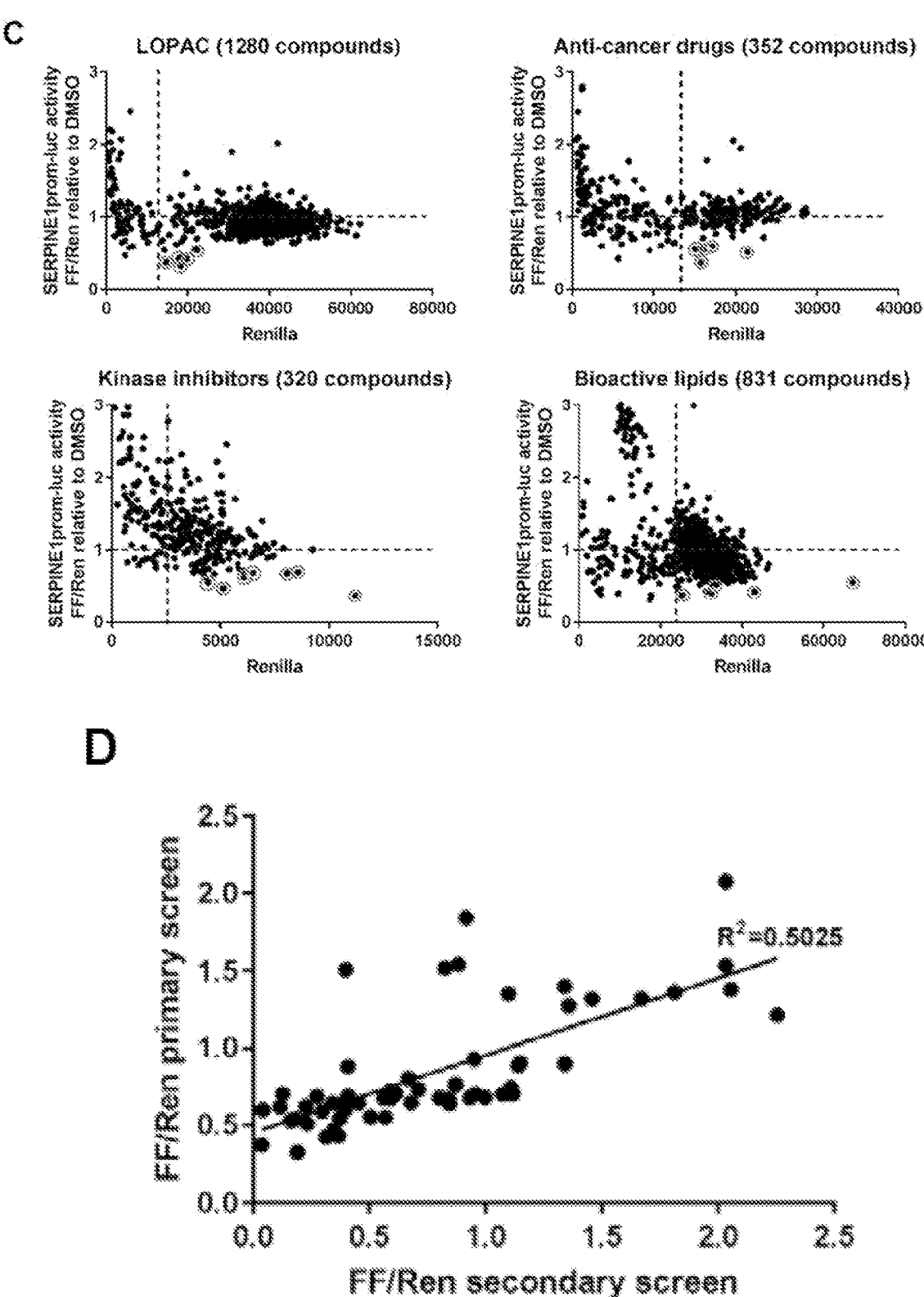
Figure 1 (C)-(D) (continued)

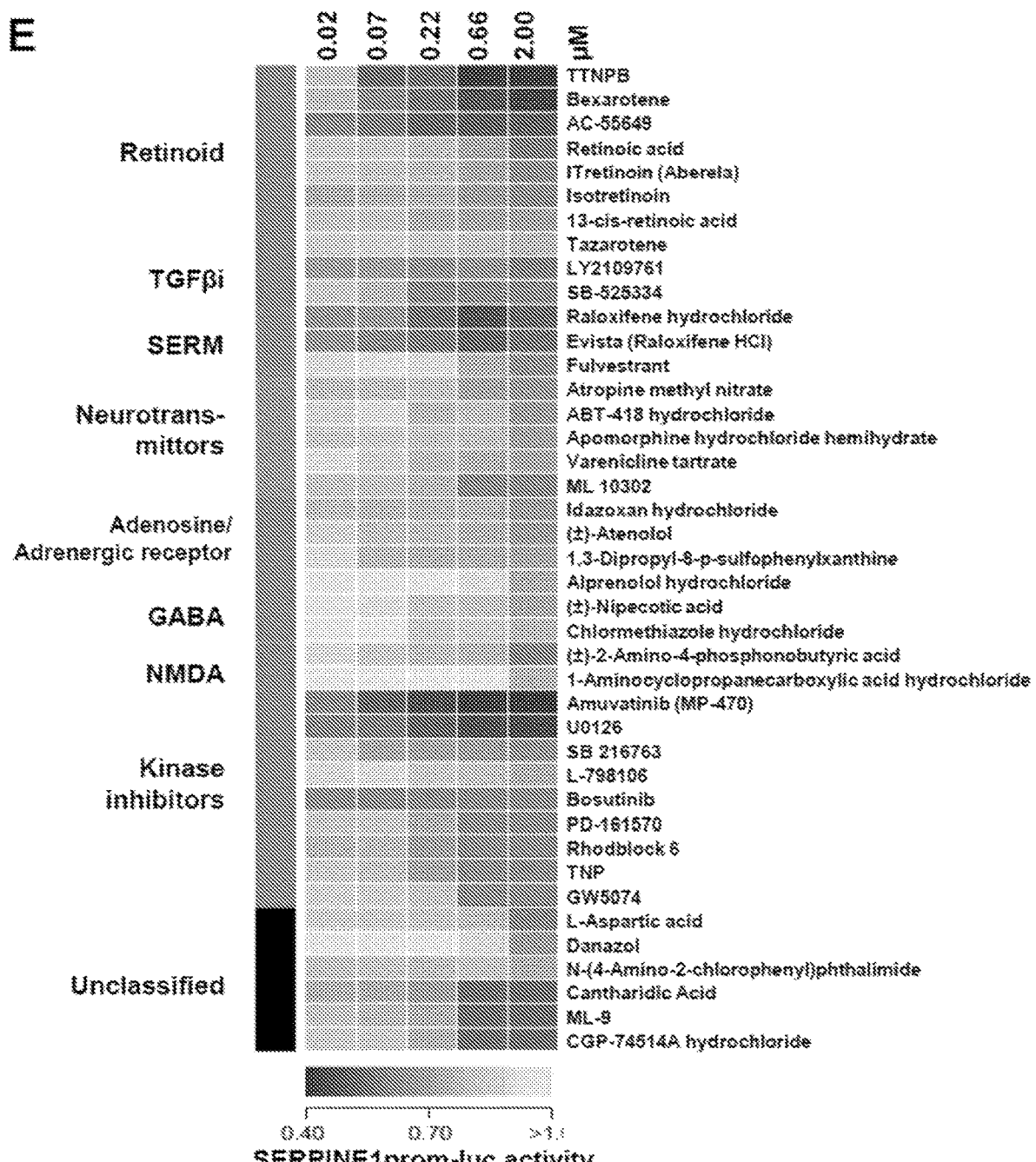
Figure 1E (end)

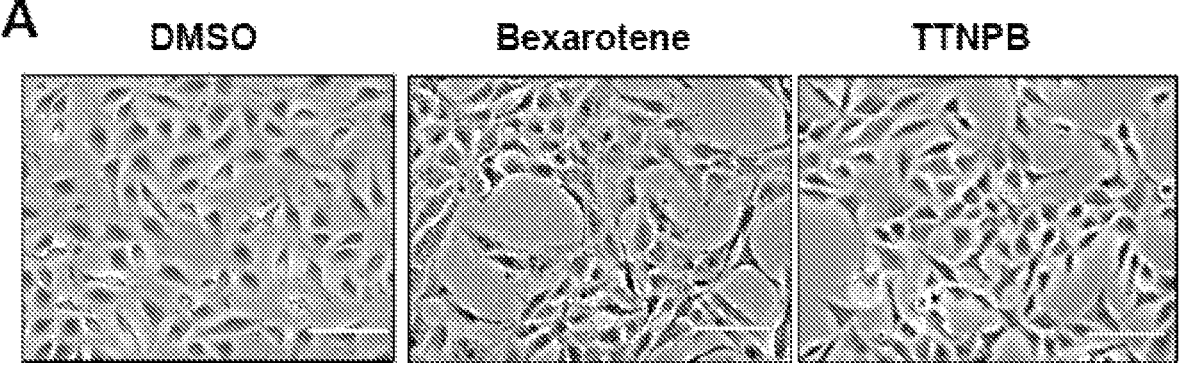
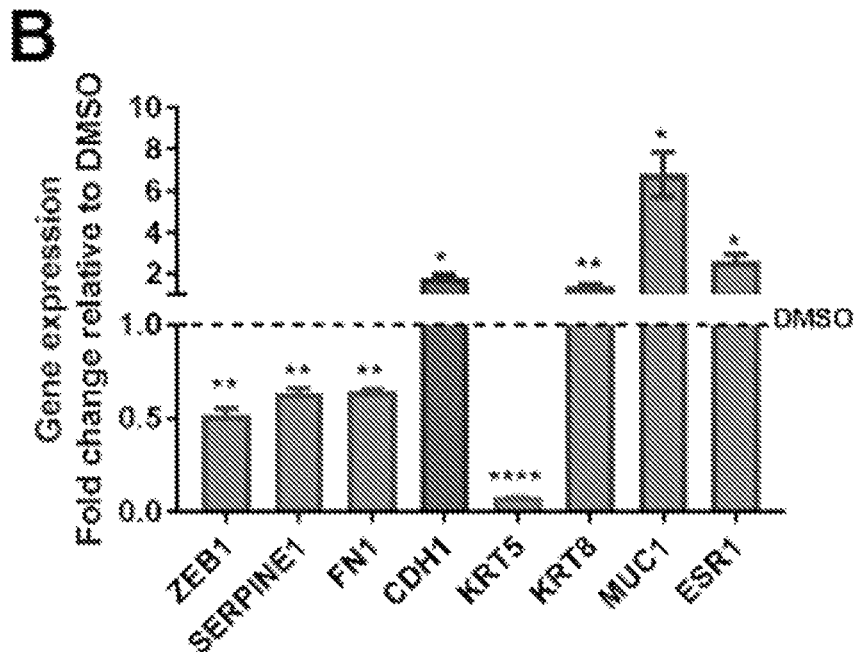
Figure 2(A)-(B) (continued)

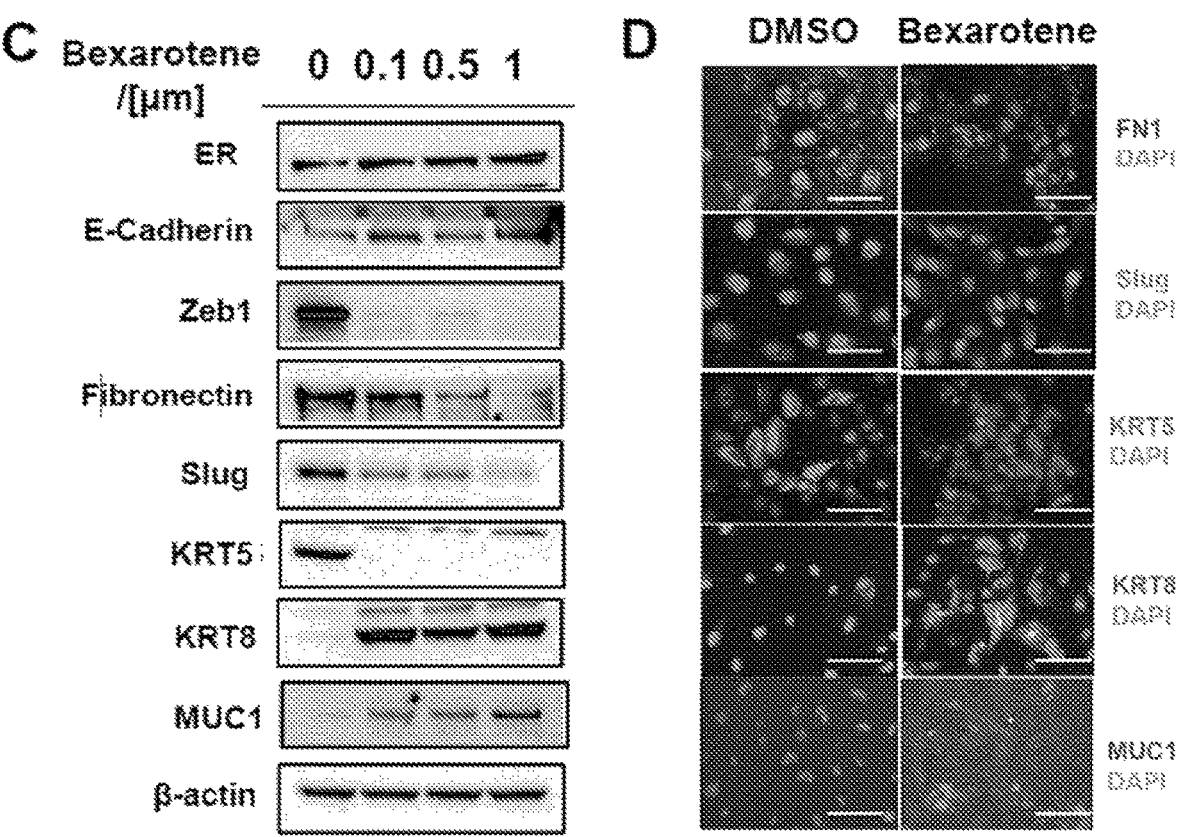
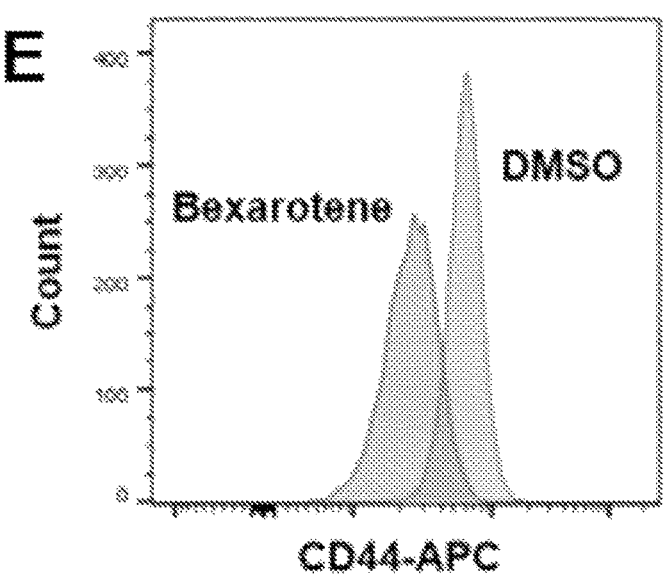
Figure 2(C)-(E) (continued)

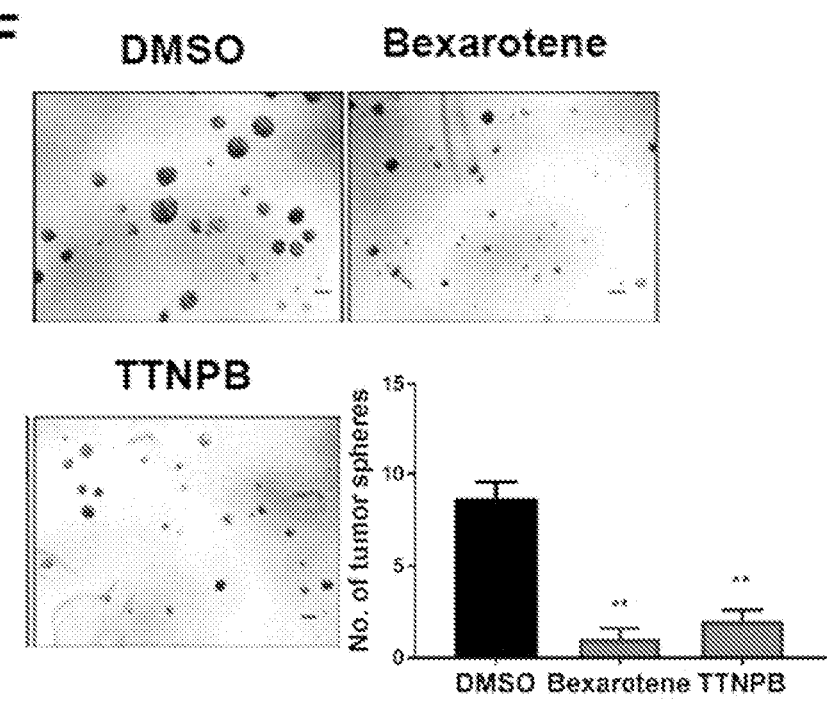
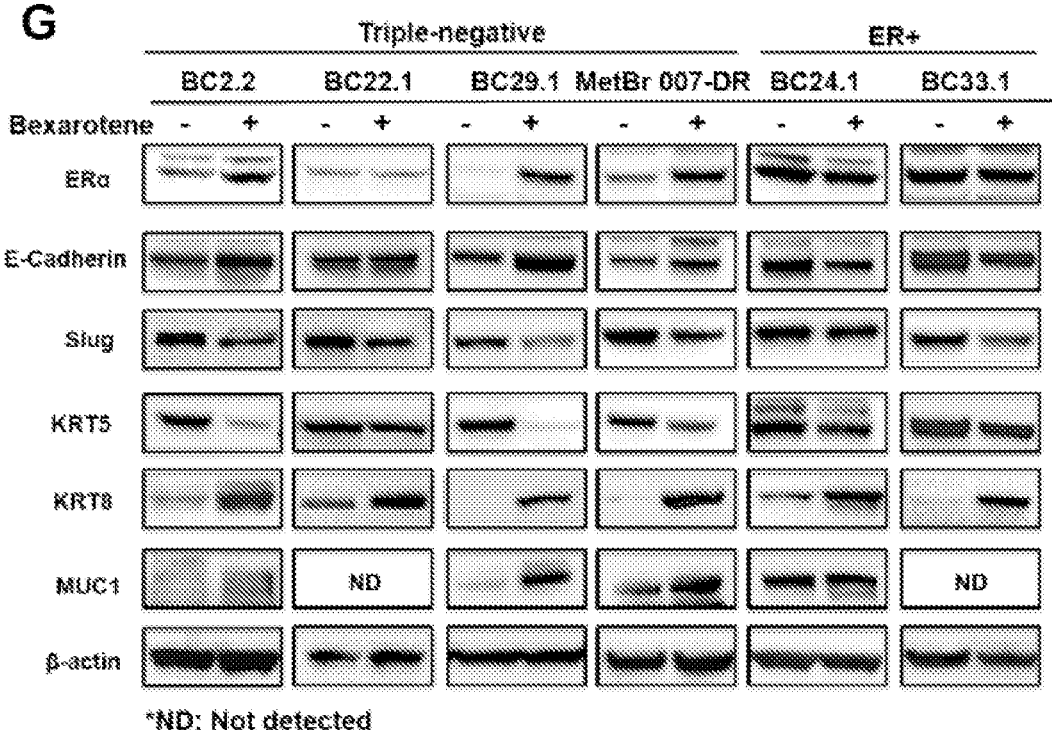
Figure 2(F)-(G) (continued)

H
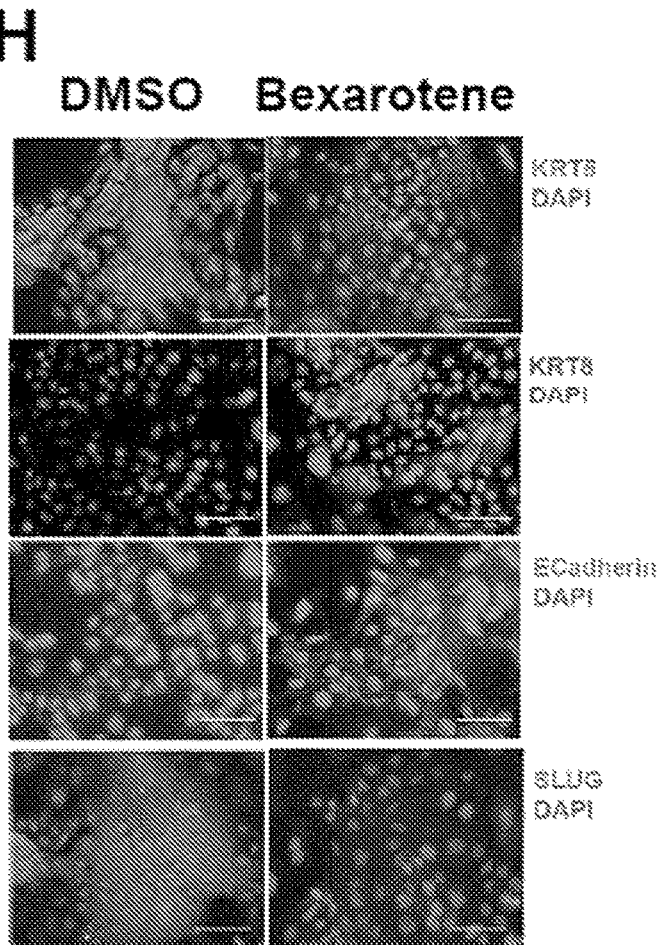
I
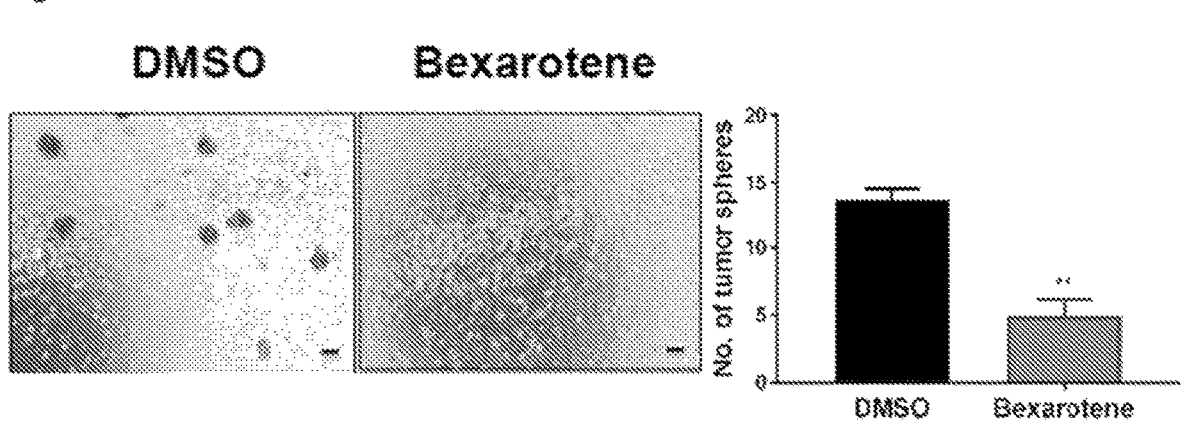
Figure 2(H)-(I) (continued)

J
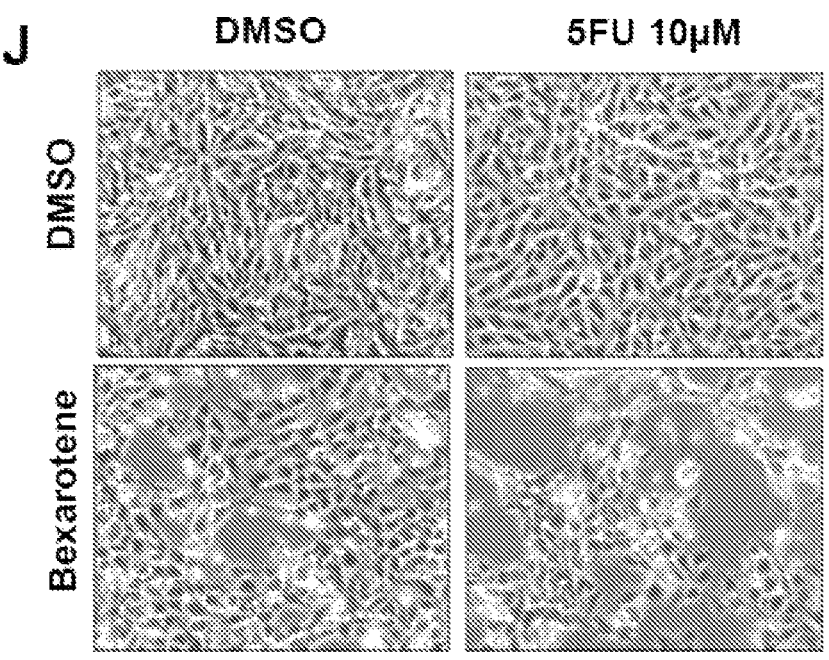
K
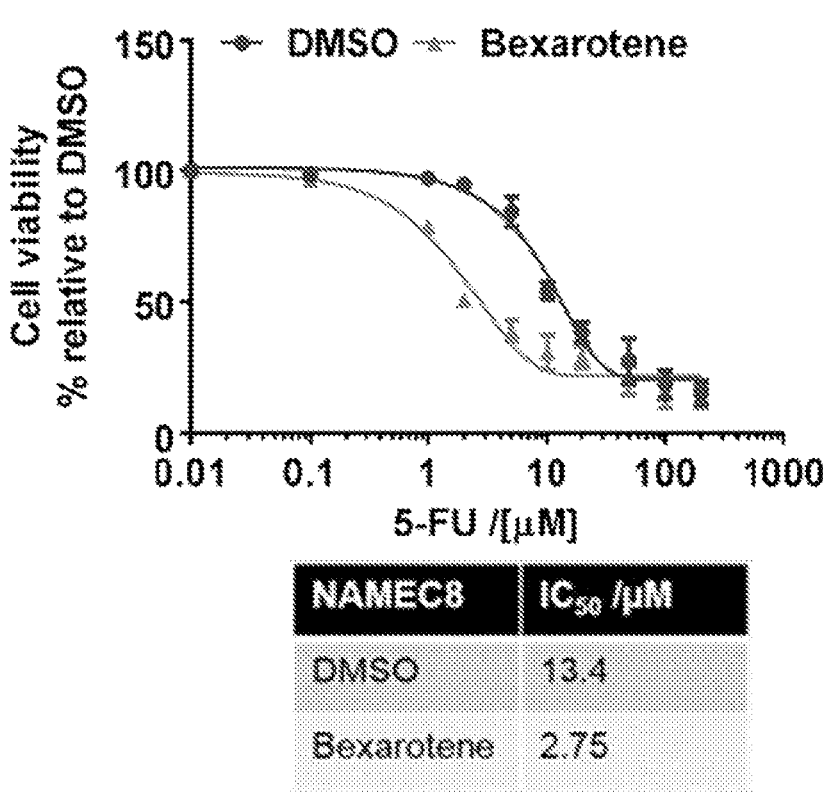
Figure 2(J)-(K) (continued)

L
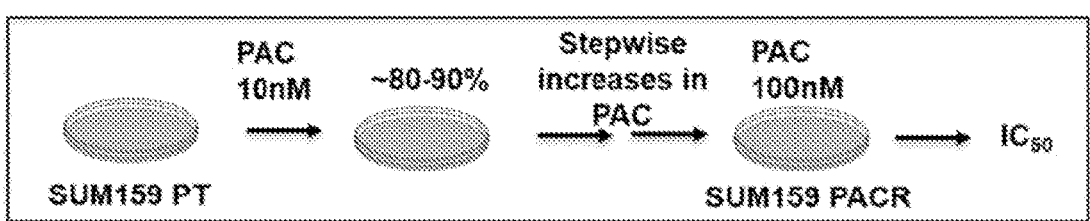
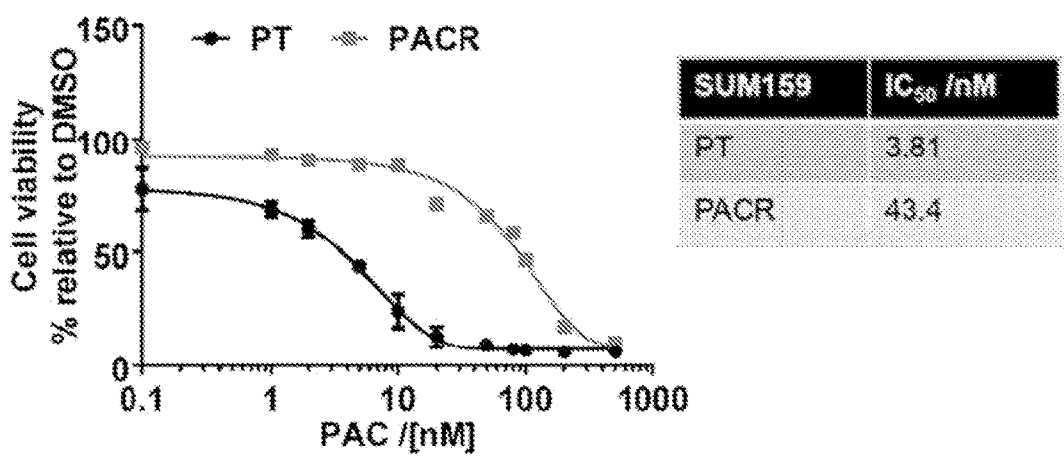
M
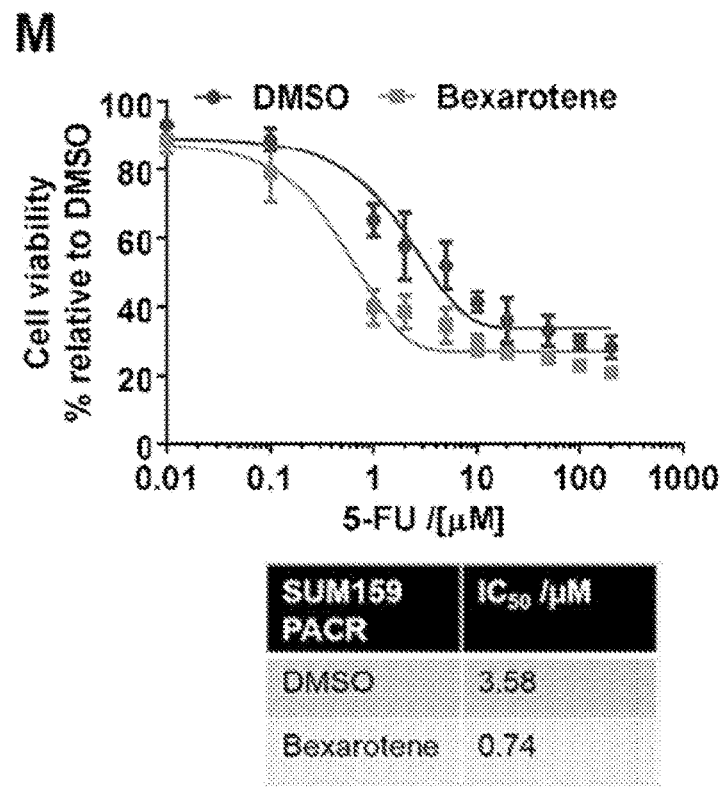
Figure 2(L)-(M) (end)

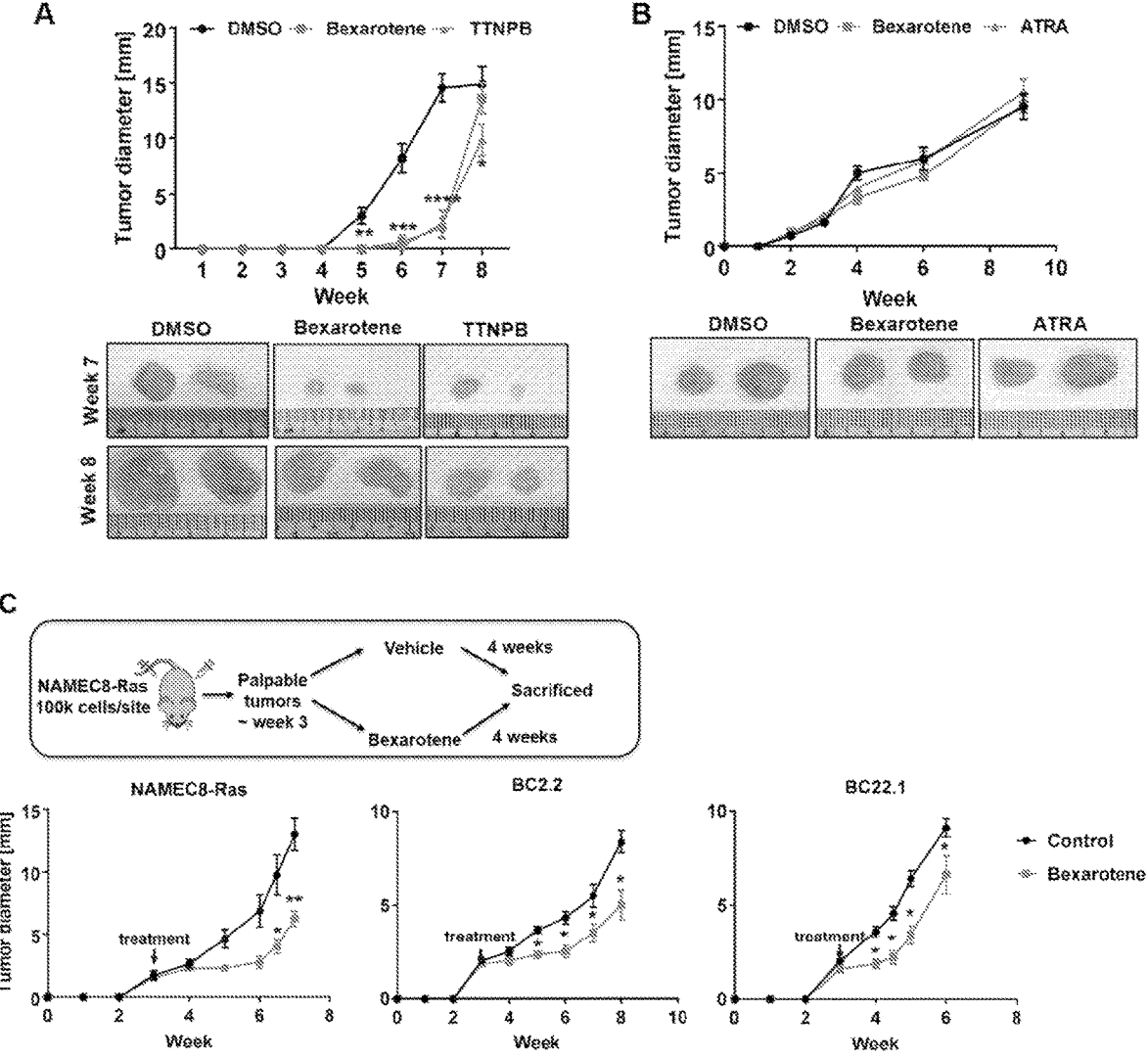
Figure 3(A)-(C) (continued)

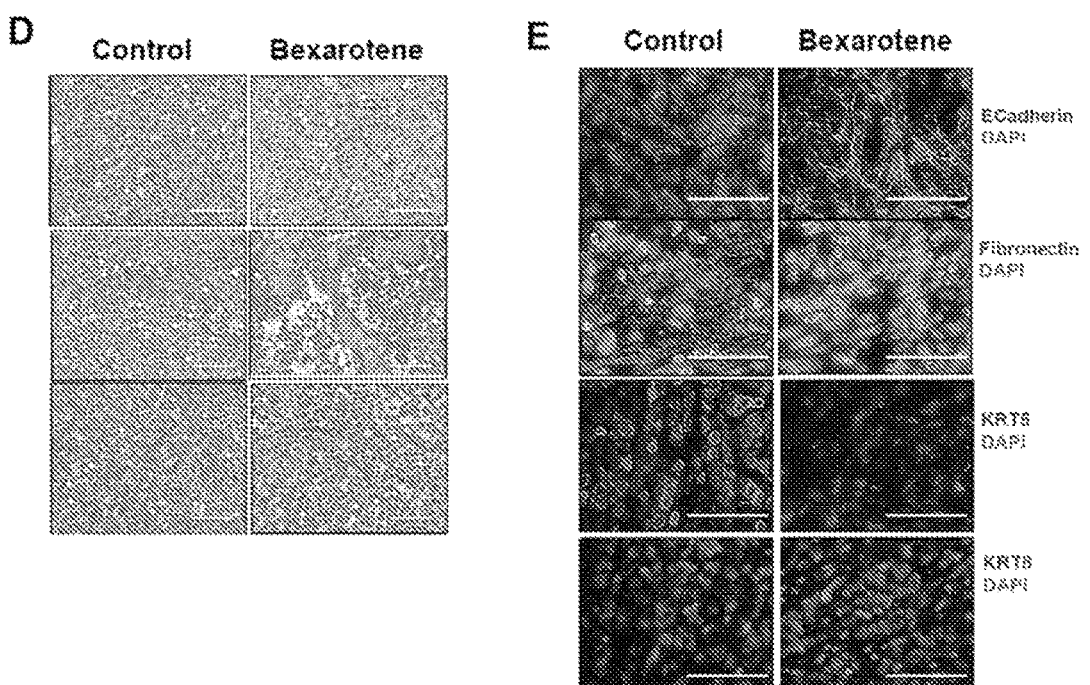
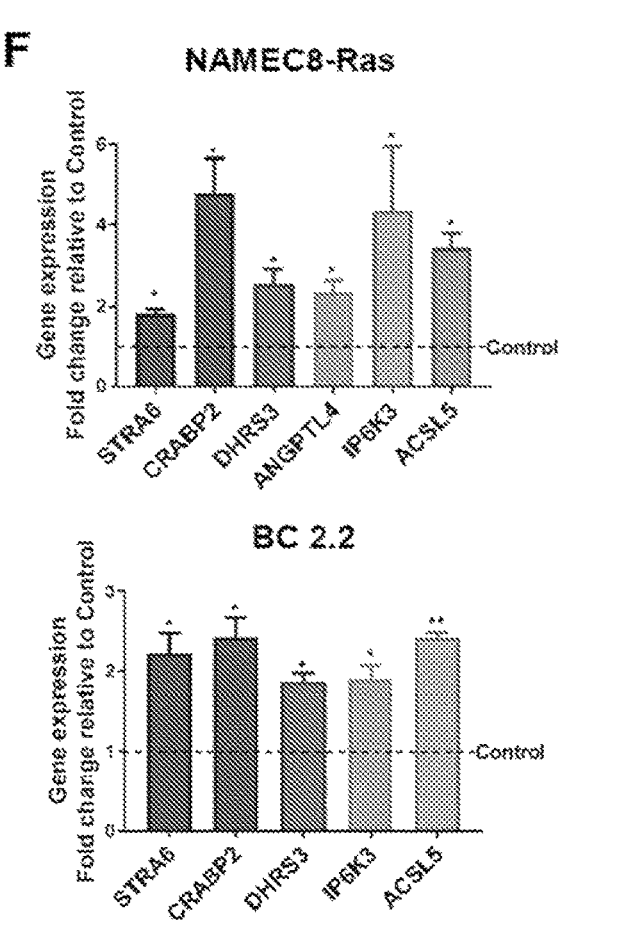
Figure 3(D)-(F) (end)

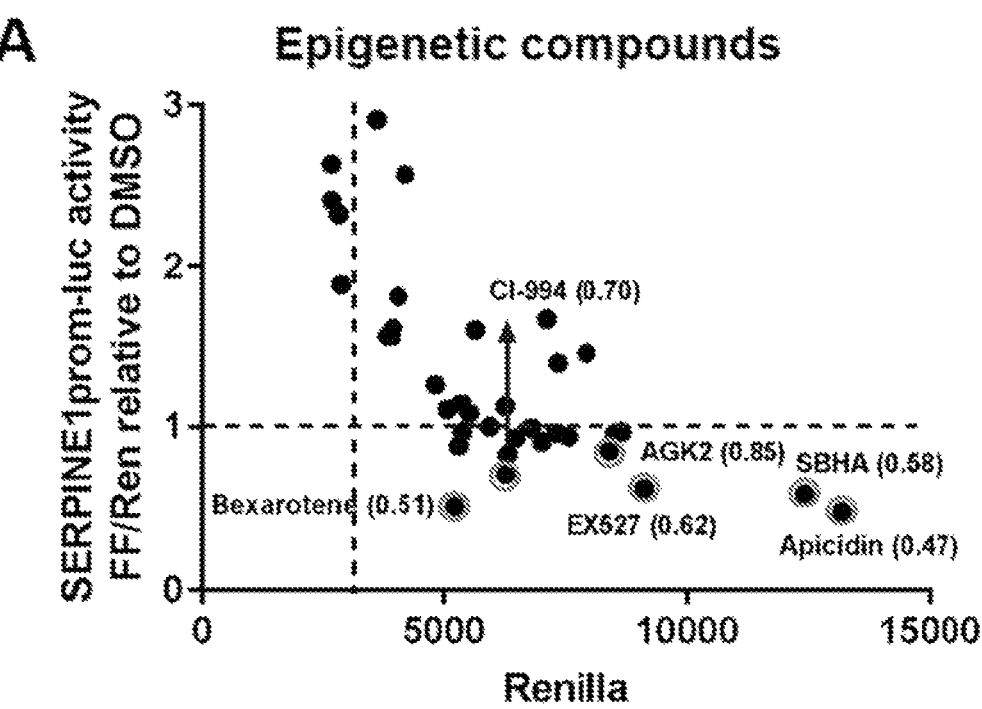
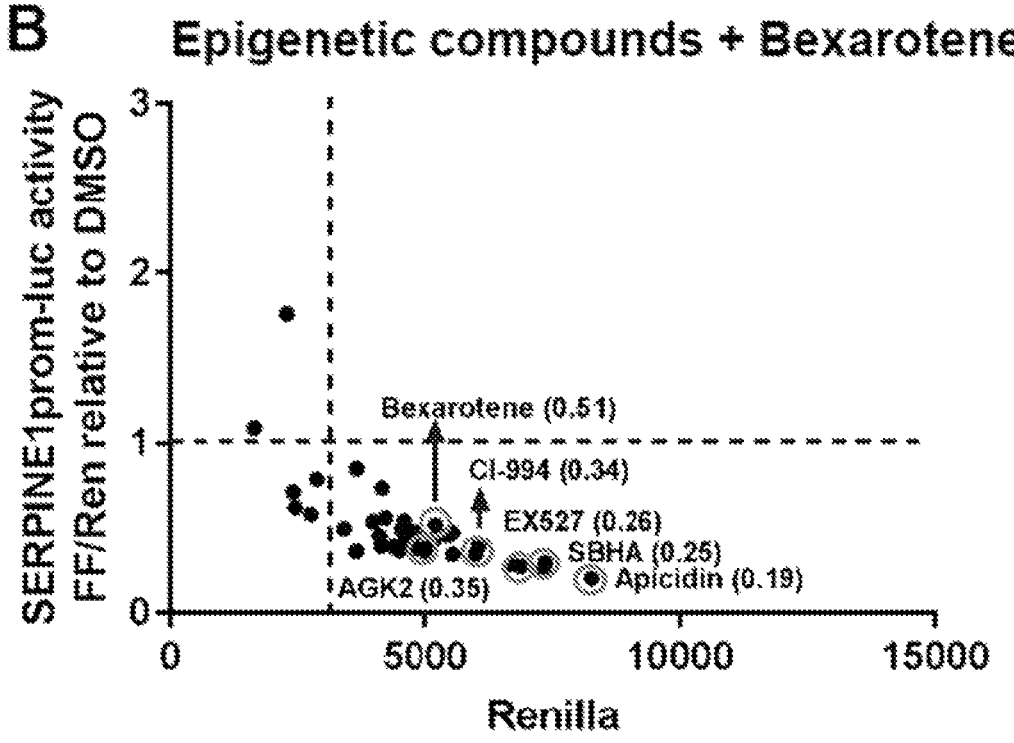
Figure 4(A)-(B) (continued)

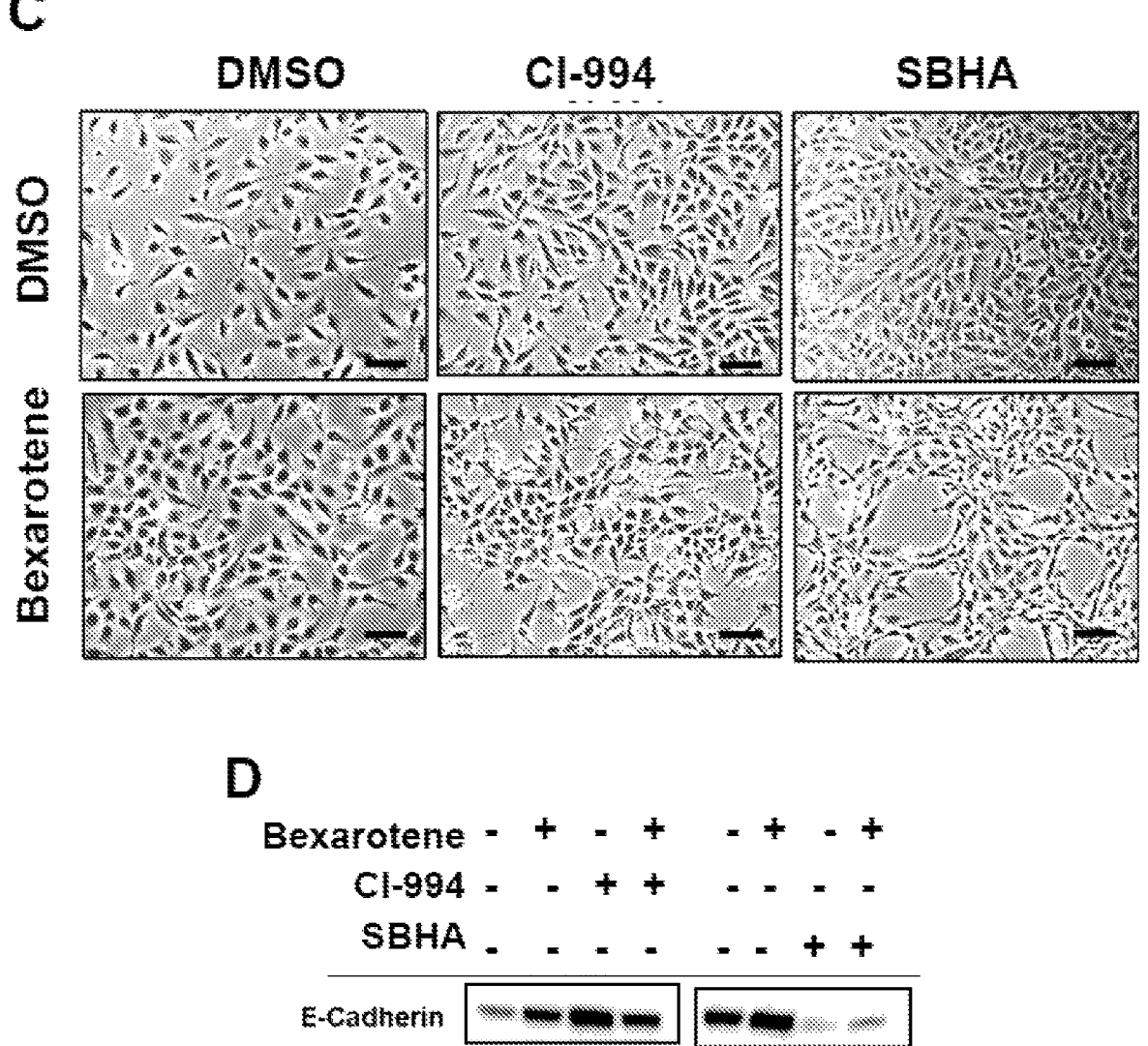
Figure 4(C)-(D) (continued)

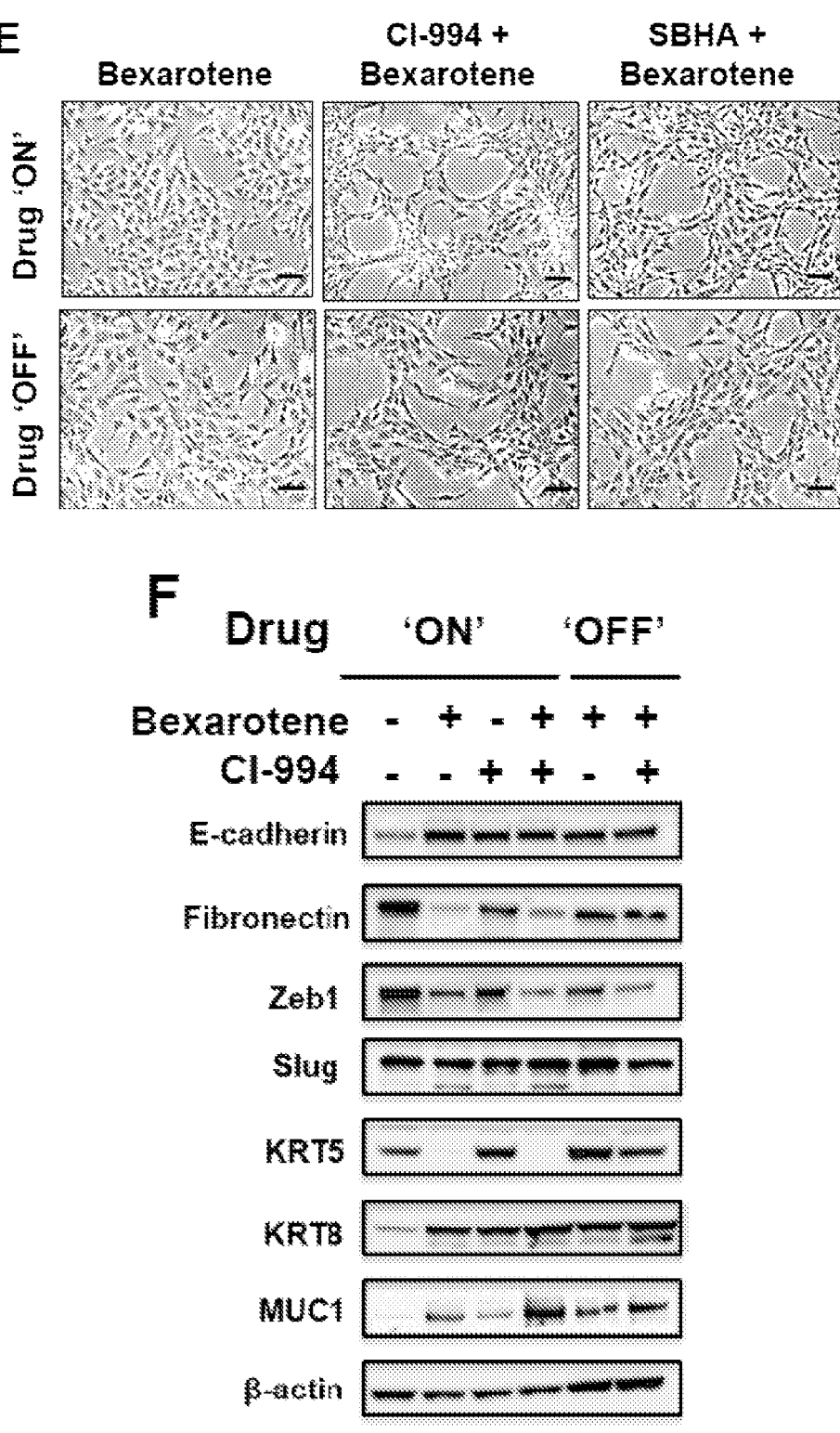
Figure 4(E)-(F) (continued)

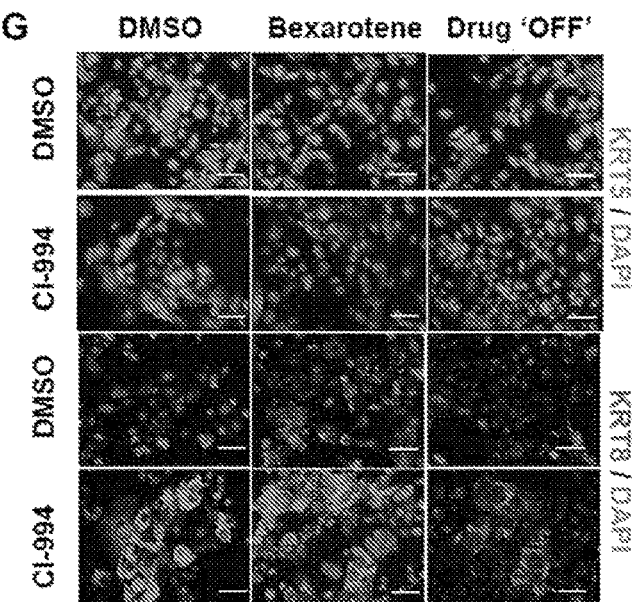
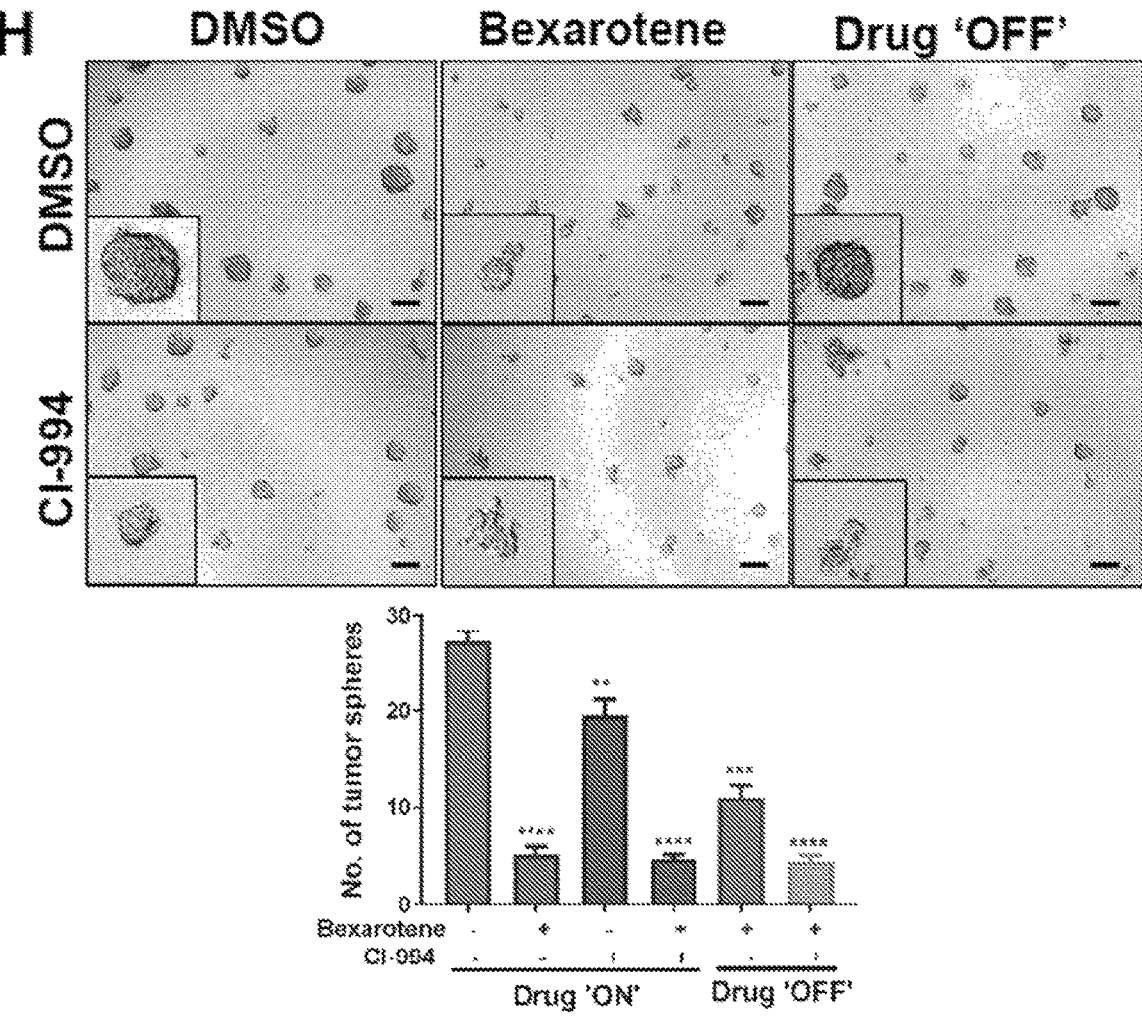
Figure 4(G)-(H) (continued)

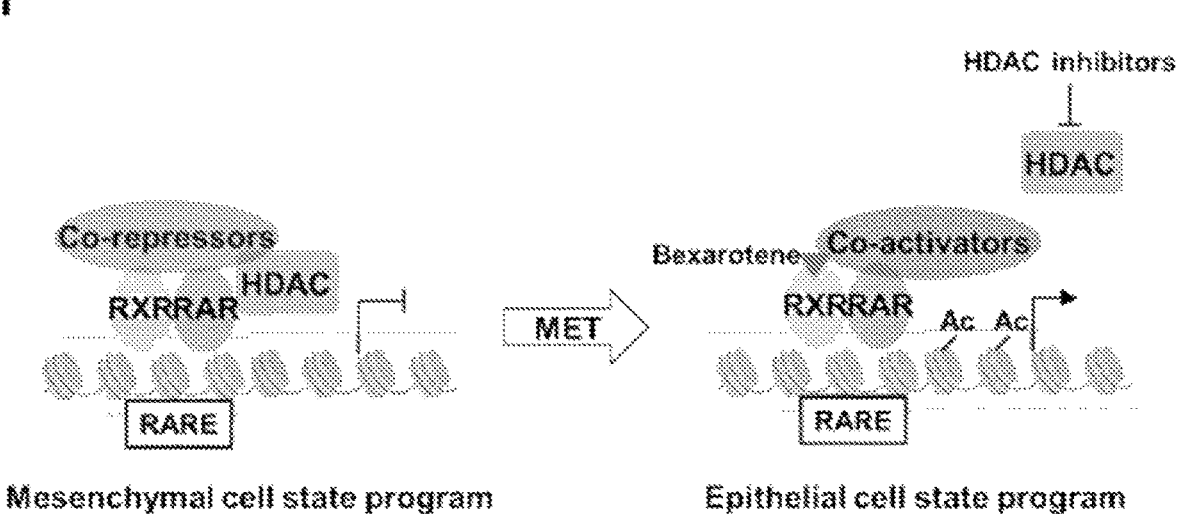
Figure 4(I) (end)

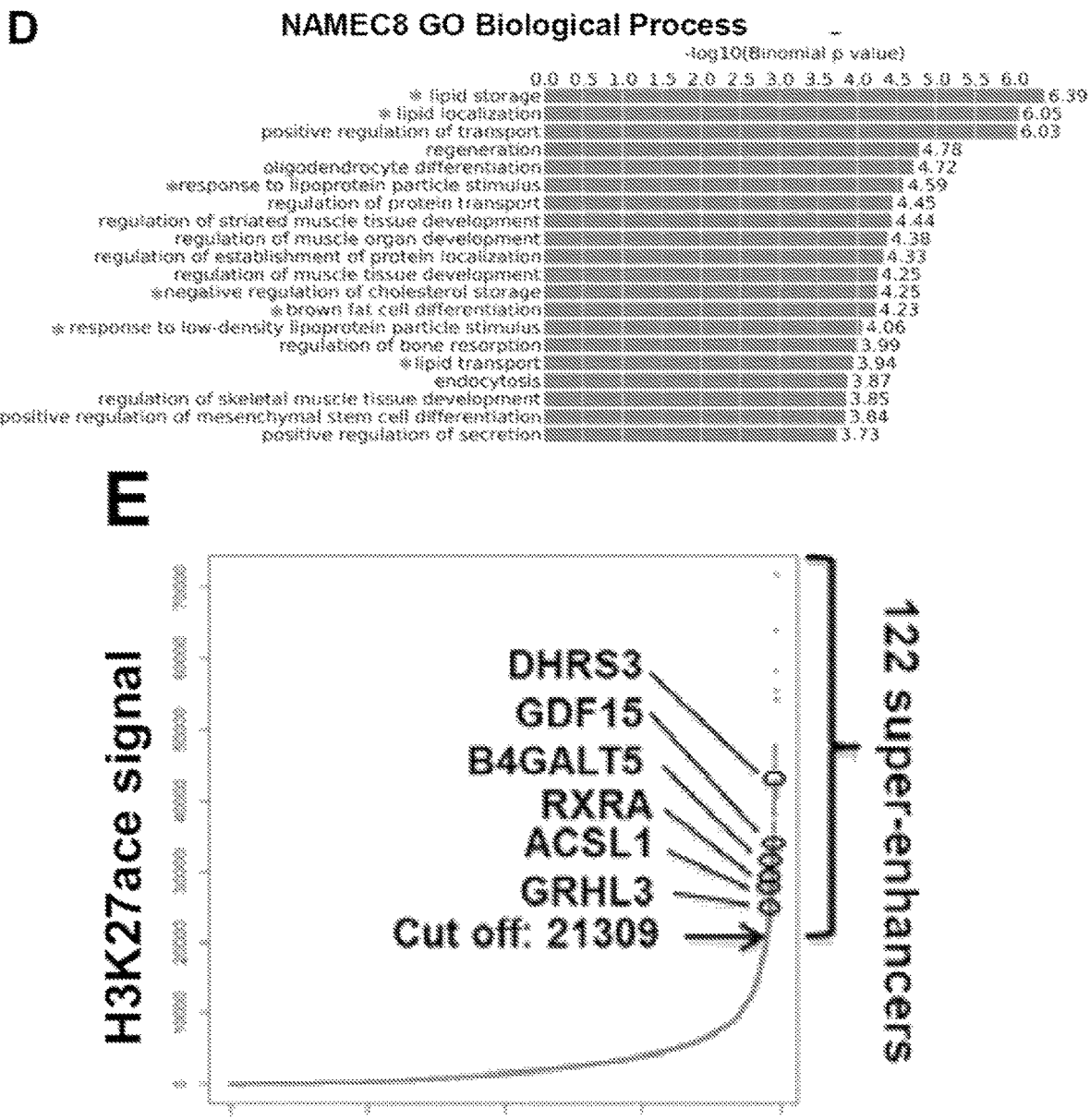
Figure 5(D)-(E) (continued)

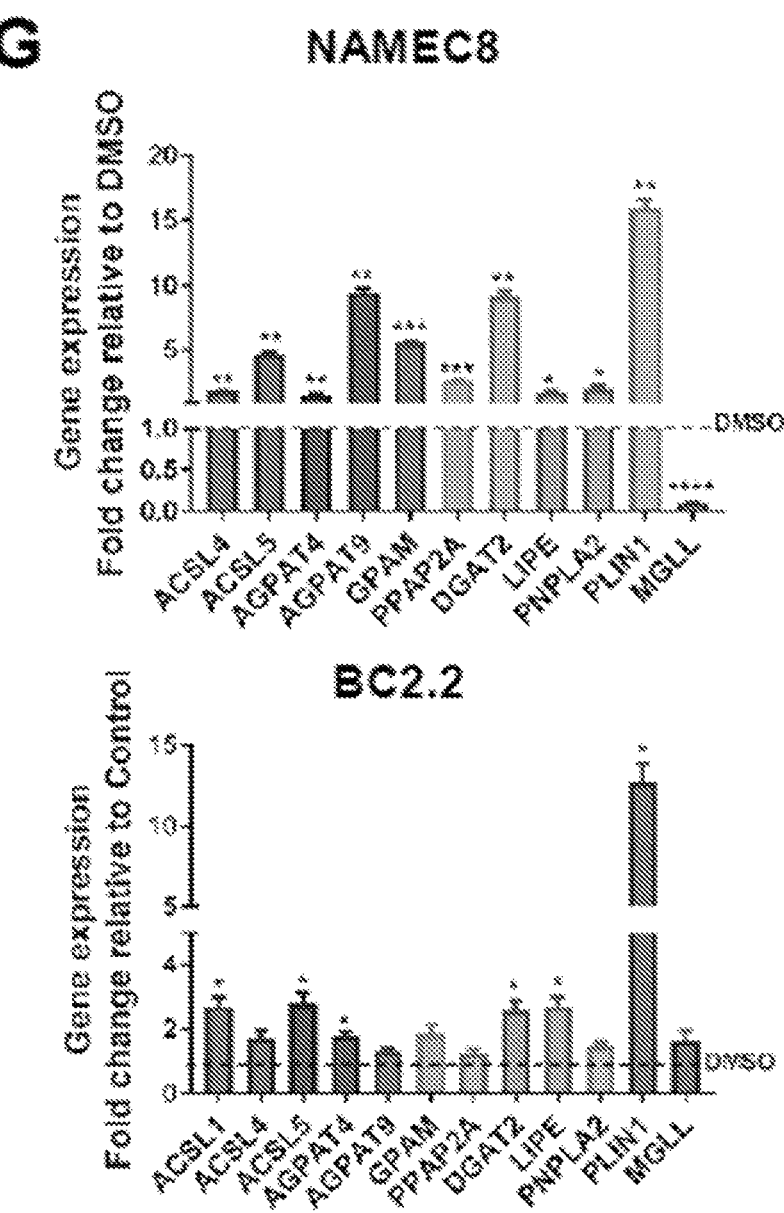
Figure 5(G) (end)

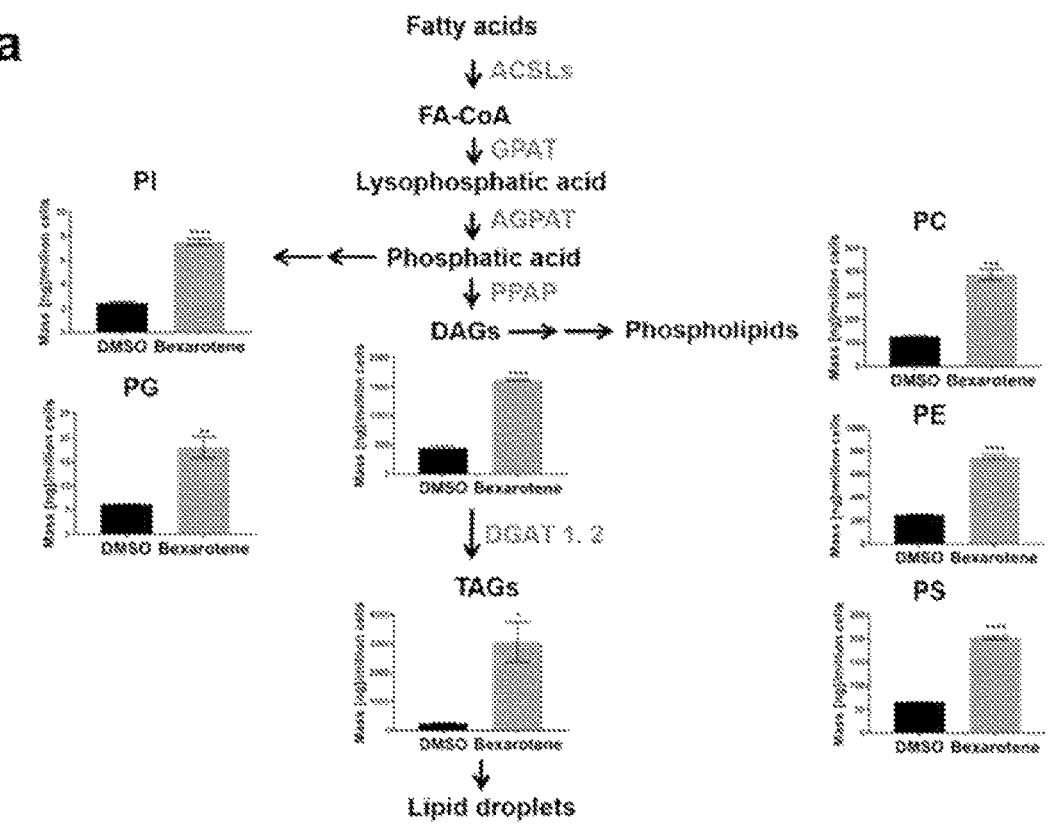
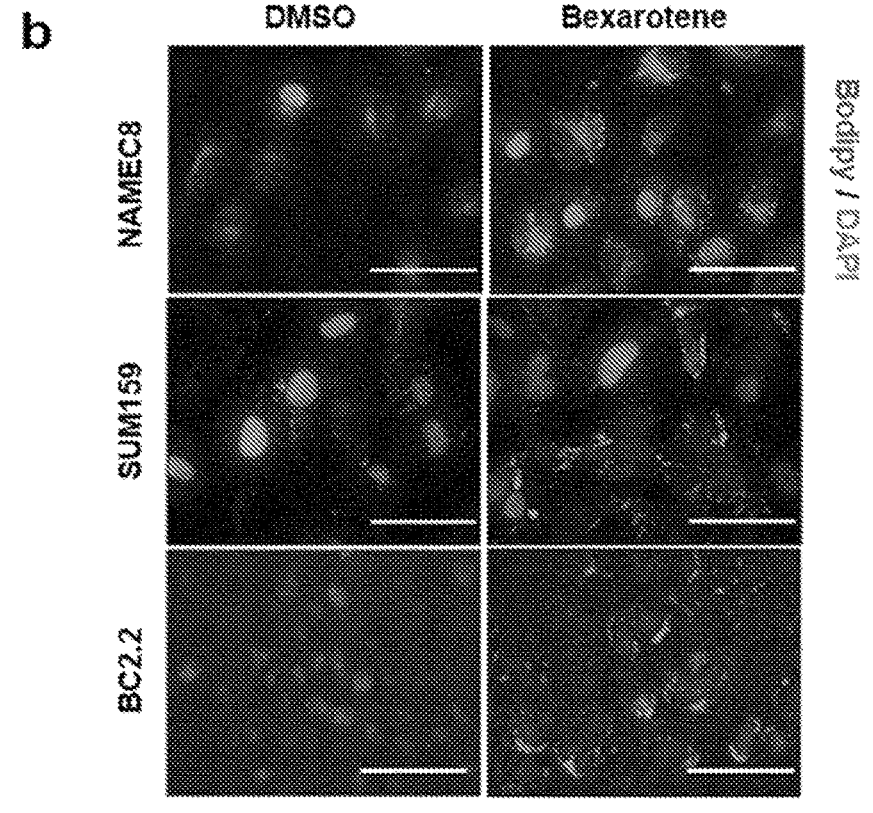
Figure 6(A)-(B) (continued)

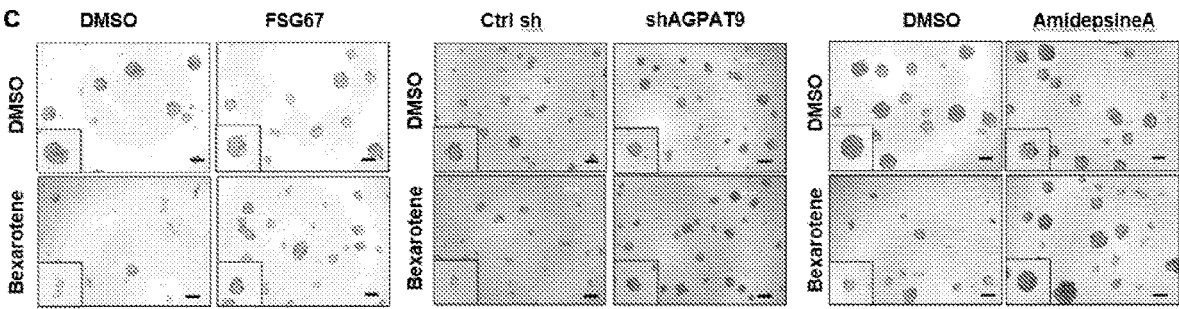
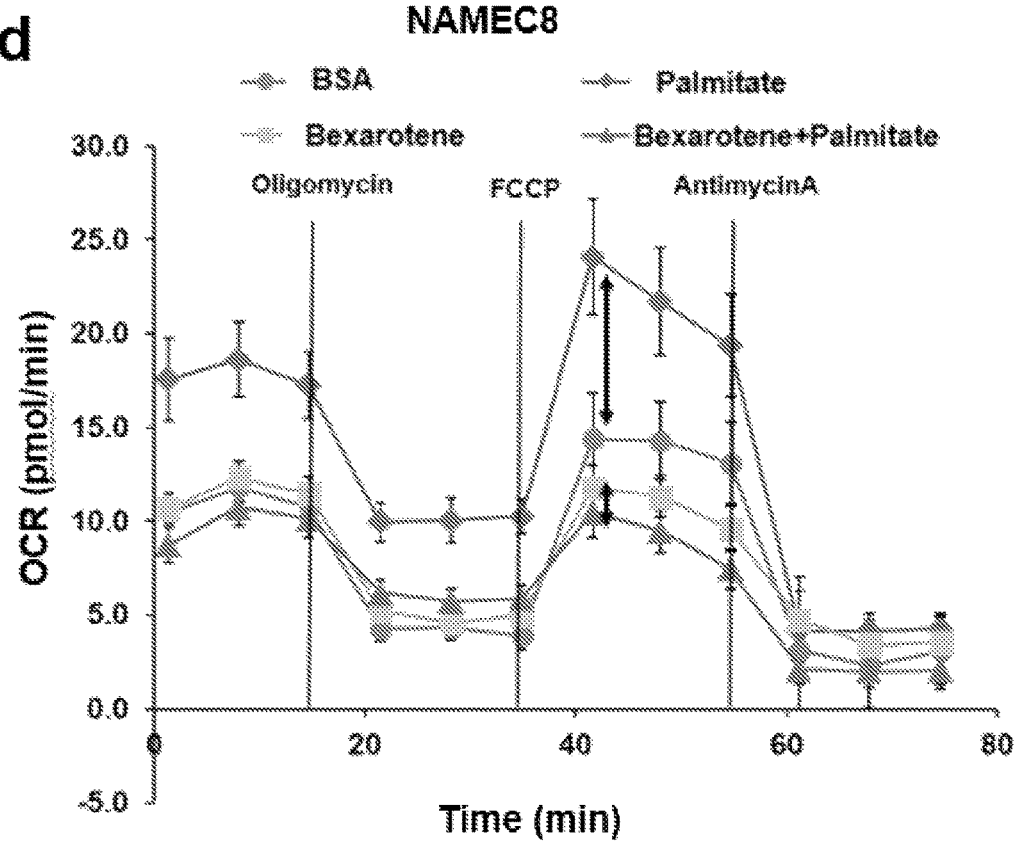
Figure 6(C)-(D) (continued)

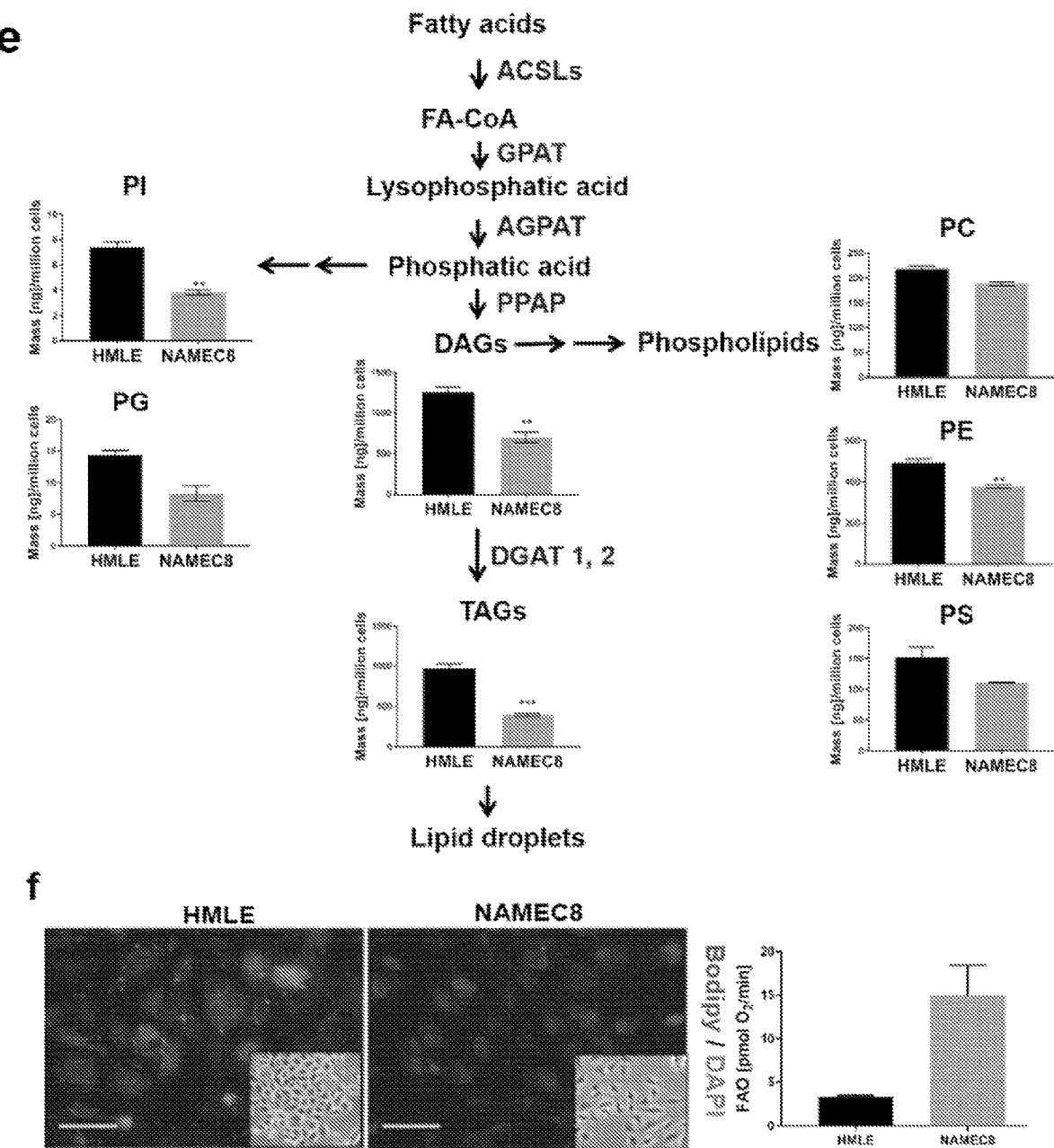
Figure 6(E)-(F) (continued)

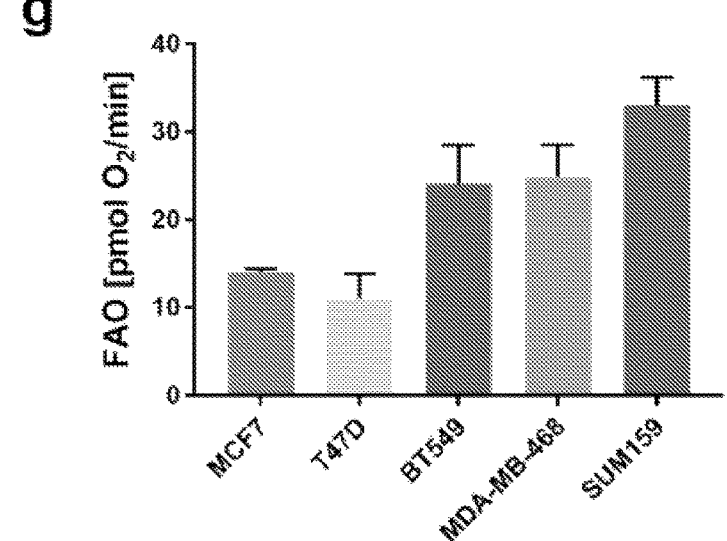
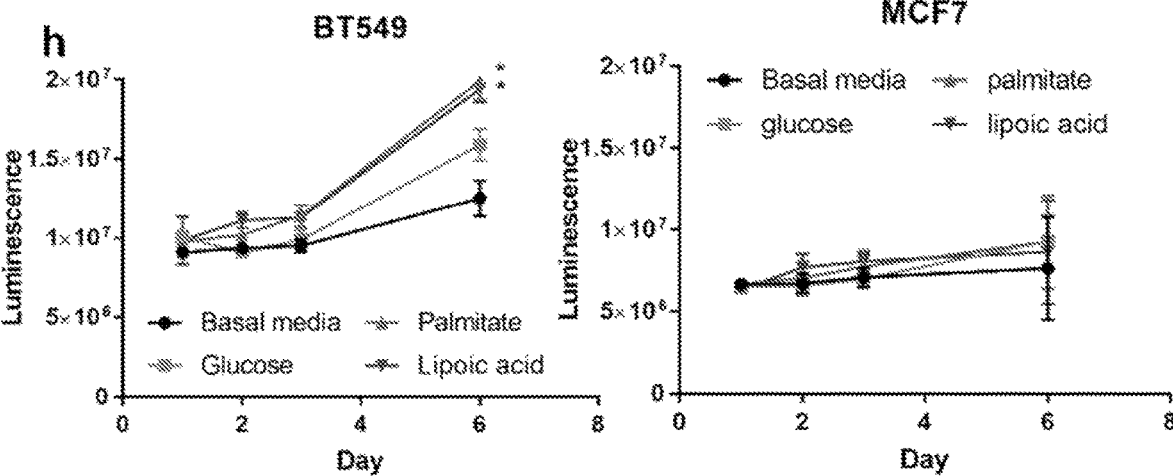
Figure 6(G)-(H) (end)

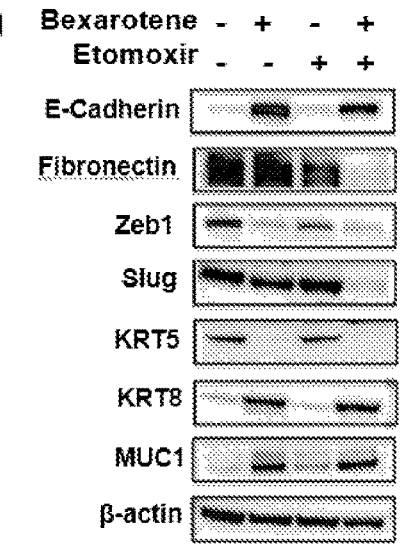
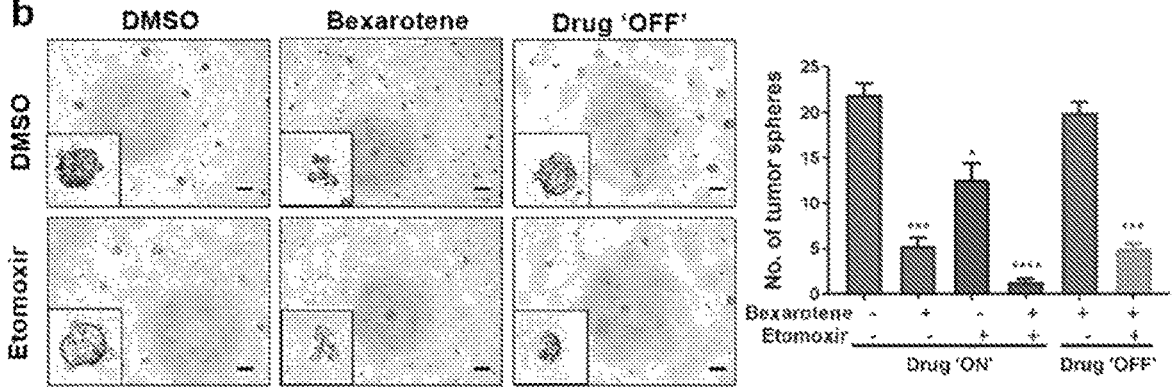
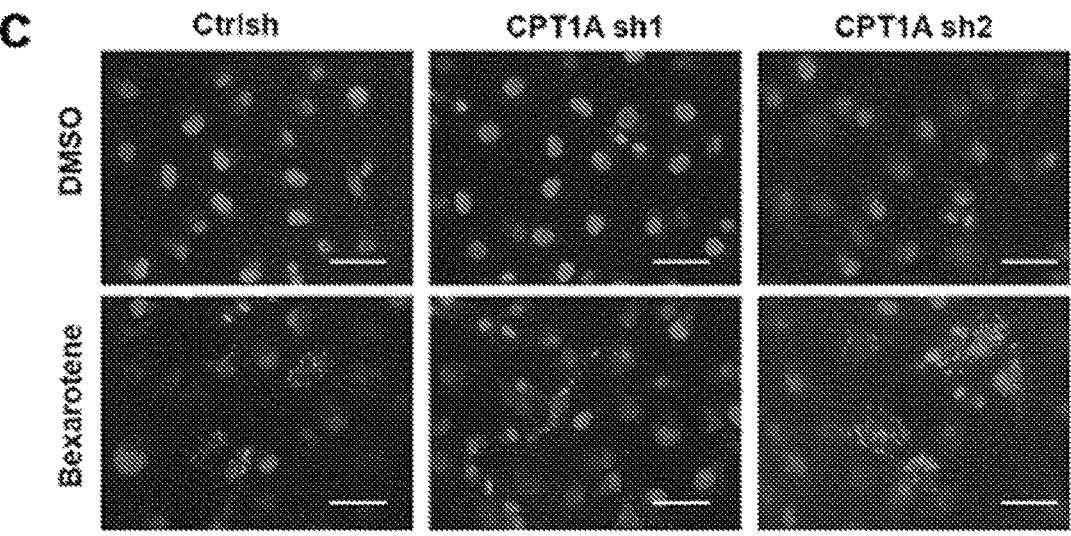
Figure 7(A)-(C) (continued)

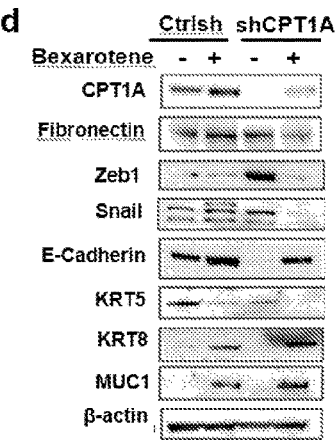
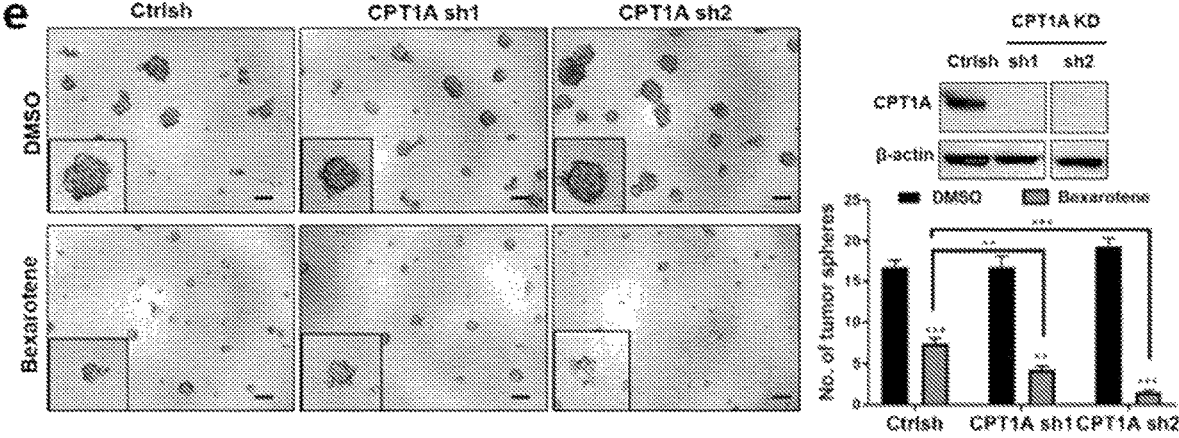
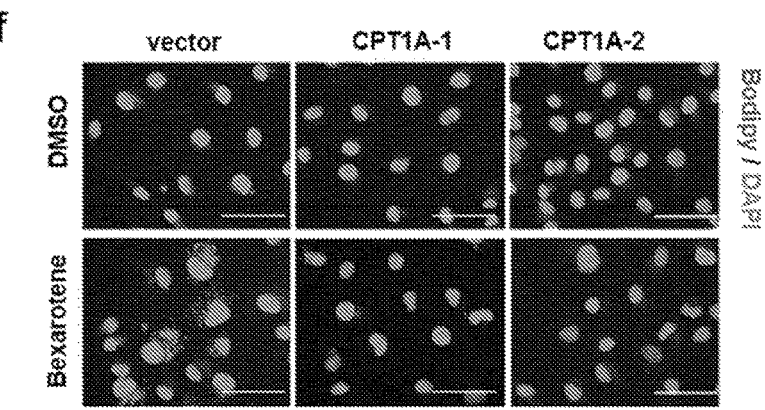
Figure 7(d)-(f) (continued)

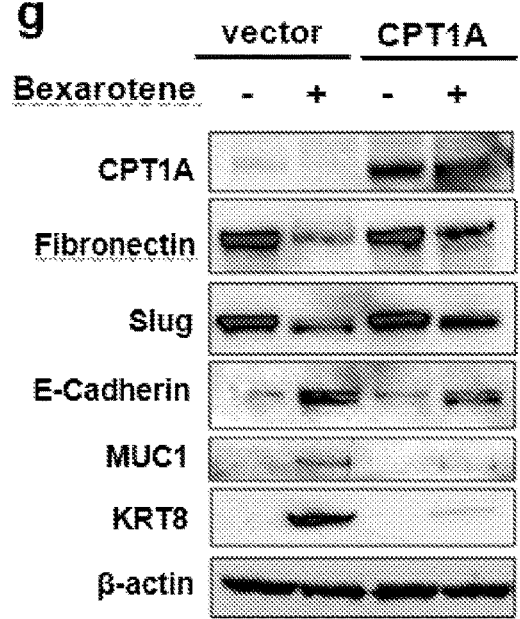
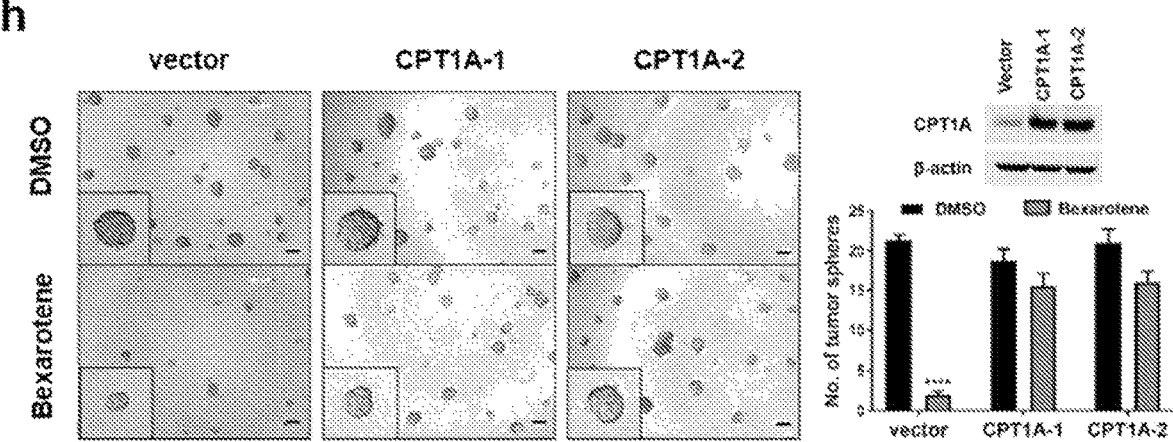
Figure 7(g)-(h) (end)

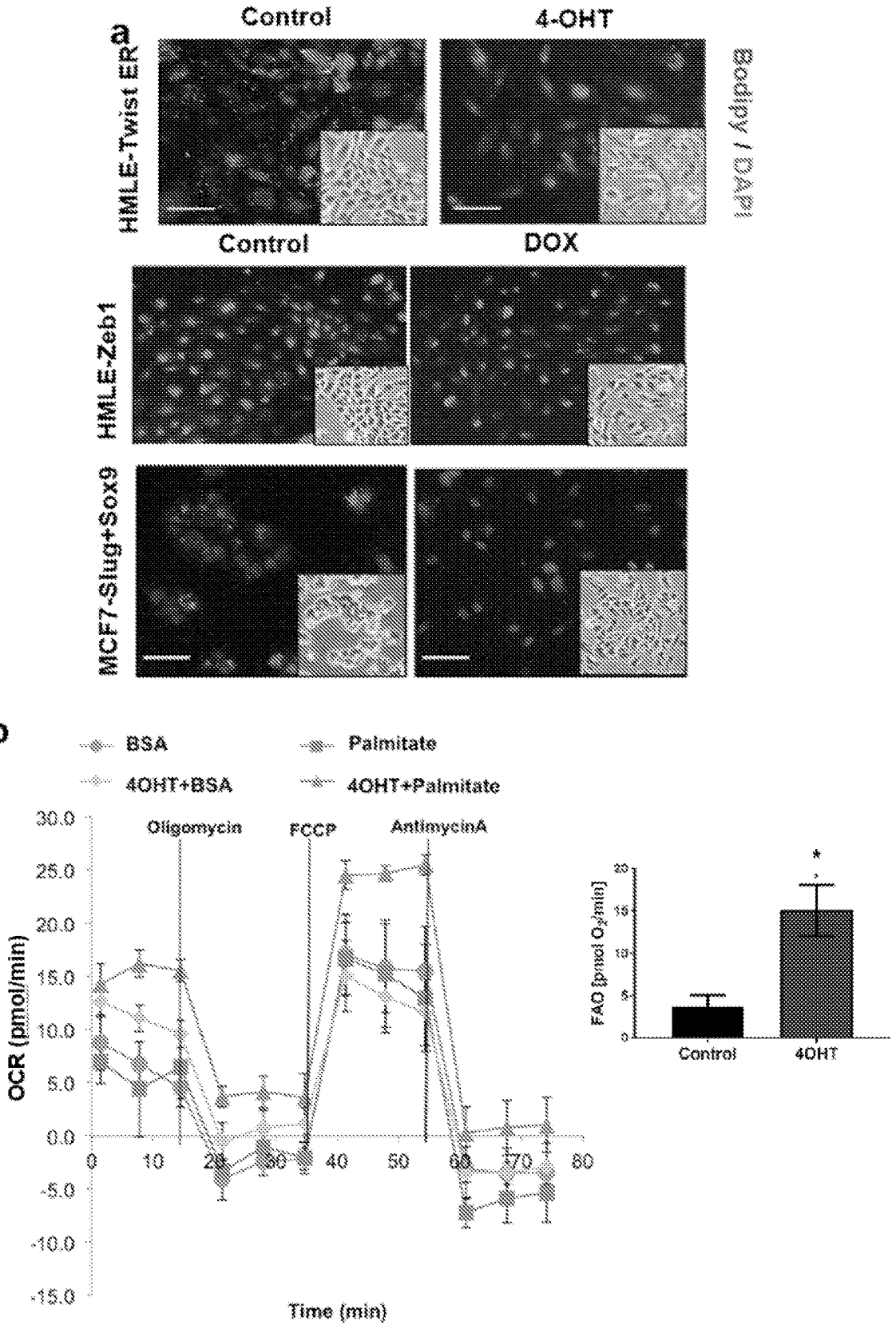
Figure 8(A)-(B) (continued)

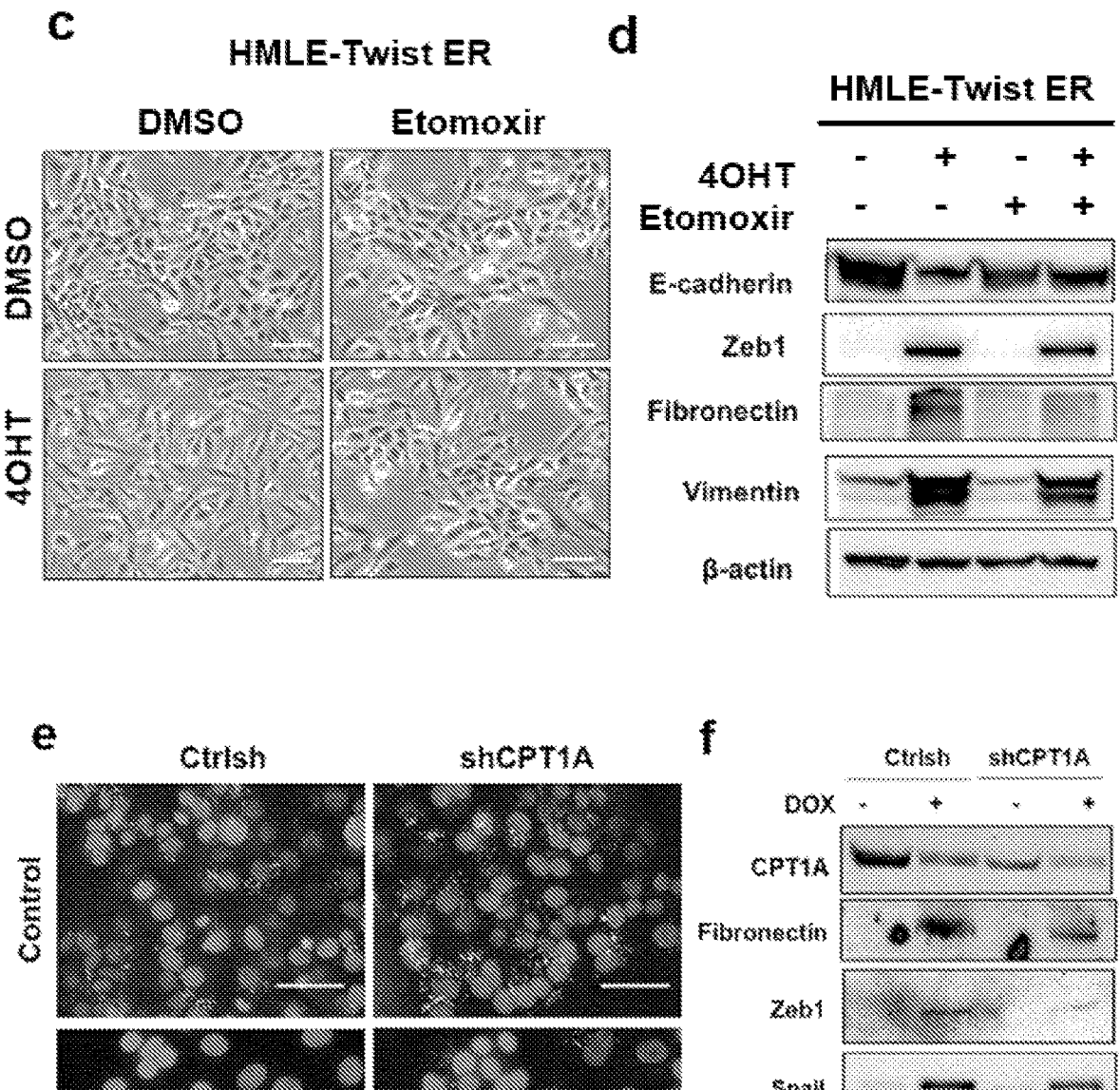
Figure 8(C)-(F) (continued)

g
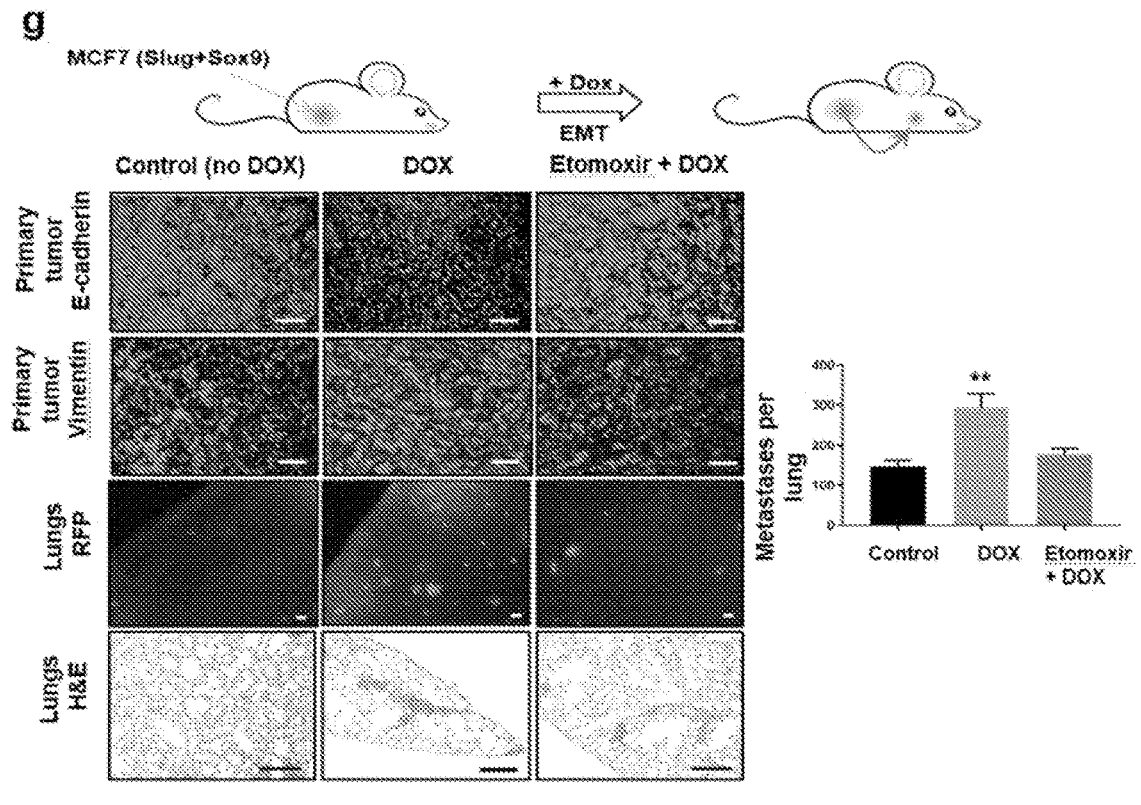
h
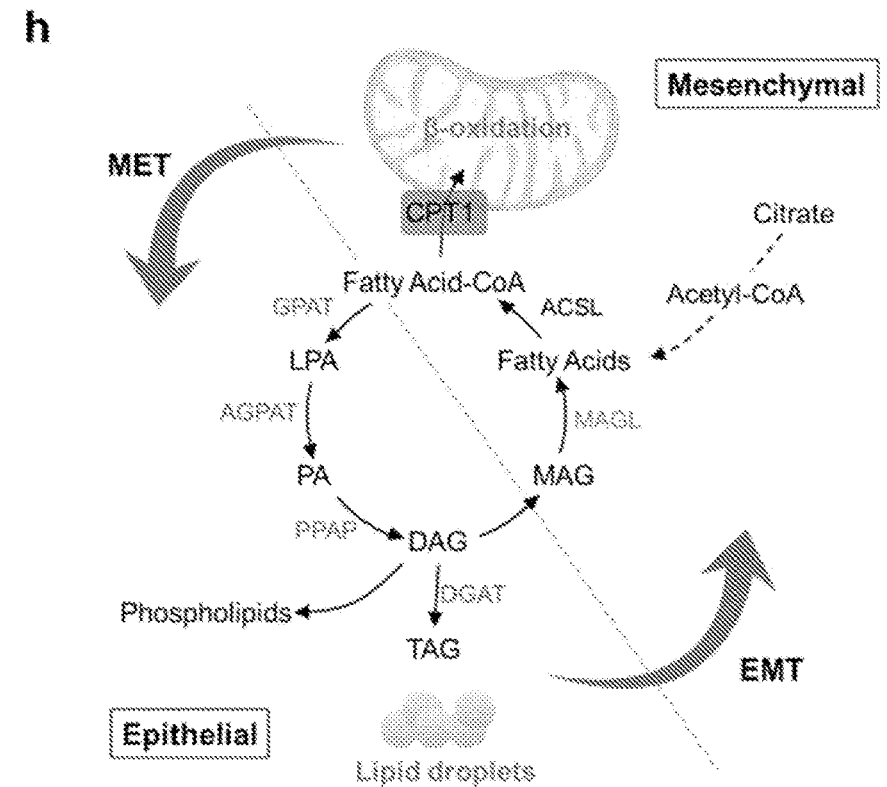
Figure 8(G)-(H) (end)

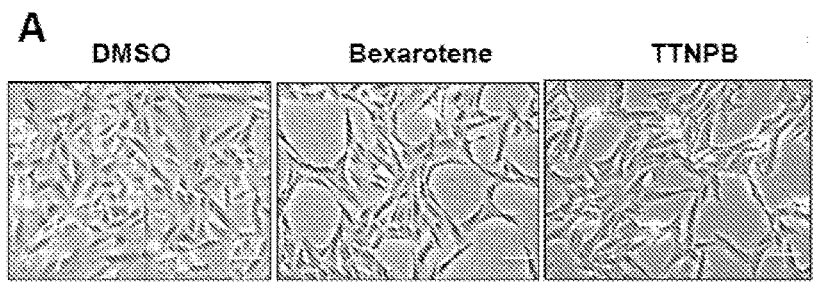
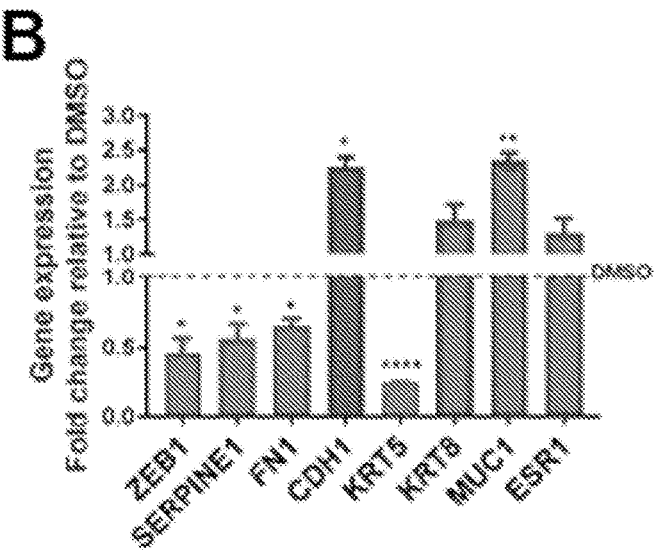
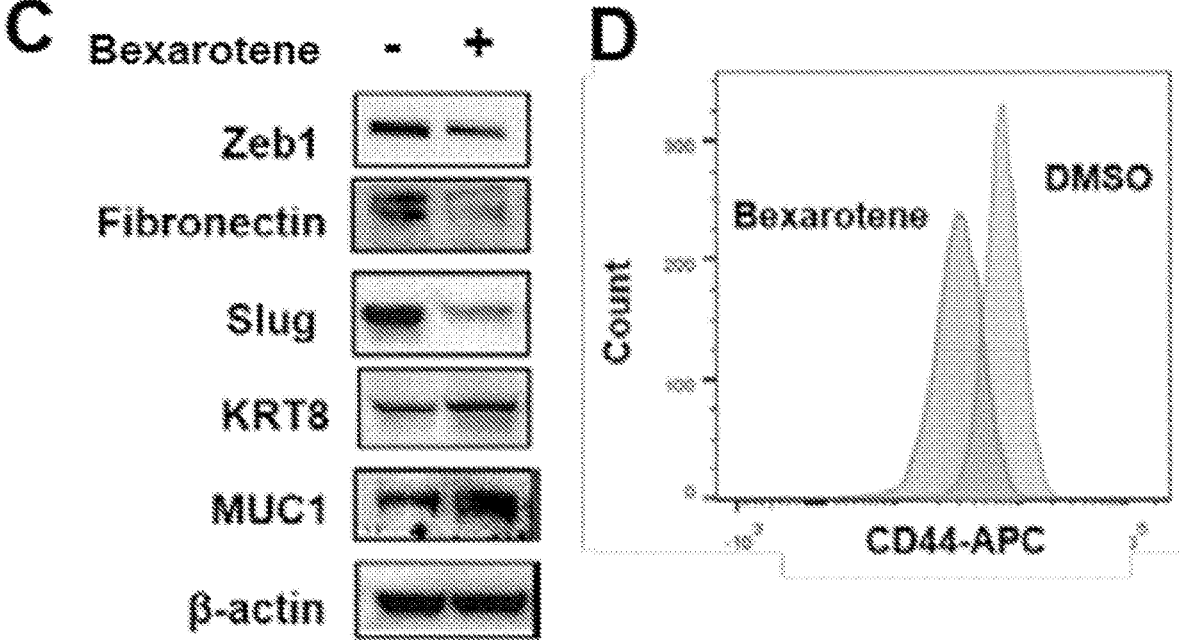
Figure 10(A)-(D) (continued)

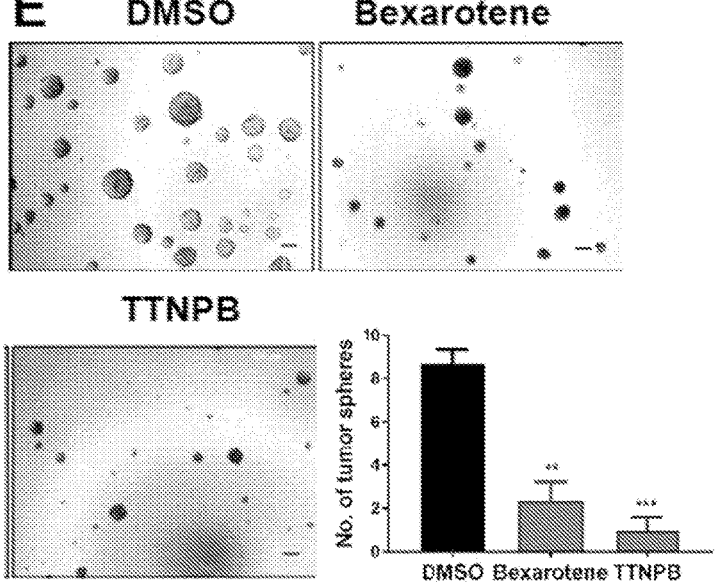
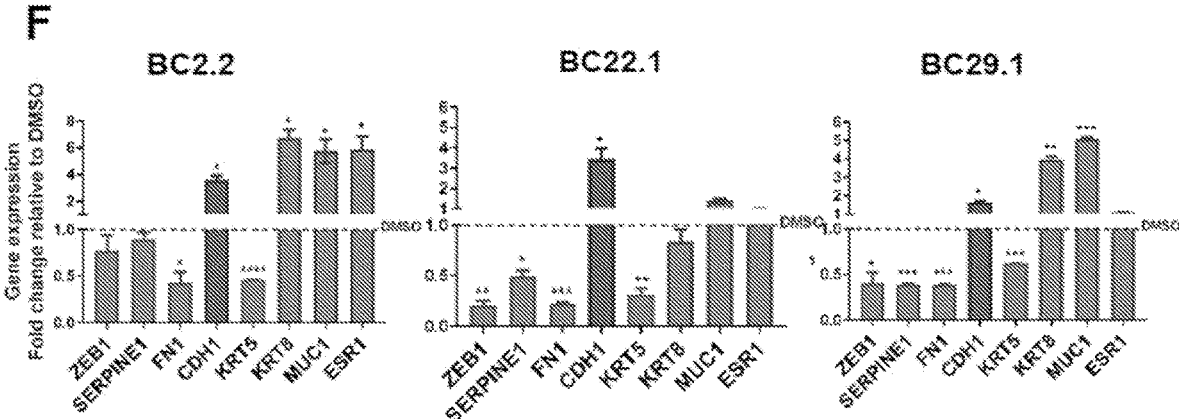
Figure 10(E)-(F) (continued)

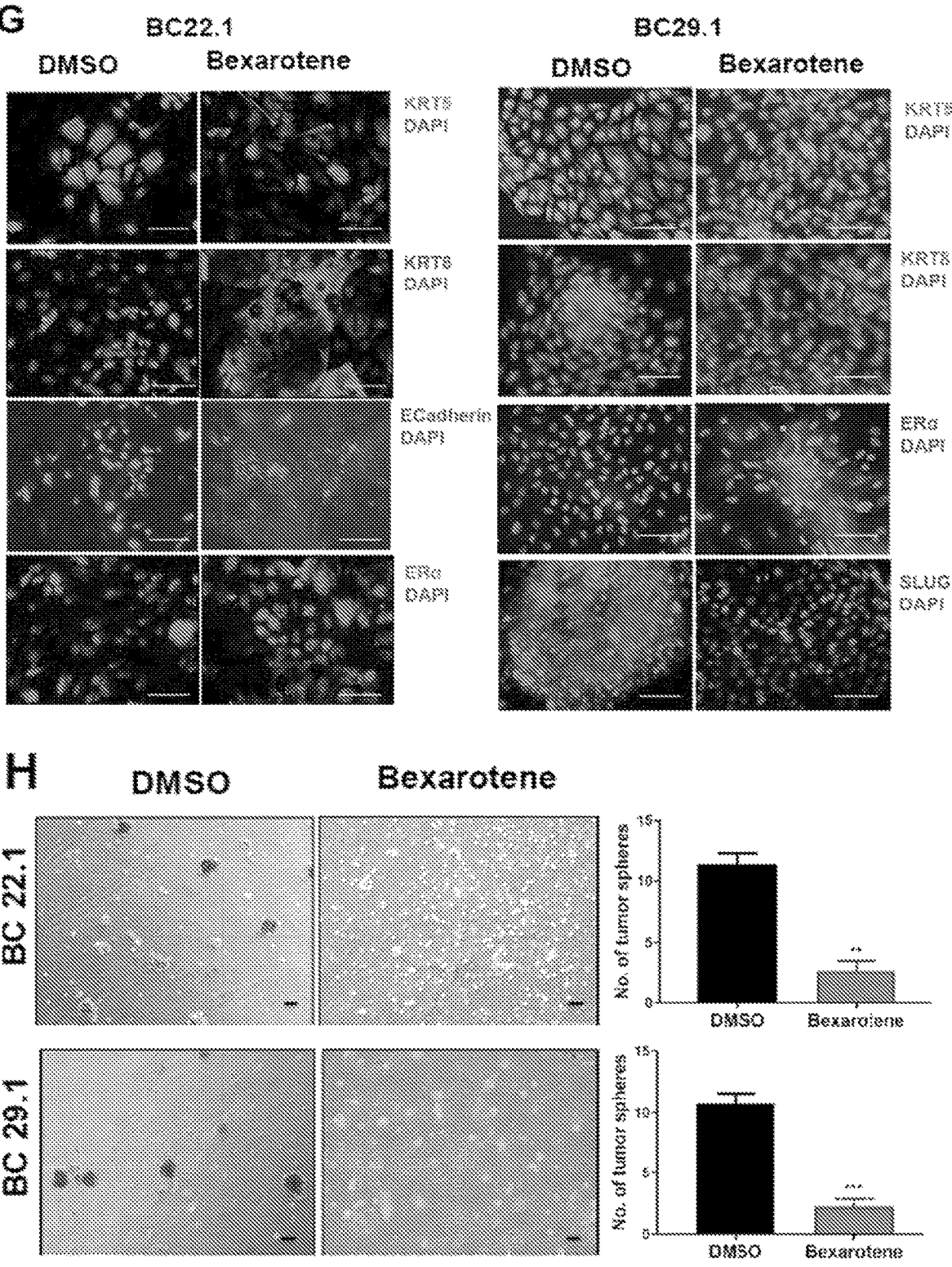
Figure 10(G)-(H) (continued)

I
J
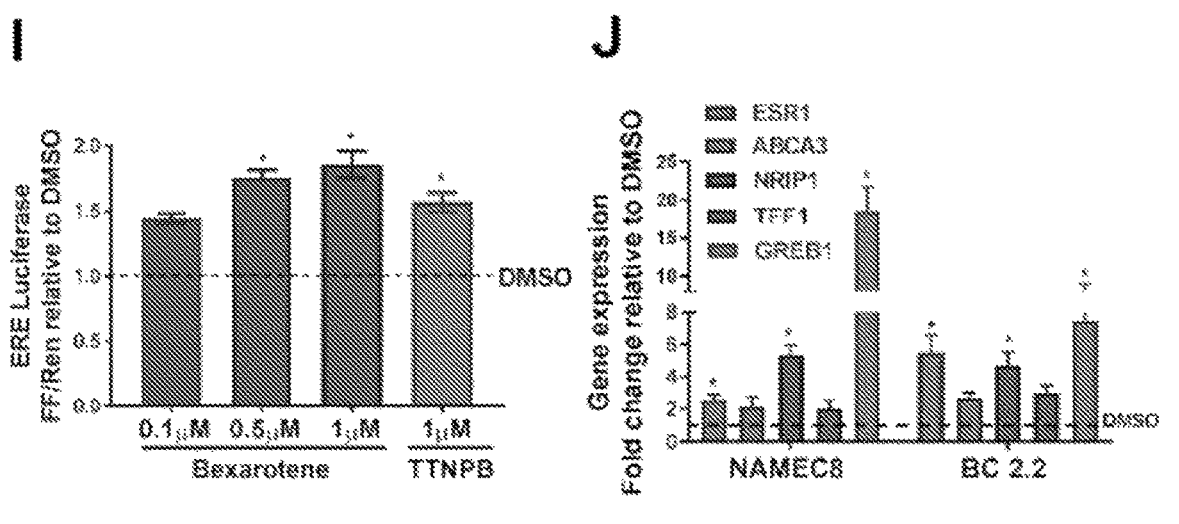
K
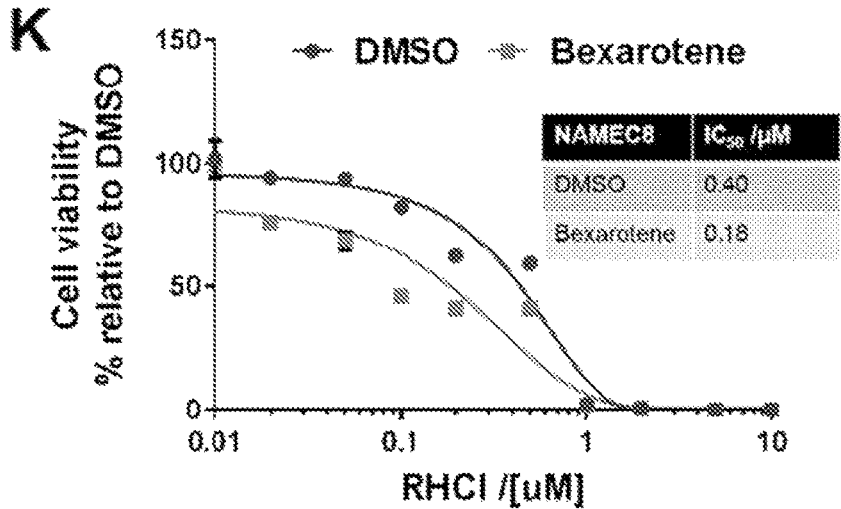
L
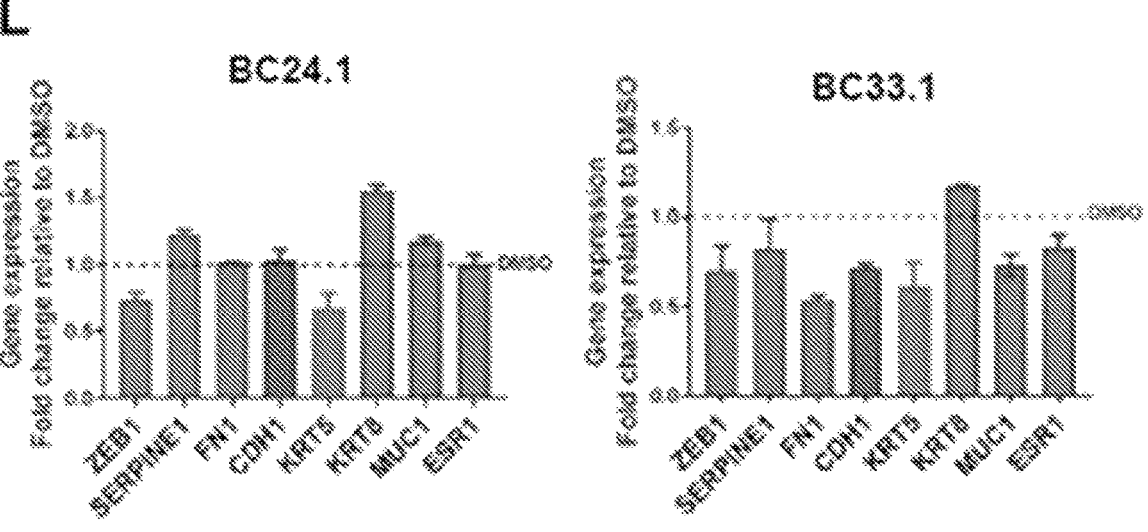
Figure 10(I)-(L) (continued)

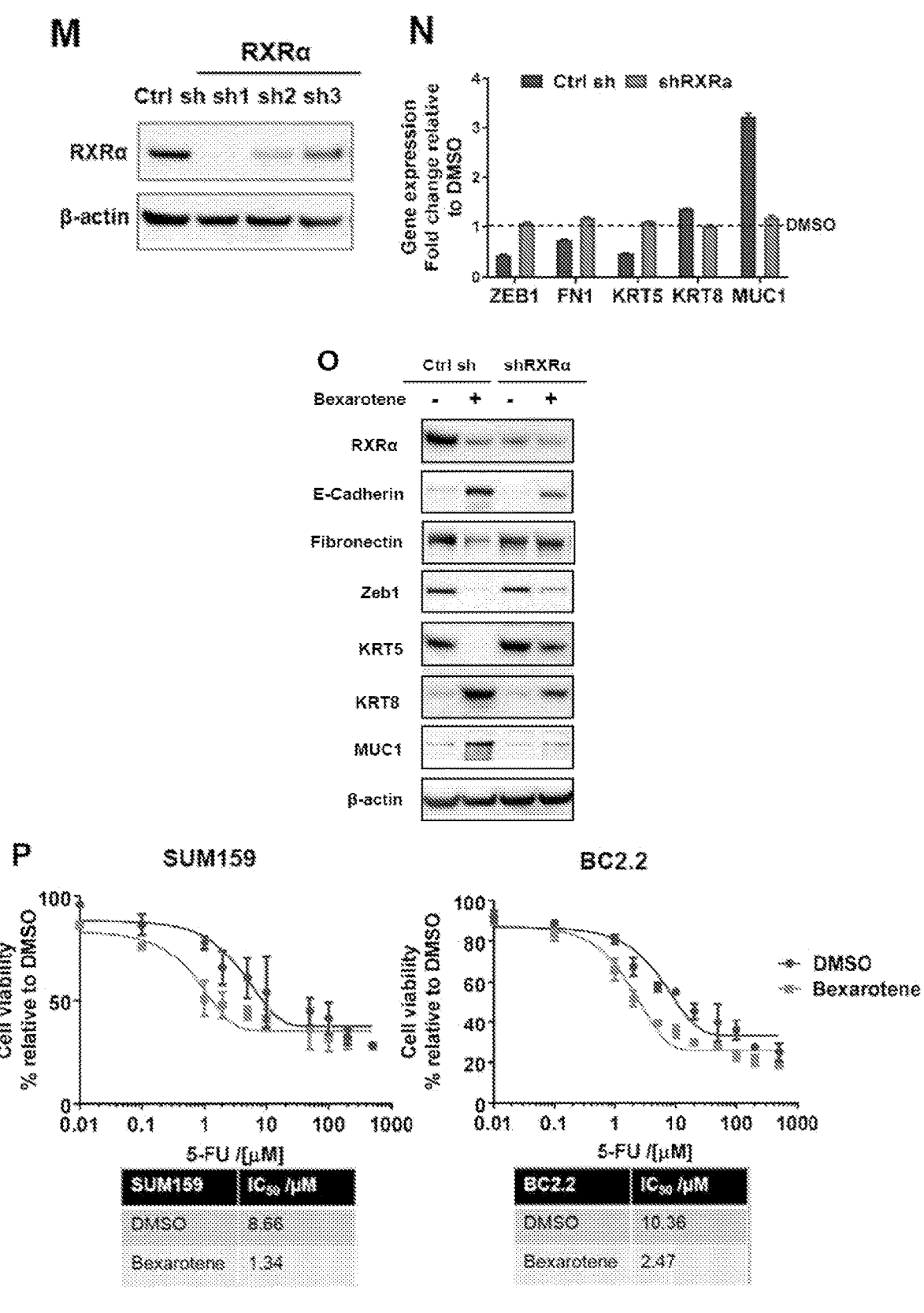
Figure 10(M)-(P) (continued)

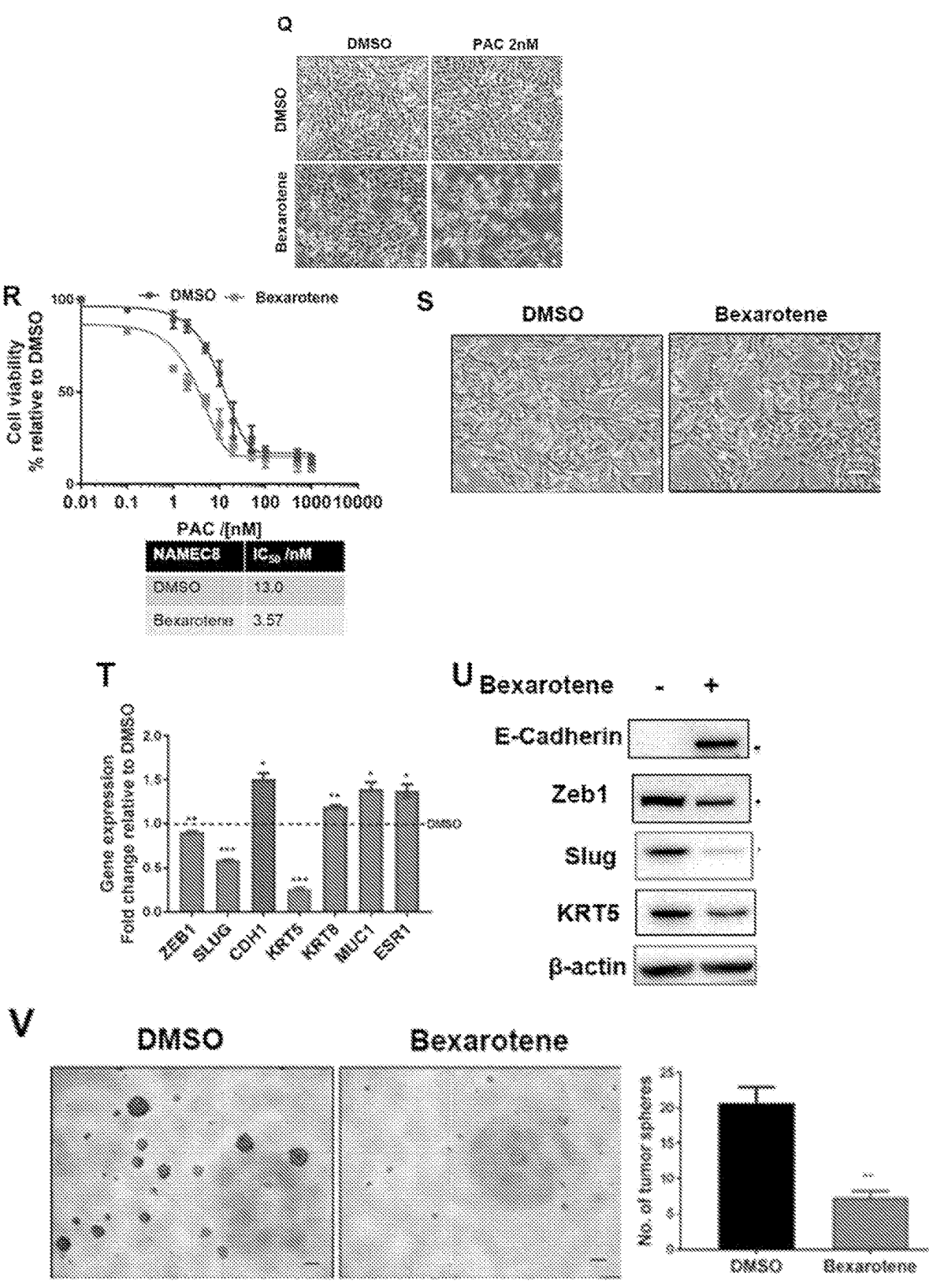
Figure 10(Q)-(V) (end)

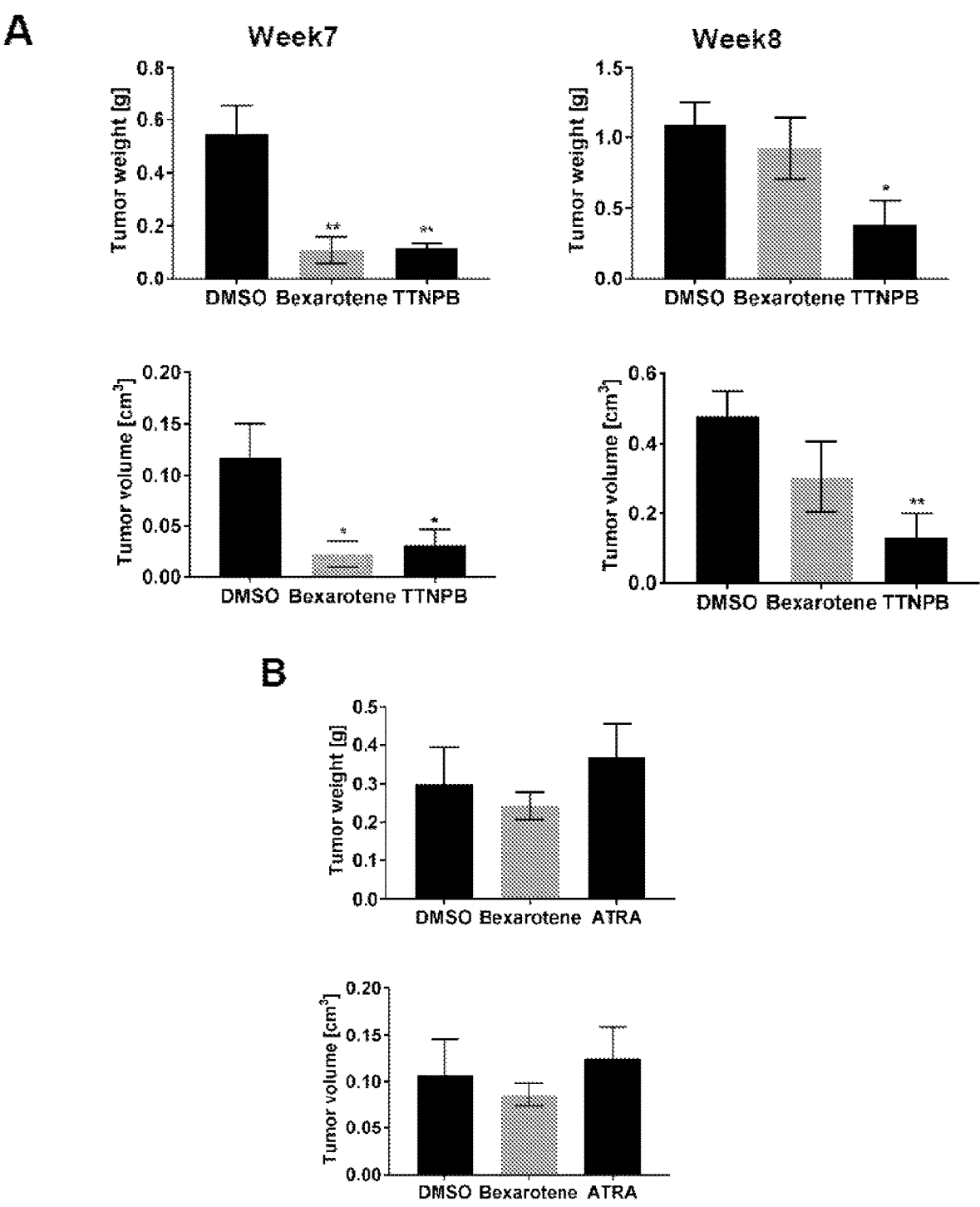
Figure 11(A)-(B) (continued)

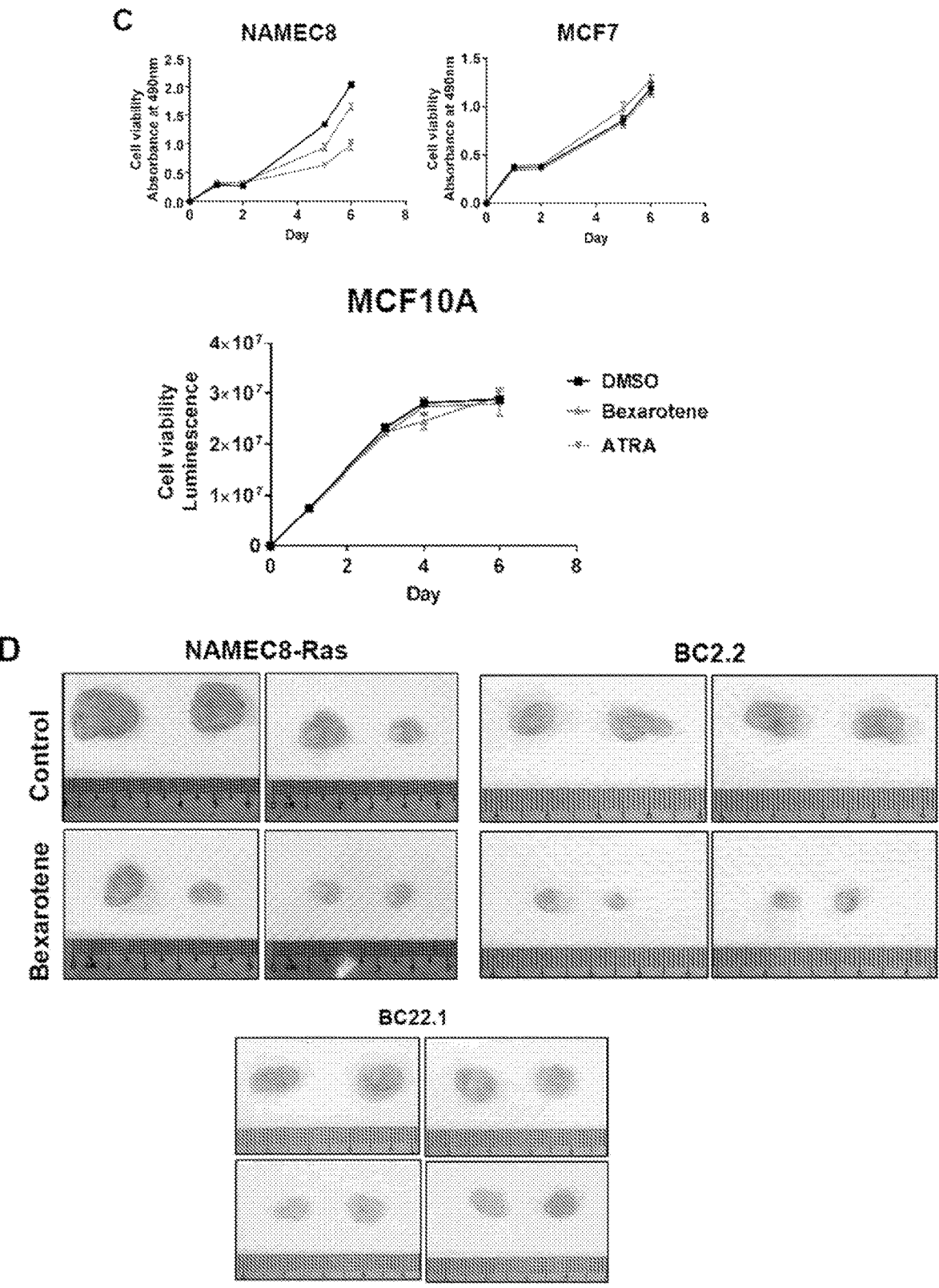
Figure 11(C)-(D) (continued)

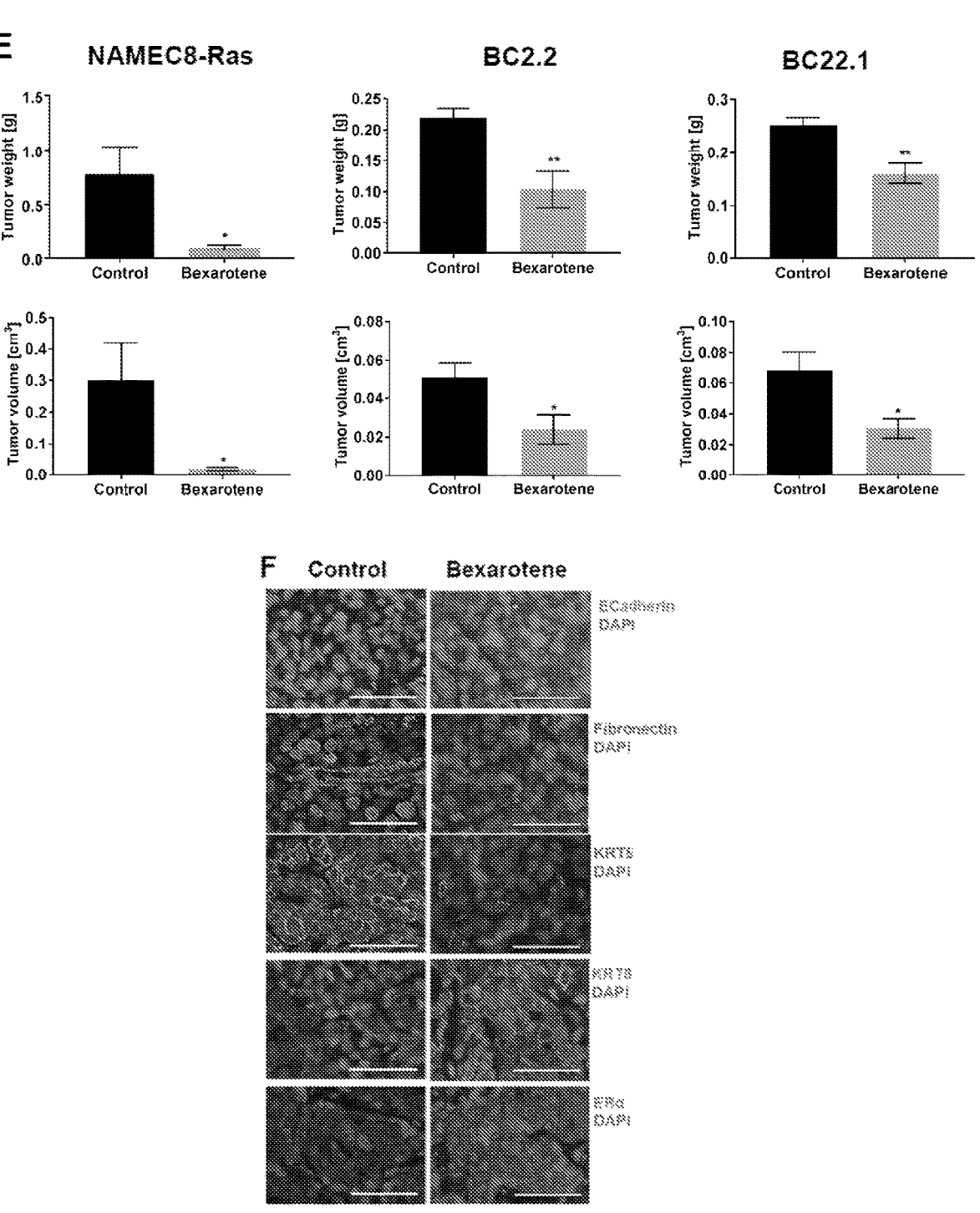
Figure11(E)-(F) (end)

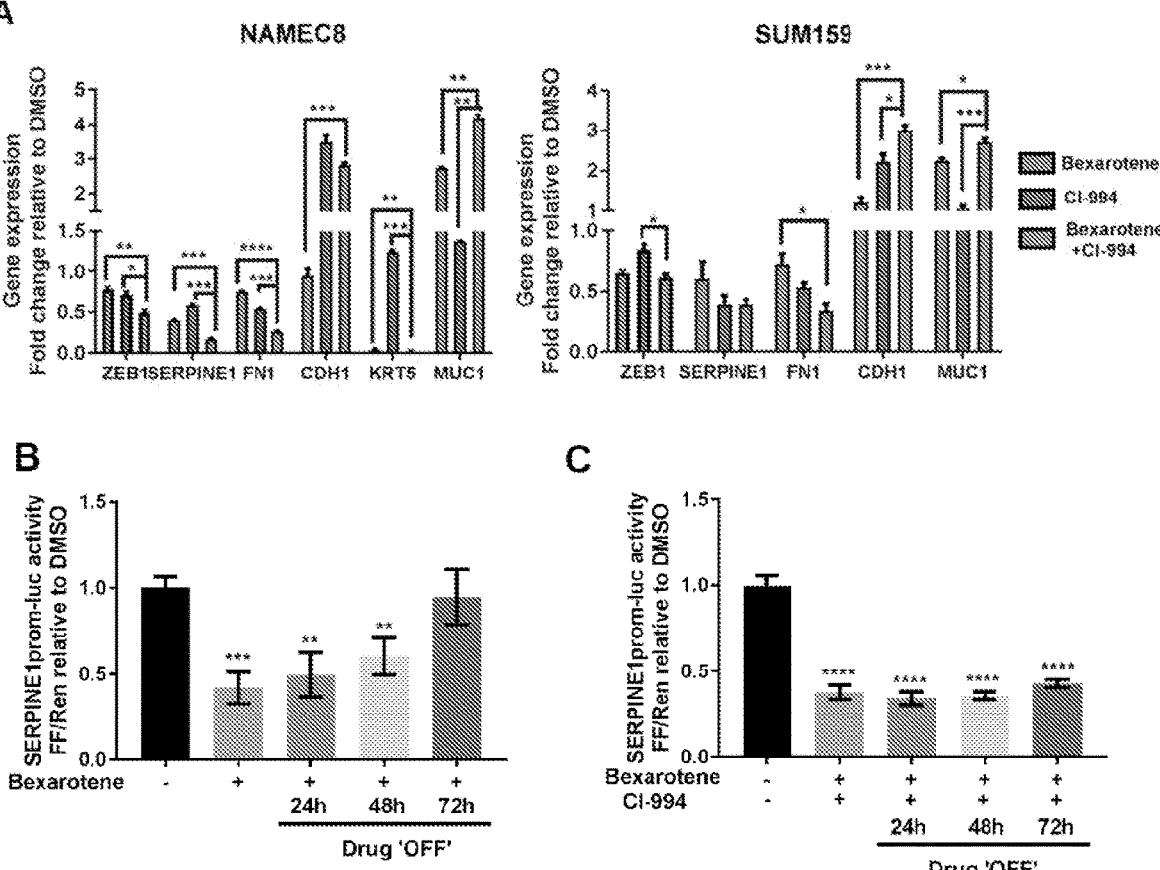
Figure 12(A)-(C) (continued)

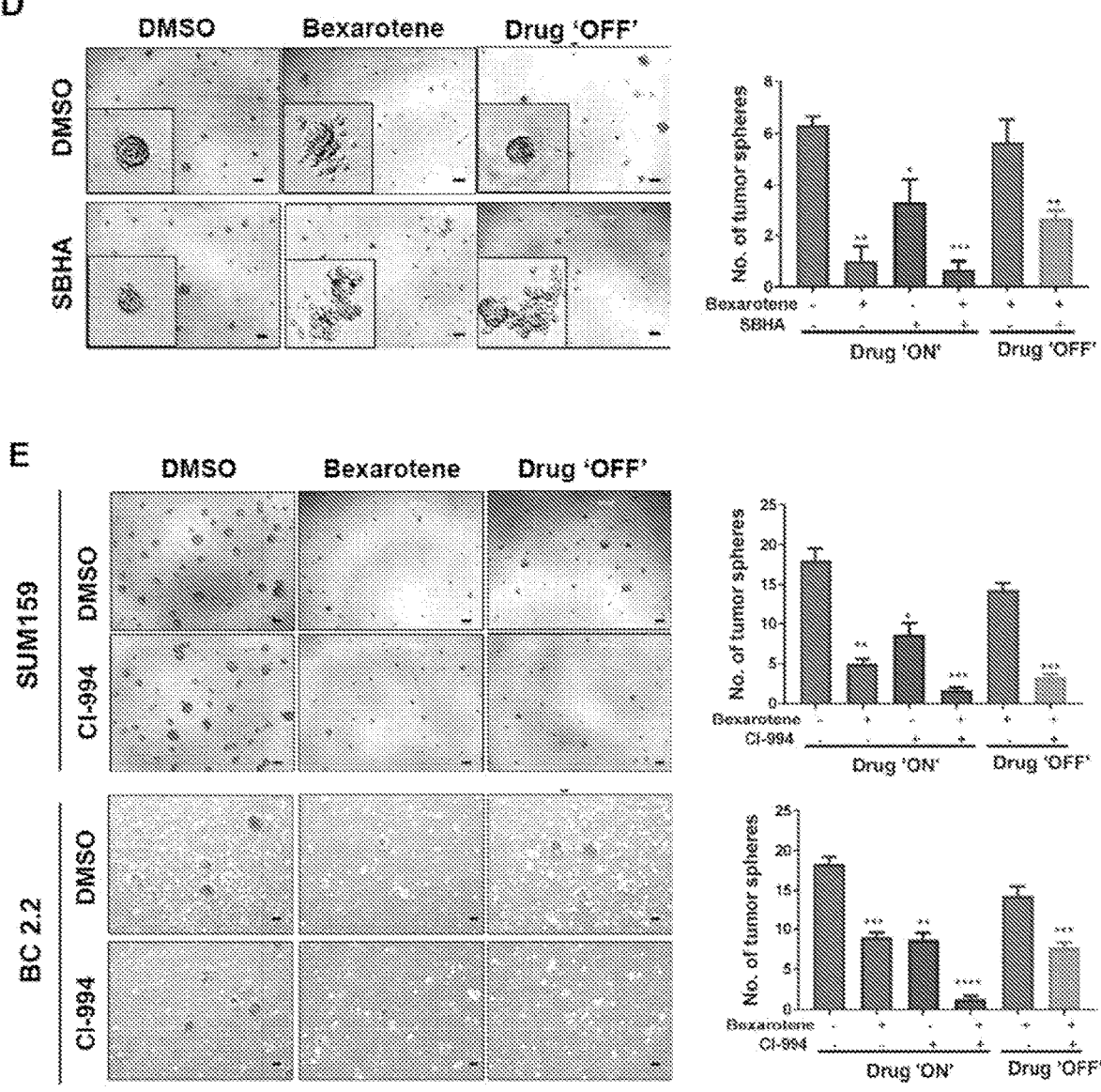
Figure 12(D)-(E) (end)

D    SUM159 Bexarotene RNA Seq
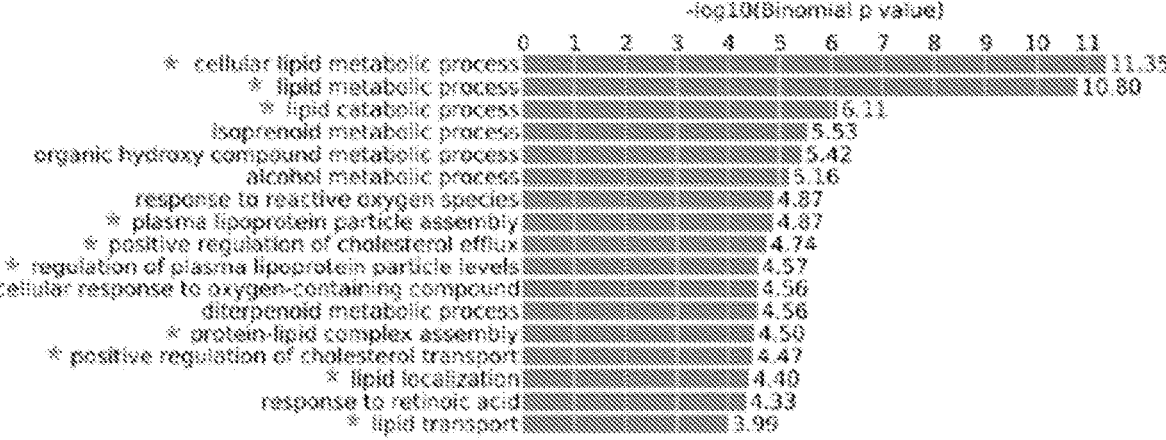
E    MetBr007 Bexarotene RNA Seq
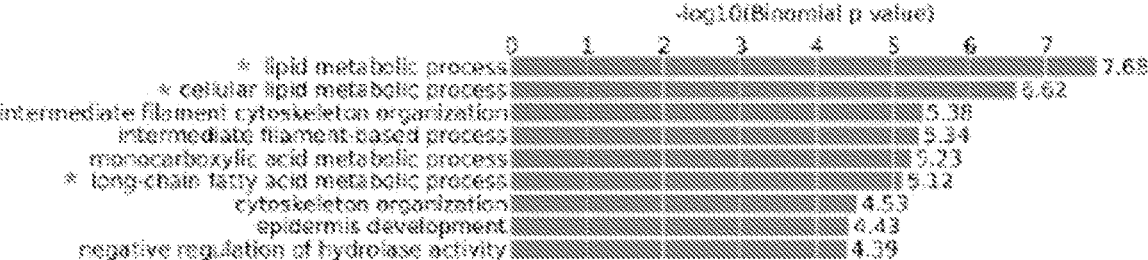
F
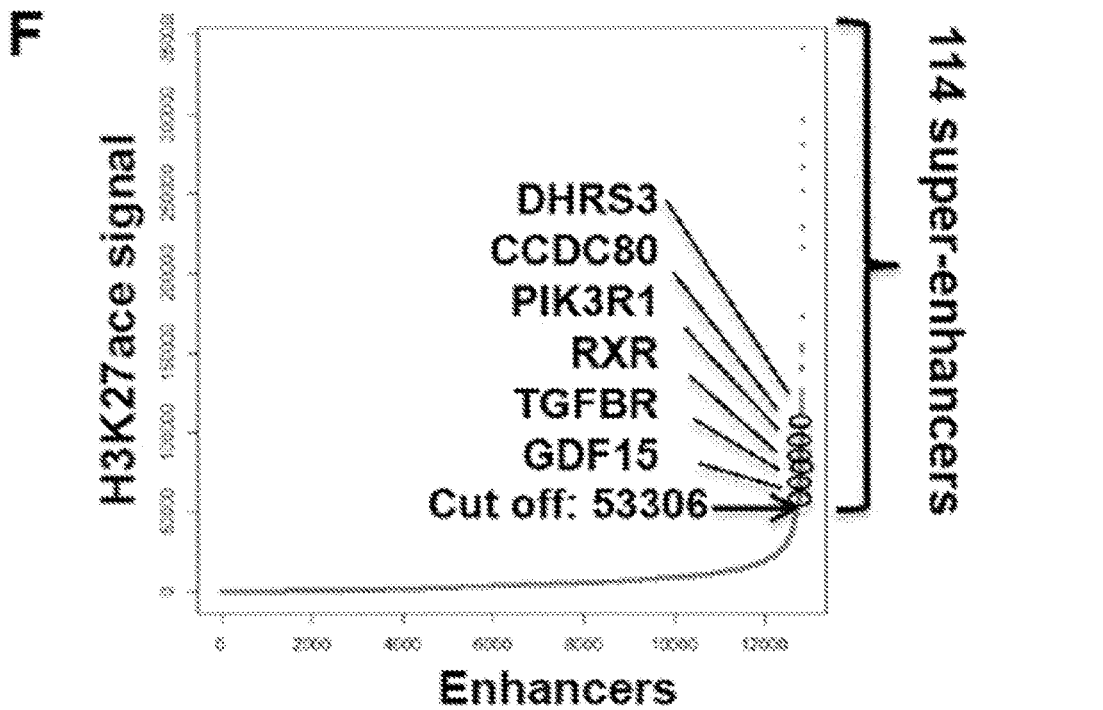
Figure 13(D)-(F)(continued)

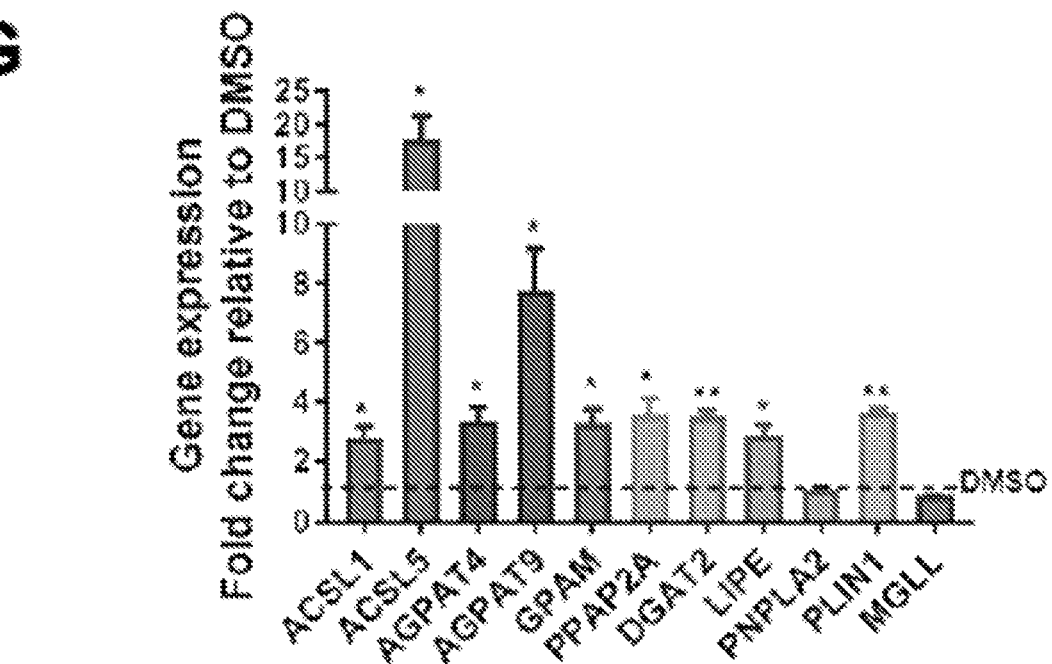
Figure 13(G)(end)

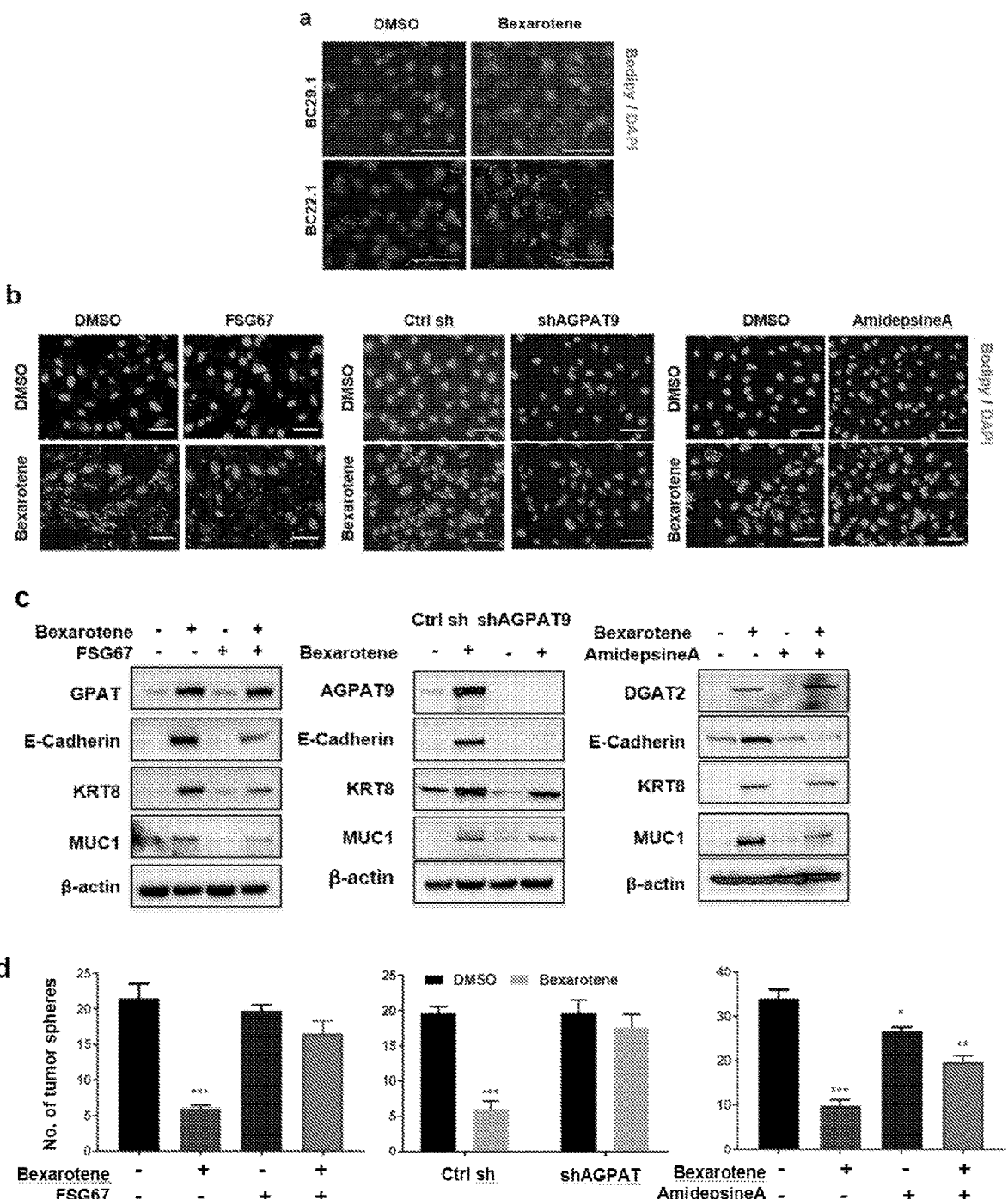
Figure 14(A)-(D)(continued)

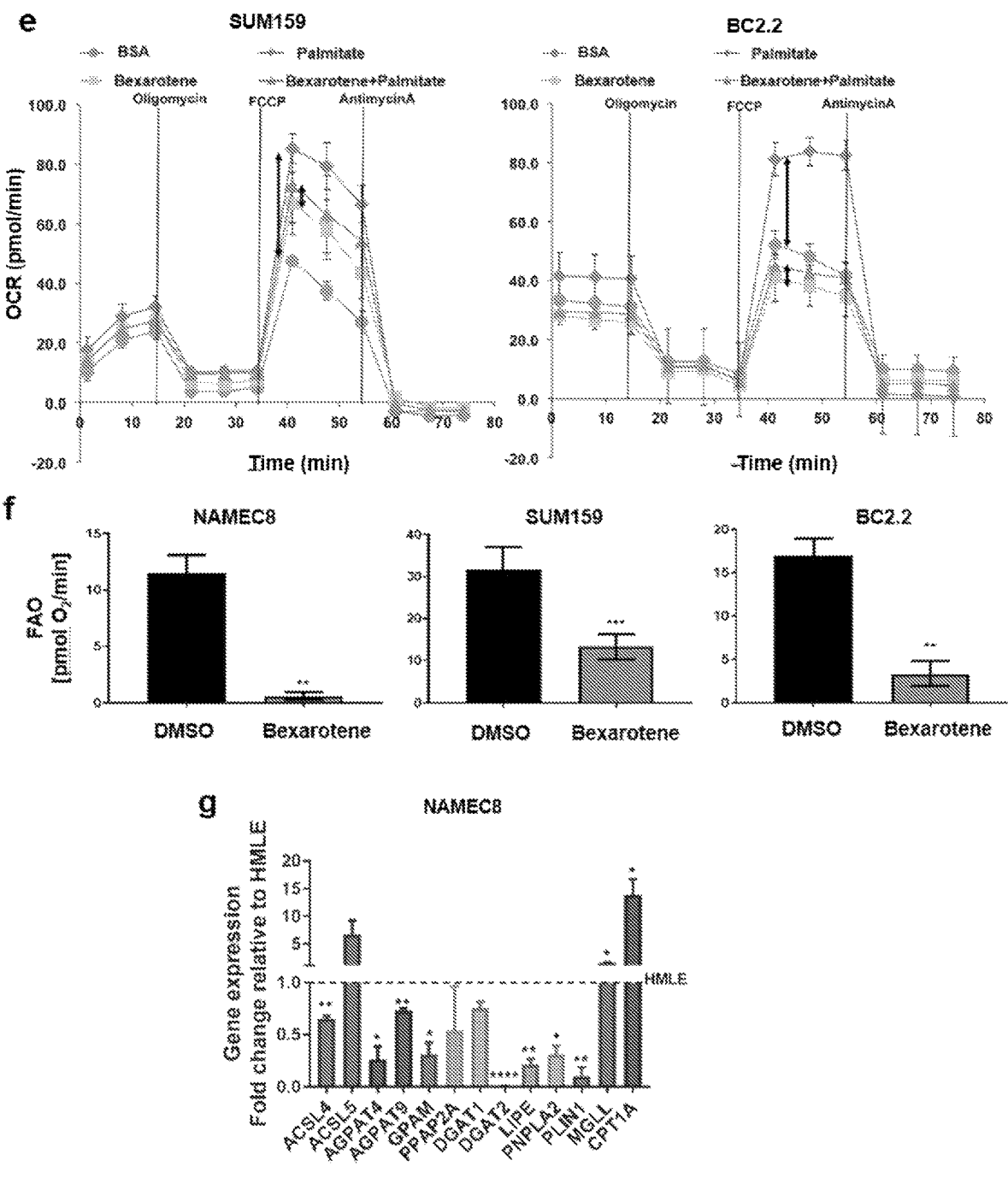
Figure 14 (E)-(G) (end)

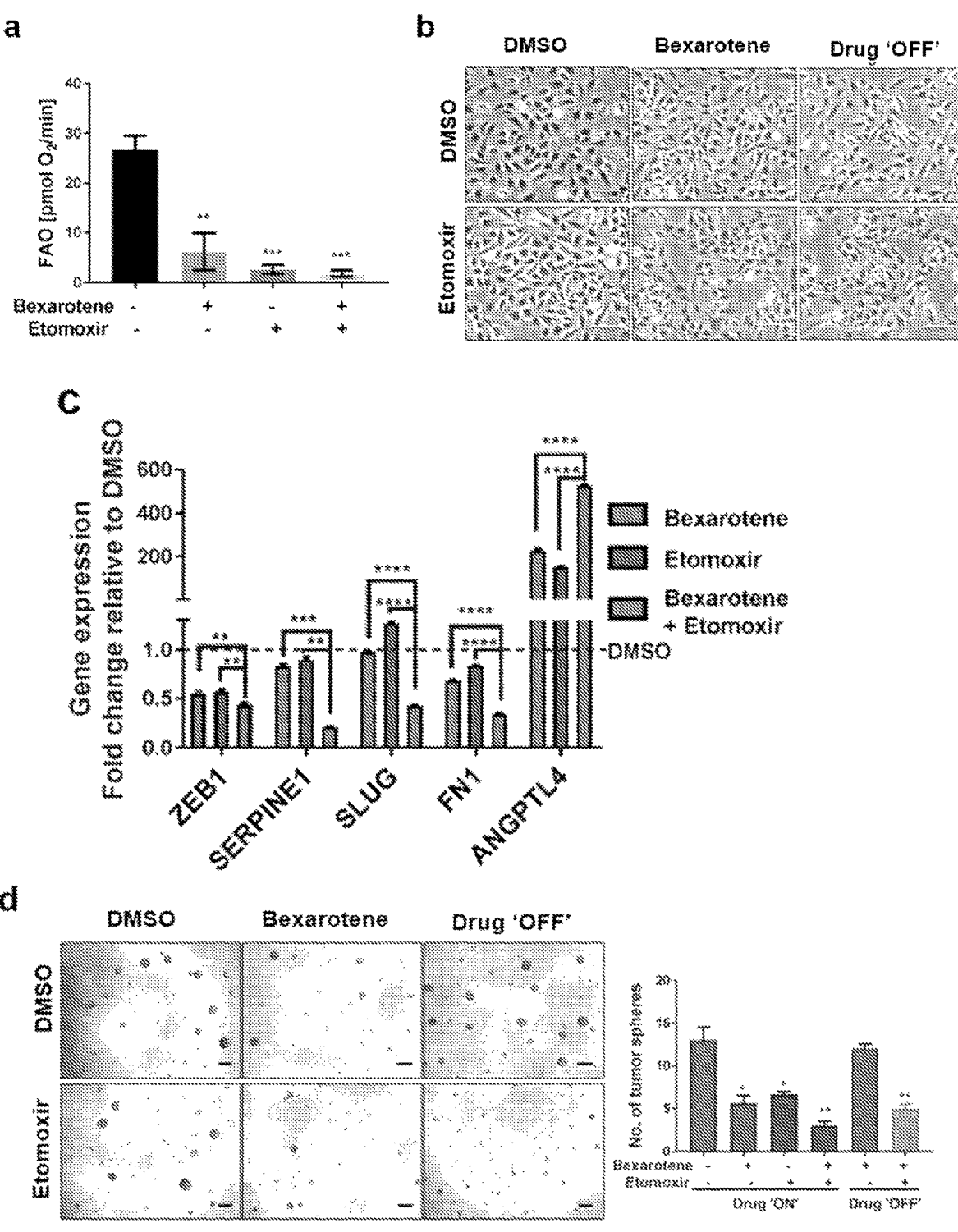
Figure 15 (A)-(D) (continued)

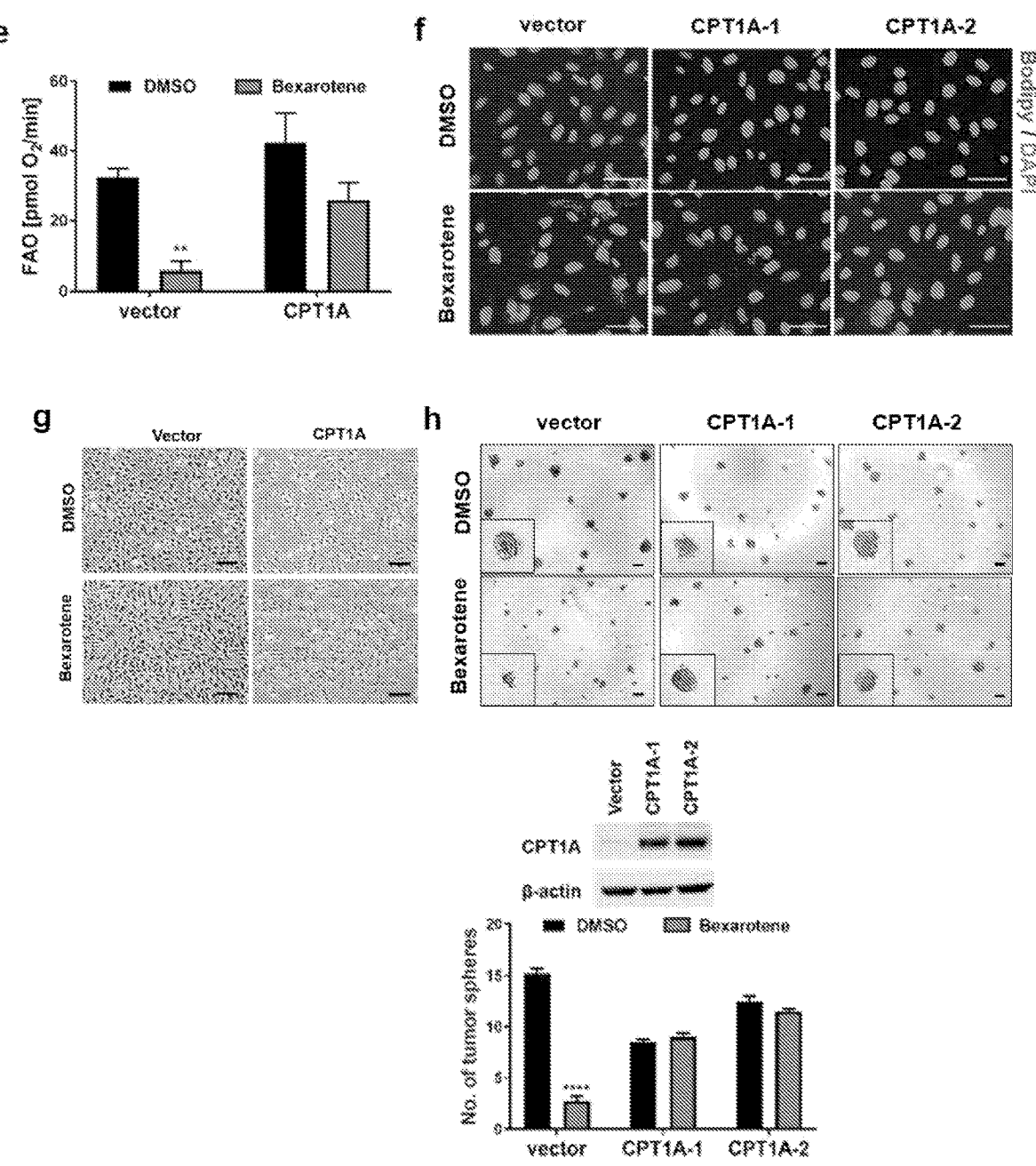
Figure 15 (E)-(H) (end)

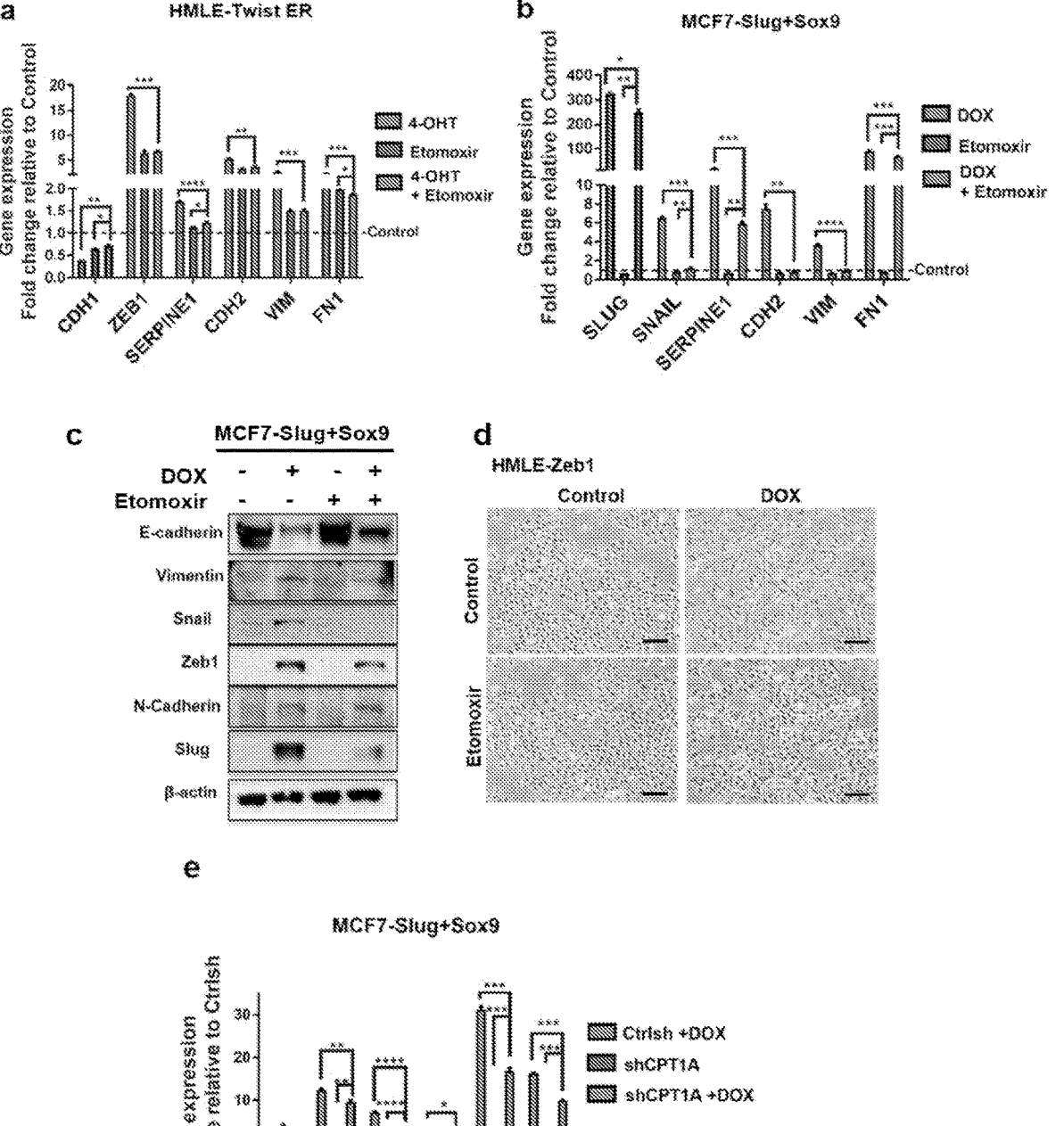
Figure 16(A)-(E) (continued)

f
A549
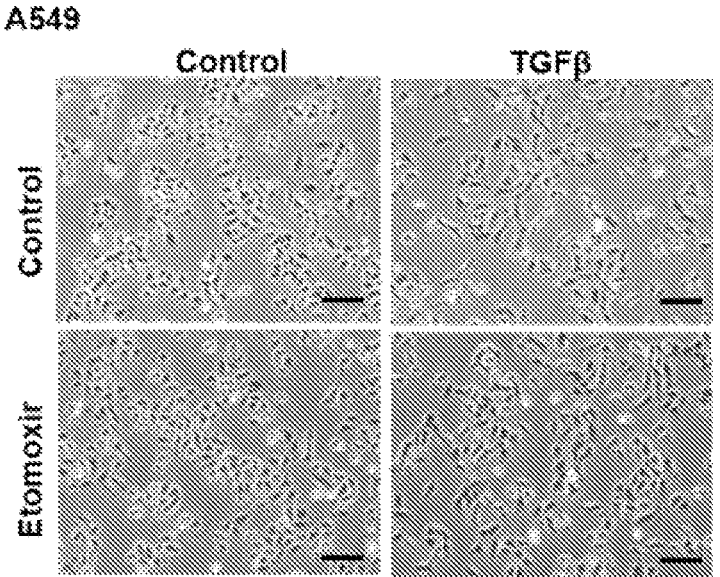
g
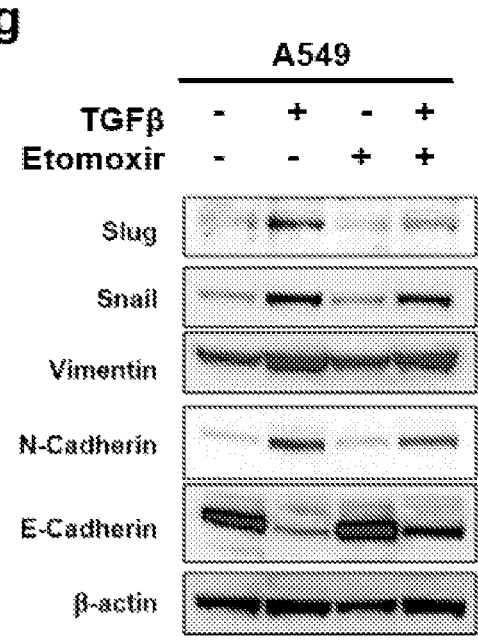
Figure 16(F)-(G) (end)

A
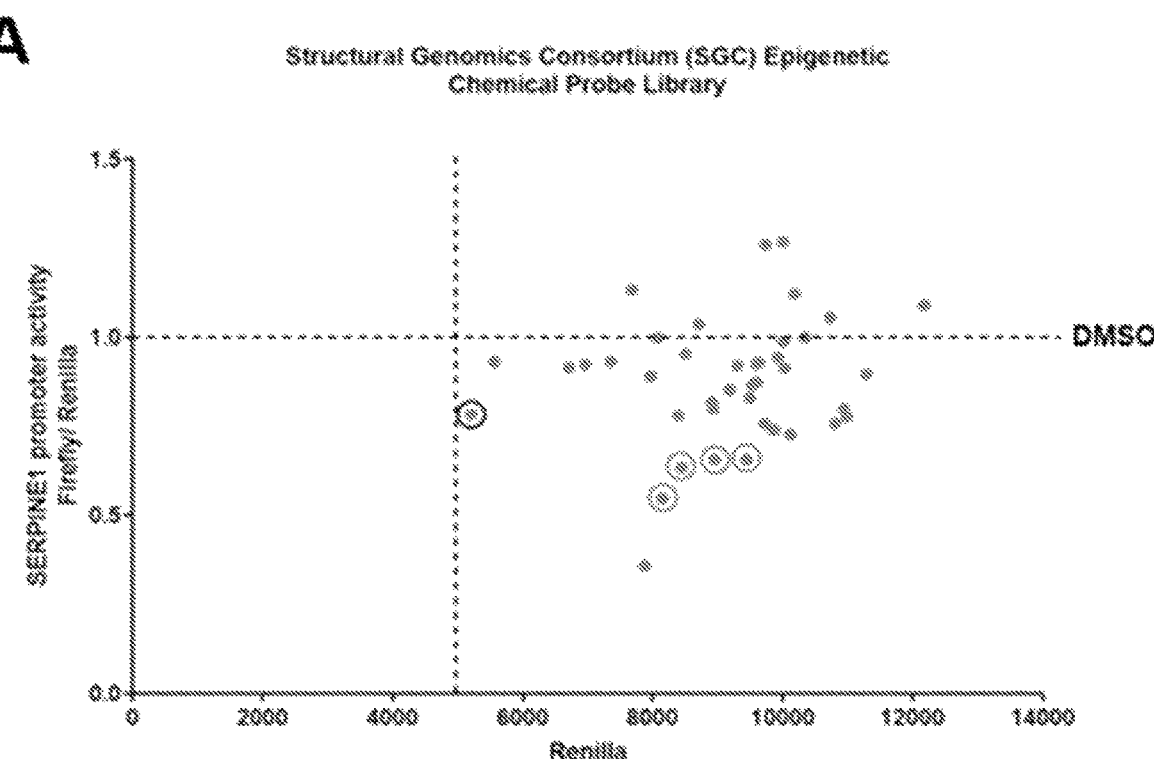
B
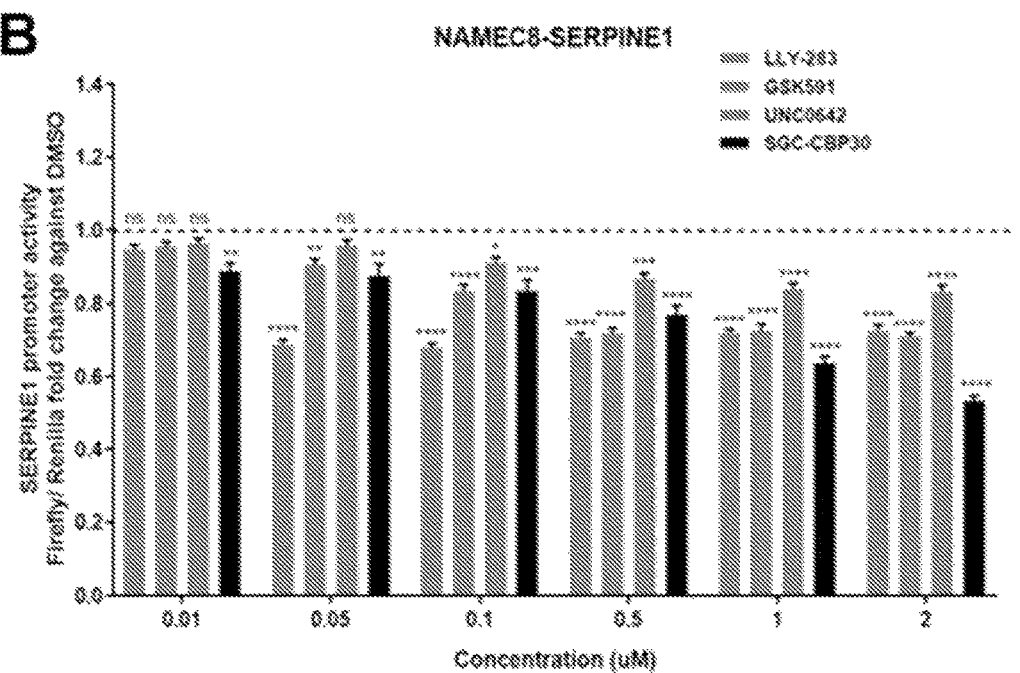
Figure 17(A)-(B) (continued)

C
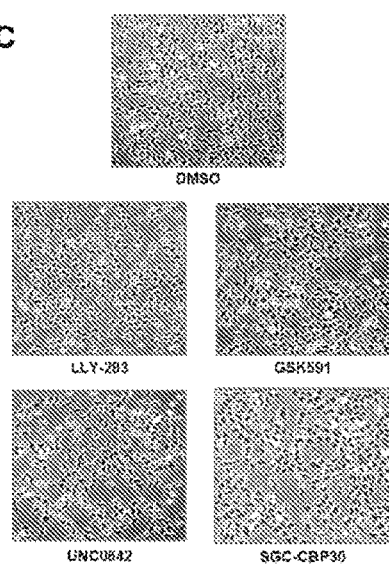
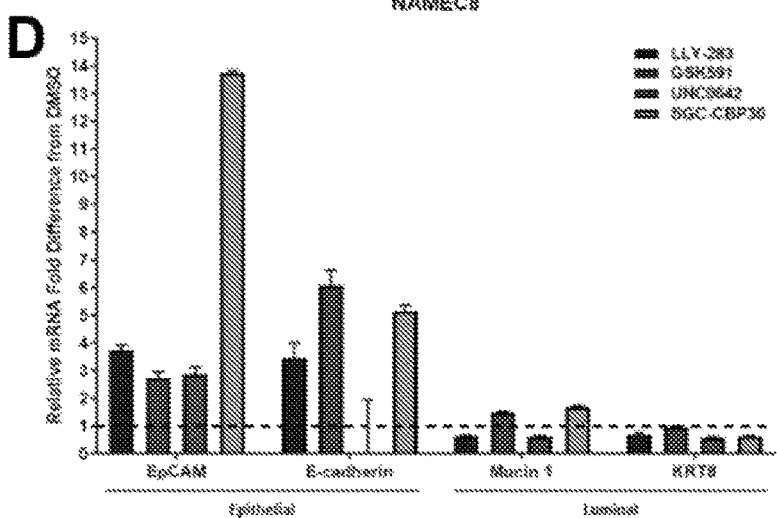
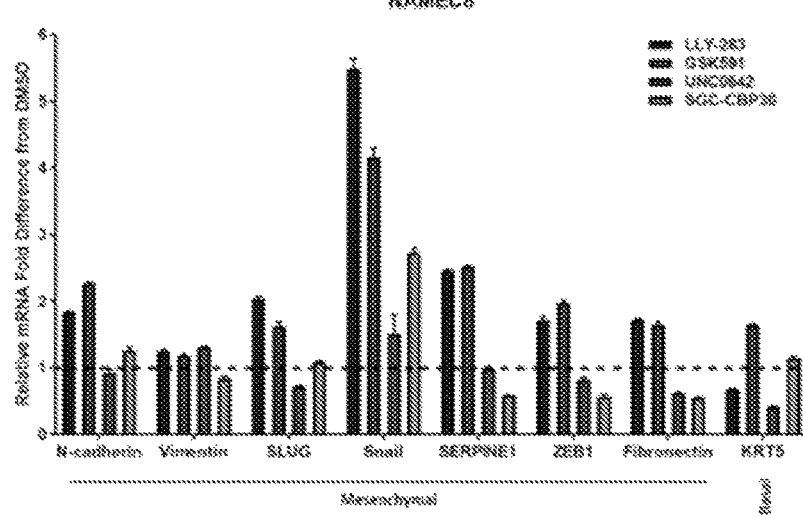
Figure 17(C)-(D) (continued)

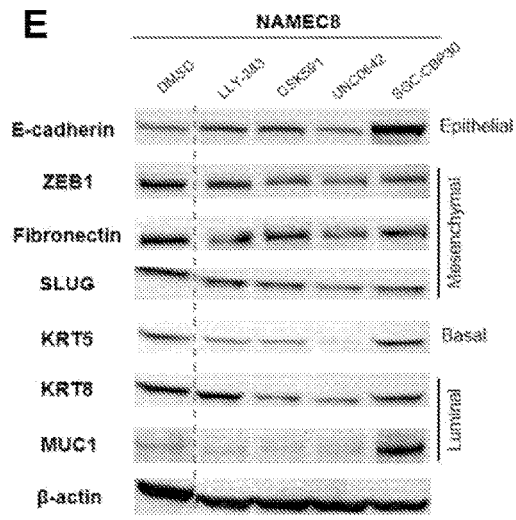
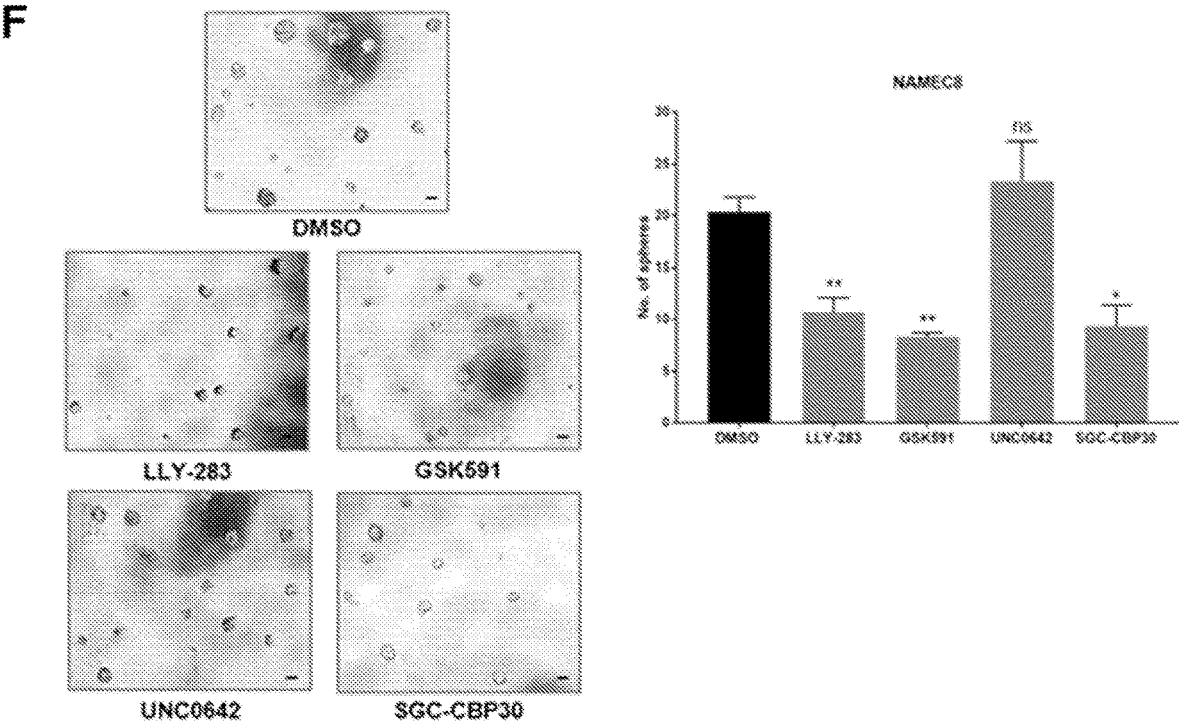
Figure 17(E)-(F) (continued)

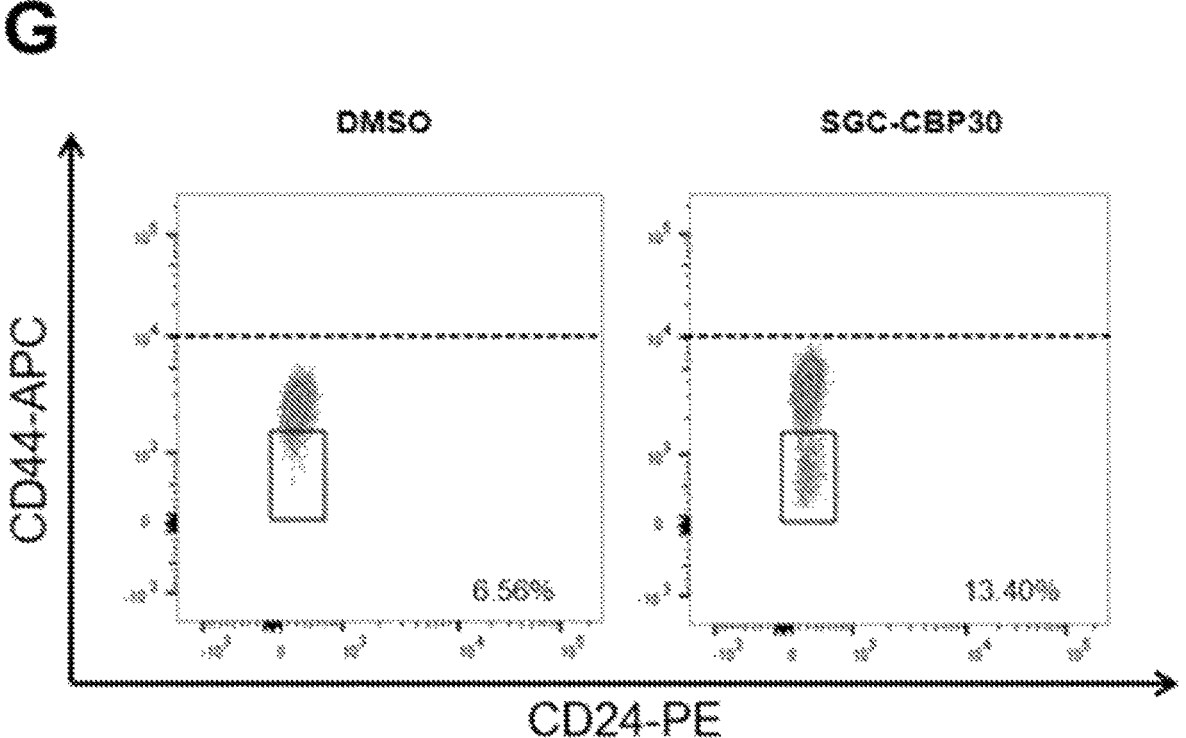
Figure 17(G) (end)

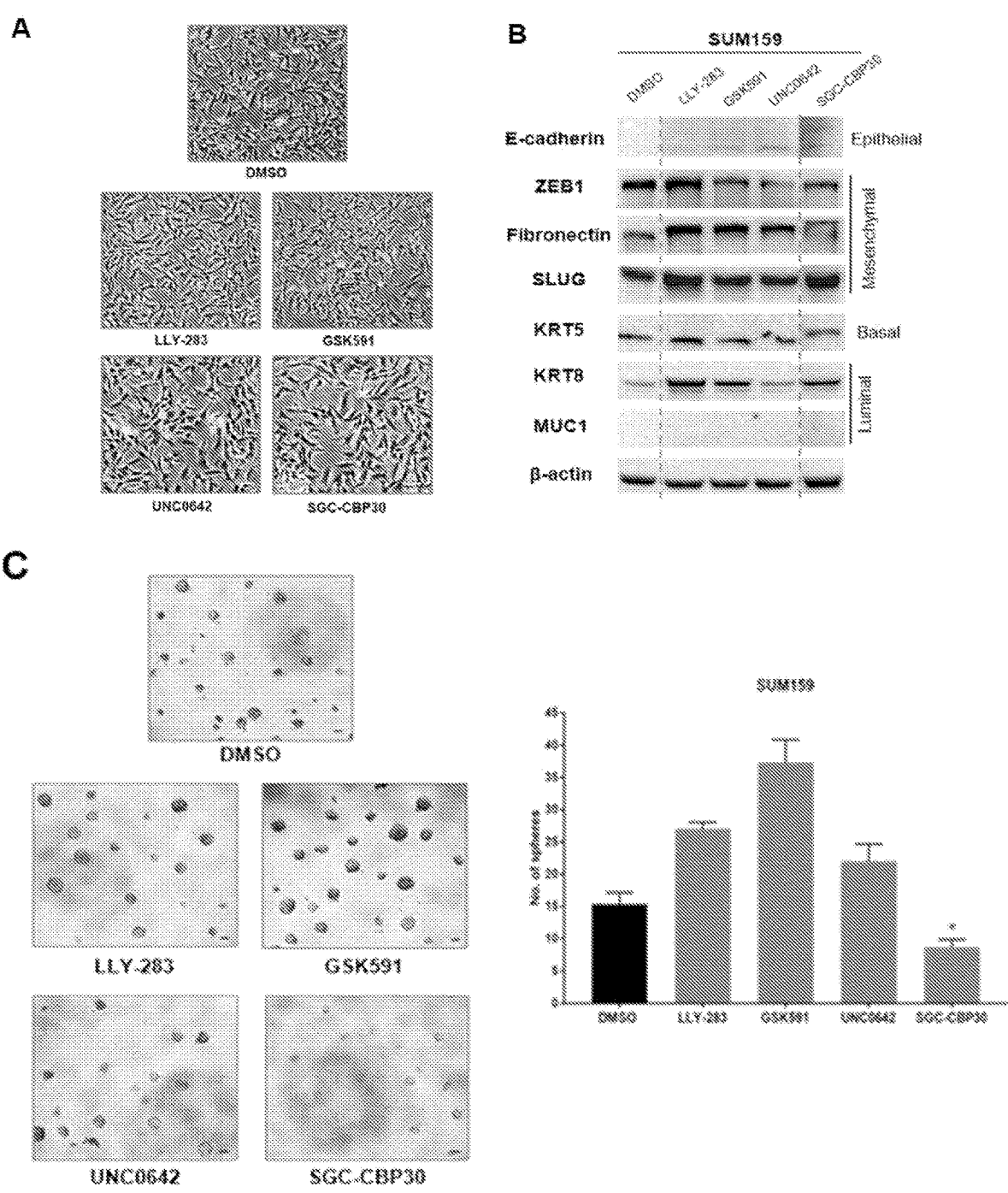
Figure 18 (A)-(C) (continued)

D
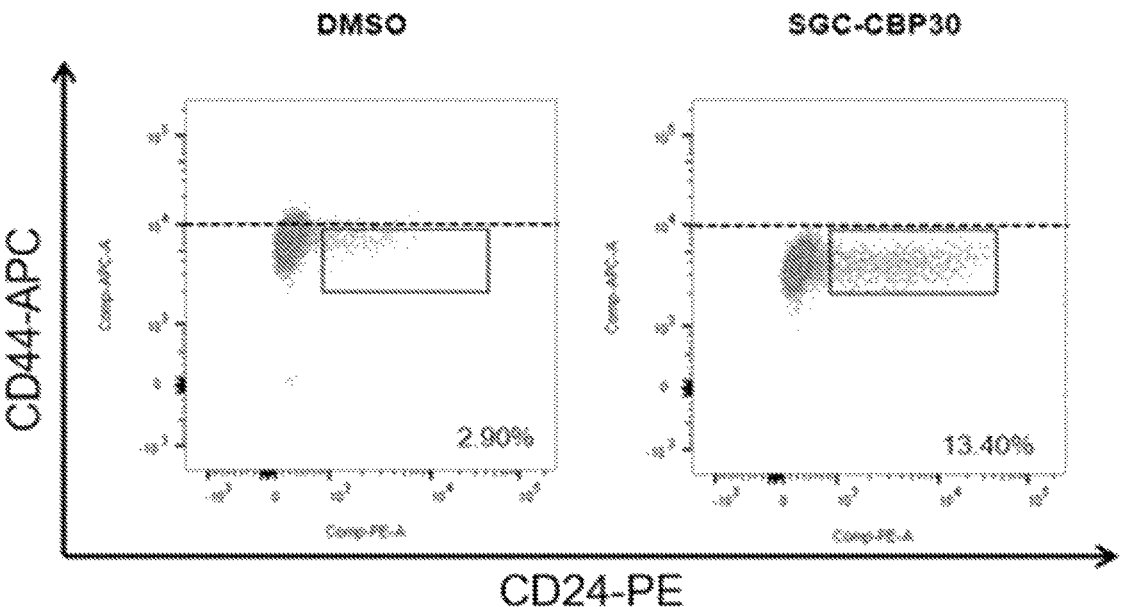
Figure 18 (D) (end)

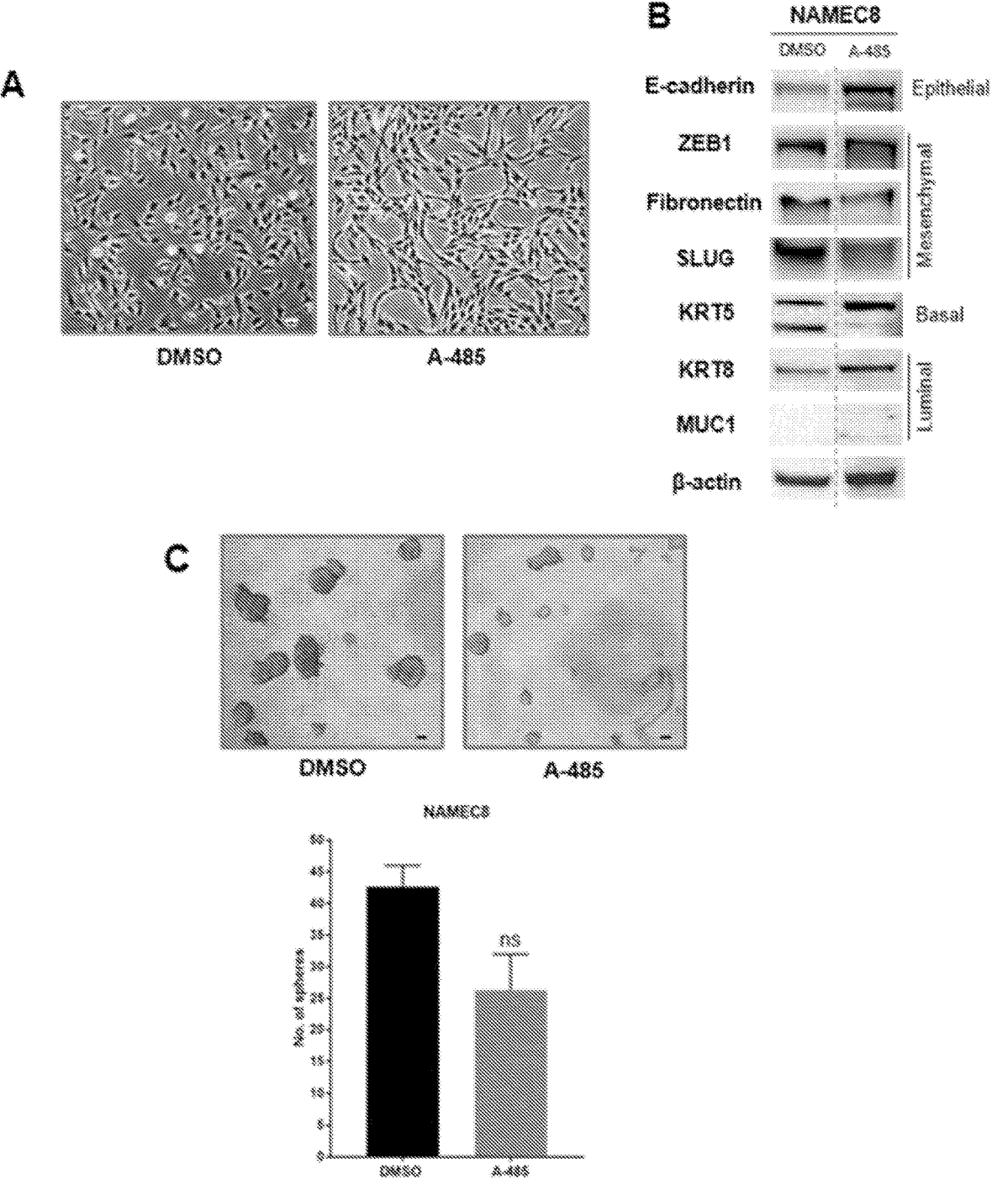
Figure 19(A)-(C) (continued)

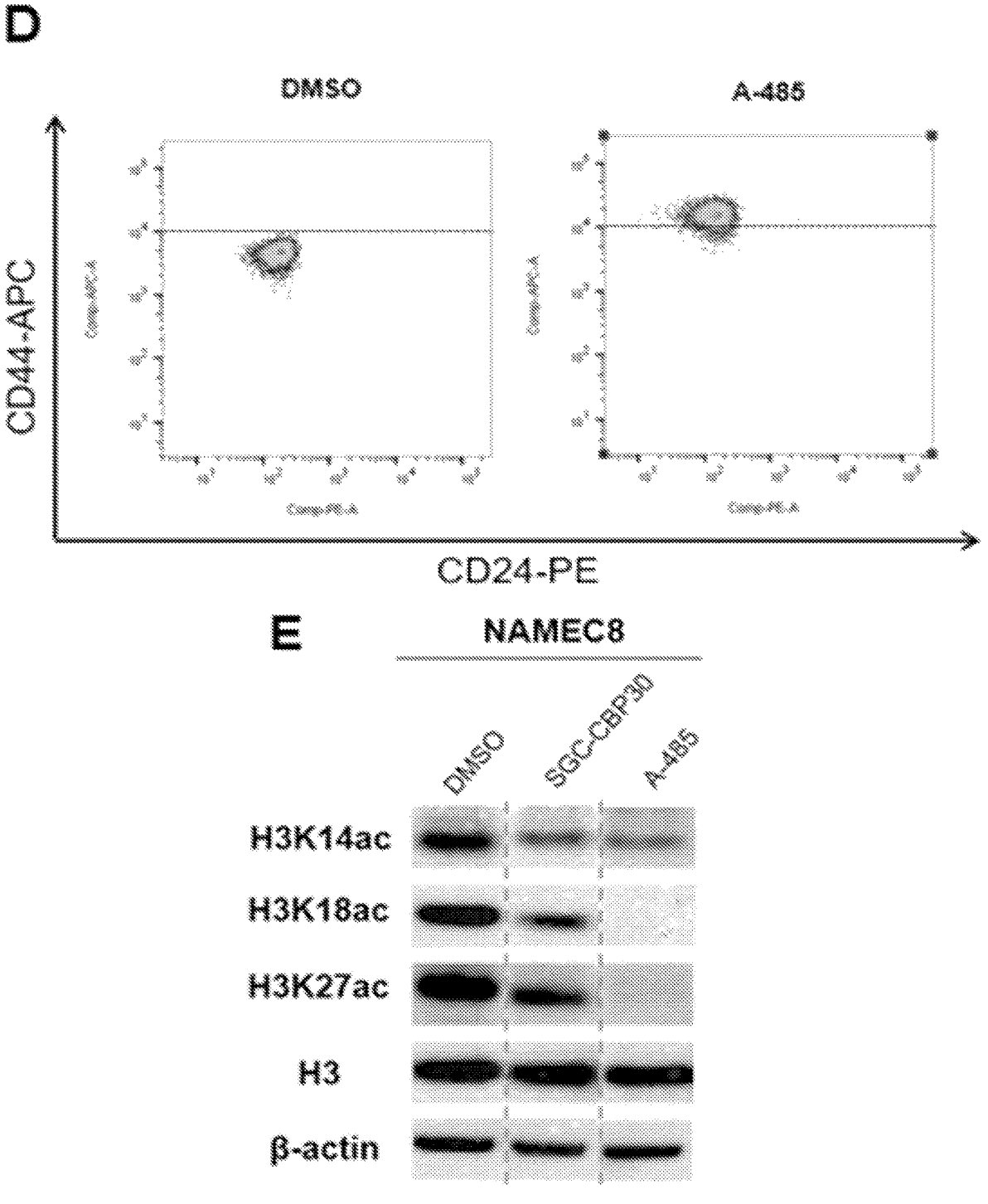
Figure 19(D)-(E) (continued)

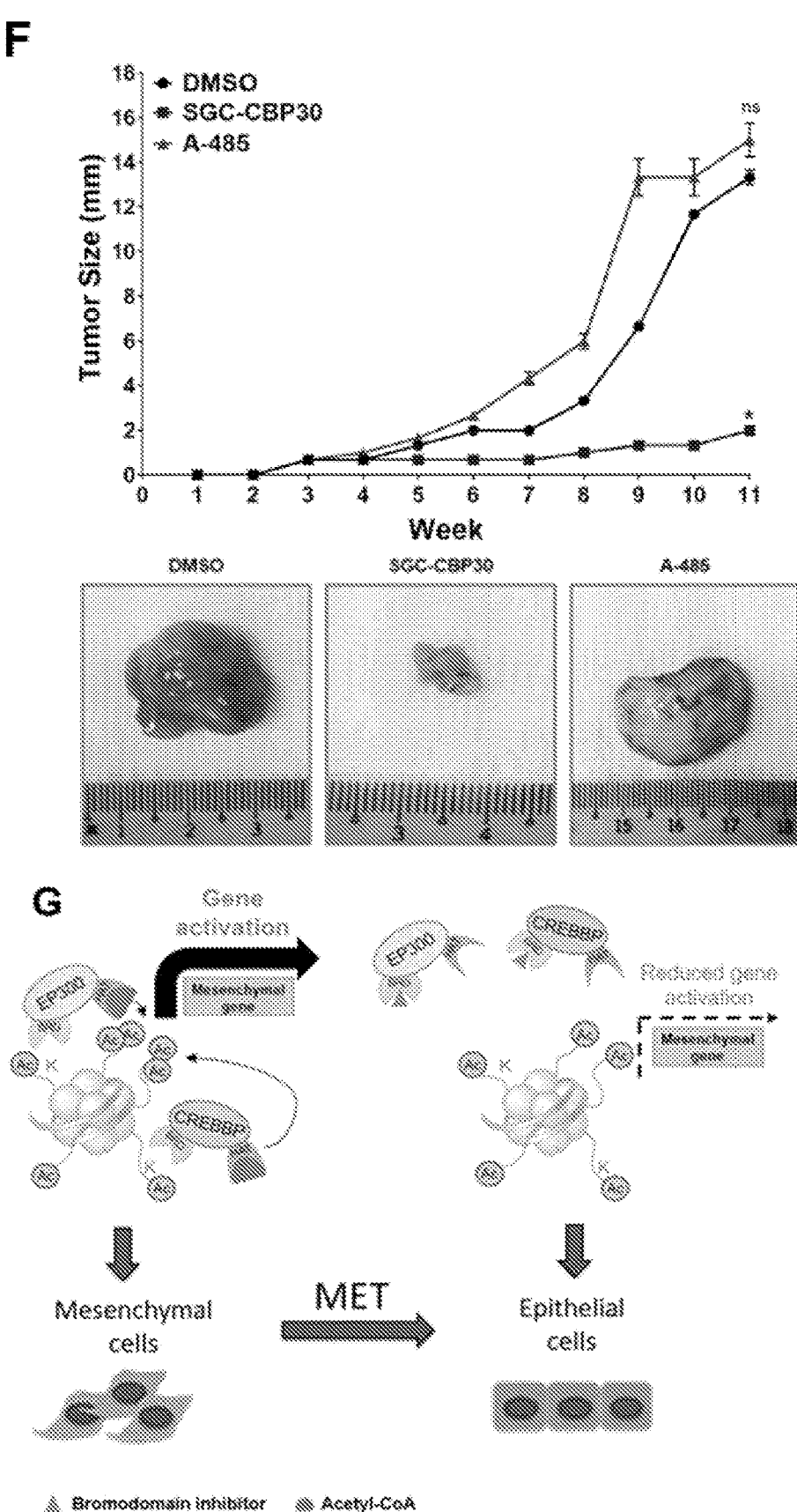
Figure 19(F)-(G) (end)

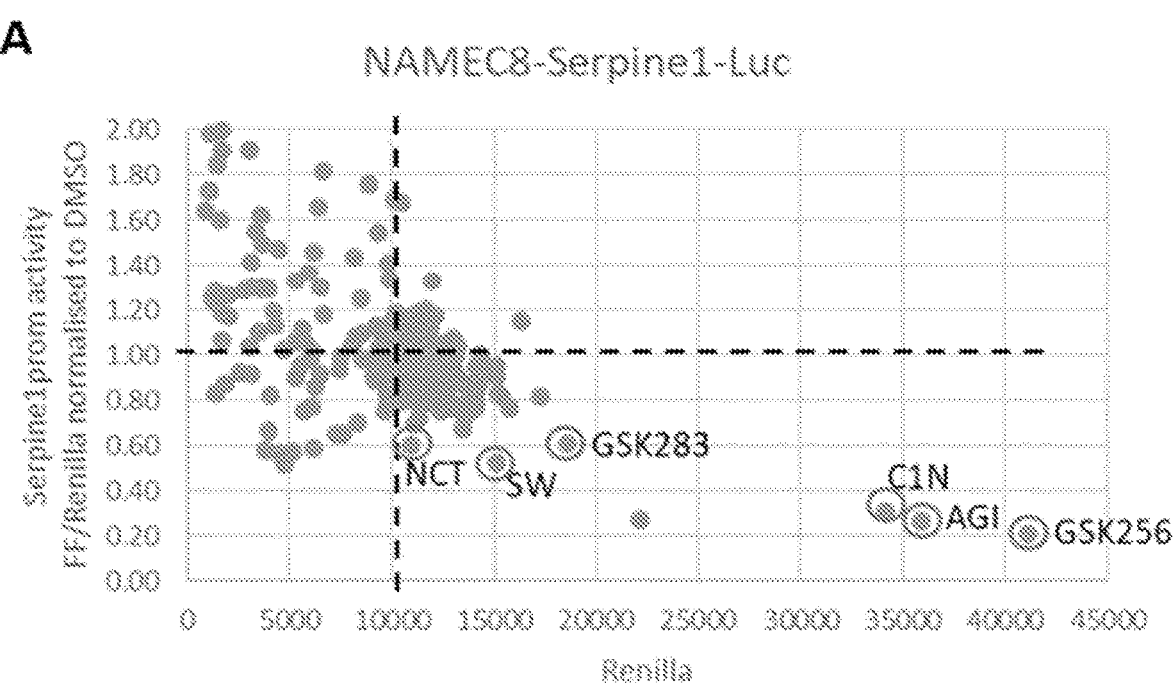

A

NAMEC8-Serpine1-Luc

B

| Compound | Target |
|---|---|
| Tanshinone I | Phospholipase |
| Hemin | Autophagy |
| Autophinib | Autophagy |
| β-Lapachone | Topoisomerase;Autophagy |
| Vps34-PIK-III | PI3K;Autophagy |
| Glutaminase C-IN-1 | Glutaminase |
| GSK256066 | Phosphodiesterase (PDE) |
| AN-2728 | Phosphodiesterase (PDE) |
| GSK2837808A | Lactate Dehydrogenase |
| Etretinate | RAR/RXR |
| Fenretinide | RAR/RXR;Autophagy |
| T0901317 | FXR;LXR |
| AGI-6780 | Isocitrate Dehydrogenase (IDH) |
| SW033291 | 15-PGDH |
| NCT-503 | Phosphoglycerate dehydrogenase |

Figure 20(A)-(B) (continued)

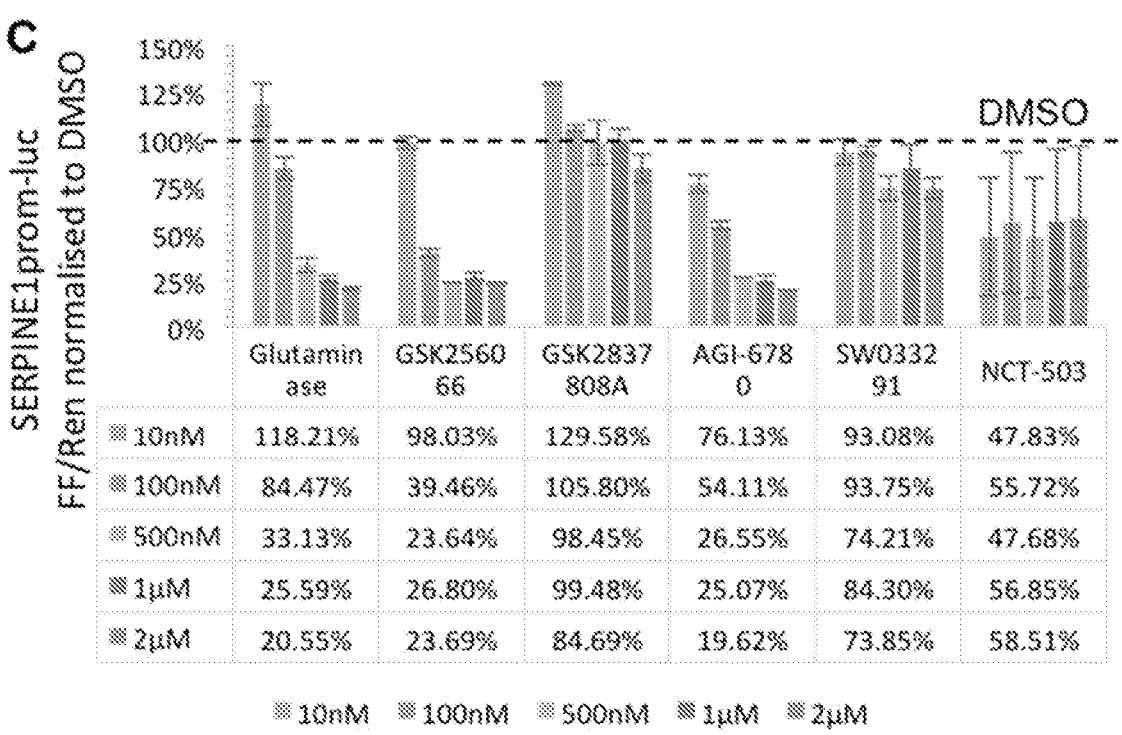
| | Glutaminase | GSK256066 | GSK2837808A | AGI-6780 | SW033291 | NCT-503 |
|---|---|---|---|---|---|---|
| 10nM | 118.21% | 98.03% | 129.58% | 76.13% | 93.08% | 47.83% |
| 100nM | 84.47% | 39.46% | 105.80% | 54.11% | 93.75% | 55.72% |
| 500nM | 33.13% | 23.64% | 98.45% | 26.55% | 74.21% | 47.68% |
| 1µM | 25.59% | 26.80% | 99.48% | 25.07% | 84.30% | 56.85% |
| 2µM | 20.55% | 23.69% | 84.69% | 19.62% | 73.85% | 58.51% |
10nM    100nM    500nM    1µM    2µM
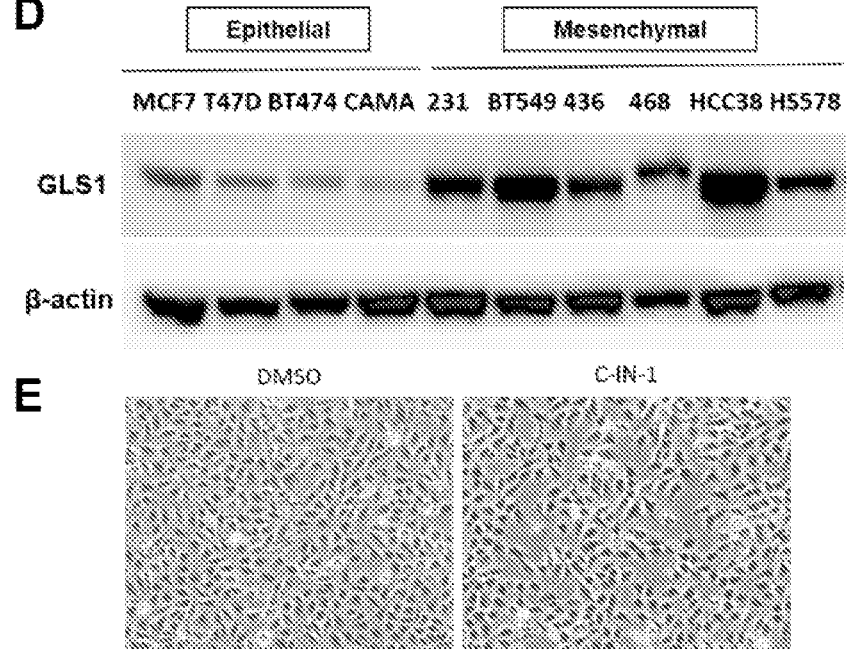
Figure 20(C)-(E) (continued)

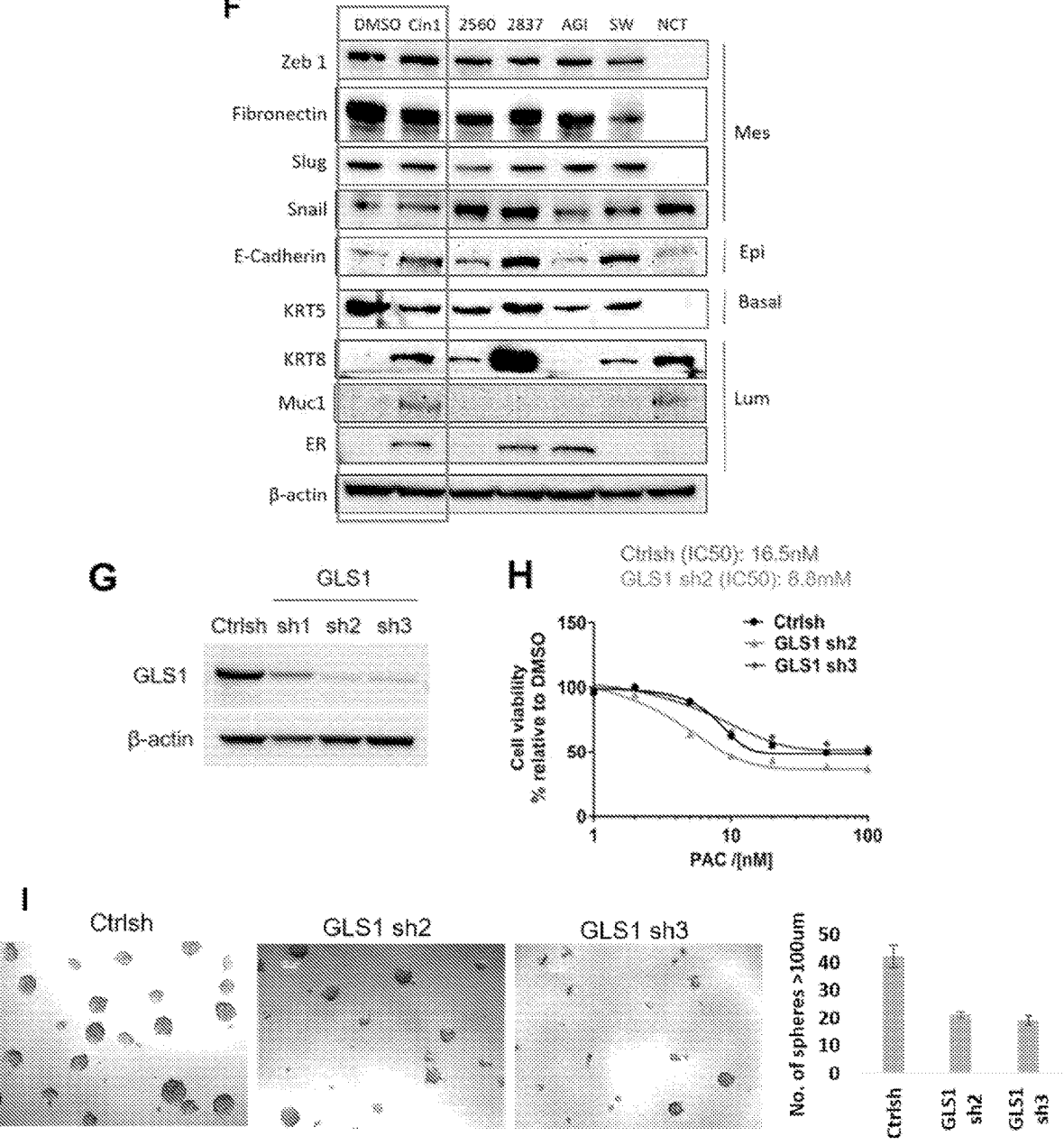
Figure 20(F)-(I) (continued)

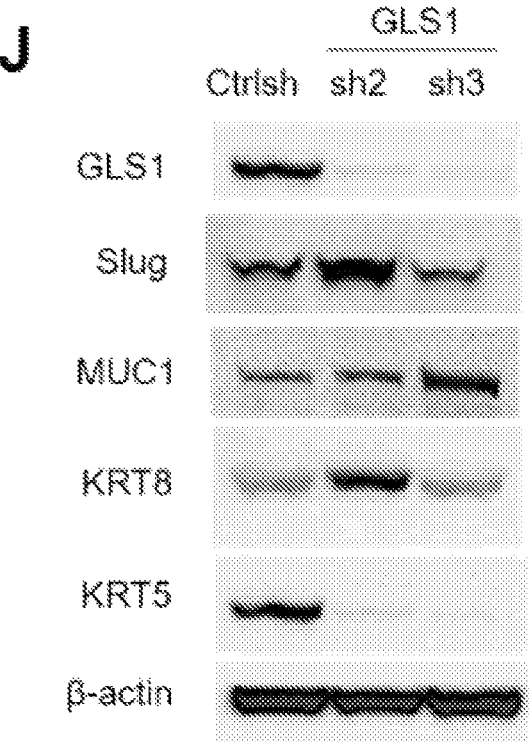
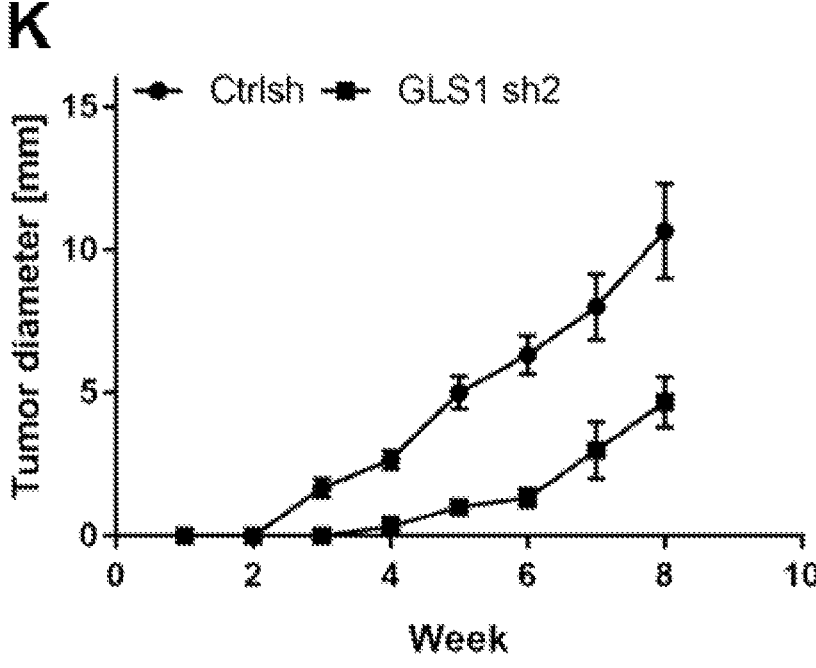
Figure 20(J)-(K) (end)

SEQUENCE LISTING

<160> NUMBER OF SEQ ID NOS: 68

<210> SEQ ID NO 1
<211> LENGTH: 23
<212> TYPE: DNA
<213> ORGANISM: Artificial Sequence
<220> FEATURE:
<223> OTHER INFORMATION: CDH1 forward

<400> SEQUENCE: 1
atggctcaag aaacatttgt cat                                          23

<210> SEQ ID NO 2
<211> LENGTH: 17
<212> TYPE: DNA
<213> ORGANISM: Artificial Sequence
<220> FEATURE:
<223> OTHER INFORMATION: CDH1 reverse

<400> SEQUENCE: 2
gagcttgcgg cccgaat                                                 17

<210> SEQ ID NO 3
<211> LENGTH: 23
<212> TYPE: DNA
<213> ORGANISM: Artificial Sequence
<220> FEATURE:
<223> OTHER INFORMATION: CD24 forward

<400> SEQUENCE: 3
gagaacagga tgccccttag aat                                          23

<210> SEQ ID NO 4
<211> LENGTH: 21

-continued

```
<212> TYPE: DNA
<213> ORGANISM: Artificial Sequence
<220> FEATURE:
<223> OTHER INFORMATION: CD24 reverse

<400> SEQUENCE: 4
aaatctgcgt gggtaggagc a                                              21

<210> SEQ ID NO 5
<211> LENGTH: 20
<212> TYPE: DNA
<213> ORGANISM: Artificial Sequence
<220> FEATURE:
<223> OTHER INFORMATION: CD44 forward

<400> SEQUENCE: 5
atcttgccac agccactgat                                               20

<210> SEQ ID NO 6
<211> LENGTH: 20
<212> TYPE: DNA
<213> ORGANISM: Artificial Sequence
<220> FEATURE:
<223> OTHER INFORMATION: CD44 reverse

<400> SEQUENCE: 6
tcggaagttg gctgcagttt                                               20

<210> SEQ ID NO 7
<211> LENGTH: 19
<212> TYPE: DNA
<213> ORGANISM: Artificial Sequence
<220> FEATURE:
<223> OTHER INFORMATION: SERPINE 1 forward

<400> SEQUENCE: 7
cgggcagctc gaagaagtg                                                19

<210> SEQ ID NO 8
<211> LENGTH: 22
<212> TYPE: DNA
<213> ORGANISM: Artificial Sequence
<220> FEATURE:
<223> OTHER INFORMATION: SERPINE 1 reverse

<400> SEQUENCE: 8
tagaggaata gcgggggatc at                                            22

<210> SEQ ID NO 9
<211> LENGTH: 22
<212> TYPE: DNA
<213> ORGANISM: Artificial Sequence
<220> FEATURE:
<223> OTHER INFORMATION: CD166 forward

<400> SEQUENCE: 9 aggggggagga gagagagatt cg                                           22

<210> SEQ ID NO 10
<211> LENGTH: 20
<212> TYPE: DNA
<213> ORGANISM: Artificial Sequence
<220> FEATURE:
<223> OTHER INFORMATION: CD166 reverse

<400> SEQUENCE: 10
```

-continued gcggagatca agaggcagaa                                                     20

<210> SEQ ID NO 11
<211> LENGTH: 29
<212> TYPE: DNA
<213> ORGANISM: Artificial Sequence
<220> FEATURE:
<223> OTHER INFORMATION: ZEB1 foward

<400> SEQUENCE: 11
cggcggatcg attcagctta tttattcca                                           29

<210> SEQ ID NO 12
<211> LENGTH: 29
<212> TYPE: DNA
<213> ORGANISM: Artificial Sequence
<220> FEATURE:
<223> OTHER INFORMATION: ZEB1 reverse

<400> SEQUENCE: 12
cggtaaacta gtgatcctct cgcttgtgt                                           29

<210> SEQ ID NO 13
<211> LENGTH: 21
<212> TYPE: DNA
<213> ORGANISM: Artificial Sequence
<220> FEATURE:
<223> OTHER INFORMATION: CDH1 forward

<400> SEQUENCE: 13
ttgcaccggt cgacaaagga c                                                   21

<210> SEQ ID NO 14
<211> LENGTH: 21
<212> TYPE: DNA
<213> ORGANISM: Artificial Sequence
<220> FEATURE:
<223> OTHER INFORMATION: CDH1 reverse

<400> SEQUENCE: 14
tggattccag aaacggaggc c                                                   21

<210> SEQ ID NO 15
<211> LENGTH: 20
<212> TYPE: DNA
<213> ORGANISM: Artificial Sequence
<220> FEATURE:
<223> OTHER INFORMATION: VIM forward

<400> SEQUENCE: 15
acccgcacca acgagaaggt                                                     20

<210> SEQ ID NO 16
<211> LENGTH: 21
<212> TYPE: DNA
<213> ORGANISM: Artificial Sequence
<220> FEATURE:
<223> OTHER INFORMATION: VIM reverse

<400> SEQUENCE: 16
attctgctgc tccaggaagc g                                                   21

<210> SEQ ID NO 17
<211> LENGTH: 20
<212> TYPE: DNA
<213> ORGANISM: Artificial Sequence

```
<220> FEATURE:
<223> OTHER INFORMATION: SLUG foward

<400> SEQUENCE: 17
taccgctgct ccattccacg                                              20

<210> SEQ ID NO 18
<211> LENGTH: 21
<212> TYPE: DNA
<213> ORGANISM: Artificial Sequence
<220> FEATURE:
<223> OTHER INFORMATION: SLUG reverse

<400> SEQUENCE: 18
catgggggtc tgaaagcttg g                                            21

<210> SEQ ID NO 19
<211> LENGTH: 20
<212> TYPE: DNA
<213> ORGANISM: Artificial Sequence
<220> FEATURE:
<223> OTHER INFORMATION: GAPDH forward

<400> SEQUENCE: 19
tggcaaattc catggcaccg                                              20

<210> SEQ ID NO 20
<211> LENGTH: 21
<212> TYPE: DNA
<213> ORGANISM: Artificial Sequence
<220> FEATURE:
<223> OTHER INFORMATION: GAPDH reverse

<400> SEQUENCE: 20
cgccccactt gattttggag g                                            21

<210> SEQ ID NO 21
<211> LENGTH: 19
<212> TYPE: DNA
<213> ORGANISM: Artificial Sequence
<220> FEATURE:
<223> OTHER INFORMATION: SERPINE1 forward

<400> SEQUENCE: 21
gcaccacaga cgcgatctt                                               19

<210> SEQ ID NO 22
<211> LENGTH: 21
<212> TYPE: DNA
<213> ORGANISM: Artificial Sequence
<220> FEATURE:
<223> OTHER INFORMATION: SERPINE1 reverse

<400> SEQUENCE: 22
acctctgaaa agtccacttg c                                            21

<210> SEQ ID NO 23
<211> LENGTH: 20
<212> TYPE: DNA
<213> ORGANISM: Artificial Sequence
<220> FEATURE:
<223> OTHER INFORMATION: ZEB1 forward

<400> SEQUENCE: 23
tgcactgagt gtggaaaagc                                              20
```

```
<210> SEQ ID NO 24
<211> LENGTH: 20
<212> TYPE: DNA
<213> ORGANISM: Artificial Sequence
<220> FEATURE:
<223> OTHER INFORMATION: ZEB1 reverse

<400> SEQUENCE: 24
tggtgatgct gaaagagacg                                        20

<210> SEQ ID NO 25
<211> LENGTH: 19
<212> TYPE: DNA
<213> ORGANISM: Artificial Sequence
<220> FEATURE:
<223> OTHER INFORMATION: MUC1 forward

<400> SEQUENCE: 25
tgccgccgaa agaactacg                                         19

<210> SEQ ID NO 26
<211> LENGTH: 21
<212> TYPE: DNA
<213> ORGANISM: Artificial Sequence
<220> FEATURE:
<223> OTHER INFORMATION: MUC1 reverse

<400> SEQUENCE: 26
tggggtactc gctcatagga t                                      21

<210> SEQ ID NO 27
<211> LENGTH: 20
<212> TYPE: DNA
<213> ORGANISM: Artificial Sequence
<220> FEATURE:
<223> OTHER INFORMATION: KRT5 foward

<400> SEQUENCE: 27
caaggttgat gcactgatgg                                        20

<210> SEQ ID NO 28
<211> LENGTH: 20
<212> TYPE: DNA
<213> ORGANISM: Artificial Sequence
<220> FEATURE:
<223> OTHER INFORMATION: KRT5 reverse

<400> SEQUENCE: 28
tgtcagagac atgcgtctgc                                        20

<210> SEQ ID NO 29
<211> LENGTH: 22
<212> TYPE: DNA
<213> ORGANISM: Artificial Sequence
<220> FEATURE:
<223> OTHER INFORMATION: KRT8 reverse

<400> SEQUENCE: 29
cagaagtcct acaaggtgtc ca                                     22

<210> SEQ ID NO 30
<211> LENGTH: 21
<212> TYPE: DNA
<213> ORGANISM: Artificial Sequence
<220> FEATURE:
<223> OTHER INFORMATION: KRT8 reverse
```

-continued

```
<400> SEQUENCE: 30
ctctggttga ccgtaactgc g                                         21

<210> SEQ ID NO 31
<211> LENGTH: 21
<212> TYPE: DNA
<213> ORGANISM: Artificial Sequence
<220> FEATURE:
<223> OTHER INFORMATION: FN1 forward

<400> SEQUENCE: 31
gagaatggac ctgcaagccc a                                         21

<210> SEQ ID NO 32
<211> LENGTH: 20
<212> TYPE: DNA
<213> ORGANISM: Artificial Sequence
<220> FEATURE:
<223> OTHER INFORMATION: FN2 reverse

<400> SEQUENCE: 32
agtgcaagtg atgcgtccgc                                           20

<210> SEQ ID NO 33
<211> LENGTH: 22
<212> TYPE: DNA
<213> ORGANISM: Artificial Sequence
<220> FEATURE:
<223> OTHER INFORMATION: GREB1 forward

<400> SEQUENCE: 33
atgggaaatt cttacgctgg ac                                        22

<210> SEQ ID NO 34
<211> LENGTH: 19
<212> TYPE: DNA
<213> ORGANISM: Artificial Sequence
<220> FEATURE:
<223> OTHER INFORMATION: GREB1 reverse

<400> SEQUENCE: 34
cactcggcta ccaccttct                                            19

<210> SEQ ID NO 35
<211> LENGTH: 22
<212> TYPE: DNA
<213> ORGANISM: Artificial Sequence
<220> FEATURE:
<223> OTHER INFORMATION: ABCA3 forward

<400> SEQUENCE: 35
ctcctctgga agaactacac cc                                        22

<210> SEQ ID NO 36
<211> LENGTH: 22
<212> TYPE: DNA
<213> ORGANISM: Artificial Sequence
<220> FEATURE:
<223> OTHER INFORMATION: ABCA3 reverse

<400> SEQUENCE: 36
gggcacattt tccgactgaa tc                                        22

<210> SEQ ID NO 37
```

```
<211> LENGTH: 21
<212> TYPE: DNA
<213> ORGANISM: Artificial Sequence
<220> FEATURE:
<223> OTHER INFORMATION: NRIP1 forward

<400> SEQUENCE: 37
ggatcaggta ctgccgttga c                                             21

<210> SEQ ID NO 38
<211> LENGTH: 23
<212> TYPE: DNA
<213> ORGANISM: Artificial Sequence
<220> FEATURE:
<223> OTHER INFORMATION: NRIP1 reverse

<400> SEQUENCE: 38
ctggaccatt actttgacag gtg                                           23

<210> SEQ ID NO 39
<211> LENGTH: 21
<212> TYPE: DNA
<213> ORGANISM: Artificial Sequence
<220> FEATURE:
<223> OTHER INFORMATION: TFF1 forward

<400> SEQUENCE: 39
ccctcccagt gtgcaaataa g                                             21

<210> SEQ ID NO 40
<211> LENGTH: 20
<212> TYPE: DNA
<213> ORGANISM: Artificial Sequence
<220> FEATURE:
<223> OTHER INFORMATION: TFF1 reverse

<400> SEQUENCE: 40
gaacggtgtc gtcgaaacag                                               20

<210> SEQ ID NO 41
<211> LENGTH: 21
<212> TYPE: DNA
<213> ORGANISM: Artificial Sequence
<220> FEATURE:
<223> OTHER INFORMATION: LIPE foward

<400> SEQUENCE: 41
tcagtgtcta ggtcagactg g                                             21

<210> SEQ ID NO 42
<211> LENGTH: 21
<212> TYPE: DNA
<213> ORGANISM: Artificial Sequence
<220> FEATURE:
<223> OTHER INFORMATION: LIPE reverse

<400> SEQUENCE: 42
aggcttctgt tgggtattgg a                                             21

<210> SEQ ID NO 43
<211> LENGTH: 20
<212> TYPE: DNA
<213> ORGANISM: Artificial Sequence
<220> FEATURE:
<223> OTHER INFORMATION: PNPLA2 forward

<400> SEQUENCE: 43
```

```
ggcttcctcg gcgtctacta                                          20

<210> SEQ ID NO 44
<211> LENGTH: 21
<212> TYPE: DNA
<213> ORGANISM: Artificial Sequence
<220> FEATURE:
<223> OTHER INFORMATION: PNPLA2 reverse

<400> SEQUENCE: 44
tttaccaggt tgaaggaggg g                                        21

<210> SEQ ID NO 45
<211> LENGTH: 21
<212> TYPE: DNA
<213> ORGANISM: Artificial Sequence
<220> FEATURE:
<223> OTHER INFORMATION: ACSL4 forward

<400> SEQUENCE: 45
catccctgga gcagatactc t                                        21

<210> SEQ ID NO 46
<211> LENGTH: 22
<212> TYPE: DNA
<213> ORGANISM: Artificial Sequence
<220> FEATURE:
<223> OTHER INFORMATION: ACSL4 reverse

<400> SEQUENCE: 46
tcacttagga tttccctggt cc                                       22

<210> SEQ ID NO 47
<211> LENGTH: 22
<212> TYPE: DNA
<213> ORGANISM: Artificial Sequence
<220> FEATURE:
<223> OTHER INFORMATION: ACSL5 forward

<400> SEQUENCE: 47
ctcaacccgt cttacctctt ct                                       22

<210> SEQ ID NO 48
<211> LENGTH: 22
<212> TYPE: DNA
<213> ORGANISM: Artificial Sequence
<220> FEATURE:
<223> OTHER INFORMATION: ACSL5 reverse

<400> SEQUENCE: 48
gcagcaactt gttaggtcat tg                                       22

<210> SEQ ID NO 49
<211> LENGTH: 22
<212> TYPE: DNA
<213> ORGANISM: Artificial Sequence
<220> FEATURE:
<223> OTHER INFORMATION: AGPAT4 forward

<400> SEQUENCE: 49
ctcagggcta atcatcaaca cc                                       22

<210> SEQ ID NO 50
<211> LENGTH: 22
<212> TYPE: DNA
```

<213> ORGANISM: Artificial Sequence
<220> FEATURE:
<223> OTHER INFORMATION: AGPAT4 reverse

<400> SEQUENCE: 50
gcttgagatg caataggaca gt                                              22

<210> SEQ ID NO 51
<211> LENGTH: 19
<212> TYPE: DNA
<213> ORGANISM: Artificial Sequence
<220> FEATURE:
<223> OTHER INFORMATION: AGPAT9 forward

<400> SEQUENCE: 51
cgctggttct cggcttcat                                                 19

<210> SEQ ID NO 52
<211> LENGTH: 22
<212> TYPE: DNA
<213> ORGANISM: Artificial Sequence
<220> FEATURE:
<223> OTHER INFORMATION: AGPAT9 reverse

<400> SEQUENCE: 52
tggcccactc taaagttttc ac                                             22

<210> SEQ ID NO 53
<211> LENGTH: 22
<212> TYPE: DNA
<213> ORGANISM: Artificial Sequence
<220> FEATURE:
<223> OTHER INFORMATION: GPAM forward

<400> SEQUENCE: 53
gatgtaagca cacaagtgag ga                                             22

<210> SEQ ID NO 54
<211> LENGTH: 23
<212> TYPE: DNA
<213> ORGANISM: Artificial Sequence
<220> FEATURE:
<223> OTHER INFORMATION: GPAM reverse

<400> SEQUENCE: 54
tccgactcat taggctttct ttc                                            23

<210> SEQ ID NO 55
<211> LENGTH: 22
<212> TYPE: DNA
<213> ORGANISM: Artificial Sequence
<220> FEATURE:
<223> OTHER INFORMATION: PPAP2A forward

<400> SEQUENCE: 55
ggcaggttgt ccttctattc ag                                             22

<210> SEQ ID NO 56
<211> LENGTH: 19
<212> TYPE: DNA
<213> ORGANISM: Artificial Sequence
<220> FEATURE:
<223> OTHER INFORMATION: PPAP2A reverse

<400> SEQUENCE: 56
cagtgtgggg cgtaagagt                                                 19

<210> SEQ ID NO 57
<211> LENGTH: 19
<212> TYPE: DNA
<213> ORGANISM: Artificial Sequence
<220> FEATURE:
<223> OTHER INFORMATION: DGAT2 forward

<400> SEQUENCE: 57
attgctggct catcgctgt                                             19

<210> SEQ ID NO 58
<211> LENGTH: 23
<212> TYPE: DNA
<213> ORGANISM: Artificial Sequence
<220> FEATURE:
<223> OTHER INFORMATION: DGAT2 reverse

<400> SEQUENCE: 58
gggaaagtag tctcgaaagt agc                                        23

<210> SEQ ID NO 59
<211> LENGTH: 21
<212> TYPE: DNA
<213> ORGANISM: Artificial Sequence
<220> FEATURE:
<223> OTHER INFORMATION: PLIN1 forward

<400> SEQUENCE: 59
tgtgcaatgc ctatgagaag g                                          21

<210> SEQ ID NO 60
<211> LENGTH: 19
<212> TYPE: DNA
<213> ORGANISM: Artificial Sequence
<220> FEATURE:
<223> OTHER INFORMATION: PLIN1 reverse

<400> SEQUENCE: 60
agggcgggga tcttttcct                                             19

<210> SEQ ID NO 61
<211> LENGTH: 20
<212> TYPE: DNA
<213> ORGANISM: Artificial Sequence
<220> FEATURE:
<223> OTHER INFORMATION: MGLL forward

<400> SEQUENCE: 61
atgccagagg aaagttcccc                                            20

<210> SEQ ID NO 62
<211> LENGTH: 19
<212> TYPE: DNA
<213> ORGANISM: Artificial Sequence
<220> FEATURE:
<223> OTHER INFORMATION: MGLL reverse

<400> SEQUENCE: 62
cgtctgcatt gaccaggtg                                             19

<210> SEQ ID NO 63
<211> LENGTH: 20
<212> TYPE: DNA
<213> ORGANISM: Artificial Sequence
<220> FEATURE:

-continued

```
<223> OTHER INFORMATION: ESR1 forward

<400> SEQUENCE: 63
cccactcaac agcgtgtctc                                        20

<210> SEQ ID NO 64
<211> LENGTH: 23
<212> TYPE: DNA
<213> ORGANISM: Artificial Sequence
<220> FEATURE:
<223> OTHER INFORMATION: ESR1 reverse

<400> SEQUENCE: 64
cgtcgattat ctgaatttgg cct                                    23

<210> SEQ ID NO 65
<211> LENGTH: 21
<212> TYPE: DNA
<213> ORGANISM: Artificial Sequence
<220> FEATURE:
<223> OTHER INFORMATION: PTGS1 forward

<400> SEQUENCE: 65
cgccagtgaa tccctgttgt t                                      21

<210> SEQ ID NO 66
<211> LENGTH: 21
<212> TYPE: DNA
<213> ORGANISM: Artificial Sequence
<220> FEATURE:
<223> OTHER INFORMATION: PTGS1 reverse

<400> SEQUENCE: 66
aaggtggcat tgacaaactc c                                      21

<210> SEQ ID NO 67
<211> LENGTH: 22
<212> TYPE: DNA
<213> ORGANISM: Artificial Sequence
<220> FEATURE:
<223> OTHER INFORMATION: HADHB forward

<400> SEQUENCE: 67
ctgtccagac caaaacgaag aa                                     22

<210> SEQ ID NO 68
<211> LENGTH: 21
<212> TYPE: DNA
<213> ORGANISM: Artificial Sequence
<220> FEATURE:
<223> OTHER INFORMATION: HADHB reverse

<400> SEQUENCE: 68
cgatgcaaca aacccgtaag c                                      21
```

METHODS FOR MANIPULATING CELL STATE TRANSITIONS IN CANCER

REFERENCE TO SEQUENCE LISTING

The content of the electronically submitted sequence listing (Name: 2021 May 12-SeqListing-S61013719-4487-0020001; Size: 12,846 bytes; Date of Creation: May 12, 2021) filed with this application is incorporated herein by reference in its entirety.

The sequence information contained in the CRF is identical to the sequence information contained in the sequence listing in the disclosure.

FIELD

The present invention relates to the field of cancer biology. In particular, there is provided a method of inducing mesenchymal-epithelial transition (MET) in a cancer cell.

BACKGROUND

Breast cancer is a heterogeneous disease that is classically stratified by receptor expression status; this necessitates different treatment strategies to achieve optimal disease control. While estrogen reception-positive (ER+) and ERRB2/HER2-positive tumors typically respond well to targeted therapies, the triple-negative breast cancer (TNBC) subtype, as defined by the absence of ER, progesterone receptor (PR), and HER2 expressions, lacks targeted approaches and remains refractory to standard-of-care chemotherapy. Limited progress has been made in carving new adjuvant regimens in the clinical management of TNBCs, and phase II and III trials for therapeutic agents against TNBCs have been short of promising. This underscores the need to explore more effective therapeutic strategies for TNBCs. The activation of epithelial-mesenchymal transition (EMT) program in cancer cells has often been attributed to the gain of resistance phenotypes, in part through the acquisition of cancer stem cell-like properties. Several studies have conceptually suggested that the reversal of the EMT program, i.e., a mesenchymal-epithelial transition (MET), may cause cancer cells to regain sensitivity to chemotherapy.

While receptor status has been one of the mainstays of clinical classification, prognosis, and management decisions, gene expression profiling has been applied to categorize breast cancer into several 'intrinsic' molecular subtypes: Luminal A, Luminal B, HER2-enriched, Basal-like and Claudin-low. Although there remains some debate, it has been observed that ER+ tumors tend to be luminal-like and express 'epithelial' marker genes such as E-cadherin, whereas TNBC bear a basal-like gene signature and express 'mesenchymal' markers that include claudins and vimentin. During cell state transitions, whether the gain of 'epithelial' or 'mesenchymal' features is indeed connected to luminal- or basal-like cancer, respectively, remains unclear. It may be possible that the MET, beyond changes in cell states, may be capable of converting basal-like breast cancer into one that is more luminal-like, characterized by the expression of ER or luminal cytokeratins.

The EMT program is well-established to be regulated by alterations in extracellular and intracellular signaling pathways. For instance, extrinsic signals such as TGFβ and PDGF lead to the activation of intracellular signal transduction cascades that ultimately result in the activation of EMT-associated transcription factors such as TWIST, SNAIL, SLUG, and ZEB1. In contrast, pathways that promote the MET appear more diverse and poorly defined. For example, forskolin-induced MET acts through the activation of cAMP pathway that results in epigenetic reprogramming, while TGFβ inhibitors have been reported to mediate MET in germline stem cells. In both instances, the precise mechanisms remain elusive. Furthermore, although it is, in principle, possible that the biochemical or genetic modulation of potential pathways such as cAMP activation or TGFβ receptor inhibition may help promote an MET, their potential for clinically relevant applications may not be forthcoming.

While the signaling pathways and transcription regulators that control cell states are well understood, other emerging aspects, particularly metabolism which contributes towards cancer cell function, remain far less understood. Altered metabolism has reemerged as a hallmark of tumors, underscoring the role of metabolic pathways in regulating tumor cell behavior, as well as their therapeutic implications. The vast majority of the studies have focused on evaluating the metabolic differences between cancer and normal cells, particularly on the demand for glycolysis. Given the phenotypic diversity and plasticity among cancer cells, little is known regarding the association and contribution of their metabolic features to functional adaptations. The shifts of cancer cells between cell states, ostensibly, necessitate different energetic requirements for supporting these functions.

SUMMARY

Provided herein is a method of inducing mesenchymal-epithelial transition (MET) in a cancer cell. In one aspect, there is provided a method of inducing mesenchymal-epithelial transition (MET) in a cancer cell, the method comprising contacting the cell with an inducer of mesenchymal-epithelial transition for a time and under conditions sufficient to induce MET in the cell, wherein the cancer cell is a basal-like (or mesenchymal-like) cancer cell. Such a cancer cell belongs to a mesenchymal subtype of cancer.

In one aspect, there is provided an inducer of mesenchymal-epithelial transition (MET) for use in inducing mesenchymal-epithelial transition in a cell in a patient.

In one aspect there is provided the use of an inducer of mesenchymal-epithelial transition (MET) in the manufacture of a medicament for inducing mesenchymal-epithelial transition in a cell in a patient.

In one aspect, there is provided a method of treating cancer in a patient in need thereof, the method comprising administering an inducer of mesenchymal-epithelial transition (MET) in combination with a chemotherapeutic agent, an epigenetic-modifying compound, an immunomodulatory agent, or an inhibitor or regulator of lipid metabolism to the patient, for a time and under conditions to treat cancer in the patient.

In one aspect, there is provided an inducer of mesenchymal-epithelial transition (MET) for use in treating cancer in patient in need thereof, wherein the inducer of mesenchymal-epithelial transition (MET) is to be administered in combination with a chemotherapeutic agent, an epigenetic-modifying compound, an immunomodulatory agent, or an inhibitor of or regulator lipid metabolism to the patient.

In one aspect, there is provided the use of an inducer of mesenchymal-epithelial transition (MET) in the manufacture of a medicament for treating cancer is a subject, wherein the medicament is to be administered in combination with a chemotherapeutic agent, an epigenetic-modifying compound, an immunomodulatory agent, or an inhibitor or regulator of lipid metabolism to the patient.

In one aspect, there is provided a method of sensitizing a cancer patient to an anti-cancer therapy, the method comprising administering a retinoid to the patient for a time and under conditions to sensitize the patient to the anti-cancer therapy.

In one aspect, there is provided an inducer of mesenchymal-epithelial transition (MET) for use in sensitizing a cancer patient to an anti-cancer therapy.

In one aspect, there is provided a use of an inducer of mesenchymal-epithelial transition (MET) in the manufacture of a medicament for sensitizing a patient to an anti-cancer therapy.

In one aspect, there is provided a method of identifying an agent that induces mesenchymal-epithelial transition in a cell, the method comprising:

a) contacting a cell with a test agent to be screened; and b) detecting the expression from a promoter of a gene selected from the group consisting of CD24, CD44, CD166, CDH1, ZEB1 and SERPINE 1;

wherein a change in expression in the one or more genes as compared to control indicates that the test agent is capable of inducing mesenchymal-epithelial transition in the cell.

In one aspect, there is provided a method of identifying a cancer patient responsive to a combination therapy comprising a mesenchymal-epithelial transition (MET) inducing compound in combination with a chemotherapeutic agent, an epigenetic-modifying compound, an immunomodulatory agent, or an inhibitor or regulator of lipid metabolism, the method comprises detecting a mesenchymal subtype of cancer in a sample obtained from the patient, wherein the presence of a mesenchymal subtype of cancer indicates that the patient is responsive to the combination therapy.

In one aspect, there is provided a method of identifying and treating a cancer patient responsive to a combination therapy comprising a mesenchymal-epithelial transition (MET) inducing compound in combination with a chemotherapeutic agent, an epigenetic-modifying compound, an immunomodulatory agent, or an inhibitor or regulator of lipid metabolism, the method comprising: detecting a mesenchymal subtype of cancer in a sample obtained from the patient, wherein the presence of a mesenchymal subtype of cancer indicates that the patient is responsive to the combination therapy; and treating the patient with the combination therapy.

In one aspect, there is provided a method of inhibiting epithelial-mesenchymal transition (EMT) of a cancer in a subject, the method comprising administering an inhibitor or regulator of lipid metabolism for a sufficient time and under conditions to inhibit epithelial mesenchymal transition (EMT) of the cancer in the subject.

In one aspect, there is provided an inhibitor or regulator of lipid metabolism for use in inhibiting epithelial-mesenchymal transition (EMT) of a cancer in a subject.

In one aspect, there is provided the use of an inhibitor or regulator of lipid metabolism in the manufacture of a medicament for inhibiting epithelial-mesenchymal transition (EMT) of a cancer in a subject.

In one aspect, there is provided a method of blocking or preventing metastasis of a cancer in a subject, the method comprising administering an inhibitor or regulator of lipid metabolism for a time and under conditions sufficient to block or prevent metastasis in the subject.

In one aspect, there is provided an inhibitor or regulator of lipid metabolism for use in blocking or preventing metastasis of a cancer in a subject.

In one aspect, there is provided the use of an inhibitor or regulator of lipid metabolism in the manufacture of a medicament for blocking or preventing metastasis of a cancer in a subject.

BRIEF DESCRIPTION OF THE FIGURES

Certain embodiments are illustrated by the following figures. It is to be understood that the following description is for the purpose of describing particular embodiments only and is not intended to be limiting with respect to the description.

FIG. 1. High-throughput chemical library screens identify retinoids as promoters of the mesenchymal-epithelial transition (A) Generation of reporter cell lines for MET screens using small molecule compound libraries. (B) Dual-glo Luciferase assay of NAMEC8-SERPINE1prom-Luc cells treated with A83-01. Data are represented as mean FF/Ren+/−SEM, n=3, **P<0.01 by Student's t-test. (C) Dual-glo Luciferase assay of NAMEC8-SERPINE1prom-Luc cells screened with LOPAC, Anti-cancer drugs, Kinase inhibitors and Bioactive lipids libraries. Data are represented as mean FF/Ren, n=3. Hits are circled in red. (D) Scatter plot of primary and secondary screens with 61 compounds. FF/Ren values from both screens were plotted and a linear trend line was computed. (E) Dual-glo Luciferase assay of 41 compounds performed at 5-point dose response. Compounds are classified according to physiological function into 9 classes. Data are represented as mean FF/Ren, n=3. Grey boxes represent doses that resulted in <50% cell viability from DMSO.

FIG. 2. Retinoids induce the conversion of basal-like breast cancer cells to become luminal and enhance their sensitivities to chemotherapy (A) Cell morphology images of NAMEC8 treated with DMSO, bexarotene (1 µM) or TTNPB (1 µM). Images are taken at 50× magnification. Scale represents 100 µm. (B) Expression of EMT and lineage marker genes of bexarotene-treated NAMEC8 cells relative to DMSO. Data are represented as mean+/−SEM, n=3, *P<0.05, P<0.01, *P<0.001 by Student's t-test. (C) Protein expression of EMT and lineage markers in DMSO vs. bexarotene-treated NAMEC cells. Bexarotene was treated at increasing concentrations of 0.1 µM, 0.5 µM and 1 µM. β-actin was used as loading control. (D) Immunofluorescence staining of EMT and lineage markers in DMSO vs. bexarotene-treated NAMEC8 cells. Images are taken at 100× magnification. Scale bar represents 50 µm. (E) Flow cytometry histogram plot of CD44 staining in DMSO vs. bexarotene-treated NAMEC8 cells. (F) Mammosphere forming assay of DMSO vs. bexarotene- or TTNPB-treated NAMEC8 cells. Images were taken at 50× magnification. Scale bar represents 100 µm. Bottom right: Bar graph showing number of spheres >100 µm. Data are represented as mean+/−SEM, n=3, P<0.01. (G) Protein expression of EMT and lineage markers in BC2.2, BC22.1, BC29.1, MetBr-007 DR, BC24.1, BC33.1: DMSO vs. bexarotene-treated cells. β-actin was used as loading control. (H) Immunofluorescence staining of EMT and lineage markers in BC2.2: DMSO vs. bexarotene-treated cells. Images are taken at 100× magnification. Scale bar represents 50 µm. (I) Mammosphere forming assay of DMSO vs. bexarotene-treated BC2.2 cells. Images were taken at 50× magnification. Scale bar represents 100 µm. Right: Bar graph showing number of spheres >100 µm. Data are represented as mean+/−SEM, n=3, P<0.01. (J) Cell morphology images of NAMEC8 treated with bexarotene, in the presence or absence of 10 µM 5-FU. Images were taken at 50× magnification. (K) Dose response graphs of NAMEC8 DMSO vs. bexarotene-treated cells to varying concentrations of 5-FU. $IC_{50}$ values are shown in the tables below. Data are represented as mean+/−SEM, n=3. (L) Schematic of process for generation of SUM159 PAC-R cells (top). Dose response graphs of SUM159 PT vs. PACR cells to varying concentrations of PAC (bottom). $IC_{50}$ values are shown in the table. Data are represented as mean+/−SEM, n=3. (M) Dose response graphs of SUM159 PACR for DMSO vs. bexarotene-treatment to varying concentrations of 5-FU. $IC_{50}$ values are shown in the table. Data are represented as mean+/−SEM, n=3.

FIG. 3. Retinoid therapy promotes MET and reduces the tumorigenicity of TNBC cells in animals (A) Tumor measurements of SUM159 pre-treated with DMSO, bexarotene or TTNPB before subcutaneous injection into NSG mice (top). Data are represented as mean diameter+/−SEM, n=6 for DMSO, n=8 tumors for bexarotene and TTNPB, *P<0.05, P<0.01, *P<0.001, ****P<0.0001. Representative images of tumors from mice sacrificed at week 7 and week 8 post-implantation (bottom). (B) Tumor sizes of MCF7-Ras pre-treated with DMSO, bexarotene or ATRA before subcutaneous injection into NSG mice (top). Data are represented as mean diameter+/−SEM, n=4 for DMSO, n=6 tumors for bexarotene and ATRA. Representative images of tumors from mice sacrificed at week 9 post-implantation (bottom). (C) Schematic of workflow for mouse xenograft experiment (top). Tumor sizes in Control mice vs. bexarotene-fed mice from NAMEC8-Ras (left), BC2.2 (middle) and BC22.1 (right) (bottom). Data are represented as mean diameter+/−SEM, n=6 for control, n=4 for bexarotene (NAMEC8-Ras), n=7 for control and bexarotene (BC2.2 and BC22.1), *P<0.05, **P<0.01. (D) Haemotoxylin and eosin staining of NAMEC8-Ras tumors formed in control mice vs. bexarotene-fed mice. Images were taken at 200× magnification. Scale bar represents 50 μm. (E) Immunofluorescence staining of EMT and lineage markers in NAMEC8-Ras tumor sections from control mice vs. bexarotene-fed mice. Images are taken at 100× magnification. Scale bar represents 50 μm. (F) Gene expression of retinoic acid response genes in NAMEC8-Ras (top) and BC2.2 (bottom) tumors formed in bexarotene-fed mice relative to tumors in control mice. Data are represented as mean+/−SEM, n=3, *P<0.05, **P<0.01.

FIG. 4. Epigenetic perturbations enhance and increase the durability of retinoid-induced cell state changes (A) Dual-glo luciferase activity plot of NAMEC8-SERPINE1prom-Luc cells treated with epigenetic compounds. Data are represented as mean FF/Ren, n=3. Hits are circled in red. (B) Dual-glo luciferase activity plot of NAMEC8-SERPINE1prom-Luc cells treated with bexarotene, plus individual epigenetic compounds. Data are represented as mean FF/Ren, n=3. Hits are circled in red. (C) Cell morphology images of NAMEC8 treated with DMSO, bexarotene, CI-994, SBHA, bexarotene+C1-994 or bexarotene+SBHA. Images were taken at 50× magnification. Scale bar represents 100 μm. (D) Protein expression of NAMEC8 treated with DMSO, bexarotene, CI-994, SBHA, bexarotene+C1-994 or bexarotene+SBHA. β-actin was used as a loading control. (E) Cell morphology images of NAMEC8 treated with DMSO, bexarotene+CI-994, bexarotene+SBHA (Drug 'ON') and retracted for 7-10 days (Drug 'OFF'). Images are taken at 50× magnification. Scale bar represents 100 μm. (F) Protein expression of NAMEC8 treated with DMSO, bexarotene, CI-994, bexarotene+CI-994, -bexarotene and -(bexarotene+CI-994). β-actin was used as a loading control. (G) Immunofluorescence staining of KRT5 (top) and KRT8 (bottom) in BC2.2 treated with DMSO, bexarotene, CI-994, bexarotene+C1994, -bexarotene, -(bexarotene+CI994). Images are taken at 100× magnification. Scale bar represents 50 μm. (H) Mammosphere forming assay of NAMEC8 treated with DMSO, bexarotene, CI-994, bexarotene+CI-994, -bexarotene, -(bexarotene+CI-994). Images were taken at 50× magnification. Scale bar represents 100 μm. Graph shows number of spheres >100 μm. Data are represented as mean+/−SEM, n=3, P<0.01, *P<0.001, ****P<0.0001. (I) Transcriptional regulation of gene expression by retinoid receptors and epigenetic regulators. In the mesenchymal cell state, RAR and RXR tend to be associated with corepressors such as HDACs, thereby inhibiting the transcription of epithelial genes. Exposure to bexarotene results in the activation of RAR and RXR, causing a change in protein interactions from corepressors to coactivators. HDAC inhibition help reinforce gene transcription activity through maintaining histone acetylation at gene promoters.

FIG. 6: Mesenchymal-epithelial transition restricts β-oxidation by channeling fatty acids towards lipid droplet storage (a) Relative lipid content, measured by LC-MSMS, in DMSO vs. bexarotene-treated NAMEC8 cells. Data are represented as mean+/−SEM, n=3, *P<0.05, **P<0.01. Upregulated genes upon bexarotene treatment were validated by RT-PCR (colored in red). (b) Lipid droplet staining in NAMEC8, SUM159 and BC2.2: DMSO vs. bexarotene-treated. Images were taken at 200× magnification. Scale bar represents 50 μm. (c) Mammosphere forming assay in NAMEC8 cells in the following conditions. Treatment with bexarotene, FSG67, or FSG67+bexarotene (left). Exposure of Ctrl sh or shAGPAT cells in the presence or absence of bexarotene (middle). Treatment in the presence of various combinations of bexarotene and AmidepsineA (right). Images were taken at 50× magnification. Scale bar represents 100 μm. (d) Oxygen consumption rate (OCR) of NAMEC8 DMSO vs. bexarotene, in the presence or absence of palmitate. Black arrows depict rate of fatty acid β-oxidation (FAO). (e) Relative lipid content, measured by LC-MSMS, in in HMLE vs. NAMEC8 cells. Data are represented as mean+/−SEM, n=3. Downregulated genes in NAMEC8 relative to HMLE as validated by RT-PCR are colored in blue. (f) Lipid droplet staining in HMLE vs. NAMEC8. Images were taken at 10× magnification. Scale bar represents 50 μm. (g) Rates of fatty acid β-oxidation (FAO) measured by Seahorse in a panel of breast cancer cell lines. Data are represented as mean+/–SEM, n=3. (h) Cell viability assay of BT549 and MCF7 grown for 6 days in basal medium (DMEM with 1% FBS, 2.5 mM glucose), basal medium supplemented with 25 mM glucose, 20 μM palmitate or 20 μM lipoic acid. Data are represented as mean+/–SEM, n=3.

FIG. 7: Induction of mesenchymal-epithelial transition is dependent on fatty acid modifier carnitine palmitoyltransferase a) Protein expression of NAMEC8 treated with bexarotene, etomoxir, bexarotene+etomoxir, -bexarotene, -(bexarotene+etomoxir). β-actin was used as a loading control. b) Mammosphere forming assay of NAMEC8 treated with bexarotene, etomoxir, bexarotene+etomoxir, -bexarotene, -(bexarotene+etomoxir). Images were taken at 50× magnification. Scale bar represents 100 μm. Graph showing number of spheres >100 μm. Data are represented as mean+/–SEM, n=3, *P<0.05, *P<0.001, P<0.0001. c) Lipid droplet staining in NAMEC8 Ctrlsh, CPT1A-sh1 and sh2 cells treated with DMSO or bexarotene. Images were taken at 100× magnification. Scale bar represents 50 μm. d) Protein expression of NAMEC8 Ctrlsh and CPT1A-sh1 cells treated with DMSO or bexarotene. β-actin was used as a loading control. e) Mammosphere forming assay of NAMEC8 Ctrlsh, CPT1A-sh1 and sh2 cells treated with DMSO and bexarotene (left). Images were taken at 50× magnification. Scale bar represents 100 μm. Protein expression showing knockdown of CPT1A (top right). Graph showing number of spheres >100 μm (bottom right). Data are represented as mean+/–SEM, n=3, P<0.01, *P<0.001. f) Lipid droplet staining in NAMEC8 vector control, CPT1A-1- and CPT1A-2-overexpressing NAMEC8 cells treated with DMSO or bexarotene. Images were taken at 200× magnification. Scale bar represents 50 μm. g) Protein expression of NAMEC8 vector control and CPT1A-1 overexpressing cells treated with DMSO or bexarotene. β-actin was used as a loading control. h) Mammosphere forming assay of NAMEC8 vector control, CPT1A-1- and CPT1A-2-overexpressing cells treated with DMSO and bexarotene (left). Images were taken at 50× magnification. Scale bar represents 100 μm. Protein expression showing the overexpression of CPT1A (top right). Graph showing number of spheres >100 μm (bottom right). Data are represented as mean+/–SEM, n=3, **P<0.0001.

FIG. 8: Impairment of fatty acid oxidation re-channels lipids towards the support of an epithelial cell state and blocks EMT a) Lipid droplet staining in HMLE-Twist ER Control vs. 40HT-induced cells (top), HMLE-Zeb1 Control vs. DOX-induced cells (middle), MCF7-Slug+Sox9 Control vs. DOX-induced cells. Images were taken at 100× magnification. Scale bar represents 50 μm. b) Oxygen consumption rate (OCR) in HMLE-Twist ER control vs. 4-OHT-induced cells in the presence or absence of palmitate (left). Black arrows depict rate of FAO. Rate of FAO in HMLE-Twist ER Control vs. 40HT-induced cells (right). Data are represented as mean+/–SEM, n=3, *P<0.05. c) Morphology of HMLE-Twist ER treated with etomoxir, in the presence or absence of 4-OHT. Images were taken at 50× magnification. Scale bar represents 100 μm. d) Protein expression of EMT markers in HMLE-Twist ER treated with etomoxir, in the presence or absence of 4-OHT. β-actin was used as a loading control. e) Lipid droplet staining in MCF7-Slug+Sox9 Ctrlsh and shCPT1A cells+/–DOX induction. Images were taken at 100× magnification. Scale bar represents 50 μm. f) Protein expression of MCF7-Slug+Sox9 Ctrlsh and shCPT1A cells+/–DOX induction. β-actin was used as a loading control. g) Schematic of workflow for mouse xenograft experiment (top). Bottom left: Immunofluorescence staining of E-Cadherin and Vimentin in primary tumors formed in Control (no DOX) vs. DOX vs. Etomoxir+DOX groups (200× magnification). Scale bar represents 50 μm. Whole-mount fluorescence lung images (100× magnification) and the histology of the lung sections (10× magnification) from lung metastases are also shown. White scale bar represents 100 μm and black scale bar represents 50 μm. Bottom right: Graph shows number of metastases per lung. Data are represented as mean+/–SEM, n=5 technical replicates, **P<0.01. h) Model illustrating differing fatty acid metabolism driving epithelial and mesenchymal cell states. In the mesenchymal cell state, β-oxidation is high with minimal lipid stores. Upon induction of MET, the epithelial cell state is characterized by inhibited β-oxidation and accumulation of lipid stores.

FIG. 10. (A) Cell morphology images of SUM159 treated with DMSO, bexarotene (1 μM) or TTNPB (1 μM). Images were taken at 50× magnification. Scale bar represents 100 μm. (B) Gene expression of EMT and lineage marker genes of bexarotene-treated SUM159 cells relative to DMSO. Data are represented as mean+/–SEM, n=3, *P<0.05, P<0.01, *P<0.001. (C) Protein expression of EMT and lineage markers in DMSO vs. bexarotene-treated SUM159 cells. β-actin was used as loading control. (D) Flow cytometry analysis of CD24 and CD44 expression in DMSO vs. bexarotene-treated SUM159 cells. (E) Mammosphere forming assay of DMSO, bexarotene- or TTNPB-treated SUM159 cells. Images were taken at 50× magnification. Scale bar represents 100 μm. Bar graph showing number of spheres >100 μm. Data are represented as mean+/–SEM, n=3, *P<0.05, **P<0.01. (F) Gene expression of EMT and lineage marker genes of BC2.2, BC22.1 and BC29.1 bexarotene-treated cells relative to DMSO. Data are represented as mean+/–SEM, n=3, *P<0.05, P<0.01, *P<0.001. (G) Immunofluorescence staining of EMT and lineage markers in BC22.1 (left) and BC29.1 (right) treated with DMSO or bexarotene. Images were taken at 100× magnification. Scale bar represents 100 μm. (H) Mammosphere forming assay of BC22.1 (top) and BC29.1 (bottom) in DMSO vs. bexarotene treatment. Images were taken at 50× magnification. Scale bar represents 100 μm. Bar graphs show number of spheres >100 μm. Data are represented as mean+/–SEM, n=3, *P<0.05. (I) Luciferase assay of estrogen receptor element (ERE) reporter activity in NAMEC8 cells treated with increasing doses of bexarotene or 1 μM TTNPB. Data are represented as mean FF/Ren+/–SEM, n=3, *P<0.05. (J) Gene expression of estrogen receptor (ER) target genes in NAMEC8 and BC2.2 treated with bexarotene. Data are represented as mean+/–SEM, n=3, *P<0.05. (K) Dose response graphs of DMSO vs. bexarotene-treated NAMEC8 to varying concentrations of Raloxifene HCl. $IC_{50}$ values are shown in the table. (L) Gene expression of EMT and lineage marker genes of BC24.1 (left) and BC33.1 (right) in bexarotene-treatment relative to DMSO. Data are represented as mean+/–SEM, n=3. (M) Knockdown of RXRα in NAMEC8 using Ctrl shRNA or RXRα shRNAs. β-actin was used as loading control. (N) Gene expression of EMT and lineage genes of NAMEC8 Ctrl shRNA and RXRα sh1 bexarotene-treated cells relative to DMSO. Data are represented as mean+/−SEM, n=3, *P<0.05. (O) Protein expression of EMT and lineage markers in NAMEC8 Ctrl shRNA and RXRα sh1 treated with DMSO or bexarotene. β-actin was used as loading control. (P) Dose response graphs of SUM159 (middle), BC2.2 (right): DMSO vs. bexarotene-treated cells to varying concentrations of 5-FU. $IC_{50}$ values are shown in the tables below. Data are represented as mean+/−SEM, n=3. (Q) Cell morphology images of NAMEC8 treated with bexarotene, in the presence or absence of 2 nM Paclitaxel. Images were taken at 50× magnification. (R) Dose response graphs of DMSO vs. bexarotene-treated NAMEC8 to varying concentrations of PAC. $IC_{50}$ values are shown in the table. Data are represented as mean+/−SEM, n=3 (S) Morphology of DMSO vs. bexarotene-treated SUM159 PACR cells. Images were taken at 50× magnification. Scale bar represents 100 μm. (T) Gene expression of EMT and lineage marker genes of bexarotene-treated SUM159 PACR cells relative to DMSO. Data are represented as mean+/−SEM, n=3, *P<0.05, P<0.01, *P<0.001. (U) Protein expression of EMT and lineage markers of DMSO vs. bexarotene-treated SUM159 PACR. β-actin was used as a loading control. (V) Mammosphere formation assay for DMSO or bexarotene-treated SUM159 PACR cells. Images were taken at 50× magnification. Scale bar represents 100 μm. Bar graph showing number of spheres >100 μm. Data are represented as mean+/−SEM, n=3, **P<0.01.

FIG. 11 (A) Tumor weight of SUM159 pre-treated with DMSO, bexarotene or TTNPB at week 7 and 8 (top). Tumor volume of SUM159 pre-treated with DMSO, bexarotene or TTNPB at week 7 and 8 (bottom). Data are represented as mean+/−SEM, n=6. (B) Tumor weight (top) and tumor volume (bottom) of MCF7-Ras pre-treated with DMSO, bexarotene or ATRA. Data are represented as mean+/−SEM, n=6. (C) Cell viability (as measured by MTS assay) of NAMEC8 (left), MCF7 (middle) and MCF10A (right) treated with DMSO, bexarotene, or ATRA, over a six-day period. Data represent mean+/−SEM, n=3. (D) Images of NAMEC8-Ras, BC2.2 and BC22.1 tumors formed in control mice vs. bexarotene-fed mice. (E) Tumor weight of NAMEC8-Ras, BC2.2 and BC22.1 tumors formed in control mice vs. bexarotene-fed mice (top). Tumor volume of NAMEC8-Ras, BC2.2, BC22.1 tumors formed in control mice vs. bexarotene-fed mice (bottom). Data are represented as mean+/−SEM, n=6. (F) Immunofluorescence staining of EMT and lineage markers in BC2.2 tumor sections from control mice vs. bexarotene-fed mice. Images were taken at 200× magnification. Scale bar represents 50 μm.

FIG. 12. (A) Gene expression of EMT and lineage marker genes in NAMEC8 (left) and SUM159 (right) treated with bexarotene, CI-994 or bexarotene+CI-994, relative to DMSO. Data are represented as mean+/−SEM, n=3, *P<0.05, P<0.01, *P<0.001. (B) Dual-glo luciferase assay of NAMEC8-SERPINE1prom-Luc cells first treated with DMSO, bexarotene, followed by compound withdrawal for 24 h, 48 h or 72 h (Drug 'OFF'). Data are represented as mean+/−SEM, n=6, P<0.01, *P<0.001. (C) Dual-glo luciferase assay of NAMEC8-SERPINE1prom-Luc cells first treated with DMSO, bexarotene+CI-994, followed by compound withdrawal for 24 h, 48 h or 72 h (Drug 'OFF'). Data are represented as mean+/−SEM, n=6, ****P<0.0001. (D) Mammosphere forming assay of NAMEC8 treated with DMSO, bexarotene, SBHA, bexarotene+SBHA, -bexarotene, -(bexarotene+SBHA). Images were taken at 50× magnification. Scale bar represents 100 μm. Graph shows number of spheres >100 μm. Data are represented as mean+/−SEM, n=3, *P<0.05, P<0.01, *P<0.001. (E) Mammosphere forming assay of SUM159 (top) and BC2.2 (bottom) treated with bexarotene, CI-994, bexarotene+CI-994, -bexarotene, or -(bexarotene+CI-994). Images were taken at 50× magnification. Scale bar represents 100 μm. Graph showing number of spheres >100 μm. Data are represented as mean+/−SEM, n=3, *P<0.05, P<0.01, *P<0.001.

FIG. 14: Mesenchymal-epithelial transition restricts β-oxidation by channeling fatty acids towards lipid droplet storage a) Lipid droplet staining of BC29.1 and BC22.1: DMSO vs. bexarotene treatment. Images were taken at 200× magnification. Scale bar represents 50 μm. b) Lipid droplet staining in NAMEC8 treated in the following conditions. Treatment with bexarotene, FSG67, or FSG67+bexarotene (left). Exposure of Ctrl sh or shAGPAT cells in the presence or absence of bexarotene (middle). Treatment in the presence of various combinations of bexarotene and AmidepsineA (right). Images were taken at 100× magnification. Scale bar represents 50 μm. c) Protein expression of epithelial and luminal markers in NAMEC8 cells in the following conditions. Treatment with bexarotene, FSG67, or FSG67+bexarotene (left). Exposure of Ctrl sh or shAGPAT cells in the presence or absence of bexarotene (middle). Treatment in the presence of various combinations of bexarotene and AmidepsineA (right). β-actin was used as a loading control. d) Graphs showing number of spheres >100 μm for mammosphere forming assay in NAMEC8 cells in the following conditions: Treatment with bexarotene, FSG67, or FSG67+bexarotene (left). Exposure of Ctrl sh or shAGPAT cells in the presence or absence of bexarotene (middle). Treatment in the presence of various combinations of bexarotene and AmidepsineA (right). Images were taken at 50× magnification. Scale bar represents 100 μm. Data are represented as mean+/−SEM, n=3, *P<0.05, P<0.01, *P<0.001. e) Oxygen consumption rate (OCR) of SUM159 (left) and BC2.2 (right): DMSO vs. bexarotene, in the presence or absence of palmitate. Black arrows depict rate of fatty acid β-oxidation (FAO). f) Graphs showing rate of FAO in NAMEC8 (left), SUM159 (middle) and BC2.2 (right): DMSO vs. bexarotene-treated. Data are represented as mean+/−SEM, n=3, P<0.01, *P<0.001. g) Gene expression of lipid-associated genes involved in TAG synthesis in NAMEC8, relative to HMLE. Data are represented as mean+/−SEM, n=3, *P<0.05, P<0.01, *P<0.001, ****P<0.0001.

FIG. 15: Induction of mesenchymal-epithelial transition is dependent on fatty acid modifier carnitine palmitoyltransferase a) Graph showing rate of FAO in SUM159 treated with bexarotene, etomoxir, bexarotene+etomoxir. Data are represented as mean+/−SEM, n=3, P<0.01, *P<0.001. b) Morphology of NAMEC8 treated with bexarotene, etomoxir, bexarotene+etomoxir, -bexarotene, or -(bexarotene+etomoxir). Images were taken at 100× magnification. Scale bar represents 50 μm. c) Gene expression of EMT and retinoid acid responsive genes for NAMEC8 treated with bexarotene, etomoxir, or bexarotene+etomoxir. Data are represented as mean+/−SEM, n=3, P<0.01, *P<0.001, ****P<0.0001. d) Mammosphere forming assay of SUM159 treated with bexarotene, etomoxir, bexarotene+etomoxir, -bexarotene, or -(bexarotene+etomoxir). Images were taken at 50× magnification. Scale bar represents 100 μm. Graph showing number of spheres >100 μm. Data are represented as mean+/−SEM, n=3, *P<0.05, P<0.01. e) Graph showing rate of FAO in vector or CPT1A-overexpressing SUM159 cells, treated with either DMSO or bexarotene. Data are represented as mean+/−SEM, n=3, P<0.01. f) Lipid droplet staining of SUM159 vector, CPT1A-1-, and CPT1A-2 overexpressing cells treated with DMSO or bexarotene. Images were taken at 200× magnification. Scale represents 50 μm. g) Morphology of NAMEC8 vector and CPT1A-overexpressing cells treated with DMSO or bexarotene. Images were taken at 40× magnification. Scale bar represents 50 μm. h) Mammosphere forming assay of SUM159 vector, CPT1A-1 and CPT1A-2 overexpressing cells treated with DMSO and bexarotene (left). Images were taken at 50× magnification. Scale bar represents 100 μm. Protein expression showing the overexpression of CPT1A (top right). Graph showing number of spheres >100 μm (bottom right). Data are represented as mean+/−SEM, n=3, ****P<0.0001.

FIG. 16: Impairment of fatty acid oxidation re-channels lipids towards the support of an epithelial cell state and blocks EMT (a) Gene expression of EMT genes in HMLE-Twist ER treated with etomoxir, in the presence or absence of 4-OHT, relative to control. Data are represented as mean+/−SEM, n=3, *P<0.05, P<0.01, *P<0.001, ****P<0.0001. (b) Gene expression of EMT genes in MCF7-Slug+Sox9 treated with etomoxir, in the presence or absence of doxycycline induction, relative to control. Data are represented as mean+/−SEM, n=3, *P<0.05, P<0.01, *P<0.001, ****P<0.0001. (c) Protein expression of EMT markers in MCF7-Slug+Sox9 treated with etomoxir, in the presence or absence of doxycycline induction. β-actin was used as a loading control. (d) Cell morphology images of HMLE-Zeb1 treated with etomoxir, in the presence or absence of doxycycline induction, relative to control. Images were taken at 40× magnification. Scale bar represents 50 μm. (e) Gene expression of EMT genes in MCF7-Slug+Sox9 Ctrlsh and shCPT1A cells+/−DOX induction, relative to Ctrlsh cells. Data are represented as mean+/− SEM, n=3, *P<0.05, P<0.01, *P<0.001, ****P<0.0001. (f) Cell morphology images of A549 treated with etomoxir, in the presence or absence of TGFβ, relative to control. Images were taken at 40× magnification. Scale bar represents 50 μm. (g) Protein expression of EMT markers in A549 treated with etomoxir, in the presence or absence of TGFβ. β-actin was used as a loading control.

FIG. 17: Epigenetic library screen to identify potent MET inducers. (A) Dual-glo Luciferase assay of NAMEC8-SERPINE1 cells screened with epigenetic library to identify MET inducers. Data are represented as SERPINE1 promoter activity (mean FF/Ren values) against renilla for cell viability, n=3. A83-01 (circled in black) was included as a positive control, and compounds with SERPINE1 promoter activity lower than A83-01 was identified as hits (circled in red). (B) Dual-glo Luciferase assay of hits from MET screen performed at 6-point dose response. Data are represented as SERPINE1 promoter activity (mean FF/Ren values) against concentration, n=3, *p<0.05, p<0.01, *p<0.001, ****p<0.0001, ns, not significant. (C) Cell morphology images of NAMEC8 treated with DMSO and epigenetic compounds. LLY-283 and GSK591 were used at 20 nM, UNC0642 and SGC-CBP30 were used at 1 μM. Only SGC-CBP30 treatment resulted in epithelial-like morphology. Images are taken at 4× magnification. Scale bar represents 100 μm. (D) qRT-PCR analysis of EMT and basal/luminal genes of NAMEC8 treated with epigenetic hits. mRNA levels are shown relative to DMSO. Data are represented as mean, +SEM, n=3. (E) Immunoblot analysis of EMT and basal/luminal markers in NAMEC8 upon treatment with epigenetic hits. SGC-CBP30 demonstrated the most drastic change as compared to the other compounds. β-actin was used as a loading control. (F) Left: Mammosphere formation assay of NAMEC8 upon treatment with epigenetic hits. A significant reduction in spheres formation and spheres size was observed in three of the compounds tested. Images are taken at 4× magnification. Scale bar represents 100 μm. Right: Bar graph representing number of tumor spheres >50 μm. Data are represented as mean, +SEM, n=3, *p<0.05, **p<0.01, ns, not significant. (G) Flow cytometry analysis of CD44 and CD24 staining in NAMEC8, DMSO vs SGC-CBP30 treated cells. Population of cells with decreased CD44 expression was observed upon SGC-CBP30 treatment, suggesting an induction towards a non-stem-like state.

FIG. 18: CREBBP/EP300 bromodomain inhibition induces MET in SUM159 TNBC cell line. (A) Cell morphology images of SUM159 treated with DMSO and epigenetic compounds. LLY-283 and GSK591 were used at 30 nM, UNC0642 and SGC-CBP30 were used at 2 μM. Images are taken at 4× magnification. Scale bar represents 100 μm. (B) Immunoblot analysis of EMT and basal/luminal markers in SUM159 upon treatment with epigenetic hits. β-actin was used as a loading control. (C) Top: Mammosphere formation assay of SUM159 upon treatment with epigenetic hits. A significant reduction in spheres formation and spheres size was observed in SGC-CBP30 treated cells. Images are taken at 4× magnification. Scale bar represents 100 μm. Bottom: Bar graph representing number of tumor spheres >50 μm. Data are represented as mean, +SEM, n=3, *p<0.05. (D) Flow cytometry analysis of CD44 and CD24 staining in SUM159, DMSO vs SGC-CBP30 treated cells. Cells expressed decreased CD44 expression and higher CD24 expression, suggesting an induction towards a non-stem-like state.

FIG. 19: CREBBP/EP300 bromodomain inhibition reduces tumor burden of basal-like TNBC in vivo. (A) Cell morphology images of NAMEC8 treated with A-485 at 1 μM. Epithelial-like morphology was observed upon A-485 treatment. Images are taken at 4× magnification. Scale bar represents 100 μm. (B) Immunoblot analysis of EMT and basal/luminal markers in NAMEC8 upon treatment with A-485. β-actin was used as a loading control. (C) Top: Mammosphere formation assay of NAMEC8 upon treatment with A-485. A reduction in spheres formation and spheres size was observed. Images are taken at 4× magnification. Scale bar represents 100 μm. Bottom: Bar graph representing number of tumor spheres >50 μm. Data are represented as mean, +SEM, n=3, ns, not significant. (D) Flow cytometry analysis of CD44 and CD24 staining in NAMEC8, DMSO vs A-485 treated cells. Cells expressed higher CD44 expression treatment, suggesting that A-485 failed to induce a loss of stem-like traits. (E) Immunoblot analysis of histone acetylation marks in NAMEC8 upon treatment with SGC-CBP30 and A-485. H3 and β-actin was used as a loading control. (F) Top: Tumor sizes of NAMEC8-Ras pre-treated with DMSO, SGC-CBP30, and A-485 before subcutaneous injection into NSG mice. Data are represented as mean, +SEM, n=3, *p<0.05, ns, not significant. Bottom: Images of tumors from mice sacrificed at week 11. SGC-CBP30 treatment significantly reduced tumor formation in mice. (G) Working model showing CREBBP/EP300-induced cell state transitions in TNBC upon bromodomain inhibition. In the absence of bromodomain inhibitors, CREBBP and EP300 could recognize acetylated lysines on histones to mediate mesenchymal gene activation, thus maintaining cells in mesenchymal state. However, presence of bromodomain inhibitors would block the reader function of CREBBP and EP300 proteins, thereby reducing the transcriptional regulation of genes required for maintenance of a mesenchymal cell state.

FIG. 20: Metabolic library screen to identify potent MET inducers. (A) Dual-glo Luciferase assay of NAMEC8-SERPINE1 cells screened with metabolic library to identify MET inducers. Data are represented as SERPINE1 promoter activity (mean FF/Ren values) against renilla for cell viability, n=3. Compounds that were identified as hits are circled in red. (B) Compounds identified as hits are compiled in the table with their respective molecular target listed in the right column. (C) Dual-glo Luciferase assay of hits from MET screen performed at 5-point dose response. Data are represented as SERPINE1 promoter activity (mean FF/Ren values) against concentration, with C-IN-1 glutaminase inhibitor showing a dose-response effect of decreasing SERPINE1 promoter activity. (D) Western blot showing GLS1 expression in epithelial and mesenchymal breast cancer cell lines. (E) Cell morphology images of NAMEC8 treated with 500 nM C-IN-1. (F) Immunoblot analysis of EMT and basal/luminal markers in NAMEC8 upon treatment with MET hits. (G) Western blot showing knockdown of GLS1 using 3 shRNA in NAMEC8. (H) Cell-titre glow assay of NAMEC8 ctrlsh vs GLSIsh2 and GLSIsh3 treated with paclitaxel. IC$_{50}$ of GLSsh2 cells is lower than Ctrlsh cells. (I) Western blot of GLS1 knockdown in NAMEC8 Hras cells with sh2 and sh3. (J) Mammosphere assay of NAMEC8 Hras Ctrlsh vs GLSIsh2 vs GLS1sh3 cells. Spheres>100 μm were counted after 7 days. (K) NAMEC8 Hras Ctrlsh and GLSIsh2 cells were injected subcutaneously into NSG mice and tumor growth was tracked over 8 weeks.

DETAILED DESCRIPTION

Inducer of Mesenchymal-Epithelial Transition

Figure 5A:
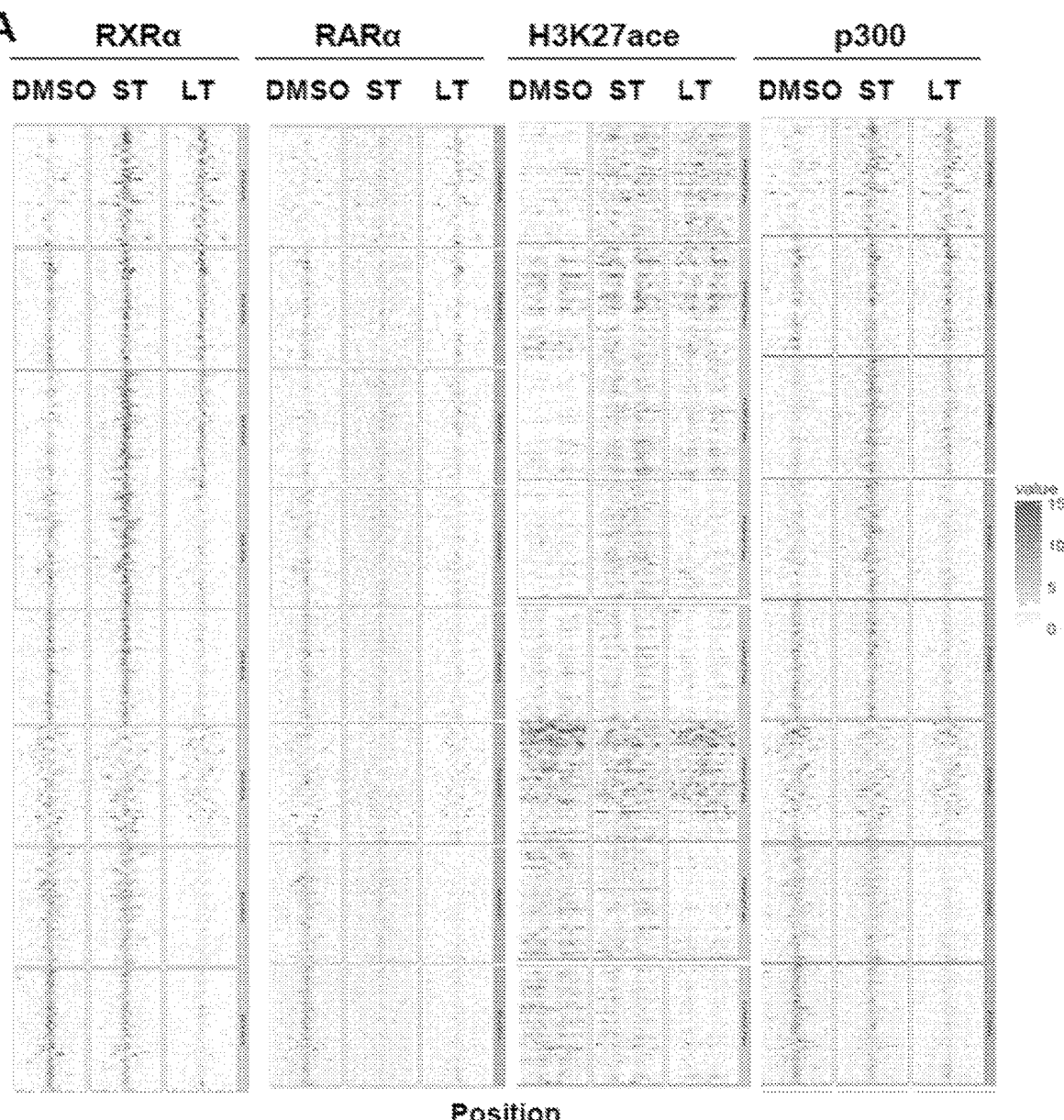
FIG. 5. Lipid metabolism genes are regulated by retinoid receptors (A) Global heat map of ChIP-seq peaks in NAMEC8 treated with DMSO, ST (short term; 7 days) bexarotene or LT (long term; 14 days) bexarotene with RXRα, RARα, H3K27ac and p300 antibodies. (B) Plots showing the occupancy of RXRα, RARα, H3K27ac and p300 at gene bodies upon ST- and LT-bexarotene treatment in NAMEC8. (C) Gene tracks depicting increases in RXRα and H3K27ac binding at STRA6, DHRS3, PLIN1, PLIN2 and ACSL5 loci, and decreases in RXRα and H3K27ac binding at MGLL locus upon ST- and LT-bexarotene treatment in NAMEC8. The x-axis shows chromosome position with the gene structure drawn below and each scale unit represents 5 kb. The y-axis shows genomic occupancy in units of rpm per bp. (D) Gene Ontology pathway enrichment analyses of genes that have increased binding to RXRα with bexarotene treatment in NAMEC8. (E) Plot of superenhancers ranked by increasing H3K27ac signals in NAMEC8 treated with bexarotene. (F) Heat map of lipid-associated genes altered upon bexarotene treatment in NAMEC8, SUM159 cells, MetBr-007DR, BC29.1 and BC22.1 cells. Data represent log 2 fold change. (G) Gene expression of lipid-associated genes involved in TAG synthesis upon bexarotene treatment relative to DMSO in NAMEC8 (top) and BC2.2 (bottom). Data are represented as mean+/−SEM, n=3, *P<0.05, P<0.01, *P<0.001.
Figure 5B:
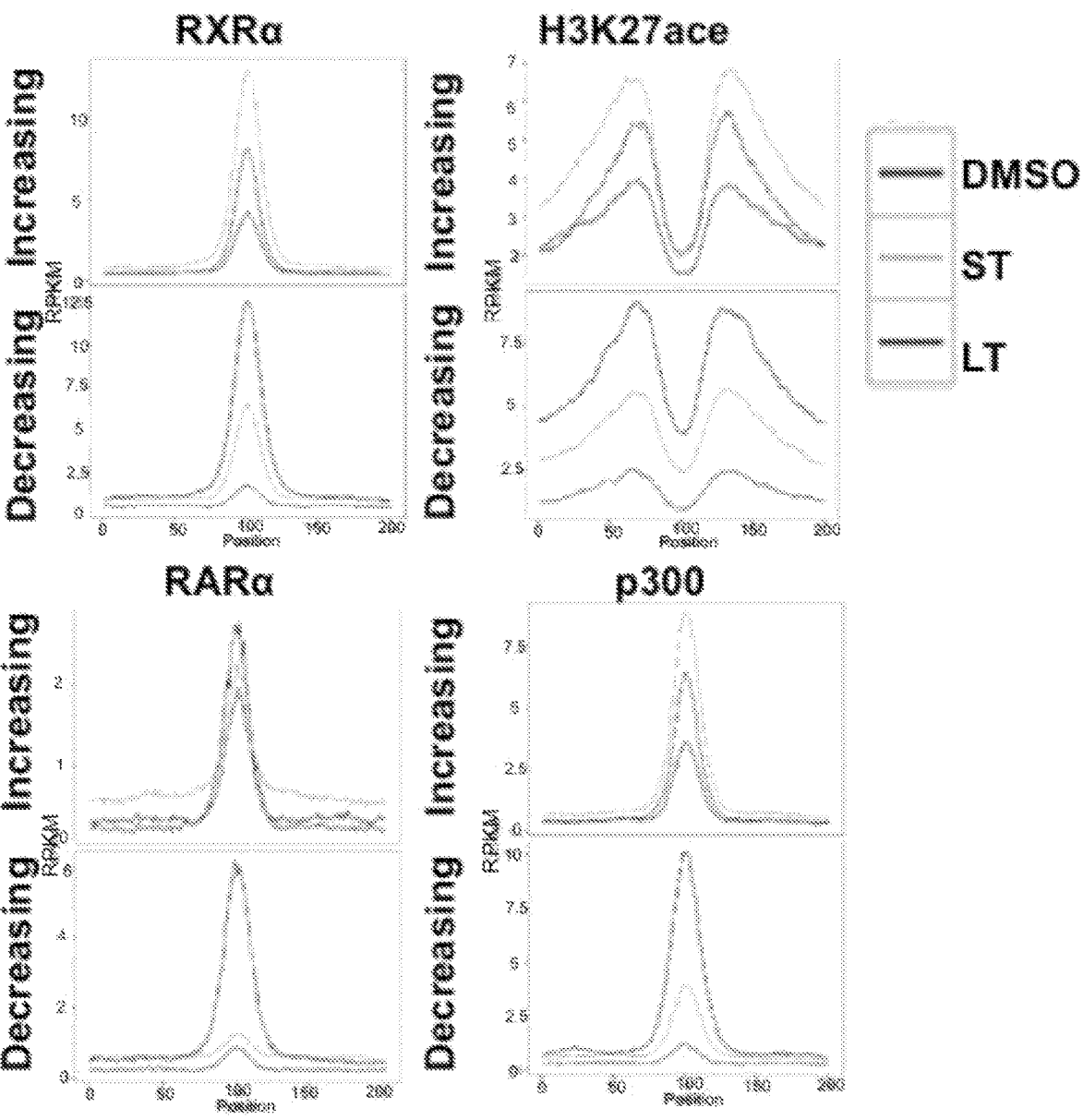

Provided herein are methods of inducing mesenchymal-epithelial transition (MET) in a cancer cell. In one aspect, there is provided a method of inducing MET in a cancer cell, the method comprising contacting the cell with an inducer of mesenchymal-epithelial transition for a time and under conditions sufficient to induce MET in the cell, wherein the cancer cell is a basal-like (or mesenchymal-like) cancer cell.

Cell state transitions can control the functional behaviour of cancer cells, governing their tumorigenicity and response to therapeutics. Epithelial-mesenchymal transition (EMT) can confer cancer stem cell-like properties and enhance tumorigenic potential and drug resistance of tumor cells. EMT may be highly activated in TNBC, contributing to recurrence and chemo-resistance. The inventors have discovered that mesenchymal-epithelial transition (MET), the reverse process of EMT, can suppress these phenotypes, and sensitize tumors to various standard-of-care therapies including chemotherapy and immunotherapy. In particular, the inventors have developed: (i) a technology platform that is useful for the identification of drugs, chemical probes, and drug targets that can improve cancer response; (ii) novel combinatory treatments that enhance anti-tumor response; and (iii) new drug targets whose activation or inhibition can reverse resistance, sensitize tumors to various standard-of-care therapies including chemotherapy and immunotherapy, and inhibit tumor growth.

In one embodiment, there is provided a method of inhibiting growth of a cancer cell, the method comprising contacting the cell with an inducer of mesenchymal-epithelial transition for a time and under conditions sufficient to inhibit growth of the cancer cell, wherein the cancer cell is a basal-like (or mesenchymal-like) cancer cell.

The term "epithelial" or "epithelial-like" is understood in the art, and can be identified by morphological, molecular and/or functional characteristics. For example, epithelial or epithelial-like cells generally have a rounded or cobblestone appearance, express the epithelial marker E-cadherin, are rapidly dividing and/or have relatively low levels of motility, invasiveness and/or anchorage-independent growth as compared with mesenchymal cells.

The term "mesenchymal" or "mesenchymal-like" is understood in the art, and can be identified by morphological, molecular and/or functional characteristics. For example, mesenchymal or mesenchymal-like cells generally have an elongated or spindle-shaped appearance, express the mesenchymal markers vimentin, fibronectin and N-cadherin, divide slowly or are non-dividing and/or have relatively high levels of motility, invasiveness and/or anchorage-independent growth as compared with epithelial cells.

The term "epithelial-to-mesenchymal transition" ("EMT") is known in the art and refers to a process whereby epithelial cancer cells take on a mesenchymal phenotype, which is believed to be associated with metastasis. In addition, while not wishing to be limited by any theory, these mesenchymal cells generally display reduced adhesiveness, increased motility and invasiveness and are relatively resistant to chemotherapeutic agents and/or radiation (e.g. treatments that target rapidly dividing cells).

The term "mesenchymal-to-epithelial transition" ("MET") is also known in the art and refers to the reprogramming of cells that have undergone EMT to regain one or more epithelial characteristics (e.g. as described above). For example, such cells typically exhibit reduced motility and/or invasiveness and/or are rapidly dividing, and may thereby regain sensitivity to cytotoxic agents.

In one embodiment, the method may be an in vitro, in vivo or ex vivo method.

The inducer of MET may be a compound selected from the group consisting of a TGFβ inhibitor, a adenosine/adrenergic, GABA or NMDA receptor modulator, a neurotransmitter, an epigenetic-modifying compound.

In one embodiment, the inducer of MET is selected from the group consisting of Amuvatinib (MP-470); Evista (Raloxifene HCl); Isotretinoin; SB 216763; Tretinoin (Aberela); 1,3-Dipropyl-8-p-sulfophenylxanthine; 5-Bromo-2'-deoxyuridine; Alprenolol hydrochloride; Amiodarone hydrochloride; Apomorphine hydrochloride hemihydrate; Atropine methyl nitrate; Cantharidic Acid; L-798106; L-Aspartic acid; Rhodblock 6; TNP; Bexarotene; PD-161570; SB-525334; 13-cis-retinoic acid; AC-55649; Raloxifene hydrochloride; Retinoic acid; Tazarotene; TTNPB; U0126; Amuvatinib (MP-470); AG-490; Abitrexate (Methotrexate); Roscovitine (Seliciclib, CYC202); PIK-294; U0126-EtOH; PH-797804; Arry-380; Motesanib Diphosphate (AMG-706); CH5132799; PIK-93; KN-62; 16,16-dimethyl Prostaglandin D2; SB 431542; Prostaglandin D2 Ethanolamide; 6-keto Prostaglandin E1; Prostratin; CAY10587; 15-deoxy-_ 12,14-Prostaglandin D2; UCM707; D 4476; 16-phenoxy tetranor Prostaglandin A2; KN-93; Prostaglandin D2-1-glyceryl ester; C-8 Ceramide; S-ethyl N-[4-(trifluoromethyl)phenyl] Isothiourea (hydrochloride); LLY-283, GSK591, UNC0642; SGC-CBP30; Tanshinone I; Hemin; Autophinib; β-Lapachone; Vps34-PIK-III; Glutaminase C-IN-1; GSK256066; AN-2728; GSK2837808A; Etretinate; Fenretinide; T0901317; AGI-6780; SW033291 and NCT-503.

In one embodiment, the inducer of MET is a retinoid. The retinoid may, for example, be dehydroretinol, didehydroretinol Tretinoin (retinoic acid), Isotretinoin, Alitretinoin, Etretinate, Acitretin, Adapalene, Bexarotene, 13-cis-retinoic acid, Tazarotene, TTNPB, Etretinate or Fenretinide.

In one embodiment, the retinoid is a retinoic acid receptor alpha (RAR-α) agonist or a retinoid X receptor alpha (RXR-α) agonist. The RAR-α agonist may be TTNPB, IRX5183, SY-1425, Etretinate or Fenretinide. The RXR-α agonist may be bexarotene.

The inducer of MET may be a modulator (e.g. inhibitor or inducer) of a metabolic enzyme or pathway. For example, the modulator of a metabolic enzyme or pathway may be a glutaminase inhibitor, a phosphodiesterase inhibitor, a modulator of autophagy, an inhibitor of phospholipase, topoisomerase, PI3K, lactate dehydrogenase, 15-PGDH or phosphoglycerate dehydrogenase.

In one embodiment, the inducer of MET is a glutaminase inhibitor. The glutaminase inhibitor may be glutaminase C-IN-1, CB839 (Telaglenastat), UPGL00004 or BPTES. The glutaminase inhibitor may be a glutaminase 1 (GLS1) inhibitor. The glutaminase inhibitor may be a glutaminase C inhibitor or a kidney-type glutaminase (KGA) inhibitor.

In one embodiment, the inducer of MET is a phosphodiesterase (PDE) inhibitor. In one embodiment, the PDE inhibitor is a PDE4 inhibitor. In one embodiment, the PDE inhibitor is GSK256066 or AN-2728.

In one embodiment, the inducer of MET is a modulator (e.g. inhibitor or inducer) of autophagy. The modulator of autophagy may be Hemin, Autophinib; β-Lapachone; Vps34-PIK-III or Fenretinide.

The inducer of MET may be an inhibitor of phospholipase (e.g. Tanshionone I), topoisomerase (e.g. β-Lapachone), PI3K (Vps34-PIK-III, Idelalisib, Copanlisib, Duvelisib, Alpelisib), lactate dehydrogenase (e.g. GSK2837808A), 15-PGDH (e.g. SW033291) or phosphoglycerate dehydrogenase (e.g. NCT-503).

The inducer of MET may be an epigenetic-modifying compound. The epigenetic-modifying compound may be an inhibitor of p300/CREBBP bromodomain, protein arginine methyltransferase 5 (PRMT5) or histone methyltransferase.

In one embodiment, the inducer of MET is a p300/CREBBP bromodomain inhibitor. The p300/CREBBP bromodomain inhibitor may be SGC-CBP30, GNE-272 or GNE-781.

In one embodiment, the inducer of MET is an inhibitor of PRMT5. The inhibitor of PRMT5 may be LLY-283 or GSK591.

In one embodiment, the inducer of MET may be an inhibitor of histone methyltransferase (e.g. G9a and/or GLP). In one embodiment, the inhibitor of histone methyltransferase is UNC0642.

Inhibitors of Epithelial-Mesenchymal Transition

The inducer of MET may also be an inhibitor of EMT. In one embodiment, the inhibitor of MET is a compound selected from the group consisting of a TGFβ inhibitor, a adenosine/adrenergic, GABA or NMDA receptor modulator, a neurotransmitter, an epigenetic-modifying compound. In one embodiment, the inhibitor of EMT is a retinoid.

In one embodiment, the inhibitor of EMT is selected from the group consisting of Amuvatinib (MP-470); Evista (Raloxifene HCl); Isotretinoin; SB 216763; Tretinoin (Aberela); 1,3-Dipropyl-8-p-sulfophenylxanthine; 5-Bromo-2'-deoxyuridine; Alprenolol hydrochloride; Amiodarone hydrochloride; Apomorphine hydrochloride hemihydrate; Atropine methyl nitrate; Cantharidic Acid; L-798106; L-Aspartic acid; Rhodblock 6; TNP; Bexarotene; PD-161570; SB-525334; 13-cis-retinoic acid; AC-55649; Raloxifene hydrochloride; Retinoic acid; Tazarotene; TTNPB; U0126; Amuvatinib (MP-470); AG-490; Abitrexate (Methotrexate); Roscovitine (Seliciclib, CYC202); PIK-294; U0126-EtOH; PH-797804; Arry-380; Motesanib Diphosphate (AMG-706); CH5132799; PIK-93; KN-62; 16,16-dimethyl Prostaglandin D2; SB 431542; Prostaglandin D2 Ethanolamide; 6-keto Prostaglandin E1; Prostratin; CAY10587; 15-deoxy-_ 12,14-Prostaglandin D2; UCM707; D 4476; 16-phenoxy tetranor Prostaglandin A2; KN-93; Prostaglandin D2-1-glyceryl ester; C-8 Ceramide; and S-ethyl N-[4-(trifluoromethyl)phenyl] Isothiourea (hydrochloride).

In one embodiment, the inhibitor of EMT is an inhibitor or regulator of lipid metabolism (or an inhibitor of fatty acid oxidation).

The inhibitor of lipid metabolism may be an inhibitor of carnitine palmitoyltransferase I (CPT1). In one embodiment, the inhibitor of CPT1 is etomoxir, perhexiline, teglicar, or oxfenicine. In one embodiment, the inhibitor of CPT1 is etomoxir.

The inhibitor of lipid metabolism may be an inhibitor of mitochondrial thiolase. In one embodiment, the inhibitor of mitochondrial thiolase is 4-bromocrotonic acid.

The inhibitor of lipid metabolism may be an inhibitor of long-chain-fatty-acid-CoA ligase (ACSL). In one embodiment, the inhibitor of ACSL is Triacsin C or a thiazolidinedione (TZD).

The inhibitor of lipid metabolism may be an inhibitor of 3-ketoacyl-coenzyme A thiolase (3-KAT). In one embodiment, the inhibitor of 3-KAT is trimetazidine, or ranolazine.

The inhibitor of lipid metabolism may be an inhibitor of Monoacylglycerol lipase (MGLL). In one embodiment, the inhibitor of MGLL is JZL184.

The cancer cell can be basal-like breast cancer or TNBC but not luminal/ER+ breast cancers. In one embodiment, the cancer cell is selected from the group consisting of triple negative breast cancer, and mesenchymal-like cancers such as head and neck cancer, lung cancer, pancreatic cancer, ovarian cancer, gastric cancer, and colorectal cancer.

The cancer cell may be a chemo-resistant cancer cell. In other words, the cancer cell may be one that is poorly responsive or essentially non-responsive to an anti-cancer therapy. In one embodiment, the cancer cell is one that is resistant to standard-of-care therapies.

The cancer cell may also be a metastatic cancer cell.

Drug Combinations

More potent and more durable cancer control can be achieved through combinatorial treatment methods involving retinoids and epigenetic regulators. The inventors have shown that several epigenetic modulators on their own could also induce MET. In combination with retinoids, they can further enhance and maintain the MET conversion phenotype.

Conversion of mesenchymal cells to an epithelial phenotype via retinoid-induced MET can also sensitize cells to immune-oncology drugs such as immune checkpoint inhibitors. The retinoids may have immunomodulatory effects by enhancing T-helper and T-regulatory cell populations, increasing type I and II interferon signalling, interferon gamma signalling, increasing cytokine-mediated signalling and activate complement cascades (Table 4A and 4B).

In one embodiment, the method further comprises contacting the cell with a chemotherapeutic agent (such as paclitaxel or 5-fluorouracil), an epigenetic-modifying compound (such as Class I HDAC inhibitors (e.g. C1-994 and SBHA)), or an immunomodulatory agent following induction of MET in the cancer cell. The method may comprise simultaneously or sequentially contacting the cell with the inducer of mesenchymal epithelial transition.

In one embodiment, the method further comprises contacting the cell with a chemotherapeutic agent. The chemotherapeutic agent may be selected from the group consisting of chlorambucil, ifosfamide, doxorubicin, mesalazine, thalidomide, lenalidomide, temsirolimus, everolimus, fludarabine, 5-fluorouracil, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

In one embodiment, the method further comprises contacting the cell with an epigenetic-modifying compound. The epigenetic-modifying compound may be a HDAC inhibitor. The HDAC inhibitor may be a Class I HDAC inhibitor. The HDAC inhibitor may be selected from the group consisting of hydroxamic acids vorinostat (SAHA), belinostat (PXD101), LAQ824, and panobinostat (LBH589); and the benzamides: entinostat (MS-275), tacedinaline (CI994), and mocetinostat (MGCD0103).

In one embodiment, the method further comprises contacting the cell with an immunomodulatory agent. In one embodiment, the immunomodulatory agent is an immune checkpoint inhibitor.

As used herein, the term "immune checkpoints" refers to a group of molecules on the cell surface of CD4 and CD8 T cells. These molecules effectively serve as "brakes" to down-modulate or inhibit an anti-tumor immune response Immune checkpoint molecules include, but are not limited to, Programmed Death-Ligand 1 (PD-L1, also known as B7-H1, CD274), Programmed Death 1 (PD-1), CTLA-4, B7H1, B7H4, OX-40, CD137, CD40, 2B4, IDO1, IDO2, VISTA, CD27, CD28, PD-L2 (B7-DC, CD273), LAG3, CD80, CD86, PDL2, B7H3, HVEM, BTLA, KIR, GAL9, TIM3, A2aR, MARCO (macrophage receptor with collageneous structure), PS (phosphatidylserine), ICOS (inducible T cell costimulator), HAVCR2, CD276, VTCN1, CD70, and CD160.

"Immune checkpoint inhibitors," as used herein refer to any modulator that inhibits the activity of the immune checkpoint molecule Immune checkpoint inhibitors include small molecule inhibitors, antibodies, antibody-derivatives (including Fab fragments and scFvs), antibody-drug conjugates, antisense oligonucleotides, siRNA, aptamers, peptides and peptide mimetics Inhibitory nucleic acids that decrease the expression and/or activity of immune checkpoint molecules can also be used in the methods disclosed herein. One embodiment is a small inhibitory RNA (siRNA) for interference or inhibition of expression of a target gene.

In one embodiment, the inducer of MET is co-administered with an immune checkpoint inhibitor, wherein the immune checkpoint inhibitor is an inhibitor of Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, IDO1, IDO2, ICOS (inducible T cell costimulator), KIR, LAIR1, LIGHT, MARCO (macrophage receptor with collageneous structure), PS (phosphatidylserine), OX-40, SLAM, TIGHT, VISTA, VTCN1, or any combinations thereof.

In one embodiment, the immune checkpoint inhibitor is an inhibitor of PD-L1. In one embodiment, the immune checkpoint inhibitor is an inhibitor of PD-1. In one embodiment, the immune checkpoint inhibitor is an inhibitor of CTLA-4. In one embodiment, the immune checkpoint inhibitor is an inhibitor of LAG3. In one embodiment, the immune checkpoint inhibitor is an inhibitor of TIM3.

The immunomodulatory agent may also be a cell therapy agent such as a T cell (e.g. a CarT cell), a natural killer (NK) cell or a dendritic cell.

In one embodiment, there is provided a method of inducing MET in a cancer cell, the method comprising contacting the cell with an inducer of mesenchymal-epithelial transition and a chemotherapeutic agent for a time and under conditions sufficient to induce MET in the cell, wherein the cancer cell is a basal-like (or mesenchymal-like) cancer cell. The inducer of mesenchymal-epithelial transition may be a retinoid such as Is Bexarotene. The chemotherapeutic agent may be paclitaxel or 5-fluorouracil.

In one embodiment, there is provided a method of inducing MET in a cancer cell, the method comprising contacting the cell with an inducer of mesenchymal-epithelial transition and an epigenetic-modifying compound for a time and under conditions sufficient to induce MET in the cell, wherein the cancer cell is a basal-like (or mesenchymal-like) cancer cell. The inducer of mesenchymal-epithelial transition may be a retinoid such as Bexarotene. The epigenetic-modifying agent may be a Class I HDAC inhibitor such as Cl-994 and SBHA.

In one embodiment, there is provided a method of inducing MET in a cancer cell, the method comprising contacting the cell with an inducer of mesenchymal-epithelial transition and an immunomodulatory agent for a time and under conditions sufficient to induce MET in the cell, wherein the cancer cell is a basal or basal-like (or mesenchymal-like) cancer cell. The inducer of mesenchymal-epithelial transition may be a retinoid such as Bexarotene. The immunomodulatory agent may be an immune checkpoint inhibitor such as an anti-PD1 antibody, an anti-PDL1 antibody or an anti-CTLA-4 antibody.

Lipid Metabolic Pathways

The inventors have shown that epithelial and mesenchymal cell states are defined by distinct metabolic pathways. A key finding pertains to differences in lipid metabolism pathways that support either the epithelial and mesenchymal cell states. These findings reveal important and novel therapeutic targets, particularly metabolic genes that can either be activated or inhibited to: (i) target or kill the more aggressive, mesenchymal subtype of tumors; (ii) cause MET conversion; (iii) block EMT and disease progression (i.e. tumor growth, invasion, metastasis, and resistance).

Without being bound by theory, the inventors have found that mesenchymal tumor cells depend more on the fatty acid oxidation (FAO) metabolism pathway through utilizing fatty acids as a source of energy substrates, whereas epithelial tumor cells tend to store fatty acids as lipid droplets. To target mesenchymal tumor cells, the key genes involved in FAO (such as ACSL, CPT1, 3-KAT, mitochondrial thiolase and MGLL) may be targeted. Inhibiting these genes can selectively kill mesenchymal tumor cells. Inhibitors of ACSL include Triacsin C (pre-clinical) and thiazolidin-ediones (TZDs) (already in clinical use for diabetes). Inhibitors of CPT1 include etomoxir (failed clinical trials due to liver toxicity), perhexiline (clinical use for angina), oxfeni-cine (pre-clinical). Inhibitors of 3-KAT include trimetazi-dine, ranolazine (clinical use for angina). Inhibitors of mitochondrial thiolase include 4-bromocrotonic acid (pre-clinical). Inhibitors of MGLL include JZL184 (pre-clinical).

Furthermore, combinations of these FAO pathway inhibi-tors with standard of care therapies may result in more potent targeting of mesenchymal tumor cells, thereby inhib-iting tumor growth, decreasing resistance, blocking metas-tasis, and improving anti-cancer response.

The inventors further found that the disruption of fatty acid oxidation can further block cancer metastasis. The use of FAO inhibitor, etomoxir, which targets the gene CPT1, can block breast cancer metastasis. Inhibition of FAO either with CPT1 inhibitors or inhibitors targeting FAO can be effective as anti-metastatic agents for cancers with strong metastatic tendencies, as well as FAO dependence such as ovarian cancer, breast cancer, oral cancer.

The method as defined herein may further comprise contacting the cell with an inhibitor of or regulator lipid metabolism following induction of MET in the cancer cell. The inhibitor of lipid metabolism may be an inhibitor of the fatty acid oxidation (FAO) pathway. In one embodiment, the inhibitor of lipid metabolism is an inhibitor of an enzyme selected from the group consisting of long-chain-fatty-acid-CoA ligase (ACSL), 3-ketoacyl-coenzyme A thiolase (3-KAT), mitochondrial thiolase and Monoacylglycerol lipase (MGLL) or an activator of an enzyme selected from the group consisting of glycerol-3-phosphate acyltransferase (GPAT), 1-acylglycerol-3-phosphate O-acyltransferase (AGPAT), prostatic acid phosphatase (PPAP), diglyceride acyltransferase (DGAT).

The inhibitor of lipid metabolism may be an inhibitor of carnitine palmitoyltransferase I (CPT1). In one embodiment, the inhibitor of CPT1 is etomoxir, perhexiline or oxfenicine.

The inhibitor of lipid metabolism may be an inhibitor of mitochondrial thiolase. In one embodiment, the inhibitor of mitochondrial thiolase is 4-bromocrotonic acid.

The inhibitor of lipid metabolism may be an inhibitor of long-chain-fatty-acid-CoA ligase (ACSL). In one embodi-ment, the inhibitor of ACSL is Triacsin C or a thiazolidin-edione (TZD).

The inhibitor of lipid metabolism may be an inhibitor of 3-ketoacyl-coenzyme A thiolase (3-KAT). In one embodi-ment, the inhibitor of 3-KAT is trimetazidine, or ranolazine.

The inhibitor of lipid metabolism may be an inhibitor of Monoacylglycerol lipase (MGLL). In one embodiment, the inhibitor of MGLL is JZL184.

In one embodiment, there is provided a method of induc-ing MET in a cancer cell, the method comprising contacting the cell with an inducer of mesenchymal-epithelial transition and an inhibitor of lipid metabolism for a time and under conditions sufficient to induce MET in the cell, wherein the cancer cell is a basal-like (or mesenchymal-like) cancer cell. The inducer of MET may be a retinoid such as Bexarotene. The inhibitor of lipid metabolism may be an inhibitor of CPT1, e.g. etomoxir.

In one embodiment, there is provided a method of induc-ing MET in a cancer cell, the method comprising contacting the cell with an inducer of mesenchymal-epithelial transition and an inhibitor of CPT1 for a time and under conditions sufficient to induce MET in the cell, wherein the cancer cell is a basal-like (or mesenchymal-like) cancer cell.

In one embodiment, there is provided a method of induc-ing MET in a cancer cell, the method comprising contacting the cell with a combination of Bexarotene and etomoxir for a time and under conditions sufficient to induce MET in the cancer cell.

The method as defined herein may comprise treating cancer in a patient or sensitizing a patient to an anti-cancer therapy.

The term "treating" as used herein, unless otherwise indicated, means reversing, alleviating, inhibiting the prog-ress of, or preventing, either partially or completely, the growth of tumors, tumor metastases, or other cancer-causing or neoplastic cells in a patient with cancer. The term "treat-ment" as used herein, unless otherwise indicated, refers to the act of treating.

The terms "subject", "patient" and "individual" are used interchangeably. As used herein, they refer to an animal. By way of example only, a subject may be, but is not limited to, a mammal including, but not limited to, a human. The terms do not require the supervision (whether continuous or inter-mittent) of a medical professional.

By "sensitizing" a cancer or a cancer cell (e.g. a cancer stem cell and/or a cancer cell with a mesenchymal pheno-type) to an anti-cancer therapy or "increasing the sensitivity" of a cancer or cancer cell to an anti-cancer therapy, it is meant that lower dosages of the anti-cancer therapeutic drug are effective to treat the cancer or kill the cancer cell and/or the cancer or cancer cell is more responsive to the same dosage of the anti-cancer drug as compared with the response in the absence of the methods of the invention.

In one aspect, there is provided an inducer of mesenchy-mal-epithelial transition (MET) for use in inducing mesen-chymal-epithelial transition in a cell in a patient.

In one aspect, there is provided the use of an inducer of mesenchymal-epithelial transition (MET) in the manufac-ture of a medicament for inducing mesenchymal-epithelial transition in a cell in a patient.

In one embodiment, there is provided a method of inhib-iting epithelial-mesenchymal transition (EMT) in a cancer cell, the method comprising contacting the cell with an inhibitor of epithelial-mesenchymal transition for a time and under conditions sufficient to inhibit epithelial-mesenchy-mal transition (EMT) of the cancer cell, wherein the cancer cell is a basal-like (or mesenchymal-like) cancer cell. This may comprise blocking disease progression of the cancer cell (i.e. tumor growth, invasion, metastasis, and resistance).

In one embodiment, there is provided an inhibitor of epithelial-mesenchymal transition (EMT) for use in inhib-iting epithelial-mesenchymal transition (EMT) in a cancer cell.

In one embodiment, there is provided the use of an inhibitor of epithelial-mesenchymal transition (EMT) in the manufacture of a medicament for inhibiting epithelial-mes-enchymal transition in a cancer cell.

In inhibiting EMT, the inhibitor may be an inhibitor of CPT1, e.g. etomoxir, perhexiline or oxfenicine.

In inhibiting EMT, the inhibitor may be an inhibitor of mitochondrial thiolase. In one embodiment, the inhibitor of mitochondrial thiolase is 4-bromocrotonic acid.

In inhibiting EMT, the inhibitor may be an inhibitor of long-chain-fatty-acid-CoA ligase (ACSL). In one embodiment, the inhibitor of ACSL is Triacsin C or a thiazolidinedione (TZD).

In inhibiting EMT, the inhibitor may be an inhibitor of 3-ketoacyl-coenzyme A thiolase (3-KAT). In one embodiment, the inhibitor of 3-KAT is trimetazidine, or ranolazine.

In inhibiting EMT, the inhibitor may be an inhibitor of Monoacylglycerol lipase (MGLL). In one embodiment, the inhibitor of MGLL is JZL184.

In one aspect, there is provided a method of treating cancer in a patient in need thereof, the method comprising administering an inducer of mesenchymal-epithelial transition (MET) in combination with a chemotherapeutic agent, an epigenetic-modifying compound, an immunomodulatory agent, or an inhibitor or regulator of lipid metabolism to the patient, for a time and under conditions to treat cancer in the patient.

The inducer of mesenchymal-epithelial transition may be administered either simultaneously or sequentially with the chemotherapeutic agent, epigenetic-modifying compound, immunomodulatory agent or inhibitor or regulator of lipid metabolism.

In one aspect, there is provided an inducer of mesenchymal-epithelial transition (MET) for use in treating cancer in patient in need thereof, wherein the inducer of mesenchymal-epithelial transition (MET) is to be administered in combination with a chemotherapeutic agent, an epigenetic-modifying compound, an immunomodulatory agent, or an inhibitor or regulator of lipid metabolism to the patient.

In one aspect, there is provided the use of an inducer of mesenchymal-epithelial transition (MET) in the manufacture of a medicament for treating cancer is a subject, wherein the medicament is to be administered in combination with a chemotherapeutic agent, an epigenetic-modifying compound, an immunomodulatory agent, or an inhibitor or regulator of lipid metabolism to the patient.

In one aspect, there is provided a method of sensitizing a cancer patient to an anti-cancer therapy, the method comprising administering a retinoid to the patient for a time and under conditions to sensitize the patient to the anti-cancer therapy.

In one aspect, there is provided an inducer of mesenchymal-epithelial transition (MET) for use in sensitizing a cancer patient to an anti-cancer therapy.

In one aspect, there is provided an inducer of mesenchymal-epithelial transition (MET) in the manufacture of a medicament for sensitizing a patient to an anti-cancer therapy.

In one embodiment, there is provided a method of inducing mesenchymal-epithelial transition (MET) in a subject, the method comprising administering an inhibitor or regulator of lipid metabolism for a time and under conditions to induce mesenchymal-epithelial transition. The inhibitor or regulator of lipid metabolism may also be used to (i) target or kill the more aggressive, mesenchymal subtype of tumors or (ii) block EMT and disease progression (i.e. tumor growth, invasion, metastasis, and resistance).

The inhibitor or regulator of lipid metabolism may be an inhibitor of the fatty acid oxidation pathway. In one embodiment, the inhibitor or regulator of lipid metabolism is an inhibitor of an enzyme selected from the group consisting of long-chain-fatty-acid-CoA ligase (ACSL), 3-ketoacyl-coenzyme A thiolase (3-KAT), mitochondrial thiolase and Monoacylglycerol lipase (MGLL) or an activator of an enzyme selected from the group consisting of glycerol-3-phosphate acyltransferase (GPAT), 1-acylglycerol-3-phosphate O-acyltransferase (AGPAT), prostatic acid phosphatase (PPAP), diglyceride acyltransferase (DGAT).

The inhibitor of lipid metabolism may be an inhibitor of carnitine palmitoyltransferase I (CPT1). In one embodiment, the inhibitor of CPT1 is etomoxir, perhexiline or oxfenicine. In one embodiment, the inhibitor of CPT1 is etomoxir.

The inhibitor of lipid metabolism may be an inhibitor of mitochondrial thiolase. In one embodiment, the inhibitor of mitochondrial thiolase is 4-bromocrotonic acid.

The inhibitor of lipid metabolism may be an inhibitor of long-chain-fatty-acid-CoA ligase (ACSL). In one embodiment, the inhibitor of ACSL is Triacsin C or a thiazolidinedione (TZD).

The inhibitor of lipid metabolism may be an inhibitor of 3-ketoacyl-coenzyme A thiolase (3-KAT). In one embodiment, the inhibitor of 3-KAT is trimetazidine, or ranolazine.

The inhibitor of lipid metabolism may be an inhibitor of Monoacylglycerol lipase (MGLL). In one embodiment, the inhibitor of MGLL is JZL184.

The inhibitor of lipid metabolism may be administered as a single agent or in combination with another anti-cancer agent such as a standard of care chemotherapeutic agent or radiotherapy to treat cancer.

In one embodiment, there is provided an inhibitor or regulator of lipid metabolism for use in inducing mesenchymal epithelial transition (MET) of a cancer in a subject.

In one embodiment, there is provided the use of an inhibitor or regulator of lipid metabolism in the manufacture of a medicament for inducing mesenchymal epithelial (MET) transition of a cancer in a subject.

In one embodiment, there is provided a method of blocking or preventing metastasis of a cancer in a subject, the method comprising administering an inhibitor or regulator of lipid metabolism for a time and under conditions sufficient to block or prevent metastasis in the subject.

In one embodiment, there is provided an inhibitor or regulator of lipid metabolism for use in blocking or preventing metastasis of a cancer in a subject.

In one embodiment, there is provided the use of an inhibitor or regulator of lipid metabolism in the manufacture of a medicament for blocking or preventing metastasis in a subject.

In one embodiment, there is provided a method of inhibiting epithelial-mesenchymal transition (EMT) of a cancer in a subject, the method comprising administering an inhibitor or regulator of lipid metabolism for a time and under conditions sufficient to inhibit epithelial mesenchymal transition (EMT) of the cancer in the subject.

In one embodiment, there is provided an inhibitor or regulator of lipid metabolism for use in inhibiting epithelial-mesenchymal transition (EMT) of a cancer in a subject.

In one embodiment, there is provided the use of an inhibitor or regulator of lipid metabolism in the manufacture of a medicament for inhibiting epithelial-mesenchymal transition (EMT) of a cancer in a subject.

In one embodiment, there is provided a method of characterizing the aggressiveness of a cancer, the method comprising detecting a mesenchymal-like lipid signature from a sample obtained from the patient. There is also provided a method of diagnosing cancer comprising detecting a mesenchymal-like lipid signature in a sample obtained from the patient.

In one aspect, there is provided a method of identifying an agent that induces mesenchymal-epithelial transition in a cell, the method comprising:

a) contacting a cell with a test agent to be screened; and b) detecting the expression from a promoter of a gene selected from the group consisting of CD24, CD44, CD166, CDH1, ZEB1 and SERPINE 1;

wherein a change in expression in the one or more genes as compared to control indicates that the test agent is capable of inducing mesenchymal-epithelial transition in the cell.

The change in expression in the one or more genes as compared to control may be an increase or decrease in the expression of the one or more genes. The control may be a cell that has not been contacted with the test agent to be screened.

The cell may be a reporter cell line engineered to express a measurable marker from the promoter of the gene from which expression is to be detected.

Provided herein are also reporter expression constructs capable of expressing a measurable marker from the promoter of a gene selected from the group consisting of CD24, CD44, CD166, CDH1, ZEB1 and SERPINE 1.

Provided herein is a platform encompassing the use of genetically-modified cancer cell lines in high-throughput small molecule/drug library screens to detect potent inducers of MET. The cell lines may detect changes in cell states, while excluding general cytotoxic drugs. This is different from other common screens that detect the loss of cell viability phenotype, as most anti-cancer drug screens are designed to measure cell kill resulting from drug treatment.

Provided herein is an engineered reporter cell line, comprising a reporter expression construct as defined herein. Also provided herein is a kit (or platform) for identifying an agent that induces mesenchymal-epithelial transition in a cell.

The control of cancer cell states, i.e. being epithelial or mesenchymal, can be employed for improving the responsiveness of cancer cell to therapy. Treatment of basal-like breast cancer or TNBC, but not the luminal/ER+ breast cancers, with retinoids and other pathway-modulating compounds induced MET. This provides an important stratification strategy for the selection of patient populations who are more likely to response to retinoid treatment. These patients have basal-like breast cancer or TNBC, bearing an activated EMT program. This MET approach can be extended to mesenchymal-like tumors of other solid cancers that include gastric, colorectal, head and neck, lung, pancreatic, liver, all of which may comprise of tumors with mesenchymal signature.

For breast cancer, stratification of patients can be performed by: (i) IHC or protein expression of tumor biopsies/resections, during which expression of ER, PR, HER2 would be assessed and hence distinguish between luminal, HER2 and basal subtypes of breast cancer; (ii) using molecular diagnostics such as PAM50 that include gene expression signatures showing a mesenchymal phenotype; and (iii) the use of IHC or protein expression of tumor biopsies/resections, during which expression of mesenchymal markers such as vimentin, fibronectin, slug, zeb1, cytokeratin 5, cytokeratin 14 and epithelial markers such as E-cadherin, EpCam, cytokeratin 8, cytokeratin 18, mucin 1 would be assessed.

In one aspect, there is provided a method of identifying a cancer patient responsive to a combination therapy comprising a mesenchymal-epithelial transition (MET) inducing compound in combination with a chemotherapeutic agent, an epigenetic-modifying compound, an immunomodulatory agent, or an inhibitor of lipid metabolism, the method comprises detecting a mesenchymal subtype of cancer in a sample obtained from the patient, wherein the presence of a mesenchymal subtype of cancer indicates that the patient is responsive to the combination therapy.

A mesenchymal subtype of cancer may refer to a basal-like (or mesenchymal-like) cancer.

In one embodiment, the method comprises treating the patient with the combination therapy.

In one aspect, there is provided a method of identifying and treating a cancer patient responsive to a combination therapy comprising a mesenchymal-epithelial transition (MET) inducing compound in combination with a chemotherapeutic agent, an epigenetic-modifying compound, an immunomodulatory agent, or an inhibitor of lipid metabolism, the method comprising:

a) detecting a basal-like cancer in a sample obtained from the patient, wherein the presence of a mesenchymal subtype of cancer indicates that the patient is responsive to the combination therapy; and b) treating the patient with the combination therapy.

Provided herein are methods of stratifying a population of patients and identifying a subgroup of patients that are likely to respond to a combination therapy. The method may comprise detecting a subgroup of patients having a mesenchymal subtype of cancer in a sample obtained from each patient.

Provided herein are methods of monitoring the response of a cancer patient to a combination therapy, comprising a mesenchymal-epithelial transition (MET) inducing compound in combination with a chemotherapeutic agent, an epigenetic-modifying compound, an immunomodulatory agent, or an inhibitor of lipid metabolism.

Select groups of patients can receive retinoids either as neoadjuvant or in combination with various standard-of-care therapies. Standard-of-care therapies may differ for various cancers. MET is characterized by changes in EMT markers, basal-to-luminal cytokeratin switch, suppressed cancer stem cell properties and enhanced sensitivity to SOC therapies, and thereby improved clinical response. The patients' tumors' response to combination therapy with retinoids can be monitored by: (i) IHC or protein expression of tumor biopsies/resections, during which expression of ER, PR, HER2 would be assessed and hence distinguish between luminal, HER2 and basal subtypes of breast cancer; (ii) using molecular diagnostics such as PAM50 that include gene expression signatures showing a mesenchymal phenotype; and (iii) the use of IHC or protein expression of tumor biopsies/resections, during which expression of mesenchymal markers such as vimentin, fibronectin, slug, zeb1, cytokeratin 5, cytokeratin 14 and epithelial markers such as E-cadherin, EpCam, cytokeratin 8, cytokeratin 18, mucin 1 would be assessed. As an endpoint clinical outcome, clinical measurements of response such as tumor size will be used. Similar approaches will be used for other cancers but with cancer-specific molecular markers.

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method steps or group of elements or integers or method steps.

As used in the subject specification, the singular forms "a", "an" and "the" include plural aspects unless the context clearly dictates otherwise. Thus, for example, reference to "a method" includes a single method, as well as two or more methods; reference to "an agent" includes a single agent, as well as two or more agents; reference to "the disclosure" includes a single and multiple aspects taught by the disclosure; and so forth. Aspects taught and enabled herein are encompassed by the term "invention". Any variants and derivatives contemplated herein are encompassed by "forms" of the invention.

EXAMPLES

Materials and Methods

Cell Lines and Cell Culture

Human mammary epithelial cell lines (HMLE) were generated as described and immortalized using retroviral vectors to express the catalytic subunit of the human telomerase enzyme, hTERT and the SV-40 Large T antigen. NAMEC8 was generated as described. Briefly, HMLE cells were grown to 50% confluency, followed by differential trypsinization for 1 minute with 0.05% trypsin. Detached cells were carefully collected and re-plated at approximately 200 cells per well of a 24-well plate. Upon expansion, wells were screened for populations that were morphologically mesenchymal and can be stably propagated. Clonal and non-clonal NAMEC cell lines were generated. NAMEC8 is a non-clonal line derived from at least 200 mesenchymal cells. HMLE cells and NAMECs were maintained in MEGM (Lonza).

HMLE-Twist-ER cells were generated as described. For EMT-induction, 100 nM of 4-hydroxytamoxifen in ethanol was added to the culture medium every 48 h to induce Twist expression. Control cells were treated with ethanol. MCF7-Slug+Sox9 cells were generated as previously described. HMLE-Zeb1 cells were generated by infection with FUW-Zeb1 and rTTA. Doxycycline was added to the culture medium every 48 h to induce Zeb1 expression. To generate tumorigenic cells from NAMEC8, cells were infected with pWZL-Blast-Ras. MCF7, MCF7-Ras, SUM159 were maintained as previously described. All cell cultures were maintained at 37° C. with 5% $CO_2$.

Primary Human Cells

Breast tissue biopsies from cancer patients were obtained from National Cancer Centre Singapore (NCCS) with patients' consent and under an IRB approved protocol (2015/2976). Tissue was digested with 1 mg/ml collagenase IV (Gibco) and 1 mg/ml dispase II (Thermo Fisher Scientific) in F12 media for 2 h while shaking in a 37° C. incubator. Cell suspension was then put through a cell strainer and centrifuged for 10 min at 1500 rpm. Cells were then washed twice and resuspended in media before seeding on irradiated 3T3 feeders as previously described. When confluent, sub-culturing was carried out by first lifting the feeders using 0.15% trypsin for 2 min. After removing feeder cells, 0.25% trypsin was added to detach tumor progenitor cells.

Patient-Derived Breast Cancer Xenograft Establishment and Therapy

Primary human breast cancer samples were obtained from the National Cancer Centre Singapore (NCCS) with patients' consent and under an IRB approved protocol (2015/2976). All animal experiments were approved by the Agency for Science Technology and Research Singapore-Biological Resource Centre IACUC (Protocol number 171286). Patient-derived breast tumor fragments (approximately 3×1×1 mm) were inserted bilaterally into the inguinal mammary fat pads of 6-8 week-old NSG female mice for initial establishment of tumors, and subsequently expanded in NSG mice once established. In this study, established tumor fragments of BC2.2 were implanted into cohorts of 6-8 week-old female NSG mice. For BC22.1, $1×10^6$ cells were injected subcutaneously into both flanks of NSG mice.

Generation of Reporter Cell Line for Screening of Compounds pGreenFire1-mCMV was cut using ClaI and SpeI and gel purified. Promoter sequences of genes Zeb1, Serpine1, CDH1, CD24, CD44, CD166 were amplified from human genomic DNA with pre-designed primers containing ClaI and SpeI restriction cut sites using AccuPrime Taq DNA Polymerase (Thermo Fisher Scientific). PCR products were then digested with restriction enzymes and gel-purified. Vector was ligated with PCR insert using Quick Ligase (Fermentas) and transformed into Stb12 competent cells. Colonies were picked and inoculated into TB media with ampicillin. Plasmids were then isolated using a plasmid miniprep kit (Qiagen) and sent for sequencing (1 stBASE Laboratories). After verifying the plasmid sequence, transfection into HEK293 cells was carried out to generate lentivirus. Transfection was carried out using FuGENE 6 (Promega). Viral supernatant was harvested at 24 h and 48 h. NAMEC8 cells were then infected twice with virus using polybrene (8 µg/µl) and checked for good transduction efficiency using Dual-Glo Luciferase System (Promega).

Screening of Compound Libraries

Stock plates of compound libraries were kindly prepared by GIS CHiP facility at 1 mM concentration in DMSO. NAMEC8-SERPINE1prom-Luc cells were seeded into 384 well plates at a density of 700 cells/well in a total volume of 50 µl, using an automated dispensing system (BioTek). 0.5 µl of compounds were then added to the wells the following day using a robotic pin transfer with a Bravo workstation (Agilent Technologies). Cells were then grown for 3 days and promoter-luciferase activity was measured using the Dual-Glo Luciferase System (Promega).

Dual-Glo Luciferase Assay

Assay was carried out according to manufacturer's instructions. To measure luciferase activity in 384 well plates, media was first removed from the plate. Firefly luciferase activity was determined by adding 30 µl Dual-Glo Luciferase substrate (Promega) to the wells and incubated for 10 min before measuring luminescence using a TECAN M1000 Pro plate reader. 15 µl Dual-Glo Stop & Glo substrate was then added to the wells, incubated for 10 min and measuring luminescence on the plate reader to determine Renilla luciferase activity. Promoter luciferase activity is then calculated by taking Firefly luciferase over Renilla luciferase.

ERE-Luciferase Activity Assay

ERE luciferase construct was kindly provided by Alan Prem Kumar, CSI, Singapore. To measure the ERE-luciferase activity, cells were seeded 24 h before transfection. ERE-luciferase (1 µg) and NSV-Renilla (0.1 µg) were packaged using Lipofectamine 2000 and transfected into NAMEC8. 24 h post-transfection, cells were reseeded into 96 well plates for drug treatment. Firefly and Renilla luciferase activities were measured with the Dual-Glo Luciferase System (Promega) 24 h post-treatment.

Lentiviral shRNA and Overexpression Constructs

Lentiviral shRNAs were obtained from the The RNAi Consortium (TRC) collection from Broad Institute. The clone ID for the shRNAs used are: TRCN0000072181 (GFP control), TRCN0000330783 (RXRα shRNA1), TRCN0000021616 (RXRα shRNA2), TRCN0000021618

(RXRα shRNA3), TRCN0000203516 (AGPAT9 shRNA). Each shRNA was cloned into lentiviral plasmid pLKO.1 (Addgene).

For overexpression of CPT1A, the ORF of CPT1A was cut from pCMV6-CPT1A (Origene Cat #RC200485) and cloned into pMN-GFP vector (gift from Yu Qiang lab, GIS). Positive clone was confirmed by sequencing and used for retroviral production. For overexpression of Zeb1, the ORF of Zeb1 was cloned into FUW-LPT2 vector. Positive clone was confirmed by sequencing and used for lentiviral production.

For production of lentivirus, plasmids were packaged into HEK293T cells with packaging plasmids using FuGENE 6 (Promega). For production of retrovirus, plasmids were packaged into PlatA cells with packaging plasmids using FuGENE 6 (Promega). Virus was harvested at 48 h and transduced into target cells. Infected cells were selected with 2 μg/ml puromycin for 7 days.

RNA Isolation, Reverse Transcription and Real-Time PCR Analysis

Cells were rinsed twice in ice-cold PBS. Total RNA was extracted using Trizol (Invitrogen) and column-purified with RNeasy kits (Qiagen). cDNA synthesis was performed with 500 ng of total RNA at 37° C. for 2 h using the SuperScript III First-Strand Synthesis System (Thermo Fisher Scientific), and subsequently diluted 5-fold. mRNA levels were measured with gene-specific primers listed below using the ABI Prism 7900HT Sequence Detection System 2.2 (Applied Biosystems). Results were normalized to GAPDH and analyzed using SDS 2.2 software.

Proliferation Assays

To measure cell growth rates, 1000 cells were seeded onto 96-well plates in triplicate. Cell viability was measured using Cell Titre Glo reagent (Promega) or CellTiter 96® Aqueous One Solution Cell Proliferation Assay (MTS) (Promega) according to the manufacturer's instructions.

Protein Extraction and Immunoblotting

Cells were harvested and scraped from culture dishes in ice-cold PBS. They were then centrifuged at 12000 rpm for 5 min at 4° C. The pellets were then snap frozen in liquid nitrogen or lysed in ice-cold RIPA lysis buffer (Thermo Scientific) and left on ice for 30 min. Subsequently, the lysates were centrifuged at 12000 rpm for 10 min at 4° C. The supernatants were then aspirated and placed in fresh tubes. Protein concentrations were determined using Coomaisse Blue. 50-80 μg total protein was mixed with NuPAGE™ LDS sample buffer and heated at 70° C. for 10 min. Samples were loaded into NuPAGE™ 4-12% Bis-Tris gels (precast polyacrylamide gel; Invitrogen™). Gel electrophoresis was done at 200V for 1.5 h and then blotted onto nitrocellulose membranes (Trans-Blot Turbo™ transfer pack; Bio-Rad). The membranes were blocked with 5% skimmed milk in Tris-buffered saline (TBS; 1st BASE) with 0.1% Tween-20 (Santa Cruz), and then incubated with primary antibodies overnight at 4° C. Thereafter, the membranes were incubated with a horseradish peroxidase (HRP)-conjugated secondary antibody at room temperature for one hour. Finally, the immunoreactive proteins were visualized by using an enhanced chemiluminescent (ECL) reagent (Thermo Scientific, 34075) with the Chemidoc™ Imager (Bio-Rad, 17001401).

Fluorescence Activated Cell Sorting (FACS)

Cells were trypsinized until they detached from the cell culture plates. Neutralization media (DMEM containing 20% FBS) was then added to inactivate the trypsin. The cells were then centrifuged at 1200 rpm for 3 min and the cell pellet was resuspended in PBS/2% FBS. Cells were stained with DAPI (1:2000) and filtered through a 40 μm strainer before sorting. FACS was done on BD Aria Fusion Cell Analyzer.

Staining of CD24 and CD44

Cells were harvested as per FACS and resuspended in 100 μl of solution containing CD24-PE and CD44-APC (BD-Biosciences) antibodies diluted in 2% FBS in PBS (1:40 dilution). Cells were stained for 45 min with vortexing every 10 min to ensure even staining. After antibody incubation, cells were washed once and resuspended in 300 μl 2% FBS in PBS. Cells were then filtered through a 40 μm strainer and analyzed on BD LSR Fortessa X-20 Cell Analyzer.

Mammosphere Assay

For mammosphere culture, cells were seeded onto 96-well ultralow-adherence plates at 700 cells/well in Mammocult medium (Stem Cell Technologies) supplemented with 4 μg/ml heparin, 0.5 μg/ml hydrocortisone and 1% methylcellulose. Spheres (>100 μm) were counted at 7-10 days later.

Immunofluorescence (IF) Staining of Cells

Cell cultures were fixed in 4% paraformaldehyde and permeabilized with 0.25% Triton X-100, followed by blocking with 1% bovine serum albumin in PBST. Cells were incubated in specific primary antibodies, followed by the appropriate secondary antibodies conjugated with Alexa Fluor-488 or -594 (Molecular Probes). Cell nuclei were then stained with DAPI and then viewed and imaged with an Axio Observer D1 epifluorescence microscope with a built-in AxioCamMR3 camera (Zeiss), using the optimal filters and 100-200× magnifications.

Generation of SUM159 PACR Cells

SUM159 cells were exposed to step-wise increases to PAC starting from 10 nM. Media with fresh drug was changed every two days and cells were split whenever they reached 80-90% confluency. Concentration of PAC was increased by 10 nM at every split until cells were able to survive at 100 nM. Cells were then subject to a cell viability assay to measure $IC_{50}$. $IC_{50}$ values were determined using GraphPad Prism software. Cells were considered resistant to PAC when there was at least a 10 fold increase in $IC_{50}$ value compared to the parental cell line.

In Vitro Measurement of $IC_{50}$

Cells were seeded in 96 well plates at a density of 2000 cells/well. Drugs (5-FU/PAC) were added in a 10-point dose-response manner the following day. Cells were allowed to grow for 3 days before cell viability was measured using the Cell Titer Glo reagent (Promega). Data were normalized to vehicle controls. Isobologram plots were generated and $IC_{50}$ values were determined using GraphPad Prism software.

In Vivo Experiments Using NSG Mice

All animal experiments were approved by the Agency for Science Technology and Research Singapore-Biological Resource Centre IACUC (Protocol number 140940). For pre-treated SUM159 and MCF7-Ras cells, $1 \times 10^6$ cells were suspended in 100 μl media containing 50% matrigel and injected subcutaneously into both flanks of female NSG mice. The NSG mice were checked for tumor by palpation once a week and tumors were harvested when they reached ~15 mm in diameter. For treatment in NSG mice, $1 \times 10^5$ NAMEC8-Ras cells were suspended in 100 μl media containing 50% matrigel and injected subcutaneously into both flanks of NSG mice. The NSG mice were checked for tumor formation by palpation and when tumors were about 3 mm, mice were randomized into two groups: vehicle (5% DMSO in corn oil) and treatment (Bexarotene, 100 mg/kg/day oral dosing). Tumor size was measured every week using Vernier calipers and mice were sacrificed when tumors reached ~15 mm or after ~4 weeks of treatment. For patient-derived cells, $2 \times 10^6$ cells were injected subcutaneously per site in NSG mice.

Orthotopic tumor transplantations of MCF7-Slug+Sox9 cells labeled with the tdTomato fluorescent protein were carried out as described previously. Briefly, $1 \times 10^6$ cells were resuspended in 30 μl of media containing 50% matrigel and injected into mammary fat pads of NSG mice. Mice were randomly divided into 3 groups (Control, DOX and Etomoxir+DOX). Mice were administered vehicle control (0.9% w/v NaCl) or etomoxir (20 mg/kg) via i.p. injections daily for 3 weeks. Doxycycline was then administered through drinking water for 2 weeks. Mice were sacrificed 10 weeks after doxycycline treatment was stopped and analyzed for lung metastases under a fluorescence microscope.

Haematoxylin and Eosin Staining of Tumor Sections

The tumor sections were fixed overnight in 4% paraformaldehyde, immersed in 70% ethanol, and sent to the Advanced Molecular Pathology Lab, IMCB for paraffinization and haematoxylin and eosin staining.

Immunofluorescence (IF) Staining of Tumor Sections

The tumor sections were fixed overnight in 4% paraformaldehyde, immersed in 70% ethanol, and sent to the Advanced Molecular Pathology Lab, IMCB for paraffinization. For IF staining, slides were deparaffinized and rehydrated in PBS. The tissues were surrounded with a hydrophobic barrier using a barrier pen and blocked with the blocking buffer (1% bovine serum albumin; BSA, 1% horse serum and 0.2% Triton X-100 in PBS) for 1 hour. They were then washed with PBS and incubated in specific primary antibodies at 4° C. overnight. The slides were washed with PBS and incubated with the appropriate secondary antibodies conjugated with Alexa Fluor-488 or -594 (Molecular Probes) at room temperature for 1 h. The tissues were then mounted on the slides using VECTASHIELD® Mounting Medium with DAPI (Vector Laboratories) and coverslip. The coverslips were permanently sealed around the perimeter with nail polish for prolonged storage. Slides were viewed and imaged with an Axio Observer D1 epifluorescence microscope with a built-in AxioCamMR3 camera (Zeiss), using the optimal filters and 100-200× magnifications. The fluorescence image analysis and the fluorescence overlay image were obtained with the Axio Vision Rel. 4.8 image software.

ChIP-Seq

ChIP assay was carried out as described previously. Briefly, the cells were cross-linked with 1% formaldehyde for 10 min at room temperature, and formaldehyde was then inactivated by the addition of 125 mM glycine. Chromatin extracts containing DNA fragments with an average size of 200-500 bp were immunoprecipitated using anti-RARα, anti-RXRα, anti-H3K27ace or anti-p300 antibody. The ChIP-enriched DNA was then decrosslinked and used for library preparation using Illumina TruSeq ChIP kit followed by analysis using Illumina sequencing.

RNA-Seq

Cells were treated with bexarotene or DMSO and lysed with Trizol. Total RNA was extracted using the Qiagen RNeasy kit (#74106). RNA integrity and concentrations were measured on a Bioanalyzer and libraries were prepared using Illumina True-Seq RNA kit followed by analysis using Illumina sequencing.

Genomic Data Analyses

For ChIP-Seq data processing, reads were aligned to human genome (hg19) using BWA aligner. The aligned reads were deduplicated using Picard Markduplicates.jar.

Peak-calling was performed using MACS2 peak-caller with default parameters Differential binding was performed using DiffBind. H3K27ac superenhancers were identified using the ROSE algorithm as described. The data for ChIP-Seq is deposited in GEO (Accession no: GSE119824).

For RNA-Seq data processing, reads were aligned to the Human reference genome GRCh37.p13 using TopHat2 and read counting was performed using featureCounts. Lowly expressed genes (i.e. those with less than 10 counts in less than 60% of the samples) were excluded from further analysis. The library sizes were then scaled by trimmed mean of M-values (TMM) method. Differentially expressed genes were identified using R package limma and put through the GREAT software for Gene Ontology pathway analysis. The data for RNA-Seq is deposited in SRA database (Accession no: SRP152713).

Lipid Extraction

Lipids from cell pellets were extracted using butanol: methanol (1:1) as extraction solvent. The extraction solvent included an internal standard mixture consisting of 17:0 LPC (Lysophosphocholine), C14 LPE (Lysophosphoethanolamine), C17 Ceramide, C17 phosphocholine, C17 phosphoserine, C17:0 PG, C8-Ceramide, DMPE (1,2-dimyristoyl-glycero-3-phosphoethanolamine), DMPG (1,2-dimyristoyl-glycero-3-phospho-(1'rac-glycerol), DMPS (dimyristoyl-glycero-phosphoserine), 12:0 DG (1,2-dilauroyl-sn-glycerol), C8 GluCer (D-glucosyl-β1-1'-N-octanoyl-D-erythro-sphingosine), 24:0 SM (N-lignoceroyl-D-erythro-sphingosylphosphorylcholine), 24:1 SM (N-nervonoyl-D-erythro-sphingosylphosphorylcholine), d5-TAG 48:0. All the standards were obtained from Avanti Polar Lipids (Alabaster, AL, USA) except for d5-TAG 48:0 that was obtained from CDN isotopes. All standards were added to a final concentration of 100 ng/ml. 100 μl of the extraction solvent including the standards were added to $1 \times 10^7$ cells in a vial containing the cell pellet. The mixture was vortexed for 15 s. The samples were then sonicated in a sonicator bath for 60 min at room temperature. The mixture was then centrifuged at 14000 g for 5 min. The supernatant was transferred to new tubes and kept at –80° C. until the analysis.

Lipidomic Analysis

Samples were analysed with a liquid chromatography-tandem mass spectrometry (LC-MS/MS) system (Agilent 1290 UHPLC connected to Agilent 6490 QQQ). A reversed phase column (Agilent ZORBAX RRHD Eclipse Plus C18, 2.1×50 mm, 1.8 μm) was used for separation. Gradient elutions were performed with Mobile phase A (40% acetonitrile/60% water with 10 mM Ammonium formate) and Mobile phase B (90% Isopropanol/10% Acetonitrile with 10 mM Ammonium formate). Quality control (QC) samples were generated by pooling an aliquot of the lipid extracts from each sample. A QC sample was injected every 10 samples during the analysis, to monitor the performances of the experimental procedures. Lipids were quantified in positive multiple reaction monitoring (MRM) mode. MS parameters: gas temperature 300° C., gas flow 5 L/min, sheath gas flow 11 L/min and sheath gas temperature 250° C. Data were extracted using MassHunter Quantitative Analysis software (Agilent). Lipids were normalized using both internal standards and cell number. Graphs and statistical analysis were done using GraphPad Prism and Mann-Whitney U test.

Lipid Droplet Staining

Intracellular lipid droplets were visualized with fluorescent Bodipy dye. Cells in culture were fixed in 4% paraformaldehyde for 15 min at room temperature, rinsed twice with PBS and permeabilized with 0.2% TritonX-100 in PBS for 10 min and incubated with Bodipy diluted in PBS (final concentration 1 μg/ml) for overnight at 4° C. Cells were washed with PBS and stained with DAPI. Fluorescence images were obtained with an Axio Observer D1 epifluorescence microscope with a built-in AxioCamMR3 camera (Zeiss), using the optimal filters and 100-200× magnifications.

Fatty Acid β-Oxidation Assay

FAO rate was measured using the mitochondrial stress test on the XF96 analyzer (Seahorse Bioscience) according to manufacturer's instructions. Cells were seeded in 96well XF96 cell culture plates at a density of 9000 cells/well in complete media. Cells were then incubated with XF modified DMEM assay medium (Seahorse Bioscience) supplemented with 1 mM glutamine, 0.5 mM glucose, 1% FBS and 0.5 mM carnitine the next day for 18 h. On the day of the assay, cells were incubated with FAO assay medium (KHB: 111 mM NaCl, 4.7 mM KCl, 1.25 mM $CaCl_2$), 2 mM $MgSO_4$, 1.2 mM $NaH_2 PO_4$ supplemented with 2.5 mM glucose, 0.5 mM carnitine, 5 mM HEPES, adjusted to pH7.4) 45 min prior to the assay in a non-$CO_2$ incubator. Seahorse XF Cell Mito Stress Test compounds (2 μM oligomycin, 2 μM FCCP, 2 μM rotenone). For inhibition of FAO, etomoxir (40 μM) was added 15 min prior to the assay. Just prior to starting the assay, XF Palmitate-BSA FAO substrate or BSA was added to the cells. Plate was then put into the XF96 analyzer and the XF Cell Mito Stress Test was run using the recommended protocol. Rate of FAO was calculated by the difference in maximal respiration when Palmitate-BSA FAO substrate was supplemented relative to BSA control.

Statistical Analyses

GraphPad Prism (GraphPad Software) v7.0 was used for statistical analyses. All data are presented as mean±standard error of mean except specified otherwise. Student t-test (two-tailed) was used to compare two groups and calculate p-values. $P < 0.05$ was considered statistically significant. Significance levels are indicated in relevant figure legends.

Example 1

To broadly understand the molecular underpinnings of the MET process and the therapeutic utility, we performed high-throughput small molecule library screens to identify classes of agents with MET-promoting properties in an unbiased manner. This led us to uncover retinoids as the most potent MET promoters, whose potency and durability could be further enhanced though epigenetic reinforcement with HDAC inhibitors. Surprisingly, beyond the classic MET marker gene and phenotypic changes, treatment with retinoids led to a basal to luminal-like transition with a switch in cytokeratin expression, as well as the reexpression of ER in some patient-derived tumor cell models. Administration of retinoids to tumor-bearing animals induced changes in tumor architecture that resembled a MET and halted tumor growth. Furthermore, for the first time, we revealed that cell state transitions in breast cancer are defined by a reprogramming of lipid metabolism, particularly the involvement of retinoids and their modulation of the switch between β-oxidation and lipid storage. Retinoids, through the retinoic acid receptor (RAR) and retinoid X receptor (RXR), bind and target key lipid metabolism genes, as revealed in genome-wide analyses. This led to a redirection of the utilization of fatty acids for β-oxidation in the mesenchymal cell state towards lipid droplet storage in the epithelial cell state. Disruptions of key metabolic enzymes mediating this flux led to the inhibition of the MET process. Conversely, perturbations to β-oxidation using the CPT1 inhibitor, etomoxir, rechanneled fatty acid flux and promoted a more epithelial cell phenotype, and furthermore were able to block EMT-driven breast cancer metastasis in animal models.

High-Throughput Small Molecule Library Screens Identify Retinoids as Promoters of the Mesenchymal-Epithelial Transition The acquisition of a mesenchymal cell state in breast cancer is often associated with more aggressive and invasive phenotypes that are also chemoresistant and cancer stem cell-like. We reasoned that the conversion of a mesenchymal to a more epithelial cell state through the process of a mesenchymal-epithelial transition (MET) may reduce the tumorigenicity and chemoresistance of cancer cells as a form of combinational therapy in breast cancer. To identify small molecule compounds that have the ability to promote MET, we utilized a mesenchymal breast cell line, NAMEC8, that is responsive to perturbation in cell states, coupled to promoter firefly-luciferase reporters as readouts for cell state changes (FIG. 1A). We tested several gene promoters that include (D) 24, CD44, CD166, CDH1, ZEB1 and SERPINE1, which have been previously shown to be associated with either an epithelial or mesenchymal cell phenotype. From other studies, TGFβ could promote an EMT in several cancer cell lines whereas the inhibition of the TGFβ pathway could either block EMT or moderately induce a MET-like phenotype. Thus, we utilized the TGFβR inhibitor, A83-01, as a positive control to evaluate the responsiveness of these gene promoters to changes in cell states (FIG. 1B). Of these SERPINE1prom-Luc exhibited the most dynamic responses when treated with A83-01, as it was downregulated by at least 50%.

We screened four chemical compound libraries (LOPAC, anti-cancer, kinase Inhibitor, bioactive lipids) containing >2700 compounds to identify classes of molecules with MET-promoting properties (FIG. 1C). Of note, in the mesenchymal NAMEC8 SERPINE1prom-Luc reporter cells, we further incorporated a Renilla-luciferase reporter that was under the control of a constitutive CMV promoter as a readout for cell numbers. The purpose was to identify compounds that alter cell states without adversely impacting cell viability (FIG. 1A). From this primary screen, the 'hit rate' was 2.19% (61 compounds). Z-score was also calculated and plotted (FIG. 8A). These were validated in a secondary screen and dose-response measurements, demonstrating a concordance rate of 83.6% (51 compounds), thus underscoring the robustness of the reporter-based screen (FIG. 1D, E and Table 1). At least 8 classes of compounds were represented, including TGFβ inhibitors, which we earlier used as a positive control. Interestingly, compounds such as adenosine/adrenergic, GABA and NMDA receptor agonists and antagonists, and some neurotransmitters, which have not been previously implicated in cell state transitions, were identified as potential regulators.

Amongst the classes, retinoids appeared to induce the most dramatic reductions in the SERPINE1prom-Luc reporter, doing so in a dose-dependent manner (FIG. 1E).

TABLE 1

| | | Avr FF/Renilla from DMSO | % Avr Renilla from DMSO |
|---|---|---|---|
| Library | Compound | | |
| AC | Amuvatinib (MP-470) | 0.23 | 213.43 |
| AC | Evista (Raloxifene HCl) | 0.60 | 70.31 |
| AC | Isotretinoin | 0.57 | 72.18 |
| AC | SB 216763 | 0.56 | 107.55 |
| AC | Tretinoin (Aberela) | 0.50 | 86.97 |
| LOPAC | 1,3-Dipropyl-8-p-sulfophenylxanthine | 0.61 | 103.45 |
| LOPAC | 5-Bromo-2'-deoxyuridine | 0.67 | 65.72 |
| LOPAC | Alprenolol hydrochloride | 0.80 | 90.18 |
| LOPAC | Amiodarone hydrochloride | 0.59 | 86.89 |
| LOPAC | Apomorphine hydrochloride hemihydrate | 0.84 | 85.06 |
| LOPAC | Atropine methyl nitrate | 0.68 | 102.95 |
| LOPAC | Cantharidic Acid | 0.40 | 74.59 |
| LOPAC | L-798106 | 0.13 | 68.99 |
| LOPAC | L-Aspartic acid | 0.71 | 99.27 |
| LOPAC | Rhodblock 6 | 0.87 | 89.97 |
| LOPAC | TNP | 0.88 | 80.47 |
| LOPAC | Bexarotene | 0.31 | 87.48 |
| LOPAC | PD-161570 | 0.39 | 74.13 |
| LOPAC | SB-525334 | 0.37 | 51.73 |
| LOPAC | 13-cis-retinoic acid | 0.37 | 84.14 |
| LOPAC | AC-55649 | 0.59 | 106.55 |
| LOPAC | Raloxifene hydrochloride | 0.37 | 95.20 |
| LOPAC | Retinoic acid | 0.35 | 88.00 |
| LOPAC | Tazarotene | 0.59 | 67.01 |
| LOPAC | TTNPB | 0.19 | 58.46 |
| LOPAC | U0126 | 0.45 | 101.92 |
| KI | Amuvatinib (MP-470) | 0.37 | 140.20 |
| KI | AG-490 | 0.47 | 64.03 |
| KI | Abitrexate (Methotrexate) | 0.56 | 55.63 |
| KI | Roscovitine (Seliciclib, CYC202) | 0.63 | 53.69 |
| KI | PIK-294 | 0.68 | 81.52 |
| KI | U0126-EtOH | 0.62 | 76.21 |
| KI | PH-797804 | 0.67 | 52.95 |
| KI | Arry-380 | 0.73 | 67.35 |
| KI | Motesanib Diphosphate (AMG-706) | 0.70 | 50.91 |
| KI | CH5132799 | 0.71 | 50.62 |
| KI | PIK-93 | 0.72 | 75.51 |
| Lipids | KN-62 | 0.43 | 67.80 |
| Lipids | 16,16-dimethyl Prostaglandin D2 | 0.48 | 52.62 |
| Lipids | SB 431542 | 0.50 | 51.90 |
| Lipids | Prostaglandin D2 Ethanolamide | 0.55 | 65.62 |
| Lipids | 6-keto Prostaglandin E1 | 0.55 | 79.67 |
| Lipids | Prostratin | 0.55 | 145.99 |
| Lipids | CAY10587 | 0.56 | 72.88 |
| Lipids | 15-deoxy-_12,14-Prostaglandin D2 | 0.57 | 68.09 |
| Lipids | UCM707 | 0.57 | 88.05 |
| Lipids | D 4476 | 0.57 | 53.26 |
| Lipids | 16-phenoxy tetranor Prostaglandin A2 | 0.59 | 82.64 |
| Lipids | KN-93 | 0.59 | 54.45 |
| Lipids | Prostaglandin D2-1-glyceryl ester | 0.59 | 58.41 |
| Lipids | C-8 Ceramide | 0.54 | 70.74 |
| Lipids | S-ethyl N-[4-(trifluoromethyl)phenyl] Isothiourea (hydrochloride) | 0.59 | 76.76 |

Figure 9:
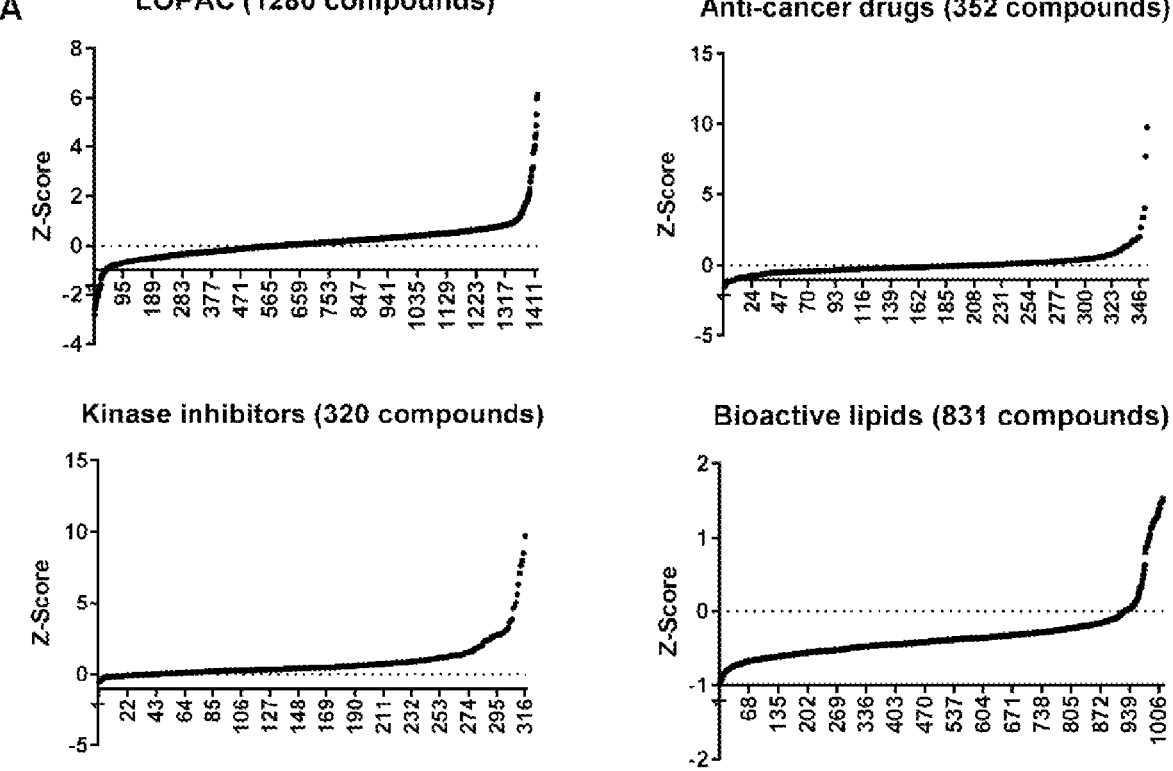
FIG. 9. (A) Z-scores for dual-glo luciferase assay of NAMEC8-SERPINE1prom-Luc cells treated with LOPAC (top left), anti-cancer drugs (top right), kinase inhibitors (bottom left) and bioactive lipids (bottom right). Data are represented as mean, n=3.
Figure 13A:
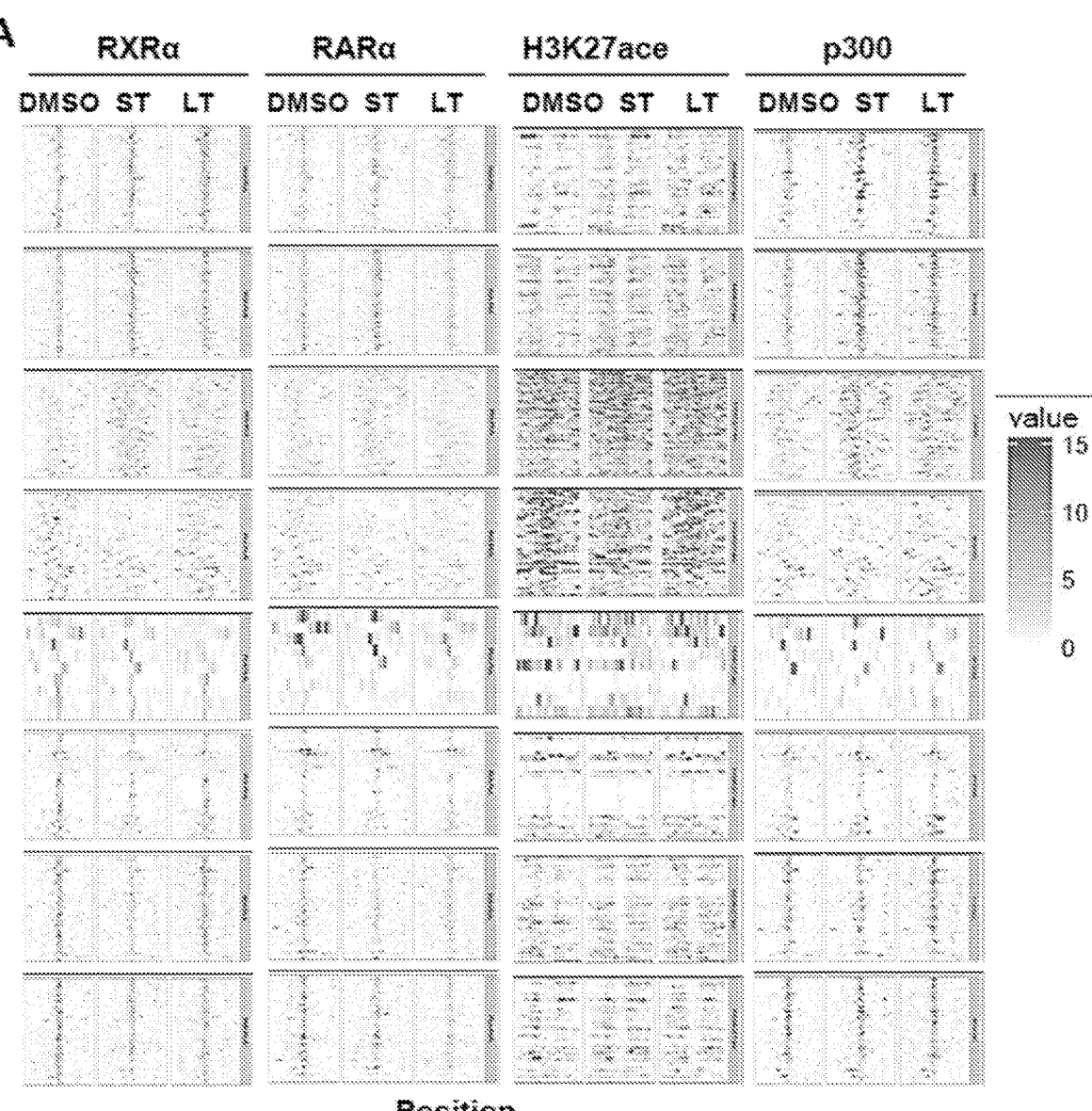
FIG. 13 (A) Global heat map of ChIP-Seq peaks in SUM159 treated with DMSO, ST (short term; 7 days) bexarotene or LT (long term; 14 days) bexarotene, with RXRα, RARα, H3K27ac and p300 antibodies. (B) Plots showing the occupancy of RXRα, RARα, H3K27ac and p300 at gene bodies upon ST- and LT-bexarotene treatment in SUM159 cells. (C) Gene tracks depicting increases in RXRα and H3K27ac binding at STRA6, DHRS3, PLIN1, PLIN2 and ACSL5 loci, and decreases in RXRα and H3K27ac binding at MGLL locus upon ST- and LT-bexarotene treatment in SUM159 cells. The x-axis shows chromosome position with the gene structure drawn below and each scale unit represents 5 kb. The y-axis shows genomic occupancy in units of rpm per bp. (D) Gene Ontology pathway enrichment analysis of genes from RNA-Seq that have log 2 fold change >1 upon LT bexarotene treatment in SUM159. (E) Gene Ontology pathway enrichment analysis of genes from RNA-Seq that have log 2 fold change >1 upon bexarotene treatment in MetBr-007-DR. (F) Plot of super-enhancers ranked by increasing H3K27ac signals in SUM159 treated with bexarotene. (G) Gene expression of lipid-associated genes involved in TAG synthesis upon TTNPB treatment relative to DMSO in NAMEC8. Data are represented as mean+/−SEM, n=3, *P<0.05, **P<0.01.
Figure 13B:
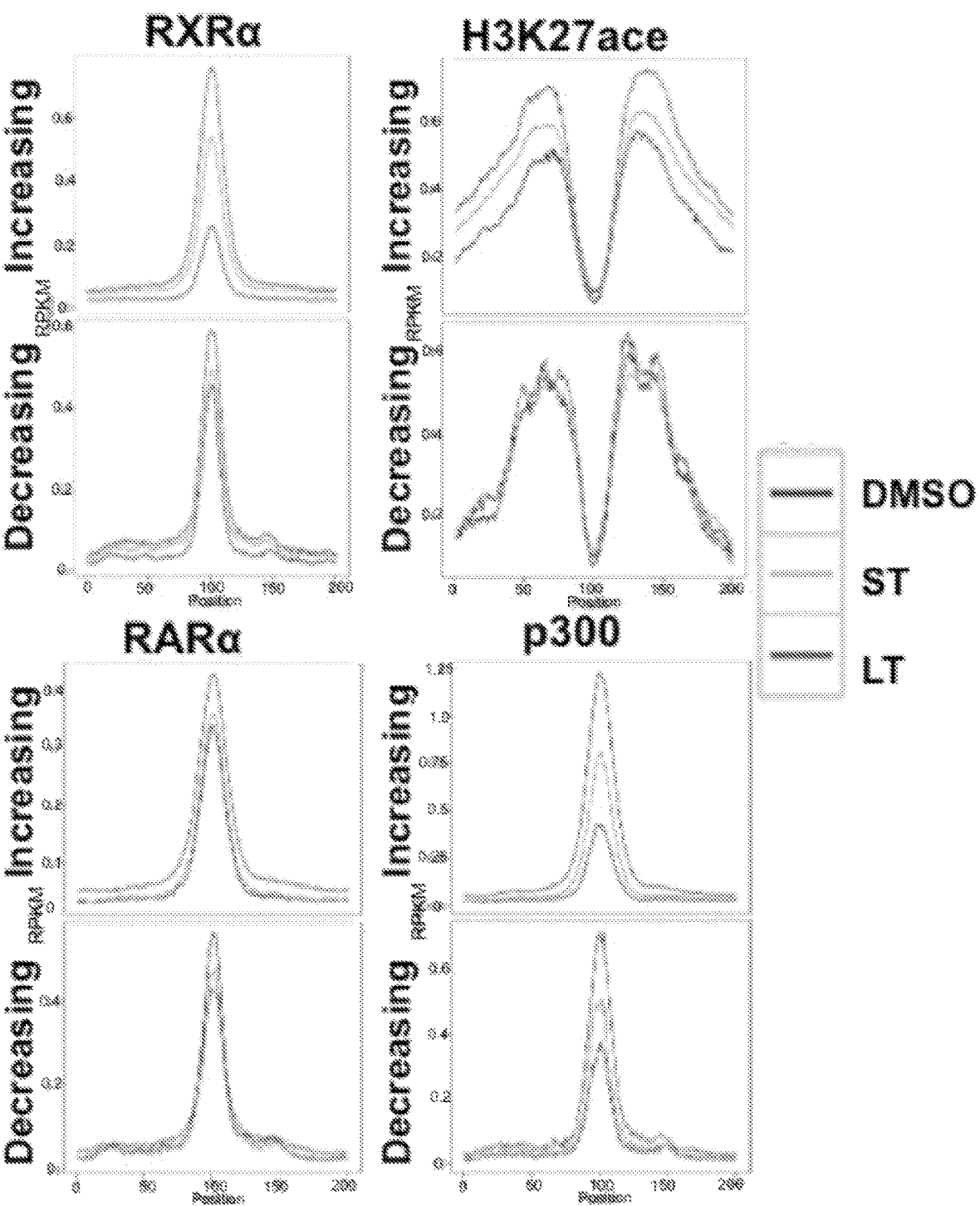
Figure 13C:
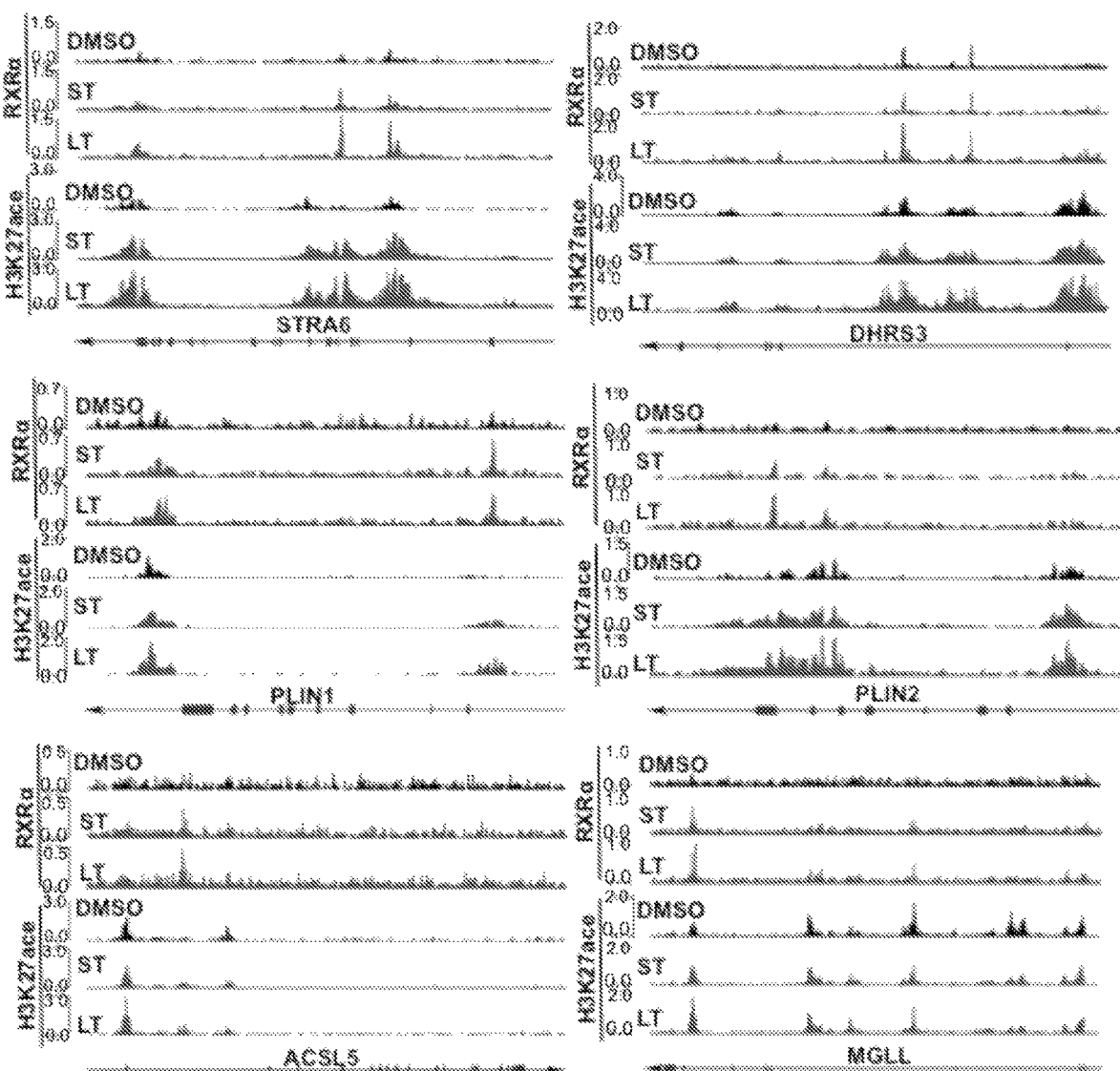

Retinoids Induce the Conversion of Basal-Like Breast Cancer Cells to Become Luminal and Enhance their Sensitivities to Chemotherapy We chose to focus on retinoids as MET-inducing agents for several reasons. First, they represent the most potent class of MET-inducing compounds in our screens. Second, they are clinically viable agents that are being used in acute promyelocytic leukemia as differentiating agents, although their utility and efficacy towards other cancers remains unclear. Lastly, the manner and mechanism by which retinoids induce changes in cell states or promote differentiation have not been well-elucidated. From our screen, we chose the strongest RARα (TTNPB) and RXRα (bexarotene) agonists for validation studies, as well as for biochemical and pathway characterization. Consistent with the downregulation of the SERPINE1prom-Luc reporter activity, which marked a mesenchymal cell state, treatment of NAMEC8 and another mesenchymal TNBC cell line, SUM159, with either bexarotene or TTNPB caused a dramatic change in morphology from scattered, spindle and fibroblastic-like cells to an epithelial-like morphology, characterized by tight clusters of epithelial islands (FIGS. 2A and 9A). This morphological change was associated with the downregulation of mesenchymal signature markers (ZEB1, SERPINE1, FN1, SLUG) and the concomitant gain of epithelial marker CDH1 (FIGS. 2B, C, D and 9B, C). For the first time, we noted a switch in cytokeratin expression from the KRT5, typically associated with basal-like, triple-negative breast cancer to KRT8, which is expressed in the luminal, ER+ subtype of breast cancer. Mucin1 (MI (1), a characteristic marker of luminal breast cancer not commonly found in TNBC, was upregulated as well. These data provided the first indications that beyond a MET, these cancer cells, which were thought to represent basal-like, triple-negative breast cancer, might have gained luminal-like features. Because the mesenchymal phenotype has been shown to be associated with a cancer stem-like state, we examined the expression of CD44 and mammosphere-forming ability of the retinoid treated cells. Both NAMEC8 and SUM159 cells showed significant reductions in surface CD44 expression via flow cytometry, and a dramatically decreased mammosphere-forming capability (FIGS. 2E, F and 9D, E).

To further assess the effects of retinoids beyond classic cancer cell lines, which tend to be homogeneous, have diverged from their parental tumors, or have altered plasticity, we generated a panel of patient-derived tumor cell lines from biopsied or resected triple-negative and ER+ breast tumors (Table 2). Consistent with our previous findings, bexarotene treatment of the patient-derived triple-negative breast cancer cell lines (BC2.2, BC22.1, BC29.1, MetBR 007-DR) increased the expression of E-cadherin, while reducing SLUG expression, to varying extents. More remarkably, however, we continued to observe the switch in cytokeratin expression from KRT5 to KRT8, along with the gain in MUC1 expression as well (FIGS. 2G, H and 9F, G). Mammosphere-forming abilities of patient-derived cancer cells were also decreased upon retinoid treatment (FIGS. 2I and 9H). Surprisingly, in three of these tumor cell lines, we noted the upregulation of estrogen receptor (ER) expression, a hallmark of ER+, luminal breast cancer. Estrogen response element (ERE)-luciferase reporter was also increased upon treatment with bexarotene or TTNPB (FIG. 9I). In support of this, ER target genes such as ABCA3, NRIP1, TFF1 and CREB1 were strongly elevated by bexarotene treatment in both cancer cell lines (NAMEC8 and BC2.2) (FIG. 9J). Since the otherwise basal-like cancer cells had now gained ER expression, we wondered if they also acquired sensitivity to anti-ER therapy that is administered for breast cancer patients harboring ER+ tumors. Interestingly, bexarotene-treated cancer cells appeared to have gained sensitivity to low doses of the selective ER modulator, Raloxifene hydrochloride (FIG. 9K). Nonetheless, we noted that the difference in drug sensitivity was a moderate two-fold, thus suggesting that the conversion from a basal to a truly luminal phenotype may be incomplete. Quite interestingly, when bexarotene was applied to the patient-derived tumor cell lines (BC24.1 and BC33.1) generated from ER+, luminal-like breast tumors, there was no dramatic change in the expression of the epithelial/mesenchymal or luminal/basal markers (FIGS. 2G and 9L), suggesting that retinoids exert their effects in mesenchymal-like but not epithelial-like breast cancer cells.

Next, we wanted to establish that the retinoids were indeed acting and signaling through the retinoic acid receptors (RXRα or RARα). Using shRNA targeting RXRα, stable knockdown was achieved in NAMEC8 (FIG. 9M). The gain in epithelial-luminal markers and loss of mesenchymal-basal markers induced by bexarotene were now abrogated in the RXRα-knockdown cells (FIG. 9N, O). These confirmed that retinoid-induced cell state changes were dependent on the RXRα receptor and its downstream activities.

The gain of a mesenchymal cell phenotype through EMT has been shown to confer resistance to broad chemotherapy. We reasoned that the reverse phenomenon, a MET, may sensitize otherwise mesenchymal cancer cells to chemotherapeutic drugs, thereby overcoming resistance. Not surprisingly, in both classic mesenchymal-like cancer cell lines (NAMEC8 and SUM159) and two patient-derived TNBC cell lines (BC2.2 and BC22.1), the exposure to bexarotene which caused a MET, was able to confer susceptibility to 5-FU or paclitaxel, standards of care for TNBC, by at least 4-6 folds (FIGS. 2J, K, and 9P, Q, R).

In the context of breast cancer management, the use of retinoids in combination with chemotherapy in treatment-naïve patients may not be feasible. For retinoids to be useful as a therapeutic agent in TNBC, it needs to be evaluated in chemotherapy-resistant cancer cells. To test this, we generated paclitaxel-resistant (PACR) SUM159 cells, which had a >20-fold increase in paclitaxel-resistance compared to the parental (PT) cells (FIG. 2L). SUM159 PACR cells changed from a mesenchymal-like to an epithelial-like phenotype, taking on a clustered morphology and bearing elevated expressions of epithelial and luminal markers following treatment with bexarotene (FIG. 9S, T, U). Bexarotene-treated PACR cells also had reduced mammosphere-forming ability (FIG. 9V), suggesting a decrease in cancer stem cell-like property. More importantly, they gained sensitivity to an alternative chemotherapeutic drug, 5-flurouracil (5-FU), thus indicating that drug-resistant cancer cells may respond to such a therapeutic strategy (FIG. 2M).

TABLE 2

Molecular information of patient-derived breast cancer cell lines.

| Patient ID | Type | Estrogen Receptor | Progesterone Receptor | HER2 receptor |
|---|---|---|---|---|
| BC 2.2 | Masectomy | – | – | – |
| BC 29.1 | Masectomy | – | – | – |
| MetBr-007-DR | Biopsy | – | – | – |
| BC 22.1 | Masectomy | – | – | – |
| BC 24.1 | Masectomy | + | + | – |
| BC 33.1 | Masectomy | + | – | – |

Retinoid Administration Promotes MET In Vivo and Reduces the Tumorigenicity of TNBC Cells in Animals We reasoned that the conversion from a mesenchymal to an epithelial cell state may cause otherwise basal, mesenchymal-like breast cancer cells to lose tumorigenicity. Ex vivo treatment of SUM159 cells with bexarotene or TTNPB indeed severely crippled their tumorigenic potential for up till seven weeks post-transplantation into immunocompromised NSG mice, although, after which, tumor growth picked up (FIGS. 3A and 10A), indicating that short-term (14 days) ex vivo treatment was not sufficient to mediate a permanent or durable change in cell state. It also suggested that the continuously enforced treatment of bexarotene may be necessary to arrest tumor growth. Interestingly, when a luminal, epithelial-like breast cancer cell line, MCF7-Ras, was similarly exposed to bexarotene or all-trans retinoid acid (ATRA), no impact on the tumor cell growth was observed (FIGS. 3B and 10B). Of note, the reductions in tumorigenicity were not attributed to the effect of retinoids in arresting cell proliferation as they maintained similar growth capacity with control cells (FIG. 10C). This clearly underscores the utility of retinoid-induced cell state changes in basal, but not luminal breast cancers.

To evaluate the efficacy of retinoids in tumor-bearing animals, we first transplanted NAMEC8-Ras cells and two other patient-derived TNBC cell lines (BC2.2 and BC22.1) into NSG mice and allowed the tumors to reach ~3 mm in diameter by week 4. One group was dosed with bexarotene and the other group with vehicle control via oral gavage daily for the duration of the study. Bexarotene-fed tumor-bearing mice showed significant reductions in tumor growth rate and burden, compared to vehicle-treated mice (FIGS. 3C and 10D, E). To understand the cause of this growth reduction, we collected the residual tumors for analyses. Immunohistochemistry of tumors showed that control tumors were grade 3 carcinoma with ductal features, whereas tumors from bexarotene-treated mice were discohesive and splayed apart. The latter also showed the presence of spindled cells with focal necrosis, fibrovascular cores suggesting possible papillary or pseudopapillary component (FIG. 3D), thus suggesting a shift in cell states. To confirm this, we performed immunofluorescence staining of EMT markers in the tumor sections. Tumors from bexarotene-treated mice now showed the expression of E-cadherin, and the loss of fibronectin, thus indicating an MET phenotype had occurred in vivo as a result of therapeutic intervention for the first time. Furthermore, there was a switch in cytokeratin expression, from the basal-associated KRT5 to the luminal-associated KRT8 in these tumors (FIGS. 3E and 10F). Since retinoids activate target genes such as STRA6, CRAPBP2, DHRS3, ANGPTL4, IP6K3, and ACSL5 through the RXR and RAR receptors which bind DNA, we analyzed their expressions in tumors of treated animals. All target gene expressions were upregulated by at least two-fold (FIG. 3F), thus confirming that the switch in cell state was mediated through retinoid target gene activities.

Example 2

Epigenetic Perturbations Enhance and Increase the Durability of Retinoid-Induced Cell state changes While retinoids could promote MET of mesenchymal breast cancer cells, the phenotype appeared to be reversible, at least partially, in the absence of sustained retinoid exposure. This pointed to inherent plasticity of cancer cells, possibly a result of dynamic epigenetic remodeling. We hypothesized that one might be able to reinforce the epithelial cell state through modifying the epigenetic landscape in combination with retinoid-induced cell state transition. As a start, we tested whether epigenetic-modifying compounds, on their own, could induce a MET. In a manner similar to our screen for MET compounds as described earlier, we screened 35 epigenetic-modifying compounds, six of which were able to downregulate the SERPINE1prom-Luc activity in the mesenchymal NAMEC8 reporter cells. While these reduced the activity by between 15-53%, the vast majority did not achieve the same magnitude caused by bexarotene treatment (FIG. 4A). We next evaluated whether the combination of epigenetic compounds with bexarotene might result in greater effects towards MET. Interestingly, several epigenetic compounds were able to produce additive benefit together with bexarotene, thereby inducing a more drastic downregulation of the SERPINE1prom-Luc activity (FIG. 4B). We focused on Cl-994 and SBHA, both of which are Class I HDAC inhibitors (HDACi).

Combined HDACi with bexarotene led to more robust changes in epithelial cell morphology and associated EMT markers (FIGS. 4C, D and 11A). For instance, ZEB1 and SLUG were more strongly reduced, whereas the gain in KRT8 and MUC1 were more apparent. Because retinoids alone did not result in a stable MET phenotype, we evaluated whether the combination might prolong the maintenance of the epithelial cell state following the withdrawal of both agents. Indeed, the reduction in SERPINE1prom-Luc activity of NAMEC8 cells treated with retinoids alone recovered after three days of drug withdrawal, whereas it was sustained in cells treated with a combination of retinoids and HDACi (FIG. 11B, C). More importantly, when the compounds were withdrawn following a seven-day treatment, the cancer cells which had undergone an MET were able to maintain the epithelial phenotype for at least another seven days (FIG. 4E, F, G). Furthermore, mammosphere-forming ability was also continually suppressed (FIGS. 4H and 11D, E). In contrast, bexarotene alone-treated cells gradually reverted to a more mesenchymal cell phenotype, with a partial reestablishment of mammosphere-forming ability. In the absence of retinoid ligands, RAR and RXR bind DNA while being associated with transcription co-repressors that include NCoR and HDAC, leading to gene silencing. When exposed to retinoids, these bind the receptors and lead to the recruitment of co-activators such as the histone acetyltransferase, p300. Simultaneously, it is likely that the inhibition of HDAC allowed for the maintenance of a gene transcription-promoting epigenetic landscape, thus resulting in a more potent and durable MET (FIG. 4I).

Lipid Metabolism Genes are Regulated by Retinoid Receptors

Figure 5C:
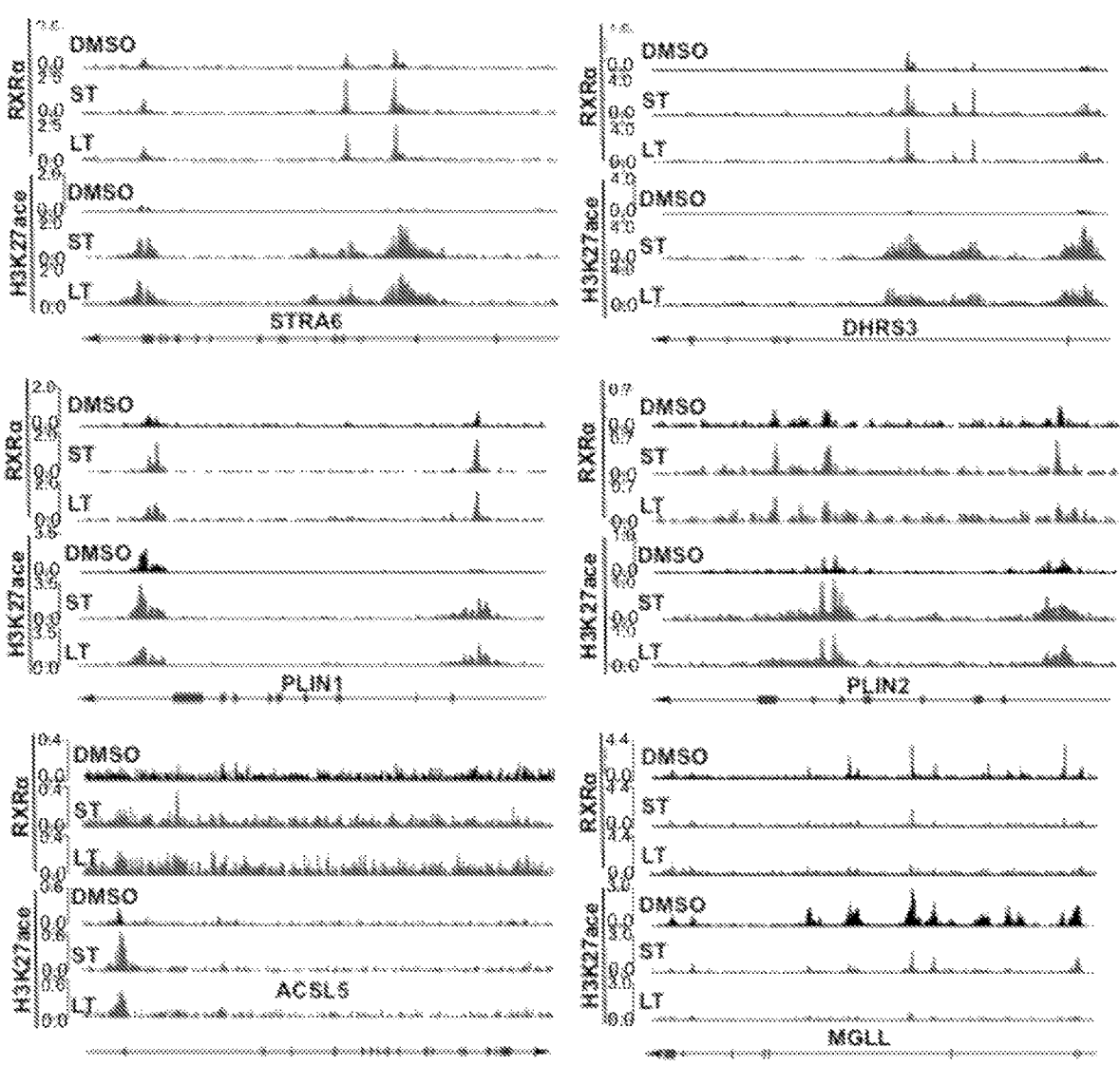

RAR and RXR are DNA-binding transcription factors and exert their influence through modulating target gene expression in the presence or absence of retinoids. Reported pathways associated with retinoid signaling include TGFβ, NFkB and Nrf2[27-29]. To understand the manner by which RAR and RXR program cell state transitions, we performed ChIP-seq to identify their compendium of target genes in an unbiased manner. We exposed the mesenchymal NAMEC8 and SUM159 cancer cells to short-term (ST: 7 days) and long-term (LT: 14 days) retinoid treatment, followed by the genome-wide analyses of target gene binding sites for RXR, RAR, and p300. Exposure to bexarotene, a RXR ligand, led to a subset of genes that became bound by RXR, as well as RAR, since both could form heterodimers. These genes furthermore showed increases in p300 binding, and H3K27ac (histone 3, lysine 27 acetylation) modification, which marks gene enhancers (FIGS. 5A, B and 12A, B). For instance, well-known retinoid target genes such as STRA6 and DHRS3 amongst others, which were original not bound by RXR in the mesenchymal cell state, became bound upon MET (FIGS. 5C and 12C).

We next sought to identify the functional pathways regulated by RXR by mapping the top RXR-bound genes using gene ontology analyses. This revealed lipid metabolism to be a major pathway that was perturbed during MET—a phenomenon that has not been previously investigated (FIG. 5D). To further test if the RXR-bound genes were associated with transcriptional changes caused by RXR activation, we performed RNA-seq of cancer cell lines and patient-derived cancer cells treated with bexarotene to detect gene expression changes. Consistent with the above analyses, genes that were upregulated at least more than two-folds showed clear enrichment in pathways relating to lipid metabolism (FIG. 12D, E). Superenhancers are features of keystone genes that help define cell states and cell lineages. Analyses of H3K27ac mark revealed key genes that contained superenhancers, upon MET. Amongst these were retinoid target genes such as DHRS3, RXR and GDF15, as well as lipid metabolism genes such as B4GALT5 and ACSL1 (FIGS. 5E and 12F). For instance, lipid metabolism genes such as PLIN1, PLIN2, ACSL5 and MGLL demonstrated clear RXR recruitment and increased H3K27ac modification upon bexarotene treatment (FIGS. 5C and 12C); this further underscores their putative role in MET.

Figure 5F:
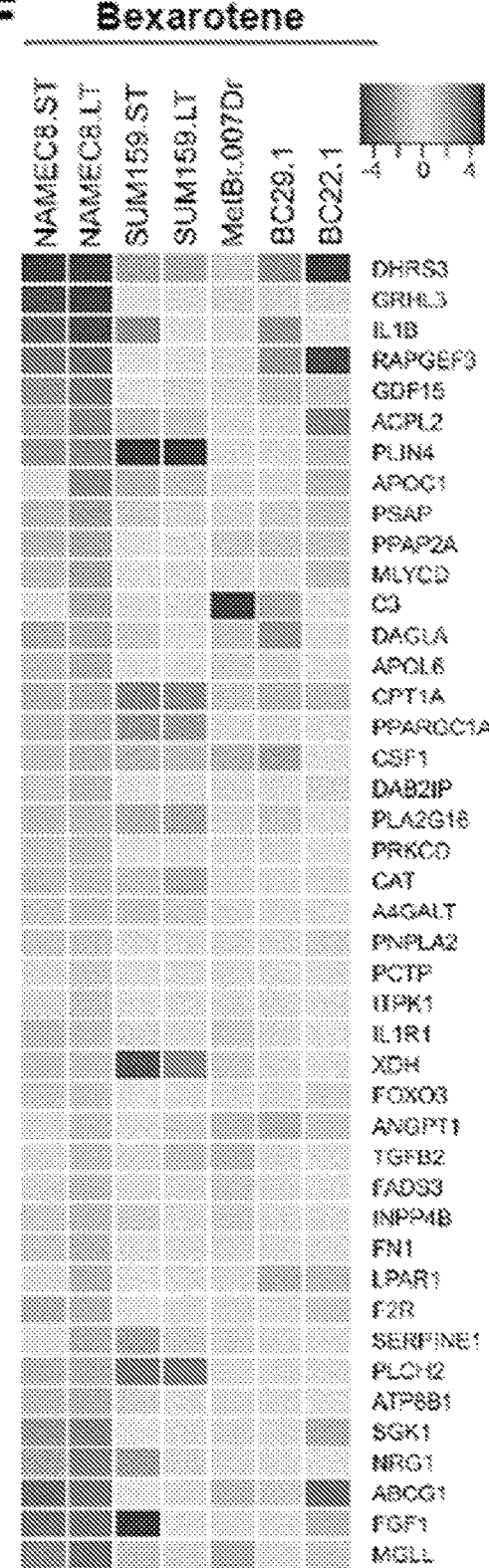

To clarify which specific aspects of lipid metabolism might be altered during cell state changes, we examined in greater detail the list of RXR target genes which showed consistent up- or down-regulation across multiple cancer cell lines and patient-derived cancer cells treated with bexarotene (FIG. 5F). Interestingly, many of the lipid-associated genes form the pathway that produces triacylglycerides (TAGs) from fatty acids. Genes involved in TAG synthesis (ACSL4, ACSL5, AGPAT4, AGPAT9, GPAM, DGAT2, PLIN1) were upregulated, whereas MGLL, a lipase involved in TAG degradation was strongly down-regulated (FIGS. 5G and 12G). Thus, these results strongly pointed to the reprogramming of lipid metabolism during MET.

Mesenchymal-Epithelial Transition Restricts β-Oxidation by Channeling Fatty Acids Towards Lipid Storage A major fate of fatty acids is their conversion and storage as TAGs. Key lipid metabolism enzymes, long-chain-fatty-acid-CoA ligase (ACSL), glycerol-3-phosphate acyltransferase (GPAT), 1-acylglycerol-3-phosphate O-acyltransferase (AGPAT), prostatic acid phosphatase (PPAP) and diglyceride acyltransferase (DGAT), which were all upregulated upon retinoid treatment, might help drive the conversion of fatty acids to intermediates such as diacylglycerides (DAG) and TAG (FIG. 4a). To demonstrate this, we determined the fate of fatty acids and their downstream intermediates using lipid-based mass spectrometry-based lipidomics upon changes in cell states. Indeed, following bexarotene treatment, lipid species such as phosphatidylinositols (PI), phosphatidylglicerols (PG), phosphatidylcholines (PC), phosphatidylethanolamines (PE) and phosphatidylserines (PS), which are the downstream metabolites of fatty acids, were dramatically increased. Accumulation of DAG and TAG species was also observed (FIG. 6a). TAGs, when accumulated, may be stored in lipid droplets. Interestingly, a clear abundance of lipid droplets was observed in mesenchymal cancer cells that had undergone an MET, whereas control-treated cells did not contain as many lipid droplets (FIG. 6b and FIG. 14a), suggesting that the fate of fatty acids might differ in the mesenchymal and epithelial cell states.

We sought to test functionally whether intermediate lipid enzymes involved in the TAG synthesis pathway were indeed necessary for the regulation of MET. Pharmacological inhibition of GPAT (using FSG67) and DGAT (using AmidepsineA), as well as shRNA knockdown of AGPAT9, all resulted in clear reductions in the accumulation of lipid droplets during retinoid treatment, when compared to vehicle treatment or control shRNA knockdown (FIG. 14b).

This was due to the blockade in MET as the gain in epithelial-luminal gene markers such as E-cadherin, KRT8, and MUC1 were suppressed when GPAT, DGAT, or AGPAT9 were functionally disrupted, even in the presence of retinoid treatment (FIG. 14c). Associated with the block in MET were the corresponding rescues in mammosphere formation ability of these mesenchymal NAMEC8 cells, clearly underscoring the importance of the TAG synthesis pathway for the epithelial cell state (FIG. 6c and FIG. 14d).

Since a more epithelial cell state appeared to be associated with greater lipid storage, we reasoned that in the mesenchymal cell state, fatty acid might be utilized as an energy source for alternative biochemical pathways such as fatty acid β-oxidation (FAO). β-oxidation is the catabolic process by which fatty acids are broken down in the mitochondria to produce acetyl-CoA for fueling the TCA cycle. Here, we used oxygen consumption rate (OCR) as a readout of TCA cycle activity. Using palmitate as a source of fatty acid, control-treated cells residing in the mesenchymal state clearly favored palmitate for energy production. By contrast, bexarotene-treated cells, which had transited to the epithelial state, showed a lower OCR when supplemented with palmitate (FIG. 6d and FIG. 14e, f), thus suggesting that the utilization and fate of fatty acids differed between cancer cells residing in different cell states. Cancer cells which are mesenchymal tend to rely on β-oxidation, whereas those in the epithelial state appeared to shunt fatty acids towards lipid droplet storage.

Having observed this switch in the fate of fatty acids utilization from β-oxidation to lipid storage in retinoid-induced MET, we wondered if cancer cells in their native cell states also manifested such metabolic preferences. Comparing two isogenic cell lines stably residing in either the epithelial (HMLE) or the mesenchymal (NAMEC8) cell state, the former indeed showed the greater accumulation of lipid species to favor TAG production and, ultimately, lipid droplets formation (FIG. 6e, f and FIG. 14g). A higher dependency on β-oxidation was reflected by higher FAO rates in mesenchymal NAMEC8 compared to epithelial HMLE and the mesenchymal cancer cell lines (BT549, MDA-MB-468 and SUM159) had similarly higher FAO rates compared to the epithelial cancer cell lines (MCF7 and T47D) (FIG. 6g). Importantly, a growth advantage was observed in mesenchymal cancer cell line BT549 when supplemented with fatty acids palmitate or lipoic acid under nutrient-deprived conditions, while epithelial cancer cell line MCF7 did not exhibit such metabolic preferences (FIG. 6h).

Induction of Mesenchymal-Epithelial Transition is Dependent on Fatty Acid Modifier Carnitine Palmitoyltransferase If cancer cells are indeed dependent on β-oxidation for maintenance of a mesenchymal phenotype, we hypothesized that inhibiting β-oxidation might be useful to promote or stabilize the epithelial cell phenotype through restricting the metabolic pathways that cancer cells rely on. Carnitine palmitoyltransferase I (CPT1) is a key mitochondria enzyme responsible for catalyzing the transfer of an acyl group from long-chain fatty acyl-CoA to form acyl carnitines. In essence, this allows for the transport of fatty acids into the mitochondria for fueling the TCA cycle and utilizing fatty acids as a source of energy. We first showed that exposing mesenchymal cancer cells to a CPT1 inhibitor, etomoxir, alone, or together with bexarotene, completely inhibited FAO activity (FIG. 15a). Although we demonstrated that bexarotene alone could cause an MET, etomoxir, on its own, was unable to do so. Nevertheless, the combination of bexarotene and etomoxir exerted a more potent MET phenotype that was more durable and sustained even when the drugs were removed for at least seven days (FIG. 7a and FIG. 15b, c). Cells that had been treated with the combination therapy also sustained the inhibitory effect on mammosphere formation after drugs were withdrawn (FIG. 7b and FIG. 15d).

To show that the enhancement of MET by addition of etomoxir are on-target, we carried out genetic knockdown of CPT1A, the major isoform of CPT1, in NAMEC8. Knockdown of CPT1A resulted in increased accumulation of lipid droplets after bexarotene treatment (FIG. 7c) and this corresponded with a stronger MET phenotype as shown by stark decreases in mesenchymal/basal proteins and increases in luminal proteins (FIG. 7d). An enhanced MET phenotype was also exhibited by greater inhibition of mammosphere formation upon bexarotene treatment in CPT1A-knockdown cells compared to control cells (FIG. 7e).

If mesenchymal cancer cells were indeed metabolizing fatty acids through β-oxidation, we reasoned that the increased activity of CPT1 through its overexpression would overcome the effects of bexarotene, and the induction of an epithelial cell phenotype. We overexpressed CPT1A in NAMEC8 cells, and strikingly, this was sufficient to overcome the bexarotene-dependent inhibition of FAO (FIG. 15e). In two cell lines overexpressing CPT1A, cells clearly showed the absence of lipid droplets even upon bexarotene treatment (FIG. 7f and FIG. 15f), further indicating an active FAO in CPT1A-overexpressing cells. This corresponded with the maintenance of a mesenchymal phenotype in CPT1A-overexpressing cells upon bexarotene treatment, as evidenced by cells growing in a scattered fashion (FIG. 15g), maintenance of mesenchymal markers and suppressed induction of epithelial/luminal markers upon bexarotene treatment (FIG. 7g). In a mammosphere-forming assay performed in CPT1A-overexpressing cell lines, mammosphere formation was rescued, even in the presence of bexarotene treatment (FIG. 7h and FIG. 15h); this suggested that the enhanced import of fatty acids into the mitochondria for β-oxidation was sufficient to overcome the effects of cell state changes induced by bexarotene. Thus, while an upstream trigger of cell state transition is necessary, the reprogramming of metabolic requirements was essential in enforcing cell states, and appeared sufficient to overcome the effect of MET inducers.

Impairment of Fatty Acid Oxidation Re-Channels Lipids Towards the Support of an Epithelial Cell State and Blocks EMT Since MET programs the fate of fatty acids towards lipid storage, we reasoned that the reverse process, an EMT, would lead to opposite outcomes. Using three different cell lines (HMLE-Twist-ER, HMLE-Zeb1, MCF7-Slug) containing the inducible expression of EMT transcription factors Twist, Zeb1 and Slug, respectively, we observed a significantly larger number of lipid droplets when cells were in the epithelial state, which were lost as cells transited to the mesenchymal state (FIG. 8a). Using HMLE-Twist-ER cells, we also demonstrated that the activation of an EMT program could reprogram the metabolic requirements of the cancer cells from lipid storage to β-oxidation, as measured by OCR (FIG. 8b and FIG. 16a).

Since the shifts in metabolic reprogramming during EMT were translated to changes in FAO, we hypothesized that the inhibition of CPT1 might have consequences on EMT progression. Exposure of the HMLE-Twist ER cells to 4-OHT induced an EMT, whereas treatment with etomoxir was able to dramatically block this transition (FIG. 8c, d). This was replicated in, yet, another inducible EMT cell line model, MCF7-Slug+Sox9, whereby etomoxir blocked Slug+ Sox9-induced EMT in MCF7 breast cancer cells as well (FIG. 16 *b, c, d*) 32. The importance of CPT1 to the EMT program was also demonstrated by genetic knockdown of CPT1A, which resulted in failure to induce EMT progression and hence maintenance of an epithelial phenotype (FIG. 8*e, f* and FIG. 16*e*). This underscores the importance of fatty acid utilization in controlling and programming cell states. The effects of etomoxir in blocking TGFβ-induced EMT is also shown in a lung cancer cell line A549 (FIG. 16 *f* and *g*).

Finally, we sought to functionally test whether the direct perturbation of metabolic pathways, in this case, fatty acid oxidation, could alter the course of EMT-induced metastasis in animal models in vivo. We utilized the cell line model MCF7-Slug+Sox9, whereby doxycycline-inducible concomitant expression of the EMT transcription factors, Slug and Sox9, in pre-established MCF7 tumor xenografts could strongly induce EMT in vivo and promote the metastasis of otherwise non-metastatic tumor cells from the fat-pads to the lungs of NSG mice (FIG. 8*g*) 32. Here, MCF7-Slug+Sox9 cells were transplanted into the fat-pads of NSG mice and drug treatment was started one week after implantation. One group of mice was administered with etomoxir (20 mg/kg per day) prior to doxycycline administration. Another group of mice were given doxycycline, while sham-treated with vehicle control. After 10 weeks, immunofluorescence analysis showed that the primary tumors of control-treated mice remained epithelial in nature with expression of E-cadherin (FIG. 8*g*). In contrast, tumors of doxycycline-treated mice showed hallmarks of an EMT that included the expression of mesenchymal marker Vimentin and concomitant loss of E-cadherin. However, tumors of doxycycline-treated mice which also received etomoxir showed retention of the epithelial features, thus demonstrating a blockade of EMT in vivo. More importantly, extensive metastatic nodules were detected in the lungs of doxycycline-treated mice, whereas the counterparts which received etomoxir had a similar number metastatic lesions as control-treated mice (FIG. 8*g*). This provided the first proof-of-concept that fatty acid oxidation is necessary for the activation of an EMT program to spawn metastases, and the pharmacological inhibition of this crucial metabolic pathway may be useful for controlling metastasis in breast cancer.

Epigenetic Regulation Governs Cell State Transitions

As EMT is a reversible process, epigenetic mechanisms such as histone modifications and DNA methylation have been found to be important in regulating the expression of EMT responsive genes. The epigenetic silencing of E-cadherin during the activation of EMT program for instance, has been well-elucidated. Furthermore, studies have also reported that various epigenetic regulators, such as the histone deacetylase inhibitors (HDACi), are able to exert differentiation effects on cancer cells. Therefore, to elucidate the molecular link between EMT and epigenetic regulation, we carried out MET and inhibiting EMT screens using a comprehensive epigenetic library consisting of a wide range of epigenetic compounds—the Structural Genomics Consortium (SGC) Epigenetic Chemical Probe Library (Cayman).

For the MET screen, a good hit corresponds to one that can induce a lower SERPINE1 promoter activity as compared to A83-01. The primary screen revealed several hits that were capable of inducing MET without adversely affecting the cell viability (FIG. 17A). These hits include inhibitors of the protein arginine methyltransferase 5 (PRMT5), G9a/GLP histone methyltransferase, and CREBBP/EP300 bromodomains. They were then examined at six different concentrations to evaluate their dose-dependent changes to SERPINE1 promoter activity with increasing drug concentrations, and to compare the MET-inducing potentials of each compound (FIG. 17B). All four compounds showed a distinct dose-dependent decrease in SERPINE1 promoter activity with increasing concentration. After which, they were then put through in vitro validation assays to test for their efficacy in promoting MET in mesenchymal TNBC cells.

Systematic Validation of Epigenetic Hits Identifies CREBBP/EP300 Bromodomain Inhibitor as a Potent MET Inducer From the MET screen, four hits (FIG. 17C, circled in red) that were the most potent in decreasing SERPINE1 promoter activity were selected for in vitro validation studies. Namely, these compounds comprise of PRMT5 inhibitors-LLY-283 and GSK591, inhibitors of the histone methyltransferases, G9a and GLP-UNC0642, and inhibitor of CREBBP and EP300 bromodomains-SGC-CBP30. These compounds were first treated in mesenchymal NAMEC8 cells to morphologically validate if they could induce a change in cell state. As observed in FIG. 3C, only treatment with SGC-CBP30 resulted in an obvious change in cell morphology from scattered, spindle- and fibroblastic-like cells, to tight clusters of epithelial islands, which is a characteristic of epithelial-like morphology. This suggests that SGC-CBP30 is potentially a stronger agent in inducing MET in mesenchymal cells as compared to the other hits. The other three compounds, on the other hand, were not observed to induce an epithelial-like morphology in NAMEC8 (FIG. 17C).

Cells treated with the hits were then evaluated for changes in the transcript and protein expression of EMT and basal/luminal markers (FIGS. 17 D and E). Similar to the morphological observation, SGC-CBP30 was shown to be the most potent in inducing an epithelial phenotype. SGC-CBP30 significantly increased epithelial marker E-cadherin expression, as well as downregulated several mesenchymal markers, fibronectin, ZEB1 and SLUG. Conversely, no apparent change was observed in cells treated with LLY-283, GSK591 and UNC0642. Furthermore, since mesenchymal phenotype is often associated with basal-like cells, and the interest of the current study is in TNBC, basal and luminal markers were also assessed upon drug treatment. SGC-CBP30 treatment was observed to increase Mucin1 (MUC1)—a glycoprotein usually expressed in luminal breast cancers (FIGS. 17 D and E). Therefore, this suggests that SGC-CBP30 not only could induce MET, but could also mediate the gain of luminal-like features in basal-like mesenchymal cells.

When cells were resuspended in mammosphere media, LLY-283 (p<0.01), GSK591 (p<0.01), and SGC-CBP30 (p<0.05) pre-treatment were observed to significantly reduce the size and number of spheres formed. DMSO pre-treated cells in contrast, were able to form spheres efficiently (FIG. 17F). As such, this suggests that upon treatment with these compounds, the in vitro stemness of mesenchymal NAMEC8 cells was reduced. Additionally, breast stem-like cells are typically characterized by the presence of CD44high/CD24-/low cell surface markers. Hence, the expression of these cell surface markers was analyzed by flow cytometry upon treatment with SGC-CBP30, since this compound exhibited a stronger MET-inducing potential across the various validation assays. FIG. 3G showed that with SGC-CBP30 treatment, a population of cells with lower CD44 expression was observed, suggesting that the expression of this classical stemness marker was suppressed. This indicates a loss of stemness when NAMEC8 cells were treated with SGC-CBP30. The decrease in stem-like properties upon treatment strongly suggests a shift away from the mesenchymal cell state, since stem-like traits are associated with mesenchymal phenotype.

In order to ensure that the effects of these hits in promoting cell state transitions can be recapitulated in cancer cells, the compounds were further evaluated in TNBC cell line, SUM159. Similar to what was demonstrated in NAMEC8, SGC-CBP30 was observed to be a stronger MET inducer as compared to the other hits, increasing epithelial features and decreasing stemness in SUM159 (FIG. 18A-D). When SUM159 cells were analyzed by flow cytometry for the expression of CD44 and CD24 cell surface markers upon SGC-CBP30 treatment, cells demonstrated a slight decrease in CD44 expression, with a population of cells gaining the expression of CD24 (FIG. 31). This suggests a transition from a stem-like state (CD44high/CD24-/low) to a non-stem-like state (CD44low/CD24high) upon inhibition of the CREBBP/EP300 bromodomains in SUM159. These data thus demonstrate that SGC-CBP30 could not only reduce the mesenchymal and basal-like features, but could also induce a loss of stemness in TNBC, potentially making it less tumorigenic and invasive.

Inhibiting the Histone Acetyltransferase Domain of CRE-BBP/EP300 Proteins Failed to Induce a Potent MET Conversion Since CREBBP and EP300 contain both bromodomain and HAT domain, we next explored whether inhibiting the HAT domain of these proteins would induce a similar phenotype as inhibiting the bromodomains. When NAMEC8 was treated with A-485, a potent and selective HAT inhibitor of CREBBP/EP300, tight clusters of epithelial islands were observed, signifying an epithelial-like cell morphology (FIG. 19A). A-485 treatment also demonstrated an upregulation of E-cadherin protein expression, with slight decrease in the mesenchymal markers (FIG. 19B). These data suggest that similar to SGC-CBP30, inhibiting the HAT domain of these proteins seemed to promote MET in mesenchymal cells. However, when the A-485 treated cells were evaluated for their in vitro stemness via mammosphere assay, there was no significant difference in sphere count from the DMSO-treated cells (FIG. 19C), indicating the limited potential of A-485 in reducing the stemness of mesenchymal cells. Interestingly, when NAMEC8 cells were analyzed for the expression of CD44 and CD24 cell surface markers upon A-485 treatment, an obvious increase in CD44 expression was observed (FIG. 19D). Consequently, the data demonstrates that inhibiting the HAT domains of CREBBP/EP300 proteins was only able to induce an epithelial-like phenotype in NAMEC8 cells, but was unable to decrease the in vitro stemness.

As CREBBP and EP300 are acetyltransferases, we next evaluated three of the most commonly acetylated histone marks-lysine 14, 18 and 27 of histone H3 (H3K14ac, H3K18ac and H3K27ac) after SGC-CBP30 and A-485 treatment. Data showed that upon SGC-CBP30 treatment, all the acetylation marks were decreased but to a lesser extent compared to A-485 treatment (FIG. 19E). As SGC-CBP30 was shown to be more potent in MET conversion than A-485, this suggests that the cell state transition might not be solely attributed to changes in acetylation status, but that the involvement of bromodomain is also essential. However, more work needs to be done to elucidate if bromodomain and HAT indeed regulate different target genes and proteins, and to explore the effects of bromodomain inhibition on MET conversion. By elucidating the mechanisms as to how inhibiting the bromodomains of CREBBP/EP300 could specifically induce cell state transitions in mesenchymal cells could serve as a novel therapeutic approach for TNBC.

CREBBP/EP300 Bromodomain Inhibition Reduces Tumor Burden of Basal-Like TNBC In Vivo Upon establishing that CREBBP/EP300-mediated epigenetic alteration could induce MET and decrease the stem-like properties of basal-like, mesenchymal TNBC cells, we next investigated the tumorigenic potential of TNBC upon CREBBP/EP300 bromodomain and HAT inhibition to determine if it could reduce tumor burden in mice. When NAMEC8-Ras cells were pre-treated with SGC-CBP30 and A-485 before subcutaneous injection into immunodeficient NOD scid gamma (NSG) mice, only SGC-CBP30 treatment resulted in significantly smaller tumors after 11 weeks, as compared to the DMSO treated cells. Tumor formation was still observed upon A-485 pre-treatment (FIG. 19F). This complements the in vitro findings that SGC-CBP30 is more potent in the MET conversion of mesenchymal cells as compared to A-485. Hence, this suggests that by altering the gene regulation of TNBC cells through CREBBP/EP300 bromodomain inhibition, cells became less tumorigenic. However, there is a need to repeat the in vivo study to ensure that this observation is consistent and reproducible. Furthermore, histological analysis need to be performed on the tumor tissues to determine if there are any morphological differences between the tumors formed by DMSO and drug treated cells. Nevertheless, our initial in vivo data suggests that inhibiting the bromodomains of CREBBP/EP300 proteins could reduce the tumorigenic potential of the highly aggressive TNBC.

Taken together, these data indicate that the CREBBP and EP300 proteins potentially have a role to play in maintaining a mesenchymal cell state. Inhibiting the bromodomain of these two co-activator proteins potentially leads to decreased transcriptional regulations, as well as modifications in the epigenetic landscape of genes imperative to maintain cells in a mesenchymal state. Therefore, we postulate that the bromodomains of CREBBP and EP300 could possibly be regulating mesenchymal genes that are associated with super-enhancers. These genes would be hyperacetylated, hence resulting in greater transcriptional activation as mediated by CREBBP/EP300 bromodomains (FIG. 19G). Inhibiting the bromodomain would impede binding of coactivators and transcription factors to the promoters of these mesenchymal genes, resulting in reduced acetylation and subsequently gene transcription. As such, we hypothesize that the induction of MET could potentially be due to the decreased transcription of genes that are important for maintenance of a mesenchymal cell state (FIG. 19G).

Phenotypic Screen for MET Inducers Against Metabolic Targets

NAMEC8-SERPINE1 cells were used in a screen with a library of 303 compounds against metabolic targets (Med-Chem Express) to identify MET inducers. A list of 15 compounds were identified as strong inducers of MET, and we selected 6 compounds to proceed with orthogonal validation in vitro: Glutaminase C-IN-1, GSK256066, GSK2837808A, AGI-6780, SW033291 and NCT-503 (FIGS. 20A and B). Dual-glo luciferase assay was carried out in NAMEC8-SERPINE1 cells treated with the 6 selected compounds at increasing concentrations from 10 nM to 2 µM. A dose dependent decrease in SERPINE1 promoter activity was observed with compounds Glutaminase C-IN-1, GSK256066 and AGI-6780 (FIG. 20C).

To investigate any possible associations between glutaminase and the mesenchymal phenotype, western blot analysis of glutaminase was carried out in a panel of epithelial vs.

mesenchymal breast cancer cell lines. Mesenchymal breast cancer cell lines were found to express higher levels of GLS1 compared to epithelial breast cancer cell lines, suggesting that GLS1 could be a determinant of the mesenchymal cell state and a potential biomarker for triple negative breast cancer (FIG. 20D).

To carry out in vitro validation of MET, NAMEC8 cells were treated with C-IN-1. A morphological change from a scattered distribution typically observed in mesenchymal cells to tight clusters of epithelial islands was induced upon C-IN-1 treatment (FIG. 20E). A corresponding change in molecular markers was observed by western blot, where mesenchymal proteins Zeb1, fibronectin, Slug and Snail were decreased, epithelial E-Cadherin was increased, basal cytokeratin 5 was decreased and luminal markers cytokeratin 8, mucin1 and ER were increased upon treatment with C-IN-1 (FIG. 20F). This provides molecular evidence for the induction of MET upon glutaminase inhibition.

Genetic knockdown of GLS1 was carried out in NAMEC8 using 3 shRNAs (FIG. 20G) followed by treatment with paclitaxel to investigate changes in chemosensitivity after MET induction. A decrease in IC50 to paclitaxel was observed in GLS1 sh2 cells compared to Ctrlsh cells (FIG. 20H), indicating an increased chemosensitivity upon conversion to an epithelial phenotype. Mammosphere assay was also carried out as an in vitro assay for stemness. A decrease in the number of spheres formed was observed in GLS1 sh2 and sh3 cells compared to Ctrlsh cells, suggesting a decrease in stemness (FIG. 20 I). Genetic knockdown of GLS1 was also carried out in NAMEC8-HRas cells and injected subcutaneously into flanks of NSG mice. A decrease in tumor growth was observed by GLS1sh2 cells as compared to Ctrlsh cells (FIGS. 20 J and K). This suggests a decreased tumorigenic potential upon induction of MET.

Example 3

Discussion

Alterations in cell states represent one emerging approach to control the response of cancer cells to therapy. In acute promyelocytic leukemia and cutaneous T-cell lymphoma, retinoids have been applied as a first-line adjuvant with curative intent. In solid tumors, however, we demonstrated that retinoids act as an inducer of the shift in cell states which primes otherwise resistant breast cancer cells to respond better to standard-of-care treatments, and may thus be clinically useful in combination therapies. In addition, retinoid-induced MET also shifts the cells from the more aggressive mesenchymal state to the less metastatic epithelial state. In small cohort studies of metastatic breast cancer patients, retinoid therapy did not result in response, possibly due to the lack of tumor molecular subtype stratification and patient selection. With new information arising from our study, we showed that the basal-like, TNBC which tend to be more mesenchymal in nature are more likely to respond. This highlights the need for biomarkers that could stratify potential responders from non-responders.

Immune checkpoint blockade therapy has shown remarkable benefit for some cancers. The attraction of harnessing the immune system lies in its common denominator approach-no matter how diverse the cancer's molecular changes are, the immune system has a natural advantage in its intrinsic ability to identify and attack cancer cells. While immune checkpoint (PD1, PD-L1) inhibitors have been effective in the treatment of certain human cancers, for examples, melanoma and lung cancer, they have not met with similar success in ER+/PR+ breast cancer; they are currently undergoing active clinical study in metastatic TNBC. Keynote 012 reported a response rate of 18% using Pembrolizumab monotherapy in a phase 1 study. Keynote 086, a phase 2 Pembrolizumab monotherapy study showed a response rate of 5%. The potential association between cancer cell states and expression of immune markers such as a PD-L1 in cell-based models has been suggested in some studies. The conversion of a mesenchymal to an epithelial cell state may elicit intrinsic molecular changes that now cause tumor cells to become more susceptible to attacks by immune cells, thereby improving the success of immunotherapy in breast cancer.

Mechanistically, there may be several routes to achieve the conversion of an MET phenotype. In our studies, retinoids are the most potent class of such inducers identified in an unbiased manner. We demonstrated, for the first time, that they act through rewiring lipid metabolism during cell states conversion (FIG. 7I). Whether lipid metabolism is indeed a driver or consequence of the changes in cell states remains to be determined. Inhibiting beta-oxidation with etomoxir was not sufficient to induce a MET, suggesting that other pathways are also necessary or that several enzymes of the FAO pathway need to be inhibited simultaneously. Nevertheless, overexpression of CPT1A alone was sufficient to block bexarotene-induced MET and the effects of bexarotene were prolonged by etomoxir treatment, demonstrating that the metabolic reprograming is a necessary feature to enable cells to shift between cell states, as well as to maintain the transition. Beyond TNBC, MET conversion could also be broadly applicable to cancers that bear mesenchymal features and prime their responses to other therapeutics.

Why do the differences in cancer cell states impose unique metabolic requirements? In embryonic stem cells, glutamine and $\alpha$-ketoglutarate ($\alpha$KG) supports pluripotency through elevated $\alpha$KG to succinate ratios that promote demethylation of DNA and histones. In cancer, cell states control proliferation, invasiveness, and tolerance to stress, which necessitate strict requirements for specific metabolites. For instance, asparagine availability promotes EMT-driven metastasis or tumor growth in general, whereas cisplatin-resistant cancer cells appear to depend on glutamine for nucleotide biosynthesis. In our study, channeling fatty acids towards $\beta$-oxidation for energy production may allow cancer cells in the mesenchymal state to tolerate fluctuations in nutrient levels during invasion and metastasis, whereas the more proliferative epithelial state may preferentially adopt aerobic glycolysis even in glucose-rich conditions, which is typical for bulk tumor cells. Thus, the addiction to specific metabolic pathways during distinct steps of cancer progression may be exploited to target cell states, and open up new avenues for anti-metabolite therapeutic strategies.

TABLE 3

| Key Resources Table | | |
|---|---|---|
| Reagent or Resource | Source | Identifier |
| Antibodies | | |
| β-actin | CST | 4970 |
| Zeb1 | SCBT | sc25388 |
| Fibronectin | BD Biosciences | 610078 |
| E-cadherin | Abcam | ab11512 |
| E-cadherin | BD Biosciences | 610182 |
| Estrogen Receptor | SCBT | sc-542 |
| Vimentin | BD | 550513 |
| Cytokeratin 5 | Abcam | ab52635 |
| Cytokeratin 8 | DSHB | 531826 |
| Mucin1 | SCBT | sc-7313 |
| Histone H3K27ac | Active Motif | 39135 |
| Keratin 8/18 | CST | 4546S |
| RXRα | SCBT | sc-553 |
| RXRα | SCBT | sc-515929 |
| RARα | Diagenode | C15310155 |
| Anti-rabbit-HRP | CST | 7074P2 |
| CD44-APC | BD Biosciences | 55942 |
| CD24-PE | BD Biosciences | 555428 |
| Anti mouse-HRP | CST | 7076S |
| Cytokeratin 8 (TROMA-I-s) | DSHB | NA |
| P300 | SCBT | sc-585 |
| Slug | SCBT | sc-15391 |
| GPAT | SCBT | sc-398135 |
| AGPAT9 | SCBT | sc-514163 |
| DGAT2 | SCBT | sc-293211 |
| CPT1A | SCBT | sc-393070 |
| Goat anti-Mouse IgG (H + L) Alexa Fluor 594 | Invitrogen | A11005 |
| Goat anti-Rabbit IgG (H + L) Alexa Fluor 594 | Invitrogen | A11012 |
| Donkey anti-Rat IgG (H + L) Alexa Fluor 594 | Invitrogen | A21209 |
| Goat anti-Mouse IgG Alexa Fluor 488 | Invitrogen | A11001 |
| Goat anti-Rabbit IgG (H + L) Alexa Fluor 488 | Invitrogen | A11008 |
| Donkey anti-Rat IgG (H + L) Alexa Fluor 488 | Invitrogen | A21208 |

TABLE 3-continued

| Key Resources Table | | |
| --- | --- | --- |
| Reagent or Resource | Source | Identifier |
| Chemicals, peptides and recombinant proteins | | |
| EGF | Sigma-Aldrich | E9644 |
| Hydrocortisone | Sigma-Aldrich | H0888 |
| Matrigel | Thermo Fisher Scientific | Cat#356231 |
| SYBR Green PCR Master Mix | Thermo Fisher Scientific | Cat#4312704 |
| Lipofectamine 2000 | Thermo Fisher Scientific | 11668019 |
| FuGENE 6 Transfection Reagent | Promega | E2691 |
| Collagenase IV | Gibco | 17-104-019 |
| Dispase II | Thermo Fisher Scientific | 17105041 |
| Trypsin | Invitrogen | Cat#25200114 |
| Insulin | Sigma- | I9278 |
| A83-01 | Sigma- | SML0788 |
| Bexarotene | Selleckchem | S2098 |
| TTNPB | Cayman Chemical | CAS 71441-28-6 |
| ATRA | Cayman Chemical | CAS 302-79-4 |
| Doxycycline hyclate | Sigma-Aldrich | D9891 |
| 4-hydroxytamoxifen | Sigma-Aldrich | H7904 |
| Polybrene | Sigma-Aldrich | H9268 |
| Etomoxir | Sigma-Aldrich | CAS 828934-41-4 |
| FSG67 | Focus Biomolecules | 10-4577 |
| AmidepsineA | APExBIO | C4872 |
| Paclitaxel | VWR | 89164-960 |
| 5-Fluorouracil | Sigma-Aldrich | F6627 |
| Bodipy 493/503 | Thermo Fisher Scientific | D3922 |
| Seahorse XF Palmitate-BSA FAO Substrate | Agilent | 102720-100 |

TABLE 3-continued

| Key Resources Table | | |
|---|---|---|
| Reagent or Resource | Source | Identifier |
| Critical Commercial Assays | | |
| Illumina TruSeq stranded mRNA kit | Illumina | #RS-122-2101 |
| Illumina TruSeq ChIP kit | Illumina | #IP-202-1012 |
| RNeasy mini kit | QIAGEN | Cat#74106 |
| SuperScript III First-Strand Synthesis System | Thermo Fisher Scientifi | 18080051 |
| Dual-Glo Luciferase assay system | Promega | E2920 |
| CellTiter-Glo® Luminescent Cell Viability Assay | Promega | G7572 |
| LOPAC$^{1280}$ | Sigma-Aldrich | LO4200 |
| Anti-cancer Compound Library | Selleckchem | L3000 |
| Kinase inhibitor Library | Selleckchem | L1200 |
| Bioactive lipids | Cayman Chemical | 10506 |
| Epigenetics Compound Library | Selleckchem | L1900 |
| Seahorse XF Cell Mito Stress Test Kit | Agilent Technologies | 103015-100 |
| Deposited Data | | |
| ChIP-Seq | GEO database | Accession no: GSE119824 |
| RNA-Seq | SRA database | Accession no: SRP152713 |
| Experimental Models: Cell Lines | | |
| NAMEC8-CD24promluc | This | |
| NAMEC8-CD44promluc | This document | |
| NAMEC8-CD166promluc | This document | |
| NAMEC8-CDH1promluc | This document | |
| NAMEC8-ZEB1promluc | This document | |
| NAMEC8-SERPINE1promluc | This document | |
| NAMEC8-pMN-CPT1A | This document | |
| SUM159-pMN-CPT1A | This document | |
| Recombinant DNA | | |
| pGreenFire-mcmv | System Biosciences | Cat# TR010PA-1 |
| pGreenFire-mcmv-Serpine1 | This document | |
| pGreenFire-mcmv-CDH1 | This document | |
| pGreenFire-mcmv-CD24 | This document | |
| pGreenFire-mcmv-CD44 | This document | |
| pGreenFire-mcmv-CD166 | This document | |
| pGreenFire-mcmv-Zeb1 | This document | |

TABLE 3-continued

| Key Resources Table | | |
| --- | --- | --- |
| Reagent or Resource | Source | Identifier |
| Sequence-Based Reagents Probes for gene promoters | | |
| CDH1 | | F: ATGGCTCAAGAAACATTTGTCAT (SEQ ID NO: 1) R: GAGCTTGCGGCCCGAAT (SEQ ID NO: 2) |
| CD24 | | F: GAGAACAGGATGCCCCTTAGAAT (SEQ ID NO: 3) R: AAATCTGCGTGGGTAGGAGCA (SEQ ID NO: 4) |
| CD44 | | F: ATCTTGCCACAGCCACTGAT (SEQ ID NO: 5) R: TCGGAAGTTGGCTGCAGTTT (SEQ ID NO: 6) |
| SERPINE1 | | F: CGGGCAGCTCGAAGAAGTG (SEQ ID NO: 7) R: TAGAGGAATAGCGGGGGATCAT (SEQ ID NO: 8) |
| CD166 | | F: AGGGGGAGGAGAGAGAGATTCG (SEQ ID NO: 9) R: GCGGAGATCAAGAGGCAGAA (SEQ ID NO: 10) |
| ZEB1 | | F: CGGCGGATCGATTCAGCTTATTTATTCCA (SEQ ID NO: 11) R: CGGTAAACTAGTGATCCTCTCGCTTGTGT (SEQ ID NO: 12) |
| Primers for RT-PCR | | |
| CDH1 | | F: TTGCACCGGTCGACAAAGGAC (SEQ D NO: 13) R: TGGATTCCAGAAACGGAGGCC (SEQ ID NO: 14) |
| VIM | | F: ACCCGCACCAACGAGAAGGT (SEQ ID NO: 15) R: ATTCTGCTGCTCCAGGAAGCG (SEQ ID NO: 16) |
| SLUG | | F: TACCGCTGCTCCATTCCACG (SEQ ID NO: 17) R: CATGGGGGTCTGAAAGCTTGG (SEQ ID NO: 18) |
| GAPDH | | F: TGGCAAATTCCATGGCACCG (SEQ ID NO: 19) R: CGCCCCACTTGATTTTGGAGG (SEQ ID NO: 20) |
| SERPINE1 | | F: GCACCACAGACGCGATCTT (SEQ ID NO: 21) R: ACCTCTGAAAAGTCCACTTGC (SEQ ID NO: 22) |
| ZEB1 | | F: TGCACTGAGTGTGGAAAAGC (SEQ ID NO: 23) R: TGGTGATGCTGAAAGAGACG (SEQ ID NO: 24) |
| MUC1 | | F: TGCCGCCGAAAGAACTACG (SEQ ID NO: 25) R: TGGGGTACTCGCTCATAGGAT (SEQ ID NO: 26) |
| KRT5 | | F: CCAAGGTTGATGCACTGATGG (SEQ ID NO: 27) R: TGTCAGAGACATGCGTCTGC (SEQ ID NO: 28) |
| KRT8 | | F: CAGAAGTCCTACAAGGTGTCCA (SEQ ID NO: 29) R: CTCTGGTTGACCGTAACTGCG (SEQ ID NO: 30) |
| FN1 | | F: GAGAATGGACCTGCAAGCCCA (SEQ ID NO: 31) R: AGTGCAAGTGATGCGTCCGC (SEQ ID NO: 32) |
| GREB1 | | F: ATGGGAAATTCTTACGCTGGAC (SEQ ID NO: 33) R: CACTCGGCTACCACCTTCT (SEQ ID NO: 34) |
| ABCA3 | | F: CTCCTCTGGAAGAACTACACCC (SEQ ID No: 35) R: GGGCACATTTTCCGACTGAATC (SEQ ID NO: 36) |
| NRIP1 | | F: GGATCAGGTACTGCCGTTGAC (SEQ ID NO: 37) R: CTGGACCATTACTTTGACAGGTG (SEQ ID NO: 38) |
| TFF1 | | F: CCCTCCCAGTGTGCAAATAAG (SEQ ID NO: 39) R: GAACGGTGTCGTCGAAACAG (SEQ ID NO: 40) |
| LIPE | | F: TCAGTGTCTAGGTCAGACTGG (SEQ ID NO: 41) R: AGGCTTCTGTTGGGTATTGGA (SEQ ID NO: 42) |
| PNPLA2 | | F: GGCTTCCTCGGCGTCTACTA (SEQ ID NO: 43) R: TTTACCAGGTTGAAGGAGGGG (SEQ ID NO: 44) |
| ACSL4 | | F: CATCCCTGGAGCAGATACTCT (SEQ ID NO: 45) R: TCACTTAGGATTTCCCTGGTCC (SEQ ID NO: 46) |
| ACSL5 | | F: CTCAACCCGTCTTACCTCTTCT (SEQ ID NO: 47) R: GCAGCAACTTGTTAGGTCATTG (SEQ ID NO: 48) |

TABLE 3-continued

Key Resources Table

| Reagent or Resource | Source | Identifier |
|---|---|---|
| AGPAT4 | | F: CTCAGGGCTAATCATCAACACC (SEQ ID NO: 49)<br>R: GCTTGAGATGCAATAGGACAGT (SEQ ID NO: 50) |
| AGPAT9 | | F: CGCTGGTTCTCGGCTTCAT (SEQ ID NO: 51)<br>R: TGGCCCACTCTAAAGTTTTCAC (SEQ ID NO: 52) |
| GPAM | | F: GATGTAAGCACACAAGTGAGGA (SEQ ID NO: 53)<br>R: TCCGACTCATTAGGCTTTCTTTC (SEQ ID NO: 54) |
| PPAP2A | | F: GGCAGGTTGTCCTTCTATTCAG (SEQ ID NO: 55)<br>R: CAGTGTGGGGCGTAAGAGT (SEQ ID NO: 56) |
| DGAT2 | | F: ATTGCTGGCTCATCGCTGT (SEQ ID NO: 57)<br>R: GGGAAAGTAGTCTCGAAAGTAGC (SEQ ID NO: 58) |
| PLIN1 | | F: TGTGCAATGCCTATGAGAAGG (SEQ ID NO: 59)<br>R: AGGGCGGGGATCTTTTCCT (SEQ ID NO: 60) |
| MGLL | | F: ATGCCAGAGGAAAGTTCCCC (SEQ ID NO: 61)<br>R: CGTCTGCATTGACCAGGTG (SEQ ID NO: 62) |
| ESR1 | | F: CCCACTCAACAGCGTGTCTC (SEQ ID NO: 63)<br>R: CGTCGATTATCTGAATTTGGCCT (SEQ ID NO: 64) |
| PTGS1 | | F: CGCCAGTGAATCCCTGTTGTT (SEQ ID NO: 65)<br>R: AAGGTGGCATTGACAAACTCC (SEQ ID NO: 66) |
| HADHB | | F: CTGTCCAGACCAAAACGAAGAA (SEQ ID NO: 67)<br>R: CGATGCAACAAACCCGTAAGC (SEQ ID NO: 68) |
| Software and Algorithms | | |
| GREAT | Stanford University | Berajano Lab |
| ROSE | Whitehead Institute for Biomedical Research | Young Lab |

Table 4: Gene Ontology pathway enrichment analyses of upregulated genes upon bexarotene treatment in NAMEC8. Immune response pathways and genes are highlighted below.

A GO Biological Process regulation of cell proliferation (GO: 0042127)
    cytokine-mediated signaling pathway (GO: 0019221)
    regulation of angiogenesis (GO: 0045765)
    positive regulation of cell death (GO: 0010942)

glycosaminoglycan biosynthetic process (GO: 0006024)
positive regulation of angiogenesis (GO: 0045766)
positive regulation of vasculature development (GO: 1904018)
cellular response to decreased oxygen levels (GO: 0036294)
positive regulation of cell proliferation (GO: 0008284)
cellular response to type I interferon (GO: 0071357)

| Term | P-value | Genes |
|---|---|---|
| regulation of cell proliferation (GO:0042127) | 1.23E−08 | COL18A1; CDKN1A; NOTCH1; CSF1; NPR3; TGFA; IFIT3; DPP4; NAMPT; CTSH; S1PR3; SOX9; TIMP1; IGFBP6; SOX7; JAG2; NGFR; KLF11; WARS; LIF; AKR1C3; AKR1C2; WNT9A; EREG; VEGFA; BCL6; IL1B; DLC1; IRF1; BHLHE40; MDM2; IL6ST; CRLF1 |
| cytokine-mediated signaling pathway (GO:0019221) | 1.99E−07 | CDKN1A; CSF1; MAOA; IFI6; IFIT3; ICAM1; IFIT2; OASL; IRAK2; HMOX1; CD36; TIMP1; GBP2; TRIM22; NGFR; PRKCD; LIF; EREG; VEGFA; BCL6;<br>OAS1; OAS2; IL1B; IRF1; IL6ST; SQSTM1; STX1A; CRLF1 |
| regulation of angiogenesis (GO:0045765) | 3.59E−07 | EGLN1; WARS; GATA6; RUNX1; VEGFA; IL1B; ADAM12; PGK1; HMOX1; CTSH; CHI3L1; ANGPTL4; HOXA5; RAPGEF3 |
| positive regulation of cell death (GO:0010942) | 1.86E−06 | PRNP; BNIP3; DLC1; DDIT4; AKR1C3; CD36; CLU; MAP3K5 |

| Term | P-value | Genes |
|---|---|---|
| glycosaminoglycan biosynthetic process (GO:0006024) | 1.99E–06 | VCAN; SDC4; IL1B; GPC1; CHST15; HAS3; HS6ST1; GPC6; CHST3; B4GALT5 |
| positive regulation of angiogenesis (GO:0045766) | 2.85E–06 | IL1B; ADAM12; GATA6; HMOX1; CTSH; CHIL1; ANGPTL4; RAPGEF3; RUNX1; VEGFA |
| positive regulation of vasculature development (GO:1904018) | 3.11E–06 | IL1B; ADAM12; GATA6; HMOX1; CTSH; CHI3L1; ANGPTL4; RAPGEF3; RUNX1; VEGFA |
| cellular response to decreased oxygen levels (GO:0036294) | 4.49E–06 | EPAS1; BNIP3; GATA6; PGK1; MDM2; HMOX1; VEGFA; CPE84 |
| positive regulation of cell proliferation (GO:0008284) | 4.60E–06 | CDKN1A; NOTCH1; CSF1; LIF; AKR1C3; TGFA; AKR1C2; EREG; VEGFA; DPP4; IL1B; NAMPT; MDM2; HMOX1; CTSH; S1PR3; SOX9; TIMP1; IL6ST; CRLF1 |
| cellular response to type I interferon (GO:0071357) | 5.04E–06 | OAS1; OAS2; IRF1; IFI6; GBP2; IFIT3; IFIT2; OASL |
| type I interferon signaling pathway (GO:0060337) | 5.04E–06 | OAS1; OAS2; IRF1; IFI6; GBP2; IFIT3; IFIT2; OASL |
| negative regulation of amyloid-beta formation (GO:1902430) | 5.22E–06 | PRNP; BIN1; APOE; CLU |
| positive regulation of cellular process (GO:0048522) | 8.40E–06 | NOTCH1; CSF1; PRKCD; LIF; AKR1C3; TGFA; AKR1C2; EREG; VEGFA; DPP4; MMP14; IL1B; DLC1; NAMPT; MDM2; CTSH; S1PR3; SOX9; CD36; TIMP1; IL6ST; CRLF1 |
| interferon-gamma-mediated signaling pathway (GO:0060333) | 8.77E–06 | OAS1; OAS2; IRF1; PRKCD; GBP2; TRIM22; ICAM1; OASL |
| negative regulation of amyloid precursor protein catabolic process (GO: 1902992) | 1.34E–05 | PRNP; BIN1; APOE; CLU |
| progesterone metabolic process (GO:0042488) | 1.34E–05 | DHRS9; AKR1C1; ARK1C3; AKR1C2 |
| cellular response to cytokine stimulus (GO:0071345) | 1.34E–05 | CDKN1A; CSF1; MAOA; TCF7; LIF; ICAM1; EREG; VEGFA; BCL6; IRAK2; IL1B; IRF1; HMOX1; CHI3L1; SOX9; CD36; TIMP1; IL6ST; STX1A; CRLF1 |

B) WikiPathway analyses of upregulated genes upon bexarotene treatment in NAMEC8. Immune response pathways and genes are highlighted below.

B WikiPathways

Nuclear Receptors Meta-Pathway WP2882

Type II interferon signaling (IFNG) WP619

Pathways in clear cell renal cell carcinoma WP4018

Benzo(a)pyrene metabolism WP696

VEGFA-VEGFR2 Signaling Pathway WP3888

Serotonin Transporter Activity WP1455

Complement Activation WP545

Photodynamic therapy-induced HIF-1 survival signaling WP3614

Hematopoietic Stem Cell Differentiation WP2849

Prostaglandin Synthesis and Regulation WP98

| Term | P-value | Genes |
|---|---|---|
| Nuclear Receptors Meta-Pathway WP2882 | 2.45E–07 | SRGN; CPT1A; G6PD; TXNRD1; TGFA; SLC7A11; SLC7A5; THBD; SLC6A8; GPAM; IL1B; SCNN1A; BHLEH40; PDK4; HMOX1; SPRY1; ANGPTL4; SQSTM1; CPEB4 |
| Type II interferon signaling (IFNG) WP619 | 9.10E–07 | OASI; IL1B; IRF1; PRKCD; IFI6; IFIT2; ICAM1 |
| Pathways in clear cell renal cell carcinoma WP4018 | 4.04E–06 | KSR1; PSAT1; BHLHE41; GRB10; PGK1; ENO2; SQSTM1; PGM1; VEGFA |
| Benzo(a)pyrene metabolism WP696 | 5.22E–06 | AKR1C1; EPHX1; AKR1C3; AKR1C2 |
| VEGFA-VEGFR2 Signaling Pathway WP3888 | 1.00E–05 | NRP2; EGR3; ITGB3; PRKCD; FHL2; ICAM1; VEGFA; EEA1; MMP14; BIN1; GPC1; GRB10; FLNB; MAP3K5 |

-continued

| Term | P-value | Genes |
|------|---------|-------|
| Serotonin Transporter Activity WP1455 | 1.34E−05 | MAOA; IL1B; ITGB3; STX1A |
| Complement Activation WP545 | 1.35E−05 | C3; C4B; C4A; C1S; C1R |
| Photodynamic therapy-induced HIF-1 survival signaling WP3614 | 1.43E−05 | EGLN1; BNIP3; IGFBP2; PGK1; TGFA; VEGFA |
| Hematopoietic Stem Cell Differentiation WP2849 | 1.43E−05 | SEC14L2; NOTCH1; CSF1; RIOK3; ITGB3; IL1B; RUNX1 |
| Prostaglandin Synthesis and Regulation WP98 | 4.56E−05 | AKR1C1; AKR1C3; AKR1C2; PTGFRN; SOX9; PTGES |
| Human Complement System WP2806 | 8.60E−05 | C3; C4A; PRNP; C1S; C1R; ITGB3; ITGA2; ICAM1 |
| Amplification and Expansion of Oncogenic Pathways as Metastatic Traits WP3678 | 9.00E−05 | NOTCH1; EPAS1; TCF7; VEGFA |
| NOTCHI regulation of human endothelial cell calcification WP3413 | 9.00E−05 | JAG2; NOTCH2; MGP; VEGFA |
| Type 2 papillary renal cell carcinoma WP4241 | 1.24E−04 | EGLN1; CDKN1A; EPAS1; TGFA; VEGFA |
| Senescence and Autophagy in Cancer WP615 | 1.50E−04 | CDKN1A; MMP14; IL1B; IRF1; CREG1; MDM2; IL6ST; SQSTM1 |
| Complement and Coagulation Cascades WP558 | 1.93E−04 | C4B; C3; THBD; C1S; C1R; CLU |

The invention claimed is:

1. A method of inducing mesenchymal-epithelial transition (MET) in a cancer cell, the method comprising contacting the cell with an inducer of mesenchymal-epithelial transition for a time and under conditions sufficient to induce MET in the cell,
    wherein the cancer cell is a basal-like (mesenchymal-like) cancer cell,
    wherein the inducer of MET is an adenosine/adrenergic receptor modulator, a GABA receptor modulator, a NMDA receptor modulator, or a neurotransmitter;
    wherein the adenosine/adrenergic receptor modulator is idazoxan hydrochloride, (±)-atenolol, or 1,3-Dipropyl-8-p-sulfophenylxanthine;
    wherein the GABA receptor modulator is (±)-nipecotic acid or chlormethiazole hydrochloride;
    wherein the NMDA receptor modulator is 1-aminocyclo-propanecarboxylic acid hydrochloride or (±)-2-amino-4-phosphonobutyric acid;
    wherein the neurotransmitter is ABT-418 hydrochloride, Apomorphine hydrochloride hemihydrate, Varenicline Tartrate, or ML 10302; and wherein the cancer cell is a cancer cell from triple negative breast cancer, head and neck cancer, lung cancer, pancreatic cancer, ovarian cancer, gastric cancer or colorectal cancer.

2. The method of claim 1, wherein the cancer cell is triple negative breast cancer.

3. The method of claim 1, wherein the cancer cell is a cancer cell that is resistant to standard-of-care therapies.

4. The method of claim 1, wherein the method further comprises contacting the cell with:

i) a chemotherapeutic agent selected from chlorambucil, ifosfamide, doxorubicin, mesalazine, thalidomide, lenalidomide, temsirolimus, everolimus, fludarabine, 5-fluorouracil, fostamatinib, paclitaxel, docetaxel, ofatumumab, rituximab, dexamethasone, prednisone, CAL-101, ibritumomab, tositumomab, bortezomib, pentostatin, or endostatin, ii) an epigenetic-modifying compound selected from vorinostat (SAHA), belinostat (PXD101), LAQ824, Panobinostat (LBH589), entinostat (MS-275), tacedinaline (CI994) or mocetinostat (MGCD0103), or iii) an immune checkpoint inhibitor selected from an inhibitor of Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, ID01,_1D02, ICOS (inducible T cell costimulator), KIR, LAIR1, LIGHT, MARCO (macrophage receptor with collageneous structure), PS (phosphatidylserine), OX-40, SLAM, TIGHT, VISTA or VTCN1, following induction of MET in the cancer cell.

5. The method of claim 1, wherein the method further comprises contacting the basal-like (or mesenchymal-like) cancer cell with an inhibitor of lipid metabolism, wherein the inhibitor of lipid metabolism is selected from etomoxir, perhexiline, oxfenicine, 4-bromocrotonic acid, tracsin C, thiazolidinediones, trimetazidine, ranolazine or JZL184.

6. The method of claim 5, wherein the inhibitor of lipid metabolism is etomoxir, perhexiline or oxfenicine.

7. The method of claim 1, wherein the method comprises inhibiting the progress of growth of a basal-like (mesenchymal-like) cancer in a patient or sensitizing a patient to an anti-cancer therapy.

8. A method of inhibiting the progress of growth of a basal-like (mesenchymal-like) cancer in a patient in need thereof, the method comprising administering an inducer of mesenchymal-epithelial transition (MET) in combination with a chemotherapeutic agent, an epigenetic-modifying compound, an immunomodulatory agent, or an inhibitor of lipid metabolism to the patient, for a time and under conditions to inhibit the progress of growth of cancer in the patient, wherein the inducer of MET is an adenosine/adrenergic receptor modulator, a GABA receptor modulator, a NMDA receptor modulator, or a neurotransmitter;

wherein the adenosine/adrenergic receptor modulator is idazoxan hydrochloride, (±)-atenolol, or 1,3-Dipropyl-8-p-sulfophenylxanthine;

wherein the GABA receptor modulator is (±)-nipecotic acid or chlormethiazole hydrochloride;

wherein the NMDA receptor modulator is 1-aminocyclopropanecarboxylic acid hydrochloride or (±)-2-amino-4-phosphonobutyric acid;

wherein the neurotransmitter is ABT-418 hydrochloride, Apomorphine hydrochloride hemihydrate, Varenicline Tartrate, or ML 10302;

wherein the chemotherapeutic agent is selected from chlorambucil, ifosfamide, doxorubicin, mesalazine, thalidomide, lenalidomide, temsirolimus, everolimus, fludarabine, 5-fluorouracil, fostamatinib, paclitaxel, docetaxel, ofatumumab, rituximab, dexamethasone, prednisone, CAL-101, ibritumomab, tositumomab, bortezomib, pentostatin or endostatin, wherein the epigenetic-modifying compound is selected from vorinostat (SAHA), belinostat (PXD101), LAQ824, Panobinostat (LBH589), entinostat (MS-275), tacedinaline (CI994) or mocetinostat (MGCD0103), wherein the immune checkpoint inhibitor is selected from an inhibitor of Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, ID01,_1D02, ICOS (inducible T cell costimulator), KIR, LAIR1, LIGHT, MARCO (macrophage receptor with collageneous structure), PS (phosphatidylserine), OX-40, SLAM, TIGHT, VISTA or VTCN1, wherein the inhibitor of lipid metabolism is selected from etomoxir, perhexiline, oxfenicine, 4-bromocrotonic acid, tracsin C, thiazolidinediones, trimetazidine, ranolazine or JZL184, and wherein the cancer is triple negative breast cancer, head and neck cancer, lung cancer, pancreatic cancer, ovarian cancer, gastric cancer or colorectal cancer.

9. A method of identifying and inhibiting the progress of growth of a cancer in a cancer patient responsive to a combination therapy comprising a mesenchymal-epithelial transition (MET) inducing compound in combination with a chemotherapeutic agent, an epigenetic-modifying compound, an immunomodulatory agent, or an inhibitor of lipid metabolism, the method comprising:

a) detecting a mesenchymal subtype of cancer in a sample obtained from the patient, wherein the presence of a mesenchymal subtype of cancer indicates that the patient is responsive to the combination therapy; and b) administering the combination therapy to the patient;

wherein the MET inducing compound is an adenosine/adrenergic receptor modulator, a GABA receptor modulator, a NMDA receptor modulator, or a neurotransmitter;

wherein the adenosine/adrenergic receptor modulator is idazoxan hydrochloride, (±)-atenolol, or 1,3-Dipropyl-8-p-sulfophenylxanthine;

wherein the GABA receptor modulator is (±)-nipecotic acid or chlormethiazole hydrochloride;

wherein the NMDA receptor modulator is 1-aminocyclopropanecarboxylic acid hydrochloride or (±)-2-amino-4-phosphonobutyric acid;

wherein the neurotransmitter is ABT-418 hydrochloride, Apomorphine hydrochloride hemihydrate, Varenicline Tartrate, or ML 10302;

wherein the chemotherapeutic agent is selected from chlorambucil, ifosfamide, doxorubicin, mesalazine, thalidomide, lenalidomide, temsirolimus, everolimus, fludarabine, 5-fluorouracil, fostamatinib, paclitaxel, docetaxel, ofatumumab, rituximab, dexamethasone, prednisone, CAL-101, ibritumomab, tositumomab, bortezomib, pentostatin, or endostatin, wherein the epigenetic-modifying compound is selected from vorinostat (SAHA), belinostat (PXD101), LAQ824, Panobinostat (LBH589), entinostat (MS-275), tacedinaline (CI994), and mocetinostat (MGCD0103), wherein the immune checkpoint inhibitor selected from an inhibitor of Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, ID01,_1D02, ICOS (inducible T cell costimulator), KIR, LAIR1, LIGHT, MARCO (macrophage receptor with collageneous structure), PS (phosphatidylserine), OX-40, SLAM, TIGHT, VISTA, or VTCN1, wherein the inhibitor of lipid metabolism is selected from etomoxir, perhexiline, oxfenicine, 4-bromocrotonic acid, tracsin C, thiazolidinediones, trimetazidine, rano-lazine or JZL184, and wherein the cancer is triple negative breast cancer, head and neck cancer, lung cancer, pancreatic cancer, ovarian cancer, gastric cancer or colorectal cancer.

\* \* \* \* \*